US009828602B2

(12) United States Patent
Freier et al.

(10) Patent No.: US 9,828,602 B2
(45) Date of Patent: Nov. 28, 2017

(54) ANTISENSE COMPOUNDS TARGETING GENES ASSOCIATED WITH FIBRONECTIN

(71) Applicant: Ionis Pharmaceuticals, Inc., Carlsbad, CA (US)

(72) Inventors: Susan M. Freier, San Diego, CA (US); Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/403,914

(22) PCT Filed: Jun. 3, 2013

(86) PCT No.: PCT/US2013/043935
§ 371 (c)(1),
(2) Date: Nov. 25, 2014

(87) PCT Pub. No.: WO2013/181665
PCT Pub. Date: Dec. 5, 2013

(65) Prior Publication Data
US 2015/0105444 A1    Apr. 16, 2015

Related U.S. Application Data

(60) Provisional application No. 61/721,993, filed on Nov. 2, 2012, provisional application No. 61/654,757, filed on Jun. 1, 2012.

(51) Int. Cl.
*C12N 15/113*    (2010.01)
*C07H 21/00*    (2006.01)

(52) U.S. Cl.
CPC ........... *C12N 15/113* (2013.01); *C07H 21/00* (2013.01); *C12N 2310/11* (2013.01); *C12N 2310/3231* (2013.01); *C12N 2310/3233* (2013.01); *C12N 2310/343* (2013.01); *C12N 2320/33* (2013.01)

(58) Field of Classification Search
CPC .................................................... C12N 15/113
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,007 B1 * | 4/2006 | Nyce ...................... A61K 31/70 435/325 |

(Continued)

FOREIGN PATENT DOCUMENTS

| | | |
|---|---|---|
| WO | WO 99/14226 | 8/1999 |
| WO | WO 2004/106356 | 12/2004 |

(Continued)

OTHER PUBLICATIONS

Caputi et al., "A novel bipartite splicing enhancer modulates the differential processing of the human fibronectin EDA exon." Nucleic Acids Res. (1994) 22(6): 1018-1022.

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71: 7731-7740.

Braasch et al., "Locked nucleic acid (LNA): fine-tuning the recognition of DNA and RNA" Chem. Biol. (2001) 8: 1-7.

Braasch et al., "Novel Antisense and Peptide Nucleic Acid Strategies for Controlling Gene Expression" Biochemistry (2002) 41(14): 4503-4510.

Branch et al., "A good antisense molecule is hard to find," TIBS (1998) 23:45-50.

(Continued)

*Primary Examiner* — J. E. Angell
(74) *Attorney, Agent, or Firm* — Knobbe, Martens, Olson & Bear, LLP

(57) ABSTRACT

The present invention provides compounds comprising oligonucleotides complementary to a fibronectin transcript. Certain such compounds are useful for hybridizing to a fibronectin transcript, including but not limited to a fibronectin transcript in a cell. In certain embodiments, such hybridization results in modulation of splicing of the fibronectin transcript. In certain embodiments, such compounds are used to treat one or more symptoms associated with fibrosis. In certain embodiments, such compounds are used to treat one or more symptoms associated with renal fibrosis.

9 Claims, 1 Drawing Sheet

(56) References Cited

U.S. PATENT DOCUMENTS

| | | | |
|---|---|---|---|
| 7,034,133 | B2 | 4/2006 | Wengel et al. |
| 7,064,207 | B2 | 6/2006 | Du et al. |
| 7,341,835 | B2 | 3/2008 | Blume et al. |
| 7,399,845 | B2 | 7/2008 | Seth et al. |
| 7,427,672 | B2 | 9/2008 | Imanishi et al. |
| 7,709,630 | B2 | 5/2010 | Gaarde et al. |
| 7,741,457 | B2 | 6/2010 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2005/0130923 | A1 | 6/2005 | Bhat et al. |
| 2005/0130924 | A1* | 6/2005 | Monia ............... C12N 15/113 514/44 A |
| 2007/0009899 | A1 | 1/2007 | Mounts |
| 2007/0031844 | A1* | 2/2007 | Khvorova ............ A61K 31/713 435/6.11 |
| 2007/0287831 | A1 | 12/2007 | Seth et al. |
| 2008/0039618 | A1 | 2/2008 | Allerson et al. |
| 2010/0197762 | A1* | 8/2010 | Swayze ............... C12N 15/111 514/44 A |
| 2012/0115923 | A1 | 5/2012 | He et al. |
| 2012/0172414 | A1 | 7/2012 | Migawa et al. |

FOREIGN PATENT DOCUMENTS

| | | |
|---|---|---|
| WO | WO 2005/021570 | 3/2005 |
| WO | WO 2007/134181 | 11/2007 |
| WO | WO 2008/046510 | 4/2008 |
| WO | WO 2008/049085 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2013/181665 | 12/2013 |

OTHER PUBLICATIONS

Chauhan et al., "Alternative splicing of fibronectin: a mouse model demonstrates the identiy of in vitro and in vivo systems and the processing autonomy of regulated exons in adult mice" Gene (2004) 324:55-63.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2): 923-937.

Elayadi et al., "Application of PNA and LNA oligomers to chemotherapy" Curr. Opinion Invest. Drugs (2001) 2: 558-561.

Englisch et al., "Chemically Modified Oligonucleotides as Probes and Inhibitors", Angewandte Chemie, International Edition, (1991) 30(6):613-722.

Freier et al., "The ups and downs of nucleic acid duplex stability: structure-stability studies on chemically-modified DNA:RNA duplexes" Nucleic Acids Research (1997) 25(22): 4429-4443.

Frieden et al., "Expanding the design horizon of antisense oligonucleotides with alpha-L-LNA" Nucleic Acids Research (2003) 31(21): 6365-6372.

GenBank Accession No. M28258.1 "Rat fibronectin gene, 1b and 2a" retrieved from the Internet on Apr. 2, 2013, downloaded from http://www.ncbi.nlm.nih.gov/nuccore/M28258.1.

Kabanov et al., "A new class of antivirals: antisense oligonucleotides combined with a hydrophobic substituent effectively inhibit influenza virus reproduction and synthesis of virus-specific proteins in MOCK cells" FEBS Lett., (1990) 259: 327-330.

Koller et al.,"Mechanisms of single-stranded phosphorothioate modified antisense oligonucleotide accumulation in hepatocytes" Nucleic Acids Research, (2011) 39: 4795-4807.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.

Kroschwitz, "The Concise Encyclopedia of Polymer Science and Engineering" pp. 858-859, John Wiley & Sons, 1990.

Kumar et al., "The First Analogues of LNA (Locked Nucleic Acids):Phosphorothioate-LNA and 2'-TmO-LNA" Bioorg. Med. Chem. Lett. (1998) 8: 2219-2222.

Letsinger et al., "Cholesteryl-conjugated oligonucleotides: Synthesis, properties, and activity as inhibitors of replication of human immunodeficiency virus in cell culture" PNAS (1989) 86: 6553-6556.

Leumann, "DNA Analogues: From Supramolecular Principles to Biological Properties" Bioorg. Med. Chem. (2002) 10: 841-854.

Manoharan et al., "Chemical Modifications to Improve Uptake and Bioavailability of Antisense Oligonucleotides" Arm. N.Y. Acad. Sci. (1992) 660: 306-309.

Manoharan et al., "Cholic Acid-Oligonucleotide Conjugates for Antisense Applications" Bioorg. Med. Chem. Let. (1994) 4(8): 1053-1060.

Manoharan et al., "Inoduction of a lipophilic thioether tether in the minor groove of nucleic acids for antisense applications" Bioorg. Med. Chem. Let. (1993) 3(12): 2765-2770.

Manoharan et al., "Lipidic Nucleic Acids" Tetrahedron Lett. (1995) 36(21): 3651-3654.

Manoharan et al., "Oligonucleotide Conjugates: Alteration of the Pharmacokinetic Properties of Antisense Agents" Nucleosides & Nucleotides (1995) 14(3-5): 969-973.

Mishra et al., "Improved leishmanicidal effect of phosphorotioate antisense oligonucleotides by LDL-mediated delivery" Biochim. Biophys. Acta (1995) 1264: 229-237.

Muro et al., "An Essential Role for Fibronectin Extra Type III Domain A in Pulmonary Fibrosis" American Journal of Respitory and Critical Care Medicine (2008) 177:638-45.

Muro et al., "Regulation of the fibronectin EDA exon alternative splicing. Cooperative role of the exonic enhancer element and the 5' splicing site" FEBS Letters (1998) 437:137-141.

New England Biolabs 1998/99 Catalog (cover page and pp. 121 and 284).

Oberhauser et al., "Effective incorporation of 2'-O-methyl-oligoribonucleotides into liposomes and enhanced cell association through modification with thiocholesterol" Nucl. Acids Res. (1992) 20(3): 533-538.

Orum et al., "Locked nucleic acids: A promising molecular family for gene-function analysis and antisense drug development" Curr. Opinion Mol. Ther. (2001) 3: 239-243.

Phanish et al., "The differential role of Smad2 and Smad3 in the regulation of pro-fibrotic TGF[beta]1 responses in human proximal-tubule epithelial cells" Biochemical Journal (2006) 393(2):601-607.

Reynolds et al., "Rational siRNA design for RNA interference" Nature Biotechnology (2004) 22(3):326-330.

Roy et al, "Downregulation of Fibronectin Overxpression Reduces Basement Membrane Thickening and Vascular Lesions in Retinas of Galactose-Fed Rats" Diabetes (2003) 52:1229-1234.

Saison-Behmoaras et al., "Short modified antisense oligonucleotides directed against Ha-ras point mutation induce selective cleavage of the mRNA and inhibit T24 cells proliferation" EMBO J. (1991) 10: 1111-1118.

Sanghvi et al., "Heterocyclic Base Modifications in Nucleic Acids and Their Applications in Antisense Oligonucleotides" Antisense Research and Applications (1993) pp. 273-288.

Sazani et al., "Therapeutic potential of antisense oligonucleotides as modulators of alternative splicing" The Journal of Clinical Investigation (2003) 112(4):481-486.

(56) References Cited

OTHER PUBLICATIONS

Shea et al., "Synthesis, hybridization properties and antiviral activity of lipid-oligodeoxynucleotide conjugates" Nucl. Acids Res. (1990) 18: 3777-3783.

Singh et al., "LNA (locked nucleic acids): synthesis and high-affinity nucleic acid recognition" Chem. Commun. (1998) 4: 455-456.

Singh et al., "Synthesis of 2'-Amino-LNA: A Novel Conformationally Restricted High-Affinity Oligonucleotide Analogue with a Handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.

Svinarchuk et al., "Inhibition of HIV proliferation in MT-4 cells by antisense oligonucleotide conjugated to lipophilic groups" Biochimie (1993) 75: 49-54.

Wahlestedt et al., "Potent and nontoxic antisense oligonucleotides containing locked nucleic acids" PNAS (2000) 97: 5633-5638.

Woolf et al., "Specificity of antisense oligonucleotide in vivo" PNAS (1992) 89:7305-7309.

White et al., "Fibronectin Splice Variants: Understanding Their Multiple Roles in Health and Disease Using Engineered Mouse Models" Life (2011) 63(7):538-546.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2013/043935 dated Nov. 5, 2013.

International Search Report for application PCT/US2013/043942 dated Jan. 10, 2014.

\* cited by examiner

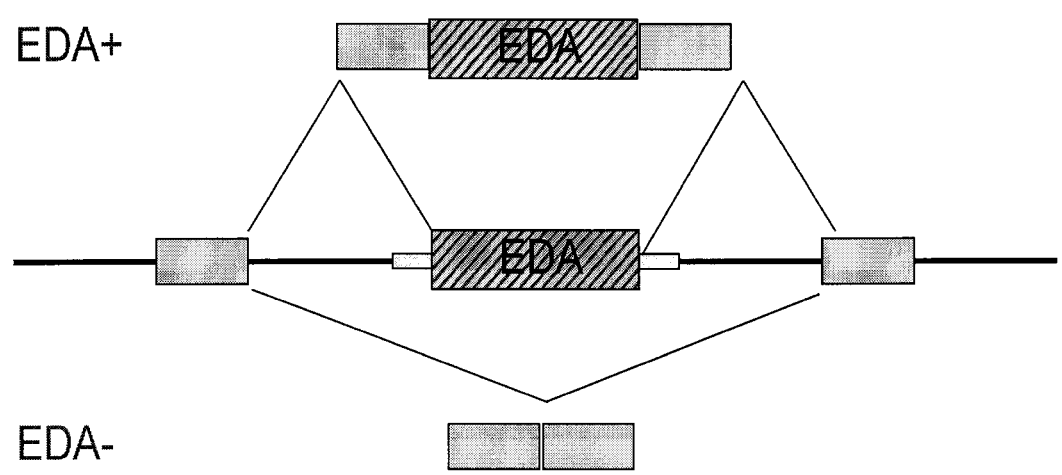

SEQUENCE LISTING

<160> NUMBER OF SEQ ID NOS: 435

<210> SEQ ID NO 1
<211> LENGTH: 76208
<212> TYPE: DNA
<213> ORGANISM: Homo sapiens

<400> SEQUENCE: 1

```
tattttatgg gttttcttcc tcacaaaata cactcctata agcagagatt cccccctcc      60 acccgaaga gaggtgacgc aatgtcctca aacactacca ccaccccaa taaaaagaa       120 aagggaaggg ggagcgtctt gcaacccctt cgcttcacac aagtccagcc actccctttc   180
ctcccagccg cttcccatcc cttcccccat ccctaaaaa gtttgatgac cgcaaaggaa   240
accgaaaaaa agttgtcttg ccccagtcct ggcgggccat cagcatctct tttgttcgct   300
gcgaacccac agtcccccgt gacgtcaccc ggagcccggg ccaatcggcg cgcggtcggc   360
tgcggcggcc ggcgggcggg cggcggggtg gggtggggcg gggcggggac agcccggcgg   420
gtctctcctc ccccgcgccc cgggcctcca gaggggcggg aggggaccgt cccatataag   480
```

-continued

```
cccccggctcc cggcgctcgg acgcccgcgc cggctgtgct gcacaggggg aggagaggga    540
accccaggcg cgagcgggaa gaggggacct gcagccacaa cttctctggt cctctgcatc    600
ccttctgtcc ctccaccgt cccttccc accctctggc ccccaccttc ttggaggcga    660 caaccccgg gaggcattag aagggatttt tcccgcaggt tgcgaaggga agcaaacttg    720
gtggcaactt gcctcccggt gcgggcgtct ctcccccacc gtctcaacat gcttaggggt    780
ccggggcccg ggctgctgct gctggccgtc cagtgcctgg ggacagcggt gcctccacg    840 ggagcctcga agagcaagag gcaggctcag caaatggttc agccccagtc cccggtggct    900
gtcagtcaaa gcaagcgtga gtactgaccg cgggctgaaa caggctgcct cagggatggg    960
accctaaagc cgaccaaagt tggggctgaa gttttgtgcg cgcgcgtgtg tgcgagtgtg   1020
tgcgcgcttt actgagagaa accagctgtg cacacaaaag gaccgagttt tgagcacgct   1080
ggttctgagg gcctgggatg ataagaccgt gcattggagg acgaggactc tgcgactttc   1140
ccgtgttcta ataaattctg cacgttcaga ttgtccttct aggaattaac caaaacttgc   1200 cttaaagag aaaaatgatg catgtctata aatttccgt ctgggattag tgtggtcctt   1260
actgctactt atttccttct gttaaataat tggtcaaata ttttcaacat ggggtggaa    1320 aggggtatt gaaatagctg tcttgtttct aactaacttg gaagagatgt aattggttca    1380
gacctcttta gggccgctca ggatacttca ccaagaacag aggttggaat tcttccgtt   1440 tttcaaagac acaccctcct tttgctttga gaaagctgct taaagttgtc cttttgact   1500 attactccaa aagaatattt aagttccttg catgttttaa aaatgtgact tcaattgtct   1560
gccttccaaa atgtttccaa ctttttatg tagacccctg gccagatgga aatgacatca    1620
ttgtatataa ctttagcaa agttaaaagg aaaaaatat gtacgtcaat attcacatga    1680
agaaaattcc ataattttgg gaaaaggaga aatgcaaatg taacgttttc cttcaattat    1740
ttgcagccgg ttgttatgac aatggaaaac actatcagat aaatcaacag tgggagcgga    1800
cctacctagg caatgcgttg gtttgtactt gttatggagg aagccgaggt tttaactgcg    1860
agagtaaacc tgaaggtaag tgacaacaag ccccatagtt agtatctttt aatacatgaa    1920
gtggtaattg ttaaactttg cattagtaag taaaaataca tacaccatt ttctaataga    1980 attacctgtc atttcctctt aagtttaaaa actgcttata tttgcttttc acatgctttt    2040 accttttaaaa caaagaaacg aatctttccc aaattagttc ctagagtctt cttttttgctt    2100 tactctccca aagttttttga tgagaaaaat gaaagatttt gtgtgtcctc cgacaaaaaa    2160
aattgcttat aaaattttaa tttattagaa agcagtctca aatcttaaac tgttagttta    2220
tgagccagaa aacactttgg ggacttacat cgtaaaatga tttgtcagcg gcagttaaca    2280
caaaaccatt agccacttca aagttctcat tcctttagga ccaatgatat ttttctcata    2340
aattatagca actctgtcag agaagcactg atcagggaa aatggaaatc ataggattaa    2400
caactgtcaa ggccttgtgg gaggtgggga tcttcgaatt gtttgtttgt ttttgttttg    2460
ttttgttttt gagacagagt cttgctctgt caccaggctg gagtgcagta gcactatctc    2520
agctcactgc aacctctgcc tccagggttc aagcaattct cctgcctcag cctcctgagt    2580
agctgggact acaggcacat gccaccacac ccagctaatt ttcatatttt tagtagagac    2640
ggggtttcac cgtattggtc agggtggtct cgaattcctg acctcaggtg atccacccgc    2700
ctcagcctcc caaagtgctg ggattacagg cgtgagccac tgtgcccggc caatcgtttg    2760 cttttttatgt gaaccttgct ttgactttct gagtcagaga ttggaatgtg aaacccttca    2820
```

```
caaatctagc tctgtcataa gttagtactt tatatggcct tttcctaaga gcctgagatt    2880
tttctacaat atgaataatt tacagaaaat ttgacaatat gtcaaggtca aaaaccatgg    2940
ccttattaga gcttaggata aaaatctgta tctctcactt cattttattc tttgaggtgt    3000
accatgttac ttgtggaata gagaagtggg ttttccttta gagggattga gtgaactaga    3060
aaagcttgta cctaagtgag gctcacatgg actttccttt tcccctcagc tgaagagact    3120
tgctttgaca agtacactgg gaacacttac cgagtgggtg acacttatga gcgtcctaaa    3180
gactccatga tctgggactg tacctgcatc ggggctgggc gagggagaat aagctgtacc    3240
atcgcaagta aggaagagat tgtgtaaaat gatgccaaaa tatcaaatat gaatttctct    3300
gttaccatca ctgtcatttt ctgttatcca tgactggata ttccgaactt tgaggtttgc    3360
ccctggtgac caggtactct taagtggtca cccaactggt tcctgtgttt cttaaagacg    3420
ggtatgagca cagatggaat cagtgtttga tgtgtgtgcg tttatgagtg tgtgtgcatt    3480
tatgagtgtg tgtgtttctg tacatagtag aaccaagaga cctcttgggt tccatttcag    3540
taagacatgc ttaggggagt tgcccatttt aaatcacctg gatatcttca agctagacaa    3600
atcatgagac ttttctgcag tgactgggaa ggtgttcatg aagagtgaac cagccatgtg    3660
ttgtctggtc ttcatgtttg caatgcagag acctcttgca cctcacagaa acagtctggt    3720
ttcttggtga ccagtaggtt atacccagga agcagatgtc actattccta gggataatac    3780
aaaattatta acccaataga gtttgctaag gaactttggg aaccgggctg attctcaact    3840
ctagtttagc taaggcactc tttccagtat gattcactgg gttaccaata gattctatta    3900
agatagtatt taagttttt aatccattct ttaaatataa gtcgtcttaa agacttctat    3960
tcaaaagaac aagtcccgtg tgaataggcc caatcaactt tccccatatt tcatgttagg    4020
gtttatccaa gttcacaggc aaatcgcaag aggcaagggt ccatagtgtt tacaatctag    4080
ttcagcattt gaatgtgcca ttgggcttaa caacttagaa aactaccagg atttccacac    4140
tttatatgca tatgtctgtt tgcttttccac caaaatgaca tttctatcct agggtaaaat    4200
acaggctctc catgctccca aaagctggag tgctgtgcct gatgtggcct tttcactgaa    4260
ttagtctcag tcttagcctg ctgtgtatga gtgaagacca agcctcccag cctttctttt    4320
ctgcttagga cccaatttcc tgtgatctct ctgggaaagc aggattcatg acctcttcct    4380
tgccatccag atttctctgt ggttttccat tgtgttctaa gcaagacact taactgaatt    4440
gactccaagt gaccagacct gttaacgttt cccctgtctc tgatgggaaa gctgttgtct    4500
gtgtctctac tttagccaac ctaagtacct accatgggtg gaatatgaga ccaaaaaaaa    4560
aaatctgttc tgccctctcc taacattttc gttgtatctt caacagaccg ctgccatgaa    4620
gggggtcagt cctacaagat tggtgacacc tggaggagac cacatgagac tggtggttac    4680
atgttagagt gtgtgtgtct tggtaatgga aaggagaat ggacctgcaa gcccataggt    4740
gtgtgagtct tagggctgag caagagctgg gatgcttagt tctaatgtgg ggttggacca    4800
gaatcacatc tacataggtc atagacctga attccagtga aaaccaataa agaaatggga    4860
attttgtttg aaataatgaa ttattatata atccatagtc ttcttacagg agttagatca    4920
aaaagtactg actacacata gaagtcttaa ctttgcttca aaagcataag gtagaattga    4980
aagatttaga atggagtcat ttcttttacc taatagctga tctcagattc ctccttcgtc    5040
aagatataat ttatttaaaa gaaaaaaaaa tgcactttg gacacatttc tatatggaat    5100
gtcctggacc gaaacatgaa atagtgtgtg cttgtcacac tctgctcatt tcttttcaaa    5160
ttaaaagttg ttgagcttct ttggatctca atcctcagtt gaatttgta agtacaagcc    5220
```

```
tgaaagtttc tggctataaa ttttactctg tttacttgtc ttctaattta gaggttttg    5280 tcttgttttg tattgttttg ctttccaata tttaaaaata gctttcttg tcattgtatt   5340 taggccactc aaaattcata attggtcatt tataattaag attggaattt tgcatatgta   5400
gtctcccaca gactagatac atacatagat ccttgctact ggaaatgctg ctgggaagtt   5460
tggggctcgc tgaaaatatg tagtccatgt acttattagg agaatggaat ttctgcctgc   5520
caactcagct tgagctttct tttgccttgg ctacttactg tgtgcttaga tgctgggtgt   5580
gtcattcttt ctgaacagag tgccacttaa aaaaaatgtg gctgaatttt tgcttacaca   5640
ctacacttta aattacaggg agcttgcaca attcaaaata acctttttt cctgttttc    5700 ttccaaattt ccctacagct gagaagtgtt ttgatcatgc tgctgggact tcctatgtgg   5760
tcggagaaac gtgggagaag ccctaccaag gctggatgat ggtagattgt acttgcctgg   5820
gagaaggcag cggacgcatc acttgcactt ctagaagtat gttttacatc tttatgttaa   5880
agattaagcc aggtattgtt ttctggattc ctagagagaa gggtaatact atgttactca   5940
gaacacatcc agtatatcag catgctttgg taacttctgg aagtcaagaa aactttcata   6000
accaacttat tccgcatctt cagagaagac tacataaata gaaaacata tcactttgat    6060 aaggttcaat ctcagctcac tgccactgac atagagttga acaaaaggtt taggtttcct   6120
tctatgtttg aaatttaaat agggcacatt cacaggctaa attgataaaa ttaaaaagaa   6180
tttatcccat aaattaaaat gatttatcta ctctggagtt agggatagtg tctctgacct   6240
aacgcatttg attagtgctg taaagaagct ggcctctggt gtctttactg ctccttctaa   6300
gattgtcttg gggtcttaat tgttgccttt gggtttgaag gctccttttt tgatattgta   6360
aactaataac agctagagag tttgttgaag taaaacagcc attaactact ggtgttgtaa   6420
ataagtttaa aatcaaatcc aaataatttg aacctgtttt atttatctag ctgaacccat   6480
ttaactacct ttaacatagc catcatccaa attcaaattc tttgctaaca aaaataggtc   6540
tctcatgaaa agtggtaacc attttgacca aagctttccc agaaacttgc tggtttatta   6600
gatattttgc atttaaaatg ttactgtgat catcagactt ccaagatctt tgtggcaata   6660
ttttagctta agacaaatta gatgtctgat tcaaacctta tctgttattt agaactcttt   6720
aaatagcaag ttgggaaaag tttctcaaag agaagtcatt tattccagaa aattttataa   6780
ggacttactt tgttcaaggt attataggg tgcagatatg aaatgaacat tagcccagcc    6840
ttcaaagagt acttagggg tcagggagat gagaaagtct tatacatatt tatcatctgc    6900
aaaacacagt attaaagatt tcaacagaaa tactgaaagt agtgctatgg aggttcaggg   6960
gatgataata cttttcgctg gggatttggg aaaaagctct aatcagtaat tataccttca   7020
tgcaaacttc tattcttgtg gtagatggat gtgggtgtgt atttgtttga acctacatca   7080
actattaatt ttttttctct aacccaggag ttgcaacaat atccaattca caaagacatc   7140
agatcctcta tactcacatc gtggcacaga gcaaatttgg attataattt aaataatcta   7200
tttaccagat aaatgcacgc atagactaat ggtcatttag ttacaaatta tcattttatg   7260
ttgatcccac tcttccagtg gagggctaac actgaataat ttggggctat tttgctagtg   7320
atttttaaat actgtagatg tttgggtata ggggaaggga aataatatt ttagtcaaag    7380 aaattgtgca tcctctacat tttttacata acaaatgaag aaagagatac taccaccttc   7440
ttatagcttc tttgtagcca ttggtgaaga ccctttgata cctgcttgcc tccccattgt   7500
tataagcttt tttttgtttg cttgtttttt tgttttgtt ttgttttgtt ttgttttga     7560
```

```
gacagtctca ccctgtcgcc caggctggag tgcaatggtg tgatctcagc tcattgcaac    7620
ctccacctcc cgggttcaag cgattctctt gcctcagctt cccgagtagc ttggattaca    7680
ggcgcccgcc accacagccg ctaattttt  tttggtattt ttagtagaga cgggggtttc    7740
accatgttgc ccaggctggt cttgaactcc tgactgcagg tgatccaccc tcctaaagta    7800
ctaggattac aggcgtgagc caccgcgctt agcctgtttt tagttttcta aagcaaggtc    7860
cctattgaaa ggcaggccat aaacagtgat gactaagaaa atcctggaa  gagcctgaga    7920 aggaaaaaga tgaaatataa tgccagagaa tgaagttagt caaaggaaca gtgtgaaaac    7980
aataaataaa tagataaatg aaaatgttat ttgacagaga gatgaaacta gactaaacca    8040
ttcagctgcc tttccactgt aacaaatgta atttcatctt tcagaagtgt aataccttgc    8100
agcaccagag ctgaatatga acatattacc aaaaatagat taccaggcat agatagcatt    8160 cctttttaa  gtttgaattg accacttgcg actctcgacc tgatgtatgt atgtgcttcc    8220
tttgtgacac agatagatgc aacgatcagg acacaaggac atcctataga attggagaca    8280
cctggagcaa gaaggataat cgaggaaacc tgctccagtg catctgcaca ggcaacggcc    8340
gaggagagtg gaagtgtgag aggcacacct ctgtgcagac cacatcgagc ggtgaggcac    8400
aggacgagca ggggcgggaa atggggaagc aggtcaagaa atatttccgc aaatccatct    8460
ttcctttgac atgccatttg aggataattt gcagtgtttc agctaataac ctaagataat    8520
ttacacatta ttggttgtta aaacttttt  taatgtcaag ttttaaattt ttcagaaaaa    8580
aagaaaaatg acatacaaat aaaccttagg gggaaaaaag ccagatttat ctccaaaaga    8640
taaaactgag ttttaaagaa tgctagcatc ataaaactta ccatggatag atcacgcaca    8700
cacgcacaca cacacgtatt ttgaatatcc aaagttcatt tgaaaggaaa tgagagttat    8760
aattaattat atgactacct ggttcttctg ctaggaaagg acaaaaaaag tgcatttgga    8820
ttttttgttt gtttgttttt gaatgaaata tacttccctg tcccgacatt gaactctttt    8880
tgtagtggaa accatccttt atatgtggtt tctatgctct ggcaaacttt gttacattct    8940
ataaagtaac acacaattat ttccttcatg tattggcatt cgaaatttta gaaattcaga    9000
gaggacttag agatggccat gaaagacatg atatctaagc attcttttta aaaaacaagt    9060
tttaatcatt tttggcatga gaaaaagatt tttacgtcat aaatgtttca taaaaatctg    9120
aagagagaaa tatggccaac aaggacgtgc actcctctca ttattttaa  tatgttttga    9180 ttaacttttt actatatgat gtgccaacat cattacgtag tgtctcagcc atccttcaat    9240
taaaaatatt aattgttcta atttttcttc ttttgatgag ttttttgtctt gctttgagca   9300 cttatgaagg tgaacaagat tagatttgat aatatctttg agttatttta ttatcattaa    9360
taaaattgct actggccaaa aaaaattata aacatcggcc acgcgcggtg gctcacgcct    9420
gtaatcccag cactttggga ggccgaggca ggcggatcac gaggtcagga gatcaagacc    9480
atcctggcta acacggtgaa accccatctc tactaaaaat acaaaaaatt aaccaggcgt    9540
tgtggcgggc gcctgtagtc ccagctactc gggaggctga ggcaggagaa tggcatgaac    9600
ccgggaggtg gagtttgcag tgacccgaga tcgcaccact gcactccagc ctgggtgata    9660
cagcgagacc ccatctcaaa aaaataaat  aaaataaaaa ataaaaaaaa ttataaatgt    9720
cagtctacca aaatagatta aaagtgtagg tgggaattaa atggggataa acactcaata    9780
aatgttagct atatatgaat attgccaata ctgaaaagat tccattgttc aaaaaagttt    9840
gagaagcaat gggttaaaca aaatggaacc tgctctgcag aatctgtgtg ttccttaca    9900 tcatactctc catggtagag tgtaggggat gggcgccatg tctccctagt acgtttgacc    9960
```

```
ttgggattct ttgtctgtga acatctttgg gttctagtgt tcagcagcac ttagggaggc    10020
actgaattca gtgtacccttt ggtctagcct cagccctgat tctgttctgc ggtgggccct    10080
ggccttcaag agaacagata tctaaaagtt gaaagaaaag atcggccggg cgcggtggct    10140
cacgcctgta atcccagcac tttgggaggc caaggcgggt ggatcacaag gtcaggagat    10200
cgagaccatc ctggctaaca cggtgaaacc ccgtctctac taaaaataca aaaaattagc    10260
cgggcgtggt ggcgggtgcc tgtagtccca gctactcggg aggctgaggc aggagaatgg    10320
cgtgaacccg ggaggcagag cttgcagtga gccgagattg cgccactgca ctccagcctg    10380
ggtgacagag tgagactccg tctcaaaaaa aaaaaaaaa aaaaaagaa aaagaaaag     10440 atcaacacat cctgttgtgt tattctgaaa ggaaagctgt cttaagagga tcaattggtt    10500
ttagaaaaaa cacaatagaa tcacaaataa tccagaggag aaataaaatg tggaaggtgg    10560
aggtgacctc cagaaaatcc aggacagctg ctgaaggcac cctctgatga gctcggttac    10620
tcagaagagt gaggatgtgt tgaaggtatc tgctgtatgg agtggcagga tgatgtctgt    10680
gattgagaaa tataatcccg gccaggcgag gtggctcatg cctgtaatcc cagcactttg    10740
ggaggccgaa gcgggtggat cccctgaggt caggagtttg agacaggagt ttgaggtcag    10800
gagtttgcca acatggcaaa accccgtctc tactaaaaaa tacaaaaaaa atcagctggg    10860
catggtggtg cgtgcctgta attgcagcta cttgggaggt tgaggcagga gaatagcttg    10920
aacccaggag gcagaggttg cagtgagccg agaccgcgcc actgcactcc agcctgggca    10980
acagagtgag accccatctc aaaaacaacc caaaaaacca aaaacaaac aaacaaaag     11040 aaatataatc ccagtagccc cagctgagct ggaggatgga gaccacttgg tagacacttg    11100 tggattatttt cctaggctaa atgcaaaagc tactgctgaa taagggacat ttttttccag    11160
tcccaggcca gtagcgacat agatttcaga gtgatctctg tgagatcctg aagatcctga    11220
ctgcagaaag tagtgaattg tcttctctca cccagttttg tgacattccc ttttcatgcc    11280
attaggatct ggccccttca ccgatgttcg tgcagctgtt taccaaccgc agcctcaccc    11340
ccagcctcct ccctatggcc actgtgtcac agacagtggt gtggtctact ctgtggggat    11400
gcagtggctg aagacacaag gaaataagca aatgcttttgc acgtgcctgg gcaacggagt    11460
cagctgccaa gagacaggta tgcattatct ttttgaagaa taggactgat gactttatta    11520
tttagttttt gaaggacaat acattttcaa tgtgaaacaa taaaacaaac aagaagcctg    11580
taatcttacc accctgtgat aacaattagg gttggcattt gaaatagttt cttccaatct    11640 tttttaattta tgtattttct ttctggtcat ggatatcatg ggtaaaaatt ttattgtatt    11700
tatctgtcta aagtgttgtt acaagagagc tactttctga ataatcatca atgttttata    11760
ttctaaatct caaatttcag cagctttgtg atgtaaacat cttccaataa cctaatatat    11820
gtattctgca ctacaaacat ggtagtcact atggcaataa caattgctac acaattctcc    11880
cccagaatag tctcatatat taattttatg gcatagatat agtcataaat attatcccaa    11940
catccttaag cagcatcctt aattgacctg tataaatata gctttacaaa tagagaaact    12000
gaggcatggc agcagaagtg gtcatgaagg acatcagcag aagaactcag gtgtcgttct    12060
atccacagta gacatggatt cctgagtaat gcatttgac tgaaattaac gagatgatca    12120
tctatactca tagcttcttc ctttgagggc acaagctcag tatctcattg aagccataaa    12180
taagcagctg ctggtgggag ataaagcatc tctgttact gacactcttt tgattatgat    12240
tgtagctgta acccagactt acggtggcaa ctcaaatgga gagccatgtg tcttaccatt    12300
```

```
cacctacaat ggcaggacgt tctactcctg caccacagaa gggcgacagg acggacatct   12360
ttggtgcagc acaacttcga attatgagca ggaccagaaa tactctttct gcacagacca   12420
cactggtgag tgtcccaagg gggagccaca gaagtgagaa aaactcactt tcatgcccta   12480
gttttatttg ccagcattct agccatttat tttgaacccg cccaagaagc atcgcttttg   12540
ttcagtttgg actcaagaga tcgcagcgct cacgtaacag ctgaggattc ttccatcttc   12600
cccagtactg ttgggaaatg acaccaaggg agtagccttc cagttcattt gatttaacac   12660
attgggatta tgatgtgatt aaagatactt gtattttgga atcagtagat gatcccacag   12720
ggctgaggaa tacaaaggat gaatgtttta gtgccttagc ttattttcca gttaaaacaa   12780
tgttttattc aaagctatca tttaatcttt tgtgggggggg gtgctgggga aatgacagtg   12840
aaagtgggat ttaaacctgt tttgaaggtg tgaaggtaaa tatgctaaga agcttagaac   12900
tatattatca gacattttt attctgagat agactgtctg tgaatgagct gcagaaacct    12960
ggctctctca gaccagtaat tctgtgtaca ttggaaagct cagcggtaat cttttccttc   13020
tttgttgtgt attgttcctg gcagttttgg ttcagactcg aggaggaaat tccaatggtg   13080
ccttgtgcca cttcccttc ctatacaaca accacaatta cactgattgc acttctgagg     13140
gcagaagaga caacatgaag tggtgtggga ccacacagaa ctatgatgcc gaccagaagt   13200
ttgggttctg ccccatggct ggtaagatga agcccttgtg ggttgtcttg tttgacaaca   13260
atttagggag tagagactaa agactagtgt ccagtttact cccatttcat tcattaacac   13320
aattttgaga caacagaaaa cttcatgtga agtgtgtttg tgtgtgtgtg tgtgtgtgtg   13380
tgtgtgtgtg atgttacatc atatacataa ggattgggaa gaataattag ataattattt   13440
atataatttt taaacctcat tgacatgatt taatgtcaaa aatataatta cttatttgta   13500
agtctggaaa tatgaatttg cacaggtttg tctttgtaaa gagcacacaa ctgagtagct   13560
tacaacattt aatatatgta tgacggcttt agtcacagag ctacaatatt gacacatggt   13620
tgtggtttga tgggcataag ctctatcact tattaataag tgccaaagtg actaaaactc   13680
aatgttttct aacaggtagg gaatctcact cttttttaa aggtccccag tttgtataga    13740
tggcgaacaa atggaaacga ataccttta cttgttttca gatttcaaga accccataga    13800 ttcccttta ttttccagtt gtagaaacaa gagcctgggc ggtaggcact gtcaagtgtg    13860
actatgagac aaagaaattg cttatacttt tatttctttc aacaaaagaa gatgctgagt   13920
ttagaagaaa aaacccactt ttgcttgtaa ttctatatcc aaacccatag ttttttattg   13980
atccagaata aactggaact gggaaaagtt atgaagctgt agttaaatcc aggcttctag   14040
aacagcaaga accctttgtg tggatgtgta gatattatct tagtttaaca tccctaacc    14100 cttcctgtaa ctattttcta tgacacgttt ggactacgtt ttctgcctcc agggctcaaa   14160
aattctaccc cttcacctga cagcacttag atgtctttga tgcacacaaa gcttcttccc   14220
aagtgagaat tcttaggatg accaaactga actgatcctt ttgcacacat acatgtttag   14280
acctggtgat catttatcaa gtgcatttct tatccatttc caaacagccc acgaggaaat   14340
ctgcacaacc aatgaagggg tcatgtaccg cattggagat cagtgggata agcagcatga   14400
catgggtcac atgatgaggt gcacgtgtgt tgggaatggt cgtggggaat ggacatgcat   14460
tgcctactcg cagcttcgag gtatgctggc tgattaacaa aaatatttga gatggcaaaa   14520
ggtacagaaa gggacacttt tttttatgaa aacttgcact atgccaaaag caggggaaga   14580
aatatggaat gccacgtcat tcattagtct actgtgcatg gtaagataag cctgaaaggc   14640
ttagcaggca gcctgctaag acaagcggca tagcaatgct aatgttctga aacactccta   14700
```

```
gcatgtaagt acttaggctg agccaaaaag atggcttcaa aagtaagaat gaaacatttg   14760
atccattcag ctttaggcta tgccactgga ttcatgtcta gaaaagatag gataatttct   14820
gtaaagaaat gaagaccttg ctattctaaa atcagatcct tacagatcca gatttcagga   14880
aacaaataca tagggactaa actttccttg ttcagattag ttttctcct ttgcacccag    14940 ctatataata tgaggaagta ttgactttt aaaagtgttt tagttttcca tttctttgat    15000
atgaaaagta atatttcggg agaaccctga gctattaata atctatgtgg ctagtgcgta   15060
gatattggtc tgaatttgtt ctccttttgt ggtgtccagt gggtaacacc atccgggagt   15120
aataattaca tgtggtgttg cagaactgaa agagaccta ataacacata gagacctcac    15180
tctatataga tcaaggagct gagacccaaa aaggaaaaag taattttctc aggatctctc   15240
aaagagtgag caacagagtt ggcctaattt atttagcgt tgtgaatact gttgacattt    15300
tatttcccaa atctaagtat ctcctcccct tcccctatt ccagagacca gaccaccaca    15360
tcatgctggg tgttagataa atatgtttaa tcttcttctt atttatccta acaagcagat   15420
atttaaagga aattatcaac taagcaagaa attttcagaa agtaagacat gtatttgttc   15480
aaatactggc ttctcacagg aaagtgtatt ttaccacatt cttacttga gcatactgta    15540 acctctgcaa aagttacaca ttttgggaag aaaaaattt ttttggcaaa aattgtatta    15600
ctgaccaaac tttgaaaaaa atgttattct atgcttgtag aaaagttatt ttagtggaag   15660
gtgttgataa ttaagtggaa gtagttgtat gctttgagaa gcatacctt tttctttcat    15720 caatggaact ttaaaaagtt tctcactcac ccacctgttt cctaaacaga tcagtgcatt   15780
gttgatgaca tcacttacaa tgtgaacgac acattccaca agcgtcatga agaggggcac   15840
atgctgaact gtacatgctt cggtcagggt cggggcaggt ggaagtgtga tcccgtcggt   15900
gagtagccct atttccctag atgagtttgc acagggggaa tggttagcaa gtttcagata   15960
agaaaagcta tgtgaaatca catgactgaa gttggctcca gactttgatc agttgcttgc   16020
aaagaacttt gcaaagtctt ctctctaata ctggaccaaa atatctcgat attggtagtc   16080
gtctggtttt tgctgaattt ggtgacaaat ttaggcttat tttaattgaa tggaatttat   16140 tctttgggttt agaatcataa agataatcca tgctattaaa agtattcttt cctttttttt   16200
ttgtttgttt ttgttttgt ttttgttttt ttgagagaga gtttcgctct tgttgcccag    16260
gctggagtgt atggcacaat ctcggctcac tgcaacctct gcttcctggg ttcaagcaat   16320
tctgctgcct cagcctcctg agtagctggg attacaggca tgcgccacca ggcccagcta   16380
attttgtatc tttagtagag atggggtttc tccatgtggg tcaggctggt ctcaaactca   16440
cttccttacc agctgtgtaa cagcatgagc aaagggtgta aatatcaccc accaaaacac   16500
tctaggtttt ttttggccg ccctttcaaaa tagaactaag caaatagtga aggctgagcc    16560
ttaaaagagc tgtgttacca gcactacaaa gtttaaggtg atccattact atttctttac   16620
caaaagagac aggttgctca ctgagaaaac aaactgataa catccgtttg tttgacgtga   16680
gattaccaga actgagagag aagcctgaga ggttttctta gaagctgctc agcaggtata   16740
ctcgtaaagt ctagttcatt catttaaatg tcaaacagtt tctttaaatt ttgaagaagt   16800
aaggaaaatg aaattattgc agattttttt cttgctattt aaatgttaag ccagttatat   16860
taatatgggt aaaaataata actaatattt aaaattaatg tgtagattat caatatacac   16920
tgaaatctaa atctttacat ttttatttag aaatattacc ttttagaaaa ctaaatattc   16980
ctcctaatag gtactttggt ttttttttta ctacaaactg tcctgtaagg taagaatgt    17040
```

-continued

```
gaacaaaata ttttttttaac tgcatatatt tgtaagaaca attgcaaatt tctatttaag    17100
ctaaatgtat gctctagcac cctgaaatta aattcgtagt tataagtctt caaggctgtt    17160
tatcttttcc ttccatgtat tttagaccaa tgccaggatt cagagactgg gacgttttat    17220
caaattggag attcatggga gaagtatgtg catggtgtca gataccagtg ctactgctat    17280
ggccgtggca ttggggagtg gcattgccaa cctttacaga cctatccaag taagtagctc    17340
tattactgca agttgagaac tgccaattgg gttataacaa cagggcagtg attattaatg    17400
ctctcatgcc taagttgggg gtctcccctc tttcccaccc ttttctcttg ttattatcta    17460
ataatcaatt gaattttga ttaaaataat ttttctctct tcctctatca agtaaaaggt    17520
agagaaggct atgaaaatgt gcctgtttat aattttactt cttaactctg taaaatattc    17580
tgttaggtta agacactctg gctaatttca tcttatatcc atacatggaa ataaaaacca    17640
ccaagtgagt tatgctggga gtaaaggttt ggggctttat attatgattc ttaacagaga    17700
agctgcatag agagatggca tgaaatgcag cataaggtac gtgttcattc aacatgtcat    17760
ctaagctccc tttgcatcaa acttttcatt tgtttgatca gttgccacca ggaacacagt    17820 atgtttgggcc aagggttgag taacttggtc aactctctgc ccacacagtt caaacactct    17880
caaatgttta ttgctgggtt tttccaggtc acaaagacat catgcctagc tgtaggtgta    17940
attagttcat ttgggggggaa aattgcattt aaatattcac tgagtgatta taataaaaca    18000
tgttaataaa acatgaaagg ctaattaaaa ggcatcagtt atttgagcaa ctgctgaggt    18060
gcaaagtctc caaagtcttc actaacgttt gactgaaaat atggcctaca ttcagaaaca    18120
aaagagtttc agggtgtcag aatctgcatg cgacagaaat taagattaac tctgtgataa    18180
aagattcact gtgacagaga acaagctatg gaacaactt ggccaaaggt agtgttagcc    18240
aagcctcatt cctccatttc ctcatctgta atatgggaag attgtagctg attaccttta    18300
atgttccatc ctaaatacta aacacccaga tgcacctttt ctaggaactt ggaagattct    18360
gcttttccca accctcagac actgtcagtg ctggggaagg tgacttcact tttgaaggct    18420
tatagcacag attgaccaac ctcctaaatt gtatttcttg gaggatttag gtgtaggaat    18480
cacttaattt tttgtaactt aatatatatt taaatctgat tgtggaagta ctataagtat    18540
atgaatggtt tgtttgttta tatgatgcaa atgatactta aatggtagaa acttctaaaa    18600
aaatgctctg tggttctat atttatgatt gttattggtg ttgcaatttg ctgaaaatga    18660
tttccttctg aatgattgag agagatcttc gtctctctca acataaggct gtccacatag    18720
ctgcttgctg gaagcattta ggtggacatg ttggagataa aatctggaaa ggaaggaatc    18780
cttgagtatt ggagtattac atgttgacct tactcctact ctttaaaaag gagaacagca    18840
agatcccact gagcatagag gtgatttcgg agggaagaga ttggaatttg acctcagata    18900
tgctctttgg tgcttatctg tatgtctggt ttgctccgtg gcctagcacg tagggcttta    18960
agagtgtggt gagaataagg gaacagcaga ttaccaacag attgtctctg agtcctgcct    19020
tgtttgttcc tcctacagag aacttggtag agttgttcaa actagcaaaa gataagaggc    19080
atttggtttg tcaataagca actagaaaag cacagatctc agcaaaataa atagagaaaa    19140
aaaggactga gtcaaaaaat cataaatgtt taacttctcc aaggcactca ctattggaaa    19200
ttattcattt agactttatt tgaaactaat tttaaaagtg tagacattgt actatctcct    19260 tttttttggta tcatctcaac tattttattg ttagtttatt catattgaat aagagaggga    19320
gtaaagattt cacaatggcg atagctagta tatgccaatt aagttaattt aaaaagttat    19380
accaactacc agtagcgaaa aaggactgtc aaaagtttaa atctaaataa tgtaaaagat    19440
```

```
gtcataattt ttaacttttc tgtctttaaa ggatacatag tataagctag agtaattata   19500
cgtagtataa gctagaatat aggaatttaa ttgatctaag aaataactga cacaaagtct   19560
ctttacttcc tgaacaaaaa catgctaaat tccatgctgt tcagtccatt tcctttaaag   19620
gtgggctatg ccacagggct agattttaaa acgtggaatt tcacaccagt gctcgaaatc   19680
ttatgaaagc aaaagggacc tctgtagttg tactccactt tggcttgagt aaaaaccact   19740
gctgtaccct ttttctttcc tttccctgcc cattttatc ctcctccttg tgtccttgtg    19800
gacatagaaa tatgattagg cttagaggtg aacagtaaag gtcatttatg ttatctttc    19860 aaaacttaat agacatttat ccatcataag cttgtccccc ctcaaaatca tgattgacaa   19920
gactaaataa agtgtatatc aggtgtctct ttatggagga aattgtagta ggatttattt   19980
aaaggatcaa tatttaaata gcccatgcc aattatcata aataattaag gacatgatat    20040
tcctagcttt cctgatttac atggaagtac gttaaatagt cacatctcca aaattttct    20100 tgaatagttg tctttaaaaa tgtgtttaca tttgtaagga tcttcataaa cagaaggggt   20160
aattcaaaga taggcatgga attgacttat gccaattgat taaaacaaac atcctgtgtg   20220
ttctgtgaaa tacatacaac tttaaaatga aaaactcata attttatgca tgaattttgg   20280
tgttcatgtg gcttggaaat atgtgcatta aatggaatta agattcaaag tatttgctaa   20340
tcttcaacca actttgaatt gttactggtg tggaagtgag catattgttt tagaatttct   20400
gaatctacat ggatatccaa gttatatatt ttttctgcta cagaaagctt tgttttccaa   20460
gagaatttaa tggcttagat aataaagttt gaaaatcaat gtatttttt tcctagaagc    20520 tttcagaaaa cttaaatctg ttaataatct ggtgaagtgc tttattacac atacaaaatt   20580
ttgctctgtt tgacagagtg tcagttagaa attcttgaaa aggttactat aagacacaat   20640
ttttatttct agtaatttaa acattgactg acatcataaa gatagtgttt taagaaaaga   20700
tagttttctg ttctgcaagc ataaatttc tagctatttc attattatct taaatggagt    20760
taacactact tagaaattga tgctacttcc cttatttcc ttttattta aacaaaagaa     20820 ccaaaaccat actttaaatt ttgttgataa cagtgatata catcaaggtg tagaaatact   20880
gaatttagta tacacttcat aaagtcattt ctgttgacaa ctgattttgg aaaaaaata    20940 aatttaatca cttaataatt tgatggatca atggtgtgat ttgggagtaa acttcttgaa   21000
taaaaataaa acttgatgtt ttttccaaac tgatagactg cttagactga tgagaaataa   21060
aactaggtct ttaattatta cctttgctat ttgtctaaga ttctacccc atttagaaat    21120 gtgtttgttt tacatcatct catatggcct ttggaatgtt gtttccttct taggtagtag   21180
attcattctt gatgaaaacc ttccaaaatt agaatttgct ttaaaagagg ctcaatacaa   21240
taagtaaatg aagtctgtgt tctgtattac attattttg taggatcgtt tcacaatttt    21300
ctcacaattc ttactttgat agtagagaaa ataaaagcaa gccaagagac tttttttaa    21360 aaatatattt tatttgctat aaacaactat gatttgcatt tctcatgtga agaataataa   21420
ttatcggcta aaaatggatt tgctgcattg attttcaacg taaatattta aaagattaat   21480
gccagataat tttattatac tcacatttaa cgacaagcaa agctgtttat aatgatgact   21540
gtccatgtac acagttttaa gttgaagtga gtgaatattc aagataatta aatgctacat   21600
tttcattttc aggctcaagt ggtcctgtcg aagtatttat cactgagact ccgagtcagc   21660
ccaactccca ccccatccag tggaatgcac cacagccatc tcacatttcc aagtacattc   21720
tcaggtggag acctgtgagt atcccaccca gaaaccttgg atactgagtc tcctaatctt   21780
```

```
atcaattctg atggtttctt ttttttcccag cttttgagcc aacaactctg attaactatt    21840
cctatagcat ttactatatt tgtttagtga acaaacaata tgtggtcaat taaattgact    21900
tgtagactga ggggattttg gttttggttt tgggttttgt ttttttgcgg tggggggggct   21960 ggtatttgga agaatttagc tctttatgtt acagaaatct tttttgcaag gacttagaaa    22020
tgataatgct taagattgtt cttgcccaat gtgggaagag aatctaaggt ttttatatgt    22080
cttgcaacct catcaaagga aaattactgg catcattttc ataatttgaa aaaaaaagcc    22140
aaattaatat atttcttttt tgattcactt tttaagtgat cattttttaaa actttacttt   22200 tgacccactg aatttattta gatagaagga aaagagatga tgggagggaa gtttagataa    22260
aggatggaag ttggttttat ttaaacaata gccctgtgat ttcctaatga aagtgacta    22320 gaaattgaag aaaccaaata aggaggatat tggtcaattt agctttagtt tctcttactc    22380
tctcaagcct gccctgttta actccaaagt tcatggctca taatttgaga aacactgttt    22440
taaacacagg agaaaaaaat gtccatttta aatcatagct attgaattct acaattacaa    22500
agaaacaaac aaacaaaatt tgaccaaccc aggcggttaa atttaaactc ttcaggaaaa    22560
atttaagctg ttaaaattat tcttttttcta aatttctaaa gtggagggac agaattttc    22620 agattttaaa gggcctccta ggtgcccaga aaattagtgg aaagaaccac gtctagacgc   22680
atctttgatg tgtcagagtt ccaaggataa aaagaaactt ttaaagtctt ctatactcag    22740
ccaggttatc aatcaaatat gagggcaaaa taatatttc agacagattt taggcagttt    22800
atcttccata tatcctttc tttaaggta tttgtagata cactccagaa aaacaagagt    22860
gaaatatgaa ggaagttgtg gggtccagca aacagtgctt ccaaatcaga cccctgatag    22920
aggtggaaaa cttttgcaatg caacaactgc gtagctggct tagaggacag ccaatacaga    22980
tggaacagaa agatgaggat gggattgagg gatcagggat tgaggtctcc aagaataaaa    23040
agggacttca tggaaaaagt aggcttgtgg ataattaatc acaggggcaa ataatgcagt    23100
taaaataaca acatgacaat caggtggagg aatgtataat aaacccaaat gtggctgggt    23160
agagtggctc acacctgtaa tcccagcact ttgggaggcc aagccgggca gattacctga    23220
ggtcaggagt tcgagaccag cttggccaac atggcgaaac cccgtctcta ctaaaaatac    23280
aaaaattagc caggcttggg ggcgcacgcc tgtagtccca gctcctcagg agctgaggta    23340
ggagaatcac ttgaacccag gaggcaaagg ttgcagggag ttgagccaag atcgcgccat    23400
tgcaccctag cctgggcaac agagcgagat tctgtttcaa aaaccccca agtgtattat    23460 aaggcaataa ttcctatacg aagcaaacta aaatgcagca atattaaggt ataaaaacaa    23520
agaggaataa ttccattgaa ccttgattct ggaaactttg atccacccag cagtcatgat    23580
gttagactca ttgaaaagaa tgtatttcta atgcatgatg cgatcggtct atagatgtgt    23640
catggaaact tggttgcaac ttcaagacaa aataaaaagt aaacatttac atgaaaaatg    23700
gtggatatgg aaggtggaga agagaggaga taacagcttt atctttcaaa atagagaatt    23760
gagagatggt accaaaagct gatgaagtaa aaaaaaaaaa aaaaaaaaaa gatacttaat    23820
ataatacttt aaattacaaa tataaacaca agaagaacaa atataatgat acaaatgtca    23880
gacactggga atgtccaaga ttctggaagg aaagggtggt attattgagc taaatcctca    23940
actttgtctg ggcacagtgg ctaaaaatta gccgggcatg gtagcatgca cctgtagtcc    24000 cagctcttg ggaggctgag gcggaaggat cgcttgagct tgagaggcgg aagttgcagt    24060
gagccaagat ggcactactg cactccagcc tgggagacag agaaagaccc tgtgtcaaca    24120
taaataaata tataaataaa tcatcaagtc tcatattaaa gactctgtaa atatgactta    24180
```

```
ttgttgacaa atgaaacaaa tagaggtgta agcatgttgt ctacatggag gcaagaccag    24240
aataatagaa aatggaaaca gattcccttg aagaggggaa tcgtgtctttt ctcattggct   24300 caatgtagtc tccgtagagt ctagaatgct tcagcacctg gcacactgct taacaaatgg    24360
tgaatgaaaa aaaaaaaaag aaaagtcatt cttttttcttc tttcacccta tgtccataat   24420
ctggccattt gcagaacttg atgtccagtg atcgaaatca acagcatcag tgcatccaat    24480
atcttctagt ctctcatctt cttattacat cattaatttt atttacttta aaattaagga    24540
tatccaaagt attatgtgag accattgcaa tgggagactt aaaagtggta taaaatgtac    24600
tttgggccag gcgcagtggc tcacgcctgt aatcccagca ctttgggagg ccaaggtggg    24660
cggatcacga ggtcaagaga tcgagagcat cctggccaac atggtgaaac cccgtctcta    24720
ttaaaaatac aaaaaaatta gctgggcatg gtggcgcata cctgtaatcc cagctactcg    24780
ggaagctgag gcaggagaat cgcttgaaac cagaaggcgg aggttgcagt gagccaggat    24840
cacgccactg cactccagcc tgggcaacaa gagcgaaact ccatctcaaa aaaaaaaaa    24900 aaaaagtaca ttgaattgga aagtcttcaa aaagcagcag tgatgaattt tttgagattt    24960
ttaacaatta caaaaattca gggttttttc taatggatgc cacctgagac tttattttct    25020
gttattttct tgtaataact aaccaaacaa gctcatgttg aaaaatgatt actaaatttg    25080
agctaattgc aatgactggt ttcaaaattt tccacagtgt atttgagtta aaatttcact    25140
gtgaagagta ctacgatcac tctcgcttat tccaaaaata taaatggaca cttgagtatt    25200
tgaattattg aggaaatggt tgactgggta atttttaaaa atcactgggc acaaaaaata    25260
tattttgact tatattagtt tagagtattt acacttgaaa gagtctcatc ttttctgaag    25320
ggtgtttctt tcatacacat tttattgcac tgagttttgt gacccatggc atattaatga    25380
agctgaacag gatgtgaaat ataaactgga agcaaaagat taaataaacc aaaattgcat    25440 ttttttctgta gtcttgtcca aaattgggta accacttctg atgggtagc tcatatccaa     25500 gaatgagtca caaaccaga ctcgttgaac ctggtatatg atgagtcaca aagcaacatt     25560
ctgcctttgt tttttcagga caagaaactt gaattgtatc ccactgagtt aaaagataaa    25620
atatatggca ttggcatttc tgtacttcag agaggaatat atctgtttgt ggtaggaata    25680
aaaaataagt gagagaggca aagcttaggt tcatcatatt atgttactga tataacacaa    25740
ttaacttggt aaaagtgaag gtgtgggtgg gcgtggtggc tcacgcttgt aatcccagca    25800
ctttgggagt ccgaggcggg tggatcacct gaggtcggga gttcgagacc agcctgacca    25860
acatggagaa accccatctc tactaaaaat ataaaattag ccaggcatgg tggcacacgc    25920
ctctaatccc agctactcgg gaggctgagg caggagaagc gcttaaacct gggaggtgga    25980
gtttgcagtg agctgagatt gagccactgc actctagcct gggcaacaag agcaaaactc    26040
tgtctcaaaa aaaaaaaaa aaagtgaagg tgcccagtgt ctgcaactat gtcaccccgg    26100
gcatatcaca tatcactctg ttttttccgtc tgtaaaacgg gagcaacaat gccattgcct    26160
tatcatcaga aggatatgga gactaaatgg gagaatgtag gtaaacagca cagagtatgg    26220
gtatcagtaa gtaaactgca gcagtttgtt gatgttaaca atagttagca ttatatctaa    26280
ctatatctaa cgatataacc attgggaatc cagttttcca tgattttcct ctagaatgga    26340
gctgcctaag tcctgcttaa gtcatttttc tttgaagatt actgaacatc atcttcaaat    26400
gttcatcctt gtaaacacgt gtgtgtgtgt gtgtgtgtgt taatttaaat tttcagaaaa    26460
attctgtagg ccgttggaag gaagctacca taccaggcca cttaaactcc tacaccatca    26520
```

-continued

```
aaggcctgaa gcctggtgtg gtatacgagg gccagctcat cagcatccag cagtacggcc    26580
accaagaagt gactcgcttt gacttcacca ccaccagcac cagcacacct gtgaccagta    26640
tgtacacaac caccctcatg cctcctaccc ccgaggttcc tagagctagg ctctcctgag    26700
gcaatgcttt ccttctcaat tcatattctt ccaggagggg caccaacgtt ttttaaaatg    26760
atgttggcga cgaggacggt aaattttcta gatgactgaa ggctgacttt cccctttctg    26820
tgactctcta ggcaacaccg tgacaggaga gacgactccc ttttctcctc ttgtggccac    26880
ttctgaatct gtgaccgaaa tcacagccag tagctttgtg gtctcctggg tctcagcttc    26940
cgacaccgtg tcgggattcc gggtggaata tgagctgagt gaggagggag atgagccaca    27000
gtacctgggt aagctcaata tgtcgctcaa gacaggttca gggcagctgc tggaaaactc    27060
tccttgtggg ggtgggtggc ctctaggcag gtggtatctg tggtttggaa ctggttgaca    27120
gctcagactg aacaaaccac cctctggcat gaggaaggga aggactgact cttttctaaga    27180 agtggccggg ttttccccaa gccactgtca catgttcctg gtccctgatg ccagctgcat    27240
catgcgccta cctgtgcaca agttcctaca gcaaaagctg tgttcttggt ggaagtaatt    27300
accaggactg cagctgacaa tgtgagcaca gtacggtcac tcatactttt caaattgtta    27360
tggtgagggg ccttttaaaaa acttcattgg cgcactgaag tgtgtgccat cgtaagcact    27420
gagttcagtg aatttgaatt cttataaagt gaacacacca caagaccagc acccagatca    27480
aggaaaagaa tatctctcta ccctcacccc atcatcttcc gccaataatc actaccctga    27540
ctcttactgc agagagctat ttttaaaaat ttggcattcg attacaaaaa ttatacgtct    27600
ttagaaaaaa agttggaaaa atgaaaggaa gaggaggag gaggagaaag gagaaagaca    27660
agaagtggtg tttccccata gtacattaat aatcacagat taggtgggtg cggtggctaa    27720
ctcctataat ctcagcactt cgggaagctg aggctggtgg atcacttgag gccaggagtt    27780
cgagatcagc ctggccaaca tggtgaacct ccatctctaa taaaaatgca aaaaaaatag    27840
ccgggtgtgt tggtgtgcac ctgtaatccc agctactcgg gaggccgagg cagaagaatt    27900
gcttgaaccg gaaaggtaga ggatgcagtg agctgaaatt gtgccactgc actccagcct    27960
gggcaacaca gcaagactct gtgtaaaaat aataataata atcactgatt agctattagc    28020
acattacctt ctagtcgctt ttccctatga atatataatt cttaaaatat ccttcttata    28080
agctgtagag tcatttgagg gactagtttg ctctgattag ttaccttttc ttttcatttc    28140
aaagatcttc caagcacagc cacttctgtg aacatccctg acctgcttcc tggccgaaaa    28200
tacattgtaa atgtctatca gatatctgag gatggggagc agagtttgat cctgtctact    28260
tcacaaacaa caggtacatg tgtgctacat agtgttaaaa gaatcttttt ctgtaaaaca    28320
caggcctgta gtagcacttc ctgactgttt gccccacttt cttctttct agcgcctga    28380 tgcccctcct gacacgactg tggaccaagt tgatgacacc tcaattgttg ttcgctggag    28440
cagaccccag gctcccatca caggtcagct aagcgtcccc ctctttggct gctatgttaa    28500
tcttaatgac atcagcaggg agggcgcaga ttctgactgc ggacctgcat atcactttaa    28560
atctccaata taatttatgg gagagggggtt tgtgtgtgtg tgtgtgtgtg tgtgtggcgg    28620 gggtgggga gttattttct atggcacatt tccccttgaa accatttcac caactccctt    28680
atacacacac accacaacat acacacaacc tgtaaagcca gctcattggc ttattaaagc    28740
aagtgttccc agggttgaag aggtgtaatt tcctgaaaac gttgctctaa gatttatcct    28800
taaggagaaa gctgagctgt cgtccttagct cattaggtga ttcaactgcc tcatcactga    28860
agttccaaaa agacacacac agtgctagac aactctgctt aggctggttc attaattgct    28920
```

```
tccctcgtct ggagctcaaa gaggaaaaat cagcttaaca tgaatatttt cacctaatgg   28980
catctctaat tgacatttat taaggatgtc aggtcttcaa ggatgacatt tattattaaa   29040
aaggttcgca tgactgttct tattttatct tcgtgctgaa tagtcattat tagaagaagt   29100
ggcaatattc aaagagtcaa aaagtatcac tggctcttca ctaatcaagc aagatgctaa   29160
gggatattag aaaagggagg atttatggtg tttctaagcc tctgtctcaa agaaaacagt   29220
gcatcttact tttgctcatg aatctgcagg gtacagaata gtctattcgc catcagtaga   29280
aggtagcagc acagaactca accttcctga aactgcaaac tccgtcaccc tcagtgactt   29340
gcaacctggt gttcagtata acatcactat ctatgctgtg gaagaaaatc aagaaagtac   29400
acctgttgtc attcaacaag aaaccactgg caccccacgc tcaggtaact tttttaagaa   29460
gacacttcct atgttatctt atcaggattg ttcctgaagg agggttgttt tgtctctgtc   29520
aacagtcctc tcattcaaga aatcttatat attagttttt ccctaaactt ctgatattta   29580
gctgaaatgt cataagtaac ttatcaaagc tggctactgg cctttctgat taaaaactga   29640
caccataacg tccatctaca aattttcccc tagaagctta agggtcattt cattttgat   29700 tcttaagtat tataaaatga ttcagtaaaa caaaaactgt tacattattt tctgcagtta   29760
tttcaaaggc tttttctaaa aaatttttta gtatcttttc ttataaccct ctcccccac   29820 caccatatga cacttcatat gctggtaact cacttattac ctattttaga taaaaggttc   29880
aaatgtcata atttaagcac tatgactgga ccatgaaaat gtgatctgat taagagacaa   29940
aacttagcaa aactctcgaa tgagaggctc aatgaactgc ctaacatatc caagaaactg   30000
gcttcttaaa agtaatcttc agcagagaat gtgaatgacc agttgactct tgtctgtcag   30060
atacagtgcc ctctcccagg gacctgcagt ttgtggaagt gacagacgtg aaggtcacca   30120
tcatgtggac accgctgag agtgcagtga ccggctaccg tgtggatgtg atccccgtca    30180
acctgcctgg cgagcacggg cagaggctgc ccatcagcag gaacaccttt gcagaagtca   30240
ccgggctgtc ccctggggtc acctattact tcaaagtctt tgcagtgagc catgggaggg   30300
agagcaagcc tctgactgct caacagacaa ccagtatgtc ttctcctatc tctatctccc   30360
ctccaaattc tccaccctca cttgcagcct gtgagaaagt gcagtaaacc attcactcag   30420
aggtgtatgg cttagagaga gggaaatacc cagccggcaa gggaatgcat agtgaacaca   30480
aagcacatta aacttgaaaa caaaactcag acaagctcca tggatgctaa gtggtaaccc   30540
atttctaaaa tacatgtacc agctgaaggg tactaagagg ggagaactga agagaatcta   30600
atttgagtgc atttttcgtg taactaaata tatctagatc aaagttaaaa tgcaggatca   30660
taacacttag agtagaattc atttaacaat agcaattgtc aagtgtctag tattactagc   30720
caccagctta tctgctcagt ttttacaagc attattctca tatttactct ttgtttgac    30780 cttaggaagg aagtcttat tattattatt ttatttattt attttttga gatggagtct    30840 cgctctgtcg ccaggctgg agtacagtgg caccatctca gctcactgga acctctacca    30900
cctgggttca agcaattctc ctgcctcagc ctcccgagta gctgggacta caggcgtgtg   30960
ccaccatgcc ctgctaattt ttgtgttttt agtagaaatg ggtttcgctg tgttggccaa   31020
gctggtctga aactcctgac ctcaagtgat ccacccactt tggcctccca aagtgctggg   31080
attacaggcg tgagccatcg tgcccagccg gaaggtctta ctagtatccg tattgaatac   31140
ttaaagaaac tgaggcttta aaaaagttct gcaacttgta gggtcacaga gataggaagg   31200
gatagagctg gctctataac ctatgtccga agcccatgct ctcaattatt atactcgact   31260
```

```
gcctcttaaa gatttcctct atttgaaagg taatttaaat ttcggtggga aaactgctgg   31320
ttattattct caagaataaa ctccacaact tatgtgattc tgatagtgca aactcaccag   31380
tatcctacca tgaatctgag gatacgttat cattactgta attactgtct aatctgaacc   31440
atgtgaaaat aacttttatt tctctagcaa agggctattc acagaatatt gcttttgacc   31500
catagagagc ttcttcttgc tgtcatttta ggaggcatat cccttttttcc ttaatctgtt   31560 tggctcagag ctaactgtga acttcagaag tgtttgtttt gccttttttaa aaataccatt   31620 gctttaatgt aactataatt tctgagactg atgcgaaagt cttgctggaa aattagactt   31680
cccaaaggat cacagtcaag caaaatggtt ccacaatttc tcatgactgg cagagttttg   31740
gcaaagtttt gtgtagcact caatctctta ctggctcagt ttttccaggg ttttgacttt   31800
cacatagtta caaccttgag gagagaaaac ttagacattc aatcaagttt caggacttga   31860
gttatgatca ttactgatct aaatatttct tggcatgttt catcttttttt cctagaactg   31920 gatgctccca ctaacctcca gtttgtcaat gaaactgatt ctactgtcct ggtgagatgg   31980
actccacctc gggcccagat aacaggatac cgactgaccg tgggccttac ccgaagagga   32040
cagcccaggc agtacaatgt gggtccctct gtctccaagt acccactgag gaatctgcag   32100
cctgcatctg agtacaccgt atccctcgtg gccataaagg gcaaccaaga gagccccaaa   32160
gccactggag tctttaccac acgtaagctg aaaattaagt gcctttttctt aactatattt   32220 acattctcta ttcttcatgc tttaaaacaa aacaaaacaa aacaaaaaaa acattaaaaa   32280
attagtacat aatttaaatc agtgatacta aaaatgtgct ccatagactg gctgctggcc   32340
cgttaattgt ttgctgctag tctgcaacaa gaaaacggt tgtgccagaa cgtaaatcac   32400
aaagcacact gcttagtaca gctgagaatt tttctgaagc cagattttct tgatgaagga   32460
agcagtgtgt taatttgcac acattgccaa gctcgctctt tcctctaggg ccagcacttt   32520
gagtaacatg ggtttaaagc agtctgttat tagaaaaatt aaattcgatt acattaaatg   32580
aatttaccaa acactagtta acgcaagaaa aaattagcac ctatgtctac attctattac   32640
tttgggcatt gaatagtaac tataaatgca gaataaaaat atctatggat tgaatgggaa   32700
ccaactaatt gaacatgaag ccaaggaaat gatttcttta tgagtgttgg ctgcagaaga   32760
ttaaagtact tttgcagacg gaatcgctct tttcttaaat tactcttgaa attcctcaga   32820
ggagaaaaat actaacaata atttttggtc atgtctatcc ttttgctcaa cattttaaag   32880
gaagtggtct taaatctccc acatatctac atcacaataa caacctctat tcacaaaccg   32940
attcctatta aatacatttc catttacatt acagagaatt atgagactcc ttatttctag   33000
ctgaacatca tttgttattt tcaactcgac attttgaatt atagaagcac ctaacataag   33060 tacttttttca gcatatattc taaccatgga ctagtttgca attttctaag agctttcaac   33120
aaatgttact cttcgactaa tttaaaagta tggatgttaa aaagcattca aaaagtccat   33180
acaagcctag tttgtaaata actatggaat tgatttccca agaaaaatac aaactttttcc   33240 ccataagaat tcatacttta agaaaaactt acttccattt aaatttactg tatgaagttt   33300
ggctcatgaa ggcttttttcc taaataatag ttaatcgtaa gcaagtaaaa ttcactttta   33360
atttgcaaat aagcttactt gaaaatttgg ctaaaatttt acacggttct aagatagtct   33420
aagatctact ctcatgaaat taatgtcttt atatttcttg taaatattca tttcttataa   33480
atgtccttca gtgaattaga atggagattt cagtgaatgc gcccttttcag tagatgtcgt   33540 ctttttactaa aatgtagaat tctatagttg tcttgttcat tccttaacat gagacatatt   33600
ttatgtagtt tcttttgttg aacacagtgc ttataaaaga aaaagcattt ttaatgatgc   33660
```

```
taacaataat taagggaagg tggtgggcca agatatttca agtacttctg aagactgata  33720
tattggatat attattttat gctttgcata atacattcat ataaaatata atgattttaa  33780
ctgaagtact gatagccaaa actaattta ttagataaag gttaacatag tgtctggaac   33840
attgtatgct ttcaaaaact atttggtgaa tagataattg agaaaggaat aataataaaa  33900
acagctaaat gaagcttata tttaaataaa ctaatgtaag cagggtattc tacaactcca  33960
tttgaacttt aagcactccc taaggctgta aacatccaca aggcttgcat gtttttgaaa  34020
ttactaaatt tctgtagttt tttactatct tactaagctg aattctggga gtaacttttc  34080
tgagtttat aacttgtgct aaattcttaa gagcaaatgt gagaaaagtt aggggaaaaa   34140
gctgtttctg gggaaaattc agcttagtct tatattgata gggcaaattt tatttcttta  34200
acagctgggc tgttcttccc taacaagacc tgccagaacc catagctcac acttagaatc  34260
acatcctttg tttgacatcg tttgtgggtt tgtggtttgg tgattttccc ataatggcct  34320
tcccaggcag agagcatcat cttaaacttg ggaagactct aggtggctgg ctcaagcaat  34380
agaaaatacc tagtcttaaa gcccaggaca gttgaggcga atataatttg taaaaaaagt  34440
tgtggttttc acagatgttc agtgaaagaa actgactgtt ctctgaattg ttttttgtgg  34500
gccattaaaa atggtcacac agggctggcc atggcatttt ggcacagtca ccagcagtca  34560
agtggtgtat aatttcagag gtactaaaag gcatcgggtc acccatccca gtcatgtccc  34620
cccaccccc accaaacacc atcaaaataa taacatacat agatgaaaca gcccactaaa  34680
ccagtagtac ctcaattcag ccattagagc tatcattatg aagtggccca cacatatatt  34740
tggcttttc tcacacaata ttttaaaat aaaaataaaa aatggctcct tagaatccag   34800
actgaaaaaa aaatgcgaga attgcgatgt tgattctaaa ttcccacatg gcaaagaaaa  34860
aaaaattgac tggagttgag ttgagactgg agtctgaaca cttttaatc cctgtttgta   34920
taactctgga gactaattct ttgtcttgcc agccattcat aatttagtat aaatgcattc  34980
agaggttttt tcccaatggg aacaaaattt gattgagatg taaagagagg aagaattgtg  35040
gagatgtcaa acatgtgacc agagctatga acacacttga taccctttgaa cttaaactta  35100
cccaactcaa aatatctggc cttctgcgat cttaccttc tacatttata ataagatttg   35160
caaggttgtt ggaaatctct atcttaactt tatatataca tgcctctttc tttctttttc  35220
tttcctttcc tttcccttc tttctttctc tttccttcct tccttccttt ctctctctct   35280
cttttcttcc tttcctttcc tttccttcct ttctttcttc ctttctttct ttctttcttt   35340
cttctttct ttctttcttt cttctttct tttctttctt tctctctcac tctctctctc    35400
tttctttctt tcttattttt ggtgctaaaa cccaaaacaa atcttttatt taaaaataag  35460
atttttttt tttttggcca ggtgtgatgg ctcatgcctg taattccagc actttgggag   35520
gccgaggtgg gtagatcacc taaggtcagg agttcgagac tggcctggcc aacatagtga  35580
aaccccatct ttactaaaaa tacaaaaatt agctggatgt ggtggtgggc aactgtagtc  35640
ccagctactt gggagtctga ggcaggagaa tcacttgaac ccaggaggct gaggttacag  35700
tgagatgaga ttgcgccact gcactccagc ctgggtgaca gagcaagagt ccatctcaaa  35760
aaaaaaattg tttaagtaaa attttatttt ctttcttttt tttttttttt tttttttttg  35820
agatggagcc ttgctctctc accctggctg gagtgcagtg gtgtgatctt ggctcactga  35880
aacctccatc tcccaggttc aggtgattct cctgcctcag cttcccaagc agctaggatt  35940
acaggcatcc accatcacac ctggctaatt tttatatttt tagcagagac aaggtttcac  36000
```

```
catgttggcc aggttggtct tgaactcctg gcctcaagtg attcacctac atcagcctcc    36060
caaagtgctg ggattacagg catgagccac tgcgcctggc caaagtaata ttttcaataa    36120
gaaaataaac agtgatgtca ggatgctaga aaatgcaaaa taaatttgtt ataattcctg    36180
attctggtga taaatactaa attttttgca gtattattct gaaagaataa tcacgtattt    36240
aaagtacaaa tctttagact tcaaagtgca tccatggtgg cagattttgt ttaaccttta    36300
tatagcatct tttattgcaa ccaaaaatag ctgaccatta ttgtggaata attcagcgta    36360 aagcttttt ttttttcttt tttgagacgg agtctcattc tgtcacccag gctggagtgc    36420
aatggcatga tctcggctca ctgcaacttc tatctccagg gttcaagcga ttcttgtgtc    36480
tcagcctccc aagaagctgg gactacaggc atgagccacc atgacagtta atttttcata    36540
tttttaatag agacagggtt tcaccatgtt tgccagcctg gtctcgaact cctgacctca    36600
agtgatccac ccacctcggc ttcccaaagt gctgggatta cagtcatgag ccaccgatcc    36660
ccgcccagca taaagctgtt tttagatcac cttctataat ttaccattgt tcttaaatta    36720
atggttaaga aacaatatga taatcagttt gtggtggcca gttttacatt ttataaggga    36780
ttttacactg acgatatagg gaaatttatt gtcatcaaag tcaaatccca acaatcataa    36840
aaagacatga attagattat ataatttcaa tgaaaggacc accttagcaa acatctaacc    36900
ccttgttact caggtatcat tcacgggcca gcagaattgg tattatctgt gtttgtcaga    36960
aatgcaaact ccctagtttt tgttggacc tccagaaaca gaatctgcat tttagccaga    37020
ccccagatga tgtgtgtggc acattaaaga ttgagaagcc tgatcctctc ccaattctca    37080
cccaatgaaa aaatatgtta catcctctat ccactgcttg gttaaactga ggttctccat    37140
aaaaatactt gttatctata tgctatgcaa tcatctgtga gtttgagttt gaatatgtg    37200 cattgattct ctctcacagt gcagcctggg agctctattc caccttacaa caccgaggtg    37260
actgagacca ccattgtgat cacatggacg cctgctccaa gaattggttt taaggtaaac    37320
tgcagatgtt cctaatctct gtgatacagc cctgagctgt ccttgtggtt cccatgtagt    37380
ggaaacaggg tgctcaggag tcaggagacc tgggttttgt cacctgcttc tgtccataca    37440
tctttgacta cattgtcagg gcctaacagt ccttccctgc ctacctcact gaattgttgg    37500
aagggtagat ggaggctgcg aaagtgtttt gcaaaggata aacattagc acgaagctgc    37560 tgcttattgt tatcttattt tctctatcct ttcctgcagg gaattacatt tcaaaaaaac    37620
atgggaaaac tttatttgat gtgttgttct aaatgagtgt gaacaagttc acaaaagcca    37680
gtttagggag accagttaaa ctcagagtca cttaaaaatc gcattttcat ccaatcagtt    37740
tcatctccaa ctgttcaaag cactgagggt gaatctctta atagaagtta agattaaggt    37800
ttccctgtgg atatctggat tcatcttctt taaagtaatg atattaggga agcggtgaat    37860
acaaatgaat atgtttaaaa gaattccatt ctttggcatt tagtgtgaag agagaaatat    37920
ttgttatcgc tggaaatcat gactcaatcc ccttgatcgt ttaaaaaaat acaccaaaga    37980
taaagtttgt aaatggccat atttatgatt atgctactca aatatagaag aactttctga    38040
agagtgccag tataccttt aattccctta ataatgtcat gctgactttc agaagcctta    38100
tgatgtgtga aggatctctc tagagttgaa cactattgga taacagtgtt acctaagttt    38160
ttgaaataga atcttaaaag gatttttaaat tatgggcata gttattctaa ttcttctctt    38220
gtaatgtatc atcctgcagt tgaagctatg tacatatctc ttcaaaaggt gtgttttgc    38280 aatacagttg ctacagggggc tggtgccttt aaatggcaac taaaaggtta attgaatgtg    38340
aataactcgt taagggaga gctcagacat tccttctagc acacacacag aaaaatagaa    38400
```

```
atgaactacc atgtgaccca cagtccctgt atacgtctgg tttgtaacaa gagattcttt    38460
atcaagcaaa acagtatgta atgacatttc tctggaacct tccattacaa gccaccttaa    38520
tgcagtttgg aagatacctc ccccacctgg gggaatttcc agctaaagta tataaaagag    38580
tccccaaatc atttcccaat aaaagtacac tgtgcagttt ctgaagagtt tacactattt    38640
aaagcataat catagcctca cagcagtaac agtcctctgg aaatatttgt ccttggtgtt    38700
tactttgcat tccttcctct agctgggtgt acgaccaagc cagggaggag aggcaccacg    38760
agaagtgact tcagactcag gaagcatcgt tgtgtccggc ttgactccag gagtagaata    38820 cgtctcacc atccaagtcc tgagagatgg acaggaaaga gatgcgccaa ttgtaaacaa    38880
agtggtgaca cgtaagaaga atttttcccc ttttctatta gtttttaaaa ctgttctact    38940
tttcgaaaaa agctagtgtc aatatcactt tttacttatg agaatggcac aggggagata    39000
tcttatcctt acttatatta ttaatgctat tcctgaattt ggagtagcag gttcaattca    39060
tgctttatat tttatggcat cagaaatgtt cttcccatgt caagaatatt tatgaactgg    39120
caagatgaaa ataatttcaa tagtattgca aaatcattaa tcataaagaa gtctttgtca    39180
gagaattact gctgtccatc atattttcat aatgtaacct atatttttat gggagggagg    39240
gagggaggga agaagcatgg aagagaggga ggtagggaag gaggaaagat tacacaggtc    39300
aagagctttg tgtcagcttt gacttttaaa atgttctttc tgcatagcat tgtctccacc    39360
aacaaacttg catctggagg caaaccctga cactggagtg ctcacagtct cctgggagag    39420
gagcaccacc ccaggtaagt ttgggatgga tcagagggca agtataacacc ataccttccc    39480 aagacaaaga ttttagaaac tgtgtttctt tcagagaaag aagggattca aattacaaat    39540
gcttagctct ccataaaaac tatagcagta catgatgtac atcatggagc agcctgcagg    39600
atgctttaat gcacgttgac ttcaatcaca ggaagcagaa caaccttaca ctagtctagg    39660
gggacaagac agatcctcac acagctgtag ggctgaagaa aagcactgtg gaaggtggct    39720
tttgctgagt gcattaaaaa ttgccaaaca aatggttgaa gtcatattac gtaatttccc    39780
ttttgtgagt tgttacagag cctaagttta ttattccctg aagttttatg aatgttttgt    39840
catgggttgc accacaaata tttaagggtg atgaaaggca gaaatacctt cattttacag    39900
aataagaaaa ctgagactta gaaaaaattg gcctactcat agtcacacat tttaaatgtt    39960
acaaaactgg gattgtaact taagtttgta gactccttct cacacccaat gtcacatatt    40020
tggaatgtaa tttttttta attatattct atgcaaactg aaaattctga ttaagggggtt    40080 tcctgaccat ttttagagct ttaaatgaag catttgtcta aattccttgt tcacatatat    40140
ttgaaaatta tttataaaat gctaaaatgt ataagatag ttgttaacaa tattcaaaca    40200
gcatgacgta ctatagcaat aacaggaaat tttagatacc cattactttt gccaaaacca    40260
catggaagtc tcaacaaacc tatggagaaa atcttaaac aaaaataaaa gttccaatta    40320
atgttgattg cattcttacc tcatatactt gttaatttaa gggatatgtt taggttatta    40380
tttagctatt tctaattta ctgtaaaatt cttgtgaaat ttttgtttaa aaaaaagtat    40440
tatatagttc ttatctttgc cggggcacag agctaaggct atcatctcta aatctgatta    40500
atgtatgcaa acacacagaa tgaaactagc tcagaatatc tcttttaatc tccctctgaa    40560
gtagagtgat tttggtaaag ttttcattat ctgcggaaac attgtttaag ccaaagctat    40620
acaatttcca gctgagttgc tctgaatttg aaactttaag ttgacaatct tcgtgcttgt    40680
tagcagcagg atcattaata tctcgtctca atggcccagc ccacacatat ggatgaccac    40740
```

```
tagcaagtgt aatgatctca atatttattt ctcattcagt tgggtttcct tgtatttgcc    40800
acattagtgt ttaccctgtt cctaatggca aaatattctg tcatctcctt gccttttata    40860
aagtttaata tactttctca ttttaatctg tccccacaga tctctagtca tcactgtttt    40920
tatttgaatg tctctcatcc ctctcaactc ttttactgcc caatttctgt gattcctgaa    40980
gacttcaaca atcaatactc tcttttttg tttgttttgt ttttttttt tgagacagag      41040 tctcactctg tcacccaggc ttggagtgca gtggcgccat ctcaactcac tgcaacctcc    41100
gtctcctggg ctcaagcgat tctcgtgcct cagcctcccc aagtagctgg gactacagac    41160
atgcgccacc aagcccagct atttttaga ttttagtag agacagggt ttaccgtgtt       41220 ggccaggctg gtctcgaact cccaacctca ggtgatctgc ctgcctcaac ctcccaatca    41280
atactctttc tagaataagt atcagcactt ttgtttctca cctttctcc tttcttggtt    41340 ctcttcctat aaatcccata gtttcagacc ttttaaatta ggagagctct ctggggaatg    41400
tgcttaaggt ggagagcgat tctatactag gcaggtagaa aggaatattc ctcagctgtc    41460
ttcaaatgat tcattaagga aaagcagggt acagtgatag gaccatgaga tttggaaaca    41520
aagaaagctt tggggaatca ctcccctggt tcaagatttc ctttaaagtg aggatcttgg    41580
cggaggttga agtgagccaa gatcacaccg ctgcactcca gcctgggtga tagagggaga   41640
ctgtctcaaa aataaaaat aaaaaaataa agtgaggatc ttagtactgc ctgaaaggat    41700
tgttgcaagc attgaataac agtgacagtg gagtcctcag taaatgccaa gtcctgcatt    41760
ccgccctgtg aatccatcat tggagtctag ttaaatatgc tctggctcac agatcctctg    41820
tgcaataact tcccttttct ttttttctcca gacattactg gttatagaat taccacaacc    41880
cctacaaacg gccagcaggg aaattctttg gaagaagtgg tccatgctga tcagagctcc    41940 tgcactttg ataacctgag tcccggcctg gagtacaatg tcagtgttta cactgtcaag     42000
gatgacaagg aaagtgtccc tatctctgat accatcatcc caggtaatag aaaaataagc    42060
tgctatcctg agagtgacac ttccaataag agtggggatt agcatcttaa tccccagatg    42120
cttaagggtg tcaactatat ttgggattta attccgatct cccagctgca cttttccaaaa   42180 ccaagaagtc aaagcagcga tttggacaaa tgcttgctgt taacactgct ttactgtctg    42240
tgcttcactg ggatgctgtg tgttgcagcg agtatgtaat ggagtggcag ccatggcttt    42300
aactctgtat tgtctgctca catggaagta tgactaaaac actgtcacgt gtctgtactc    42360
agtactgata ggctcaaagt aatatggtaa atgcatccca tcagtacatt tctgcccgat    42420
tttacaatcc atatcaattt ccaacagctg cctataaaat agttttgtcc ctgtatgtga    42480
gcactgaaac agcatttggt tgacacatct agttttcat cttgcagttt caaatccttc     42540
tttttgaaaa ttggatttta aaaaaagaa gtaaaagtca caccttcagg gtgttctttc     42600
ttgtggcttg aaagacaaca ttgcaaaggc ctgtctaagg ataggcttgt ttgtccattg    42660
ggttataaca taatgaaagc attggacaga tcgtgtcccc ctttggactc ttcagtagaa    42720
tgcttttact aacgctaatt acatgttttg attatgaatg aactaaaata gtggcaatgg    42780
ccttaacctt aggcctgtct ttcctcagcc tgaatgtgct tttgaatggc acatttcaca    42840
ccatacattc ataatgcatt agcgttatgg ccatgatgtt gtcatgagtt ttgtatggga    42900 gaaaaaaat caatttatca cccatttatt attttttaac cttcttcatg caagcttatt     42960
ttctactaaa acagtttggg aattattaaa agcattgctg atacttactt cagatattat    43020
gtctaggctc taagaatggt tttgacatcc taaacagcca tatgatttt aggaatctga     43080 acagttcaaa ttgtacccctt taaggatgtt ttcaaaatgt aaaaaatata tatatatata   43140
```

```
tattccctaa aagaatattc ctgtttattc ttctagggaa gcaaactgtt catgatgctt  43200
aggaagtctt ttcagagaat ttaaaacaga ttgcatatta ccatcattgc tttaacattc  43260
caccaatttt actactagta acctgatata cactgcttta ttttttcctc ttttttcccc  43320
tctattttcc ttttgcctcc ccctcccttt gctttgtaac tcaatagagg tgccccaact  43380
cactgaccta agctttgttg atataaccga ttcaagcatc ggcctgaggt ggaccccgct  43440
aaactcttcc accattattg ggtaccgcat cacagtagtt gcggcaggag aaggtatccc  43500 tattttgaa gattttgtgg actcctcagt aggatactac acagtcacag gctggagcc   43560 gggcattgac tatgatatca gcgttatcac tctcattaat ggcggcgaga gtgccctac   43620 tacactgaca caacaaacgg gtgaattttg aaaacttctg cgtttgagac atagatggtg  43680
ttgcatgctg ccaccagtta ctccggttaa atatggatgt ttcatggggg aagtcagcaa  43740
ttggccaaag attcagatag ggtggattgg ggggataagg aatcaaatgc atctgctaaa  43800
ctgattggaa aaaacacat gcaagtattc ttcagtacac tctcatttaa accacaagta   43860
gatataaagc tagagaaata cagatgtctg ctctgttaaa tataaaatag caaatgttca  43920
ttcaatttga agacctagaa ttttttcgtct taaataccaa acacgaatac caaattgcgt  43980
aagtaccaat taattataag aaatatatca ccaaaatgta ccatcatgat cttccttcta  44040 cccctttgata aactctacca tgctcccttct ttgtagctaa aaacccatca aaatttaggg 44100
tagagtggat gggcattgtt ttgaggtagg agaaaagtaa acttgggagc attctaggtt  44160
ttgttgctgt cactaggtaa agaaacacct ctttaaccac agtctgggga caagcatgca  44220
acatttaaaa ggttctctgc tgtgcatggg aaaagaaaca tgctgagaac caatttgcat  44280
gaacatgttc acttgtaagt agaattcact gaatggaact gtagctctag atatctcaca  44340 tgggggaag tttaggaccc tcttgtcttt ttgtctgtgt gcatgtattt ctttgtaaag   44400
tactgctatg tttctctttg ctgtgtggca acttaagcct cttcggcctg ggataaaata  44460
atctgcagtg gtattaataa tgtacataaa gtcaacatat ttgaaagtag attaaaattt  44520
tttttaaata tatcaatgat ggcaaaaagg ttaaggggg cctaacagta ctgtgtgtag   44580
tgttttattt ttaacagtag tacactataa cttaaaatag acttagatta gactgtttgc  44640
atgattatga ttctgtttcc tttatgcatg aaatattgat tttacctttc cagctacttc  44700
gttagcttta attttaaaat tacattaact gagtcttcct tcttgttcga aaccagctgt  44760
tcctcctccc actgacctgc gattcaccaa cattggtcca gacaccatgc gtgtcacctg  44820
ggctccaccc ccatccattg atttaaccaa cttcctggtg cgttactcac ctgtgaaaaa  44880
tgaggaagat gttgcagagt tgtcaatttc tccttcagac aatgcagtgg tcttaacaag  44940
taagcagttg aatgtatctg ttccataaat attaacctag agcatagcaa atgaattcta  45000
aattctcaag taggaggagc taagagcaag agagctgcaa ccaagctaca aactaaactc  45060
tgaattcaat gcacagctcc attaattttg aaagatgtaa tgtttgttgc tatcttaata  45120
tacttttgat atctacagct ttaaaaaaat catagtggaa aaacacctgc aggaaagttc  45180
catgacttca aacaaattct gcttctaaat aagcacgtaa aaataagtga atatcaagag  45240
aaattatatg actaaatcta aatctttaga gaaaaaatg agaactgaaa atagtgtcac   45300
catatgtgct ttattctcat tttatttaaa aaagtgtcag cagttgattg atttaggatt  45360
tgaatactta gaaaagtgac tgattgtttg gtctagatta gaatgttgtt gtgaagagag  45420
tcagaagttt aatttgtact tcaaaaagaa tctgttagaa ggatttctca gaagactgag  45480
```

```
agcttagaaa aaaaactgac attaaataaa taacaacaat ttatggaaat tgtctctttc   45540
tagtcccaac cattatagaa tagacatctt ttgttaaaga ataaaacagt aggctgcaag   45600
atggtgctgt gtttcacata aacagtgctt tttattattt tcactgtaat agtcaaatat   45660
ataacaacag caaagattc tacataaggg aaaaatagct tacatttagg tacattacca    45720
agtattagtc tgaaaacatc tacctttcaa acataattta gataatgaaa cacaaagaag   45780
agcagctcag cgtgaccata atcttggttt cttactttgt ggctgagggc aagaatatct   45840
ttatattggc atatccacca ccccagggct gttgcttctg ttctagagca ccctggaatc   45900
actaattaca gcatcaccca gtatacaagc ccctgcatca caatgtctgt cccttagccg   45960
tagacctgtc acatgctaat catgtgttct aagaccttat tataatccta atgctacaga   46020
tgacctcagg gtagcccctc tccctcctag caaagtcatt attatcctct tttaaagatg   46080
aagcaaacca gtgcagtggc tctcgcctgt ataatcccag cactttggga ggctgaggtg   46140
ggccaattgc ttgagcccag gagttcgaga ccagcctggg caacacagtg agaccaagtc   46200
tctacaaaaa atacaaaaat tagccgggca tggtggtgca cacctgtggt ctcagctatg   46260
taggaagttg aggtaggagg atcacctgag cctggggagg ttgaggctgc agcaagccat   46320
gatcgtgcca ctgcactcca gcctgggtga cagagtgaga ccctgtctca aaaaaataaa   46380
caaacaaata aacatgaagc cgtcgaggtc cccagcagtt aagtaaattg ccactggcca   46440
gctagtatgt ggaaatgga atccaggcat ctggtcctcc attctggcac ttttccaaac    46500
ttttgtaggg ggctttatag aaacgctgaa gggcaaatgg tgtgcagggg aatgagggtt   46560
tagtgagtag gagttccaaa tttagaaacc tcactctctg tatcttttag atatacaaat   46620
atttaccata tattacagtt gcctctagtg ttcagtacag taacatgctg cacaggctca   46680
tagcctagga gcaataggct agaccacata gcttatagct taggtgtgtc aaaggctcta   46740
ccatctaggt tttttgtttt gttttgtttt gttttgtttt tgagacggag tctccctctg   46800
ttgcccagga tggagtgcag tggcacgatc tgggctcact gcaacctcca ccaccaaggc   46860
tcaagtgatt ctcctgcctc agcctcccga gtagctggga ttacaggcgt gagccaccac   46920
gcccagctaa ttttttttgta tttttagtag acgaggggtt tcaccatgtt ggccaggctg   46980
gtttcaaact cctgacctca agtgatccac cctcctcggc ctcccaaagt gctgggatta   47040
caagcccatc taggtttgtg taggtacact ctatgatgct tacacaataa aatcaccaaa   47100
tcacacactt atcaaaatgt atctccacca ttaagctatg cctgactgtg tatcaaaatg   47160
gaagaagaag ctgggcacag tggctcacgc ctgtaatccc agcactttga gaggccaagg   47220
cgggtggatc acaaggtcag gatttccagt ccaagcctgg ttaacacggt gaagccccgt   47280
ctctattaaa aatacaaaaa ttagccaggc atggtggcag gcacctgtaa tcccagctac   47340
tcaggagtct gaggcaggag aatcacttga acccaggagg cagaggtttc agtgagccaa   47400
gatcacacca ctgcactccg gcctgggcaa cagagtaaaa cctcgtcaaa aagaaaaaat   47460
aataaaaata aaaaaaaatg gaacaagata ctcagggatg tatatttaat ttttttaaaaa  47520 atattctgct ctcattttaa tatggcagaa ccgattgctt tctaagtgtg ctttttttcc   47580
agtaaaggtt aattattaag accactagtc ctggcctggg tcaatcccag tatgatcctg   47640
ggcaagtaaa ttaaagaaga taacttctct gtgcctcagt ttttttttgt tttgttttt    47700 gttttttcat ttacaaaatg gagataattg tagtaaatca aatttttaga ggtgataggt   47760
ttgttcattt cttgaatgcg gtgatggtct cccaagtcac acatatgtaa aaacccatca   47820 cttttaaagat atgcagtacg ttgtatgaca agaaattgct tttaaaagga gcaaactacc   47880
```

```
ttccagggtt gttgtgaggc ataaatggca atccacagca ccacagcaag gattatcatg    47940
tgccctccag agacatactc tcaggtggat gcgagaaata tccagctgtt gcagcaactt    48000
catcccactc gaaatccagc tgagtcacac tcacaggtgg aatggagggc ttcgagaggc    48060 catgggcaa ggtgaccctt ccttatcatc taattacaga ccttctcaag gtctgttcac     48120
tgaacacttc gctgtagtgt tcacttaggt gtaagtaggc tataggactg gacatttgga    48180
tatttcatca gttcaaatag tcctgggcgt gctttagttt ctcatgcttt tgagcagagt    48240
tttaaaataa gccccatttg cccctacaga tctcctgcct ggtacagaat atgtagtgag    48300
tgtctccagt gtctacgaac aacatgagag cacacctctt agaggaagac agaaaacagg    48360
tgagtggtgt tggcagtatg actatccagt agcttttgcc tatcaattct gtataacaaa    48420
tgaaatgcta cttctaaaaa tacatctcca tttttgttg tcatggtgtg tgtaccttg      48480 tcatcacagt atgattttat cgctggtctc aaaaactaaa agatacctta ctcaacaatc    48540
acctagactt tcagtcacta acaaattaag aaatttgttg tctgtccttt taaaaaacat    48600
tttctaagaa gatctttgtt atttagattt agcagacatt cctttttcatt aggcagctct   48660 gtctaatggc tgacccaaca ctcattgtca tctatttgtc ttcctttact aagccagcaa    48720
gtttacattt tcttttact taataaaata tgcatttact agaaggaagt tgaattgaat     48780
ctcataaata ttacatactt aaatatgaat gcttttaatt ttttctttca aaaggtacac    48840
tttagtgtat tcattaattt atttatagtc cacttgcttc caaaaaggac ttatgatatc    48900 ttagttttggt ttcttattga aaagaactag taaatgctgt aactgaaaca gaaatttgct   48960
ggaagtccca gagactaagt gatttgaatt tgcaacaaac tctgaatttt tgtgcatttt    49020
tgaaaaatgc attttcaaa actgtcaatt cacgaggaat tatcagcatt gtaatttgtc     49080
tgggataatg tctttagttt cagaaagttt tgtgtttggc atcattacca ctctgttgac    49140
atataaattt cctcttgagc ttaggaggct tctctgagag tcaaacattt actttgagag    49200
tgggcagatc ttgctttact tggaaggata cacttacagg atagaaacac agaatacttg    49260
aacactgaag aatttgaaaa tgtcaattct cagaagatct tgaacactta tctccaaatg    49320
tgacacagaa acttactgta ataaccccta aaatctgctt gaattactta gcacaagaaa    49380
aaaatgaatg cttgagctgg ctattttgaa ttgagtcaat ttaagatttt aaaattcata    49440
tgtagcttag aatcagtaca tcttactctt tggtttatgg caaatcatgg tattgatgag    49500
acaggaacga aatgttggat gtacgttaat ttcccctaca ccttcctcac ttcctaaact    49560
ggtggtgtct tttctttttt ttttctcttc ctcccccggg tgggaaaaac aggtcttgat    49620
tccccaactg gcattgactt ttctgatatt actgccaact cttttactgt gcactggatt    49680
gctcctcgag ccaccatcac tggctacagg atccgccatc atcccgagca cttcagtggg    49740
agacctcgag aagatcgggt gccccactct cggaattcca tcaccctcac caacctcact    49800
ccaggcacag agtatgtggt cagcatcgtt gctcttaatg gcagagagga aagtccctta    49860
ttgattggcc aacaatcaac aggtaacttt tcttgtctgc aaagaaactc agaagacttt    49920
cctacccagt tggtagattc tgtaaagtag cttgctgttg tctgtcatca gctctcaaaa    49980 aaaaaaaaa aaaaaaaaa aatagatcat tgtcatggta catggagagg gaagtgagaa      50040
aatgtggaga aacatcttcc ttagaatatg gtaaagaagc ccgggcgtgg tggcagtaaa    50100
gaagataatt ttttcctct caagaaattt ctcacctgat ttgggtattt atgcatttct     50160
aataacacaa gttttgttga aaatgtagaa aattggccgg acggggtggc tcacgtcagt    50220
```

```
aatctcagca ctttgggagg ccgaaatggg cagatcactt gaggtcagaa gttcaagacc   50280
agcctggcca acatagtgaa accccatctc tactaaatat acaaaaatta gcaaggtgtg   50340
gtggcatgca cctgtaatcc cagctactgg ggaggctgag gcaggagaat ctttgaacct   50400
gggaggcgaa ggttgcagtg agctgagatc aggccattgc actccaacct gggtgacaga   50460
gcaagaccct gtctcaaaaa aaaaaaaaa aaagggcca ggcgcaatgg ctcacgcttg   50520
taatcccagc actttgggag gccaaggcgg gtggatcacg aggtcaagag atcgagacca   50580
tcctggccaa catgatgaaa cctcgtctct actaaaaata caaaaattag ctgggcgtgg   50640
tggcatgcac ctgtagtccc agctactcag gaggctgagg caggagaatt gcttgaaccc   50700
aggaggcgga ggttgcagta agccaagatt gtgtcactgc actccagcct ggtgacagag   50760
ggagactctg tctcaaaaaa aaaaaaaaaa aaggtggaaa actgaacact gtttcaaagt   50820
acctttaaaa atataatttt agggtaatag tgtcattgtt cttagcagat agaggctgaa   50880
gtacttacgg gaacagtagc atcatgttat ctgtatttta gtctcaagtc gtcaagccag   50940
agacaaatac ctaagggaag ggtatatagg tgttcattgt attactttt ttttttttt   51000
tttcttcctg aaatggagtc ttgctctgtc gcccaggctg gagtgcaatg gtgggatctt   51060
ggctcactgc aacctctgcc tcccaggctc gagcaattct cttgcctcag cctcccaagt   51120
agctgggact acaggtgccc gccaccacgc ccggctaatt tttgtatttt tagtagagat   51180
gggattttac catgttggcc aggctggttt tgaactcctg acctcaaatg atccaccgc   51240
ctcggcctcc caaagtgctg ggattacagg cgtgagccac cacgcccggc cttgtatcac   51300
tttttttttt ttttttttt ttaacttttc tgtagttttg aaattttcc aaataaaatg   51360
ttgagggaaa aaaactcttc cccaaatttg aaataatcat tttatcacaa tttgaatggg   51420
ctctgtaacc ccttatcttg aattcgtcat aatataaaat tctgctaatt acacgtagta   51480
tttacatgat tgtatggaag aatcattaag acaattatct ggaaaatgaa caaacagtaa   51540
atctgaatat tgtttgaaaa ttacggatgt gaaaagtttc cctttttttt ctagtttctg   51600
atgttccgag ggacctggaa gttgttgctg cgaccccac cagcctactg atcagctggg   51660
atgctcctgc tgtcacagtg agatattaca ggatcactta cggagagaca ggtacagcag   51720
taaaatgcta ttttacactc tgattaaatc agattctgtt gtggataacc tgaaagccca   51780
acagtgaaca aagaattaaa gaaactttgg caagtccatt caacggagcc cttgtttttt   51840
ccaagaaaat acgtaagata tagatgatat aatttgttct aaacccaaa taaaagttg    51900
tttatatact acaactagag ggggaacggc agagctgagg aaataaaagg attgtaaatt   51960
cacaaacata ttatcagtgg tggaaataag tgattttat tttttcttct ctttactttt   52020
ctgtatttc caaatttat ttaaaaggaa tgtattctgt taaaagtttt aaaaaggaca   52080
caatgcatgc aatcctgggt tgagggctta ccttctccca cttctaatgc tactctacta   52140
ctcagtgaca tttttaaagct gaaatgttaa aacagcgcta actgtaattt tctctcaatg   52200
tttatacact taccaaggtt tgctacatgc ataaataccc ctttctgttc aagatagcgc   52260
tctttaaaag ggaataagca agaagatgtg atttacatgc tgctataaat gtggtaattc   52320
aattaatcag taatacccaa gtagctctaa acccctcaca ctctgaacta accctttttc   52380
atacaggagg aaatagccct gtccaggagt tcactgtgcc tgggagcaag tctacagcta   52440
ccatcagcgg ccttaaacct ggagttgatt ataccatcac tgtgtatgct gtcactggcc   52500
gtggagacag ccccgcaagc agcaagccaa tttccattaa ttaccgaaca ggtacaaact   52560
tctactctgg ggtgacacca gctttttactt attcagatac tgttttgcaa tgttctccca   52620
```

```
aggtattttt ctaattgtag aatagatttt cctttttaat gagcaacaac ctgcagctag   52680
cacctgcagc gaacagagtt ttgagccaga taaagaagga agcaccccaa gggcaggaag   52740
ttcagtcagt tttgtcgata tattccgcat gtctgcaata cgacaggcat agagagtgtt   52800
cagtaagtat ttgtgggaaa agaatggatg agttgataaa gtaggaagag acacctgctt   52860
gtggaatgta gcttctttgt gaatgaagca accatctcaa aaataggaaa tggtattgag   52920
atgcctgccc catccctcta aaagctctct ctgtattctt tcgagaagaa atacctttct   52980
catgtaagcg atcattcgaa tatgtaccag acctagagag gaggacttgt ccaatcttgt   53040
ctccaaggac tggggcttca ctggtttctc cctgctttta tttgtagaaa ttgacaaacc   53100
atcccagatg caagtgaccg atgttcagga caacagcatt agtgtcaagt ggctgccttc   53160
aagttcccct gttactggtt acagagtaac caccactccc aaaaatggac caggaccaac   53220
aaaaactaaa actgcaggtc caggtaagaa tcatctgcat ctcggccagg tgcggtggct   53280
cactcctata atcccagaac tttgggaggc tgatgcgggc agatcacttg aggttaggag   53340
ttcgagacca gcctggccaa tatggcgaaa ccccgtctgt actaaaaaat acaaaaaaat   53400
tagctgggca tggtggcttg tgcctgtaat cccagctact caggaggctg aggcaggaga   53460
atggcttgaa gtctggaggc agaggttgca gtgagccaag atagccccac tgcactccag   53520
cctgggtgac agagtgagag actccatctc agggaaaaaa aaaaaaaaag agtaatctgc   53580
atctcatata caacaggata gatggggtag gaccacctaa tattctttt tatataaatg    53640 gctaccttgt tgtgagtact atgtatttt ttgtcctatg tcatcattgt ccccattcat    53700
gagttcaggg ctcaagatca ttatcaaccc ttttcacagt agaagtctta agtgcatttc   53760 tgttttaca tggatagttc tatttagtga tatggacatc ttaaattact agattcaccc    53820
ttctggtttt gtttatcatt cacactaaga agagataaat ggcctaactg acttttcag   53880 ctctttttag ctatgttgtc tttgttttta aatagaatac ttgtgaaatt aggatcttaa   53940
ggcaatttat tagagtcaag ttaattttca ttttttctga gagcagtatc actaattgtt   54000
gggggcatca tattaagttt tagatcttat ccttgagtgt gacttcactc ccatatggta   54060
atttgtatta gcaatgaaca ggtttgtcca agaggaaatc aaagtctgac tctccatatt   54120
tttgttacaa ttctgcaaat aaaaattcta ggccaccata tgtttactac caaactctag   54180
acgccacttg aggactttat agtggatgac gtggatgttg catttgcttt tcactcccct   54240
tgcagatcaa acagaaatga ctattgaagg cttgcagccc acagtggagt atgtggttag   54300
tgtctatgct cagaatccaa gcggagagag tcagcctctg gttcagactg cagtaaccag   54360
tacgtaacca ctgcttggtt tccatttca aagtcaaatt ttgttcttgg gtgtctgaat    54420
gcccacgaca tgtcttttgc aattacacat agggaaagtg aacttgttgg ttagtttatg   54480
tcttgagctg agcccttac gaacatcttt tttccttctc agtgccaagc gaggaattta    54540
cagagaaaga agttgtgaaa ccaccatagt tagttgctgt gctttgaatt tcttttgctc   54600
aaatggcctc agcgaaatct tatttgccta tagcaaatct acaaaaaatt ttcctagacc   54660
gtcttttcta caactggatg gtaaagttga ttgaagtgtg cctcatgtag ctttatgttt   54720
ggggcatttg aagggctatg gctggaccag agtgtaatat aaatgcttaa tagagagggg   54780
aaaagaagag tgtaagaacc attataggc tgggctcacg cctgtaatcc cagcattttg    54840
ggaggctgag gcaggcggat cacgaggtca ggagttcgag accagcctga ccaacatggt   54900 gaaacccat ctctactaaa aatacaaaaa ttagccagtc gcggtggcac gtgcctgtaa    54960
```

| | |
|---|---|
| tcccagctac tcaggaggct gaggcagaag aatcacttgg acccaggagg cagaagttgc | 55020 |
| agtgagccaa gatcatgcct ctgcacccca gcctaggtga tagagtgaga ctccatctca | 55080 |
| aaaaaaaaca aaacaaaaca attataacaa tttgaatctg acattgcaaa tcagctttac | 55140 |
| cacttccaag gtatagaaaa tccaggtcta tgagactaac atcacattgt aaaaatcaaa | 55200 |
| tcgtggtaga atatctttaa attaatataa atacatcccc attgtgggga catttttgcag | 55260 |
| ggtatctgct tatctcacat acacctatgt tttaataagt gatgcaacat tgcatatttt | 55320 |
| ctaaaccaag aaaaattaag caagtgttta agtgatttt ccttttgata gtgggttaat | 55380 |
| tggacttcat caaagaaaat ggtatctgca aaactgcttt gcatgttata aaatgctta | 55440 |
| tttcacaact tgcttttcac ataacctctt accattaatt tgcctaacag acattgatcg | 55500 |
| ccctaaagga ctggcattca ctgatgtgga tgtcgattcc atcaaaattg cttgggaaag | 55560 |
| cccacagggg caagtttcca ggtacagggt gacctactcg agccctgagg atggaatcca | 55620 |
| tgagctattc cctgcacctg atggtgaaga agacactgca gagctgcaag gcctcagacc | 55680 |
| gggttctgag tacacagtca gtgtggttgc cttgcacgat gatatggaga ccagccccct | 55740 |
| gattggaacc cagtccacag gtatatggtt aattgcacca ccaggtgccc atgggagcag | 55800 |
| cggctttatg ccctactgaa tgaattatgc ttcactgggc tattgattcc cgtgtaaggg | 55860 |
| tgaaaagaa ttattaggaa agatcctctt taaagaggaa tggtaagaaa caataaaact | 55920 |
| taggtgatat ttaaggaaac aagtctgatt aaaagaaatt ttggagtatc ctggcttata | 55980 |
| cacaagacca taaagcaaga catttgaaga ggatactaaa gttgtggatt atttcctaag | 56040 |
| ctctgactcc ctgtgattac cctcactatg tataaagaaa agaagtttgg cattacagag | 56100 |
| cttacttata aaaaggaacc caaactcggg catttcatag cagcatgatt ctgagcacac | 56160 |
| gtgggtaaga ccttcttct ctggttagat atcatatgct ggtgtataat tagcttaaat | 56220 |
| gattgtgatt tagacaccta ggaaataatc aatagggcaa ttgctttcca taatacttta | 56280 |
| tcttcttgtg ctttatttct gaagcagagt agaatgctaa agatgtatcc tagtgacagc | 56340 |
| ataaacccta gaggtgacag tctgtattat tgcttttcgc ttctcttttc tgcttctgtt | 56400 |
| gggagccagt tttcttctta cgccgcatta cagagagaac gtcaaattta gcagccatat | 56460 |
| ctgccatagg gtccaaataa agagacaata aaacattat tctctctttt ttggatggaa | 56520 |
| tactgcgtga atggttatc catacaaaga tactttatgt agaatagaaa aaggaggccg | 56580 |
| ggtgcagtgg ctcacacatg taatcctagt gctttgggag gctaagccgg gagcactgat | 56640 |
| tgaggccagg agttcatgat cagcctgggc aatgaagtga gaccccgtct ctacaaaaaa | 56700 |
| atatgaaaaa attagcgagg tgtggtgaca catgcctgta gtcccagcta ctcaagaggc | 56760 |
| tgaggtagag gatcacttga gcctacgagt tcaaggctgc agtgagctat gataactcca | 56820 |
| ctgcactgcc gcctggatga cacagagaga ccgtttctaa attaattaat taacaatttt | 56880 |
| aagaaagaaa aagggccatt gcttattttt ccatacaaaa gtaaaataaa tcataatggc | 56940 |
| caataagcca atgtaacttt ttttttaag ggaaagcaaa acttgtaaaa cctaaaatct | 57000 |
| cttagagttt tggcatttac ccaaatgttt tcagtgattc tgagaattgg tggatataaa | 57060 |
| acacatttct cagcaaacac tttcttcatt ttgcatccct tactgtacgt actttcttgt | 57120 |
| actgaatctt tgcttgacca gggaacccac ctagcccaac aagaacaatc cattctactt | 57180 |
| cttggaactc actttatttt cctttcccc catttcctat aagataacct ctaaccaatg | 57240 |
| acaatctcga cagctattcc tgcaccaact gacctgaagt tcactcaggt cacacccaca | 57300 |
| agcctgagcg cccagtggac accacccaat gttcagctca ctggatatcg agtgcgggtg | 57360 |

```
accccccaagg agaagaccgg accaatgaaa gaaatcaacc ttgctcctga cagctcatcc   57420
gtggttgtat caggacttat ggtaagacat gaccgttgtt cattggaata aagatggaga   57480
tcatctctaa cacagtttct aaggtggtga aaatataata tcataataaa tctaactgtt   57540
cttttcctct gcatcaaata atcttattgt aattttatat caacgaatt cctttatgtt    57600 gacctaagtt ttccagatga ctattgggac agaattttat aaatagcttt ggattttgtg   57660
cagctctttt agatgtattg tgcttatttt aaaaggttgt gggggcaat ttacatatcc     57720 attggttgaa tgcataaatc gacttagtta tgcattttct gagctctgtt accttggtaa   57780
agaatatttt acagtttgta ccagtctacc ttgagcctac cctcattaaa cattttaaa    57840 atccttccag acatacatgc agaaaactgc taggaaccta ggggactgat gtacctctta   57900
acataaggcc aatttcaggg gaaactacag aaagagggtt cagagacaaa atggaacatt   57960
ctctttgcct ctctatgata aggaaaaaat tatgatttac acctgtcaga tcataaaaaa   58020
gaaaaatacg ctaataccca cttttctcat ttttttttacc agcttagttt aagtatataa  58080
tctatggctt acttaagctt aaccgctaag agcattttaa aattgataaa tacatttatc   58140
acctgcactg taggaatgaa attaatctag gaattttcaa ggttgtgggt tttgctggtt   58200
tgtttatttt ttattttcta accattgcat ttacctaatg ctgtagtgaa actccttggg   58260
tttcagttga ggacgttgct aaagctcacc atgcccttat ttctctaggt ggccaccaaa   58320
tatgaagtga gtgtctatgc tcttaaggac actttgacaa gcagaccagc tcagggagtt   58380
gtcaccactc tggagagtaa gtaacaaaat gtcttcatat ggacaaacct tctgtataga   58440
caaaaattaa agaatggtaa atcagtgggg ttcagtggct catgtctaaa atccaagcac   58500
tttgggaagc tgaggcggga gcgtcacttg aggccaggag tttgagacct acccgggcaa   58560
atagcaaggc cctgtctctt aaaaaaaata aaataaataa aataaataat tttttagatt   58620
tatatgttaa cagtggaatg agtcctaatt tgaaaatcaa tttgattgcc ttttgacgc    58680 atgactgtca tcttttatac tccttcagaa aggggtctac tgacccataa aatggaatca   58740
cttcataagc ttataatgtt gatattatgg actatgactg acatctagtt tatgctctac   58800
ttgttagaat ttgtttcat agagctaagc ttggggagac cccactggct tctgctatat   58860
cttaacaatg catattaggc cattcttgca ttactataaa gaaataccgg agactgggta   58920
atttctaaag aaaagaggct taattggccc acaggccagc aggctttaca ggaagcatgg   58980
tgctggtatc ttcttggctt ctagggaggc cttgggaagc ttactcatgg tggaaggcca   59040
agggggagca ggcacatcac atggctgtgg caaaagcaag accgagagag agagagagtt   59100 gggggggag gaccttatac atttaaatga cccagtctct tgagaactca ctgtcataaa    59160
gagggcacca agccacaagg gatctgcccc catgatccaa acacctctca ccaggcccca   59220
cctccagcat tggagattac aactcaacag agatttggac agggacaaat atccaaatta   59280
tatcacagca cagtaaccat tggaccaaat caggcttaga ttctagtctt ctgttatatc   59340
aataccttga tgtatgcctt ttcaaaagtc aggtaaagtg tcaaagtttt atcatttata   59400
aaagagggat ggcattgtac ctgttgagag aaaatacaaa atacttgccg taatattaga   59460
cacacacaca cacacacaca cacacacact ctctctctct ctcacacaca catacacaca   59520
cacacacaca aaattgttag ctggccatgt tattgtaact cctaccacac atattttac    59580 attataatac attaataatt ttaatattta ttgaagtatt tgtagatact ataaagccag   59640
ccctgggaac cactggtagt atctataaag cttttcagct cttcaaaata aaatgtctga   59700
```

```
gaggtagata ttttcctatt ttctaattac agttgacctt tctctctgaa tgccaaagga    59760
gataatctac acattactag ttatatattt cttgaaatgg atgaatttga tatataccaa    59820
ggaaacgttt taaaatacca aaactttaca tggatgagcc aagcaggcac taatctctag    59880
ctatgctcct gtgcagatgt cagcccacca agaagggctc gtgtgacaga tgctactgag    59940
accaccatca ccattagctg agaaccaag actgagacga tcactggctt ccaagttgat     60000
gccgttccag ccaatggcca gactccaatc cagagaacca tcaagccaga tgtcagaagc    60060
tacaccatca caggtcaggg aactcattgc actaaccaca tttgttaaca aatacccaca    60120
atgtaaacgg gcttattaac tgttctacga ctgacactga taaaatttat tttcagtgtt    60180
atcatcataa cccagtttta gaacgttatt ttcatgctat gatcagaaat agttttgtcc    60240
tttgaatgcc tgattttgtg taatatttgt catggaaatt gcgtaagtgt caatcaacaa    60300
gtttgatctt ccatcattgt gcccttctt  atttaaaaaa ttgtaacata aggtttaaaa    60360
ctaaagaaa  taaaaaacag tgatgtatag atcttagcat taaaaagcat agttaatata    60420
aaagtaaaca ataccactta ataaaggcca aaattgtaac cgaagaatat tcaatatctg    60480
aggtctttt  tagcttttta aaattgtgat tccaaggctc aactattgac catctgatta    60540
cggtaaagag aaaacctcaa taagtggctg accccattc  tgcaagaggg cctcttccaa    60600
catagcattt ttgcattcca gaatttactt taccagtgtc cttgtctgta tcagtgattc    60660
actttcgaga tatgtttctt gttaacagtt aacatccata gcatgctcta ctttactgtt    60720
caaatgtgga ccactttggt agtctatata aatatgggat gatagaagaa cccagaaaaa    60780
ttgcaggcta gcttgagaat tctcctagta aaaagcaaga actgttaaaa atcatctctt    60840
ctcaaatccc aggtttacaa ccaggcactg actacaagat ctacctgtac accttgaatg    60900
acaatgctcg gagctcccct gtggtcatcg acgcctccac tggtaactat accttctact    60960
gaggaaatgc cattgacttg tatgcaatca gtttcatgaa ctcaaaaaac aaatgtgagg    61020
cgtatatttt tgtattatag attccagaga atcttgtttc cggttacag  tattctcaga    61080
ttctttaag  tgtgtttaga acggctcggg agaaagtgt  gggagtaatt tcttggtta     61140
tttgccttct tagagactta attttgtttt ctttcagcca ttgatgcacc atccaacctg    61200
cgtttcctgg ccaccacacc caattccttg ctggtatcat ggcagccgcc acgtgccagg    61260
attaccggct acatcatcaa gtatgagaag cctgggtctc ctcccagaga agtggtccct    61320
cggccccgcc ctggtgtcac agaggctact attactggta ttgctgcttc catgctgtca    61380
ttttccttct tactacctag gacacatgaa gtccttagca aactcccaca gcgtctttga    61440
tactgtgtca tgagaatgcg aaactctgtt cctgataacc tcaaaaagca ttctctgtgt    61500
aggagtggta gagcctaata catcccaaaa ggcatgagtg aaggaaaatg caatttcaag    61560
actgtactaa tggcatgact agactcatgt tttcctttcg ctgcaagttt gccagatacc    61620
tgtcaattca gtcctggaga aagatatttt tcaaagcata ctagctgatt gtgattctgt    61680
cattacactc agctctctat agatatggca atcttgcagg acttgccagt gcaccacctg    61740
ccattgacct tgttgaccac tatcacagga taggtcttga ggcagagcag tcccaaccac    61800
ccacattgga agaatgcctg gaatgggaa  taagagttgt ctaccttggt gggaaagact    61860
ataagcctct agtattattt tgcccaaga  gatgaaatat ttaaactatc tgtattagtc    61920
tgttttcata ctgctataaa gaggtttaat tgactcacag ttccgcatgg ctggggaggc    61980
ctcagaaaat gtacaatcat ggtggaagga aaagcaggca tgtcttacat ggcagcagga    62040
gagagaagca cacaggagga acttccagat acttacaaaa ctatcagatc ttgtgagaac    62100
```

```
tcactatcat gagaacagcc tgggggaacc accccatgat ccaatcacct cctctcctca   62160
atacatgggg attacaattc cagatgagat ttggatgcag acacagagcc aaaccatatc   62220
agtctgtata gagtatcacc tggactttaa aattcccaca gaacatacag acattagaag   62280
gagacactgg cttttagaa ttgggggaa caggaaaata gaagcagaca tgagaggaat    62340
tgaactagac acttcccaca gaggctgcac aaacactggc caatctctcc tacccttcac   62400
ttgcctttag tttcactttt cattgatctg ccactgagga ctgcttggtt attaggccta   62460
agtagattca tgtatataat ctgcaggact ctctttcaaa tttatattcc agtggtggta   62520
tatgatgctg atagatttc ttaaattcaa aaggcaaat aagaccacgt taaaagaata    62580
ccctggaaag gccaggcgcg gtggctcacg cctgtaatcc cagcactttg ggaggccgag   62640
gcaggcagat cacaaggtca ggagatcgag accatcctgg ctaacacggt gaaaccccat   62700
ctctactaaa aatacaaaaa caaaattagc caggcgtggt gatgggtgcc tgtagtccca   62760
gctactcggg tggctgaggc aggagaatgg ctgaacctgg gaagcggagc ttgcagtgag   62820
ccgagatagc accactgcac tccagcctgg gtgacagagc cagactccat ctcaaaaaaa   62880 aaaaaaaaa aaaaaaag aataccctgg aaaagttagc caaaaatgt ctattcaggc    62940 gtcagatatg atagtaagat aattagtttg cgatgcggac tttatatgca ggatatttgg   63000
gtgtttatgg aggaaaagtg aagtcgattt taccttcaag aggccaacag ccagctggag   63060
aggaagtgcc tgctcccagt agcgtctgct ggtgagaccg acttccactt gactagctga   63120
gcccattgac ataatgtgat ggttctattc tcccttcagg cctggaaccg ggaaccgaat   63180
atacaattta tgtcattgcc ctgaagaata atcagaagag cgagcccctg attggaagga   63240
aaaagacagg taagagtatc ttgcaggtaa caaggagaaa gataggacaa aactaataac   63300
aaatgagcaa tcttgcaata tgaaaaggtt ctccatgttt tgatgcattt cttgtgattt   63360
tttttatcta acagcatagt gtatatattg tattctttaa taggagaaat aatttaacat   63420
gcactgcaga gtttggtttt attttttttc tttactacag ccactcaata taaagccttg   63480
ttattcacct tttaaaaatt caaacaagat gttaaaatgt aaaagaagag ctatcattgc   63540
tcttctttta taccttctgt tgaatttaa aatgtttcct tttttaaagg agggagaaa    63600 acctctcaca tttatcttta tttggtttct acaacttaga gctaaataat gtcttacttt   63660
tgcatccagt ttcagttaat ttcaagaaaa tgtgtattcc tgatatagga aaatttcaaa   63720
aatgaacatg tgtgttttat ctattttac catttcaaac catgaaaaac tgttgagcca   63780
aacctctgta attctcatac ttatgacact gatatgatta gtctggattc tacttcctac   63840
aacttgcttc tcaaatttaa aaaagaaaga gagaaagaga aagactgcac atttcagttc   63900
cattaggtct aatttgagca gaggcagctt ctacggggct cagcggttta aagctgtgtg   63960
tatgataaat tcatactaac acttttttct ttctaaacta taaagaaacc tttgagaaaa   64020
atcctaaaga tttctttctg gaaaaagtgt tttgtgatct cagaactgct cattttctgg   64080
tggcttttat caaattgatg aacagtcatt gttgcctgaa tcgattatta tcattgctgc   64140
tacttcctgg agcttaatgc gctttgcttt tttggctcta acctctctcg gctagacgag   64200
cttccccaac tggtaacccct tccacacccc aatcttcatg gaccagagat cttggatgtt   64260
ccttccacag ttcaaaagac ccctttcgtc acccaccctg ggtatgacac tggaaatggt   64320
attcagcttc ctggcacttc tggtcagcaa cccagtgttg ggcaacaaat gatctttgag   64380
gaacatggtt ttaggcggac cacaccgccc acaacggcca cccccataag gcataggcca   64440
```

```
agaccatacc cgccgaatgt aggtgaggaa atccaaattg gtcacatccc cagggaagat    64500
gtagactatc acctgtaccc acacggtccg ggactcaatc caaatgcctc tacaggacaa    64560
gaagctctct ctcagacaac catctcatgg gccccattcc aggacacttc tgagtacatc    64620
atttcatgtc atcctgttgg cactgatgaa gaacccttac aggtaattaa ttgttctctt    64680
cacttctcat ggggcagcac agaaaggaat aagttaggta actgaagtga ccagccctcg    64740
aataaaaagt ggcttcatgg ccgggtgtga tggctcacgc ctgtaatccc agcactttgg    64800
gaggccgagg caggtggatc atttgaggtt aggagttcaa gaccagcctg gccaacatgg    64860
tgaaacctcg tctcttgaaa aaaaaaaaa aaaaaagtg gctccacttt tagaacctct    64920
tagaagatgg cacatttaag ccctgctttt ttttttttt aaatcccaat atggctctac    64980
tttggaggac ataccagaga gtcactagct tttatttcat agagaaatg aaactatttc    65040 tcttattctc acacatttga ggttcctttt tgagtaagat agatgattct agaaaagaaa    65100
gatattctac ctgaatttcc atttgtgtgc agaagtctaa aacactacct ttacgatttg    65160
tccttgaaga accccactat ctacaacata tctaaagaaa aaaaaaaaca ggcgaagctg    65220
tgcatagcag ctgataagtg attgattctc taaaacgtat attatttaat ttgtgttgac    65280
agtatccatt tttttttttc cccgagatgg agtcttgctc tatggccctg gctggagtgc    65340
agtggcgtga tctcggctca ctgcaacctc tgcctcccag gttcaagcaa ttctcctgcc    65400
tcagcctccc aaatagctgg gattacaggc atgtgccacc gcacccagct aattttgta    65460 tttttagtag agacggggtt tcacgatgtt ggccaggatg gtctcgatct cctgacctcg    65520
tgatccgccc gccttggcct cccaaagtgc tgggactaca agcatgagcc acccactaca    65580
cccggcccac tgacagtatc aattttatt gtgttgttac ttttagaaag tggcagaatt    65640
taaaaactga caacactgta ggaaatttat gagcttagaa acatgagttt gaggatttgc    65700
ccaactgttt taaggactcc acactggggt cagatgtcac ctggaggagc atgaccgtgt    65760
ctcccatata gcgcagtgtc caggttttat gtgaagcaaa catggccagg gcttccagag    65820
ggcttatgca gacctgcgac tgaagcaaga tcaatggcag gccgtctcta gtattgtcga    65880
gggctcctgt taactacgga gcacgtaggg agattgttgg caggaaaatc tggcaggaac    65940
gatggcccct atccttgttc catttctctc ctcagctggt taggaccact ataccctccc    66000 tcttttttt tttttttgttt tttgttttttt gtcttccttt gctttgttta aacagtgagg    66060
gttattggta agaggagagc ccgtgtcatt cctcactata atgctttctc tctgctttgg    66120
atgtaccgat aattgcagtt cagggttcct ggaacttcta ccagtgccac tctgacaggc    66180
ctcaccagag gtgccaccta caacgtcata gtggaggcac tgaaagacca gcagaggcat    66240
aaggttcggg aagaggttgt taccgtgggc aactctggta tgtaaacacg tactatttag    66300
acacaggctc ccctctgctg tacaccagag atgggctttt ctgttgactg tacctttgtt    66360
gccattgtct tttatctttt gggatttaat gcaacacatc aacatgaaat aaatgagcaa    66420
ctttatatta aattaatctc tcccccacct cctgccatat cctgttgtct tcacaaaatg    66480
catacgtaat tgacagactc tcaaatggtg atatgattat agatctggaa gggatttcaa    66540
atattattta gtacaacact ctgagtcctt acttctgagt atctgagttg atataggca    66600 caggtttcct gatgtctttt cccagaccct ctccatctca ccatgctgct gtcctcttga    66660
gtgattaaat actgaaacga ttacctataa agaaaatacc ccttctgcag acatggggac    66720
agttggcttt tgctcctgat ataaaatgct accaacattg tgcatttctg tctgcagaga    66780
atgttattcc aatgttattt ccattttttt ccaatgttat ttccattttt ttttctgact    66840
```

| | | | | |
|---|---|---|---|---|
| atacaggtta | aaagcttcta | tagaggttaa | aagatcatta | actcttcttt gtagcacctg 66900 |
| ggaaatcctt | ttaaatcaat | agcgtgccac | ctggctgctc | aatttgcagc agctgaaaat 66960 |
| tcaccaaggc | acatgagata | ggggataatc | aaaaccgtga | atccccaatc ttccaacagg 67020 |
| agagttctct | actccacacc | aacagagagt | gctaagtcct | gtctatgcca agtgacagat 67080 |
| tttattccta | aggccagttg | tttaatttta | gcccttccc | tcatctgata gaagactgtg 67140 |
| ctactttaca | tgtataaatt | cctgtgaatt | aagcagttga | gcatttggct ggagagaggt 67200 |
| tgggaggaga | ttattttgtg | tttgttgtat | acatatccca | cagtaatgct tatctttgcc 67260 |
| ttttgtggtt | ttactagtag | aatgccacgt | gaacagaatt | ttcaagagca aaaaggtctt 67320 |
| tgtgcttttc | taagtcattt | tttttttttt | ttttttaaaga | ttccatctct ttaactttag 67380 |
| ttaggatgga | atttgaactc | ctggctcttt | tgagtataga | accccctagt aacaatttaa 67440 |
| gttccttcca | tttttctttt | aaactcctta | ttcccagcag | cagtattcta cattctaacc 67500 |
| aggttctccc | agctttgaga | cgtctcagac | ttaccagttc | tccaaaacgc tatttttcttt 67560 |
| aagggtgaca | ccttttaaaa | attaggcacc | tcaaatatct | actgcttttg agcttttgag 67620 |
| ttttgcactg | taaaagaaa | aatacacagt | gggatttttaa | gtcaaattag tttatctaat 67680 |
| ttttagggaa | taatttgaag | catgctttgt | ttgcatagat | ttttttaaaa taagctttttc 67740 |
| caaatcataa | agagataaga | tcttaggtaa | catgaagaga | ctcccttact tattcctaaa 67800 |
| tcatctatat | tccaagggca | ttttcttatt | tggaacagtt | gacctcactg ataaagctgt 67860 |
| ctcaccacta | taataacaat | gtccaaaatc | taggctttct | gcactattat gcaaaaatta 67920 |
| caataataaa | agtgaaaatt | acattataat | ggtatattaa | aatgctaaga cttttgcatt 67980 |
| ataagcaaaa | gacagccttt | aataattatt | ctttatttag | tgaacatttt ctaagtcttg 68040 |
| gaaaagggtc | aatgttttga | attcatggcc | ttatataatc | ttcacaagat tccccaggag 68100 |
| gtatagatat | ttttattatt | acgctagtat | tgcagatgag | ggaagcaagg cagagtggta 68160 |
| ttaaatagct | ggcccaaggt | cactcaggta | ccaatggaga | ggcatcatta gtctttgcat 68220 |
| cccactaaag | ttctccacta | gcttcaattg | cctcaagatc | tgttccatgt tctatgaagt 68280 |
| agtttcaaca | gaaatggcaa | ttatcttaga | agcaaggaa | aaataaaaga tgggcttcct 68340 |
| gtcgggtgcc | tgtgacaggt | gtcacatcta | accatggttt | tttagagcag ttaatgcctt 68400 |
| gatagaacag | atgaatgcct | cttaatcctc | ctggaattct | tgttttagat taagtcattg 68460 |
| tatacagtca | ttcgattttc | ttcttatggt | ccaaatcgat | taataagatg tctcttttg 68520 |
| cttttcttc | cttttcttca | tagtcaacga | aggcttgaac | caacctacgg atgactcgtg 68580 |
| ctttgacccc | tacacagttt | cccattatgc | cgttggagat | gagtgggaac gaatgtctga 68640 |
| atcaggcttt | aaactgttgt | gccagtgctt | aggctttgga | agtggtcatt tcagatgtga 68700 |
| ttcatctagt | gagtagttgc | tttgtccatc | cacttccgtg | tttgtctcct caagttccat 68760 |
| gcatgcactc | atgtgccaag | gaagcatgtt | tggaagacac | aggttcttcc aaacatgaag 68820 |
| caaacaagag | aatactgttt | gactcgaagt | aatattttgc | atcatagaaa aatgatggga 68880 |
| aattttactt | gttggacatt | gcttcatttc | aagggttgta | tgccaataca actattaatt 68940 |
| acacataaga | ttatggtgct | aatttgattt | ttgaaatttt | ctgtgaaaac aaatggataa 69000 |
| agacttttgg | aaccaggtct | atttaagagt | attagagaca | cagaaaaacc tcaaatctct 69060 |
| tttaatcttc | agtgttgaat | gagatcagag | gtgaacattt | agactcaaaa acagcctcct 69120 |
| tcaacataaa | ccaaacatgc | acatatcata | gtacccatgc | acacactttt gcgtcacaca 69180 |

```
catagcccag gtagcttgaa cgttgctaga aatatgaaag aaaaaacaga taatctgctt    69240
ttagatcatt aaaaatcaac ttgaattgat aaatgtttga ttttcaaatt ctaatacgtt    69300
ttaattttca aattttttaa gttaaaatgt gcctaggaaa tatctattat gctttgagat    69360
taggattaga atttataaac cttttcattta ttctttgtgt ttaggagatg tgatgattat    69420
tgacaattgg ttcatttta taggtgttga ccgttatgcc tataaataag cctcctatag    69480
acatacagaa atcatatcct gtggaattag aatataagac ttggtaaaag agattttcaa    69540
agtattttac ttaacttgta tacttgaaat catttaatcc agactgaagt tgtaaaagcc    69600
agccagtgtt ttcaatatag acttccatgt ttgaccatct gaaaatgaaa aacactaaaa    69660
acatcacatg ctgtttagga gctggaaatt ttaatatttg acttcaagta gatggttttt    69720
aactcctgaa atcgaactac gtttaagttt gtatgtttat tacctgtttg agcacttagg    69780
tgcaattgtg ggagcgggga tgtcaagttc atttatgtga ctctttggct caacttacat    69840
aatctttgtt ttgatatcac agttgtctaa ttatttact ttgtagctta aggcaggctg    69900
aattgttgat aaaatggaaa aagtagtata ttgttatata agcttctgag gtgtgttttg    69960
ttgtataagc cctggaggtt aaaaagtcat cccttatgta tagtagttaa aggcataaaa    70020
ctgtgacttt tagatattcc acagaaccag acttatttga tgtggataat aaccaatgat    70080 ttagcattt gtttgctttt gttttatttt atccgggttc attttttact cttcccatgt    70140
acatgaaaca ggtggtggcg tgtagagatc agctgatcct tgttttatgg ttaattgaac    70200
tactttgtat ccagggtttc tgcaaatcca aaagtgattt ttcatctagg atctattcct    70260
aacagtctac tccaatccca ctttagtttt ccacaatttt aaatcttaat agtgagaatt    70320
caaatgaaag tcatttcatt tgactattct gatgacatga ttgtggcaga ataaattggg    70380
tcttaaaatg ccctagaaaa tggtaaatga taaaaaataa tattttaaaa ttcaaccaaa    70440
gaaatggccc attggccagg tgtggtggct cacacctgta atcccagcac ttttggaggc    70500
tgaggcgggt ggatcacctg agctcacgag tttgagacca gcctacccaa catggtaaaa    70560
ccccatctct acaaaaaata caaaaaaaaa aaaaaaaaaa aaaatagcac tgtggggagt    70620
gcctgtaatc ccagctactc aggaggctga ggcaggataa ctgcatgaac ccaggagatg    70680
gaggttacag tgagccgaga ttgcaccact tcactccagt ctgggcgaca gagaaagact    70740
ttgtctcaaa aaaaaaaaa aaaataaaaa gtaaataaat aaataaaata aatgcccat    70800 tatagggtt tttatcttta acttgctatt tttccagatc atggttctga agaccctgtg    70860
acacgtccca gttcacctac tgtcttgtga gtcagaatat acaaataact ttttggtcct    70920
gactttcccc accctacag gatggtgcca tgacaatggt gtgaactaca agattggaga    70980
gaagtgggac cgtcagggag aaaatggcca gatgatgagc tgcacatgtc ttgggaacgg    71040
aaaaggagaa ttcaagtgtg accctcgtat gtcatcacag atcattttta gtgccttatt    71100
aagcattctc actttcatta tcaggctgta actctcattc acagaaatga ttggagactt    71160
taggtctcct tgaggagtga acagtgggtt tcttaatctt ttgatttggg aaagtggaga    71220
caagcttcaa aaatgagtca tgatttaatg ttattacagg acactttagc acttgtccaa    71280
cctgagtatt ttgaccatta tctgcagtaa aatgctacaa agaagcttta ttggtctgta    71340
gattcaactt ttaaaatatg atttccatct tcccgttgga ccctttccag tgtattaggt    71400 ctaattttg gaagtgccac cctaagatct gtatagcagt actgctctta gggatgattc    71460
acataaatat gtggtgtttg cgctgtgatg atacaaattt aggacagaaa tagaacccac    71520
ccctagatca agtctgcagt attgttctca gcttatgcgt gcatctgtct tgtgtctata    71580
```

```
tgcagatgag gcaacgtgtt atgatgatgg gaagacatac cacgtaggag aacagtggca   71640
gaaggaatat ctcggtgcca tttgctcctg cacatgcttt ggaggccagc gggtaagact   71700
ggatgtgcca ggctccctac aagttagata agataaaggg tgggctcctg caaggatgtg   71760
tcgtacacac aggagggggca gagacccttc ggaagtatta aaataccaca tttcctgttg   71820
gcatacaact gctgacatag agctctagag cagctctatg tctaccttac atgccattca   71880
ttctttctat tactcttagt agaaagaatg aatgaatggc atgtagagta ccaaaaacac   71940
aagtcttgag tcattcttaa tagcaacacc tgtcatttat atgatgttag aatcattttc   72000
ctaagctccc tagcatgtca gagatactat ttacactgaa aaatagtgaa gcagagatac   72060
tattcaaatt aattagtggt aaatagaatg tgtttcattt cagccggttc tccccatcct   72120
gggcagcctg agaccctccc ctcccctact attctcaggc tgcttctatt tttcagcaaa   72180
gtgttaagtg cagtgtagct ctaggcctcc aactccattc tgatggacag gtgtcccatg   72240
gcaacgttgt taaatatttt gaataatatc tcagatgtaa gaaatgcca cttcttttaa    72300 cctctctctt gattcagaac agatgcttgt tataggtcta gcactgtgct aagtagtata   72360
ggaaaaacag aggaaatgag aaatggcttg gctcttaatg atatagttga agatgttaaa   72420
ttagcataca tttcaaagtc aagctaatta agttctaagt gggtctgaca aatacagttc   72480
tgggtaggct ggaattagca agaaagagaa gcatgaactg gctgaggttt acgatgacta   72540
aggtttagtt gggaggggag aaagcagaga gacacacccc ctgggataga aaggagctgg   72600
cccaggtggg cttttggtgag ccaaccctct gcctgctgtc ttctggtaag aaaatagatg   72660
ggaagaagtg gcttatggag ggccttggca acccattatt taagccagta cttctcaacc   72720
atttctaaaa tatgcccagt ataacaaaaa ataataagcc tttctctaat atgatttcaa   72780
atttcaaaat gaaattatgt gtaactcaaa agcaatggaa tgtgacagcc ctttgttttc   72840
aacgaagaca tgccctccca gcaactcccc aaatcctggt gggtgagggg catgcttcac   72900
actcaagggt gagactcatt ggttaatgcc aaatgcatta accaattaca ggtatccaag   72960
atgcaaagaa acatgatgga aaatagtctt tgggaaaatt aatctggcag caggggtgtt   73020
caggggcctg tcttggctcc accaggggca gcccatggaa actactatga tcttgtttca   73080
cccccagtga ttacatgggg agggaggtgc tcccaattct gatggaggag aattggagat   73140
tggaatttag attgaattca gtatctctct ctgtctctct ctctctctct ctcccattaa   73200
cacttacaac gactgtgatt gtatgacctt agaactcagt cattctggta tgaaattgtg   73260
tgatggagaa tgaatttgct gggaagttga ttttggtctc acttcagcat cttctcatta   73320
tttatgcaca tgaaaccttt catgtgcgac acttattcta ttctcaagtg ctaaatgaaa   73380
catttaagac aggagtggaa actgttcact ttctcatatg aaagcaagat tcagtgattc   73440
tgtaaggagg tagtcactgg tattgtgtta ggtattaagg ggcatatgtg cttaaacaga   73500
gaaatatgtc taaatatttt aaattctaat ataaaaaaga aagtgactgt attatttagg   73560
gctgcatttt agttgtaaga aaaaagtcca actcaagcaa aaatggccca cacaatggaa   73620
cagtcccagg acccaccggc ttcaggggct gctccagcaa tggcgcccgg actccctctt   73680
gctccgcgtg ccttcccatg cactggcttc gtgcttcagc ggggtctctg ctgatggtgc   73740
cattgatgac tgacctccat gagcttgctt taccccctgc cagcttaaga acagtagtga   73800
aagagaacat gtgtgtcctc ccatttccag taaaaacttc aggcaggagc ctcactggct   73860
cagcttggtc ccgtttccat ctcccatgcc atctccggcc aggtgacagg ctaccatgtc   73920
```

-continued

```
actgcctagg gaagtttagg aagagagtgg caaagtggtg cattagaaag aacatggcca    73980
ggtcacccca cctcctgggc ggcaggccca actccaccag tggtccactg tgtgacttcc    74040
ctgctccctc taagcaagtc actcctctcc tctgggtctc tgtttcctta cctataaaat    74100
gagaacgttt cttcatgtga tctcaagtcc cttttaaaat cgctaggatt ctttgaaaac    74160
cttttctatc atctagtgca gagaacttgt tgaggaagtt gggattggaa tgagcctcag    74220
cagatgggca aggtttgaat aggaagagaa gagacatttc aggagaaaga aacaacatag    74280
agagacagat gtaggtataa gatatggtaa taagccaaaa tgtattaaga gttataaatg    74340
catgaaatca tcatcaaagc ttgcttagtg attaactgct tatattttgc cagtgcatat    74400
gatgtgacat ttttctttaa ctcaaacact aaattacgat gtcctcaggt tatcataaac    74460
cccatttgac ttcatgcctc tactctctca gggctggcgc tgtgacaact gccgcagacc    74520
tgggggtgaa cccagtcccg aaggcactac tggccagtcc tacaaccagt attctcagag    74580
ataccatcag agaacaaaca ctgtaagtgc attagcagca caagtgtgtt ccctcatact    74640
agacagtctc tttctacagg tatctttctt cagaatgaac caagtgtttt aattaattaa    74700
aaaaaaaaac aactcataaa tgacttaagt gaaacactgt attccataat atagtttaag    74760
ttataattta tgtaactctt gaacatctcc tattgcccag tatgctgcta ggttcttgaa    74820
actaggaaga aatattatcc tatctataag cagctgtcat gagtccccac ctccccgcat    74880
tttttttttct gtacacttta cagtatttgc cactaatttt ttttttcctt ctttttttta    74940
acagaatgtt aattgcccaa ttgagtgctt catgccttta gatgtacagg ctgacagaga    75000
agattcccga gagtaaatca tcttttccaat ccagaggaac aagcatgtct ctctgccaag    75060
atccatctaa actggagtga tgttagcaga cccagcttag agttcttctt tctttcttaa    75120
gcccttttgct ctggaggaag ttctccagct tcagctcaac tcacagcttc tccaagcatc    75180
accctgggag tttcctgagg gttttctcat aaatgagggc tgcacattgc ctgttctgct    75240
tcgaagtatt caataccgct cagtatttta aatgaagtga ttctaagatt tggtttggga    75300
tcaataggaa agcatatgca gccaaccaag atgcaaatgt tttgaaatga tatgaccaaa    75360
attttaagta ggaaagtcac ccaaacactt ctgctttcac ttaagtgtct ggcccgcaat    75420
actgtaggaa caagcatgat cttgttactg tgatatttta aatatccaca gtactcactt    75480
tttccaaatg atcctagtaa ttgcctagaa atatctttct cttacctgtt atttatcaat    75540
ttttcccagt attttttatac ggaaaaaatt gtattgaaaa cacttagtat gcagttgata    75600
agaggaattt ggtataatta tggtgggtga ttattttttta tactgtatgt gccaaagctt    75660
tactactgtg gaaagacaac tgttttaata aaagatttac attccacaac ttgaagttca    75720
tctatttgat ataagacacc ttcggggaa ataattcctg tgaatattct ttttcaattc    75780
agcaaacatt tgaaaatcta tgatgtgcaa gtctaattgt tgatttcagt acaagatttt    75840
ctaaatcagt tgctacaaaa actgattggt ttttgtcact tcatctcttc actaatggag    75900
atagctttac actttctgct ttaatagatt taagtggacc ccaatatttta ttaaaattgc    75960
tagtttaccg ttcagaagta taatagaaat aatctttagt tgctctttc taaccattgt    76020
aattcttccc ttcttccctc cacctttcct tcattgaata aacctctgtt caagagatt    76080
gcctgcaagg gaaataaaaa tgactaagat attaaaagta tttgaatagt ataatatgga    76140
ggagttttat cttagggaaa ccccatggta tgataacccc catctaacat gtcttacttt    76200
gggtcagc                                                            76208
```

```
<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
ggagagagtc agcctctggt tcag                                              24

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgtcaactgg gcgctcaggc ttgtg                                             25

<210> SEQ ID NO 4

<400> SEQUENCE: 4

000

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
gcaaattaat ggtaa                                                        15

<210> SEQ ID NO 6
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 6
ttaggcaaat taatg                                                        15

<210> SEQ ID NO 7
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 7
tctgttaggc aaatt                                                        15

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 8
atgtctgtta ggcaa                                                        15
```

```
<210> SEQ ID NO 9
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 9
tcaatgtctg ttagg                                                     15

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
cgatcaatgt ctgtt                                                     15

<210> SEQ ID NO 11
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 11
gggcgatcaa tgtct                                                     15

<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
tttagggcga tcaat                                                     15

<210> SEQ ID NO 13
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 13
gtcctttagg gcgat                                                     15

<210> SEQ ID NO 14
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 14
ccaatcaggg gctgg                                                     15

<210> SEQ ID NO 15
<211> LENGTH: 15
<212> TYPE: DNA
<213> ORGANISM: Artificial sequence
<220> FEATURE:
<223> OTHER INFORMATION: Synthetic oligonucleotide
```

-continued

```
<400> SEQUENCE: 15
ggttccaatc agggg                                                    15

<210> SEQ ID NO 16
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 16
actgggttcc aatca                                                    15

<210> SEQ ID NO 17
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 17
tggactgggt tccaa                                                    15

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 18
ctgtggactg ggttc                                                    15

<210> SEQ ID NO 19
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 19
tacctgtgga ctggg                                                    15

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
atatacctgt ggact                                                    15

<210> SEQ ID NO 21
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 21
aaccatatac ctgtg                                                    15

<210> SEQ ID NO 22
<211> LENGTH: 15
```

```
<212> TYPE: DNA
<213> ORGANISM: Artificial sequence
<220> FEATURE:
<223> OTHER INFORMATION: Synthetic oligonucleotide

<400> SEQUENCE: 22
aattaaccat atacc                                                      15

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
gatcaatgtc tgttaggc                                                   18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
cctgtggact gggttcca                                                   18

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ccttccctga aggttcctcc                                                 20

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
gtaacccgtt gaaccccatt                                                 20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
ccatccaatc ggtagtagcg                                                 20

<210> SEQ ID NO 28

<400> SEQUENCE: 28

000

<210> SEQ ID NO 29
<211> LENGTH: 68651
```

```
<212> TYPE: DNA
<213> ORGANISM: Mus musculus
<220> FEATURE:
<221> NAME/KEY: misc_feature
<222> LOCATION: (45900)..(45900)
<223> OTHER INFORMATION: n is a, c, g, or t
<220> FEATURE:
<221> NAME/KEY: misc_feature
<222> LOCATION: (45905)..(45905)
<223> OTHER INFORMATION: n is a, c, g, or t

<400> SEQUENCE: 29
tttcccttcc cacaaaatac actctggtgt gcacagactt ttctcagagg tgacgcaatg      60
ttctcaaaca ccaccacagc caccaattta aaaaaaaaaa agttaagaga tgaggggggt     120
aagccttacc accccaggct tccttaggct ccagcccctc cctcccttc cttcgagtct     180
acatcacttt acagccgttt cccatcccta cccccaatcc tcctcccaaa agtttgacga     240
ccgcaaagga aaccagaaag gggaaaaaag ttctctagtc ccagacctgg cgggagatca     300
gcatctcttt tgttcggggc gaacccaccg taccccgtga cgtcacccgg actctgggcc     360
aataggcgcg cggtcggcgg cggctgcggc ggcaggaggg gcgggaggag tcggaccgga     420
ccctcctccc cggcgcgcag ggcctcgtgg ggggcgggaa ggtactgtcc catataagcc     480
tctgctcttg gggctcaacc gctcgcaccc gctgcgctgc acaggggag aaaaggagcc     540
cagggtgtga gccggacaac ttctggtcct ctccttccat ctccttaccg gcgtccccac     600
ctcaggactt ttcccgcagg ctgcgagggg acccacagtt cgtggccact tgcctcctgg     660
ggagggcgac tctcctccca tccactcaag atgctcaggg gtccgggacc cgggcggctg     720
ctgctgctgg cagtcctgtg cctggggacc tcggtgcgct gcaccgaagc cgggaagagc     780
aagaggcagg ctcagcaaat cgtgcagcct caatccccgg tggctgtcag tcagagcaag     840
cgtgagtacc gacagtctgg ttcaaaccgg ccggcggcag ggatgggttg gtcctcaagc     900
gcccgctcaa gttgtggcta aagttttttgc gcgcgtgcgt ggctgtgcga acgtgtgtga     960
gtgcgcgctt tatcgaggga aaccagctgt ggacacaaaa ggcttaggtc tgaacaggct    1020
ggttgctggt gaagtggagg taggaccgt ctgttcttcc cctcaagtgc gctaacaaat    1080
tctacacctt cagttcgccc ttccaggaac caaaacgtgt gaaagagaaa agagacacga    1140
acttacaaat tttacatcag agattattgt ggttccctg atccttattt tctttatcag    1200
caaatagctg gttaaatatt taacacgggg aggaggtgag actatctaaa taggtagttt    1260
cttaccaact tgaaagagat gttagttggc tcagtgcttt gggggggggg gggtagccta    1320
ggattctttc cccaagagca aggatagcca tttctcttcc agtttttcag agacacactc    1380
ttcctttatc ttgggctaga ggaaaattta aaagttctcc ctccttttttt tcttttttctt    1440
ttcttttctt ttctttttctt ttttttttct ttttttttttt tttttttttt ttttgccatg    1500
atctcacact gtagcctaag ctagcctggc attctcctgt gttgtccagg cttgtgtgtt    1560
caacttggga gcaattcttc tgcctcagtt tctacagagc tggggttatt ggcatagtca    1620
tcaagacacc caacttaagt tttctttctt gtcttttgt tgttgttgtt aagagtattg    1680
aagccctcag gatttaaaag taatttctat ttctggcctc tcagagtgtt tcaagtctgc    1740
tgaggtagtt cccctgccca taaggacatg acgtcattgt ataacttta cccaagttaa    1800
aagataagaa ggaaaaaacc cctaaacatc catctacata aacaatgctt aaatctttga    1860
ttagctagtt tccacatctg aactttagtg gaatattgct tttaagagtt tttttgtttg    1920
tgcaggctca ccaagtcagt tggcaaaatt cagtagtttt gtagggggaaa aaagagaggg    1980
```

```
agggatggaa ctgttaataa ctttccccat caattcttcg cagctggctg ttttgacaat    2040
gggaagcact atcagataaa tcagcagtgg aacggacct  acctaggcaa cgccctggtt    2100
tgtacctgct atggaggaag ccggggtttt aactgcgaga gcaagcctga gcgtaagtgg    2160
aaggcagtct gggccctggc agagatgatg ctctaagtaa aaccacattt gccttctcct    2220
cctccctgct ccagtcgctt gtaattccct cttattagac ttcttgcact ggcttttcac    2280
atgctcttac ctctaaaaca aatgtaatcc acacgagtct ccaaagccgc cttttattc     2340 tcttggagct tttgattaga aaatgagagg ttttgcgtgt ctcccttcaa aaagaaaact    2400
tataaaagtt tgcttataaa agtttaattt attagaaagt gatctcggat cttttggctc    2460
ccaattatgg gccagaagtt gctttgaggc actgggttgt aaagtgattt gttagctgca    2520
gttccgtgaa aaaacaaaa  acaacaaccc actaccactt cggagactcc tgaagcccct    2580
tgatacgctt ccggtgagct acagcagtcc cttcagagag gctgctgagg gagggtacag    2640
gacaaatgtt tcagtggggc tgacaaaggc cagccactgc tgggaggccg gcaaccttca    2700
aactgtttgt gtcccttgtg acccttgaat tgatttccct ggtttgagac tggaatttgg    2760 aatcttttcct ctgcaactca gctggtcaca gggtgtggct ttttcctggg aactctttac    2820
attataaata agggaaccgc tgagagctgg ccaaaggtca agagctctgg ttttattaaa    2880
gcctaactta aaaacttgtc tctcttaagt ttcagagtcg ccatgtatgt gtgtgagact    2940
cacatggact tttttttttt cccctttcca cagctgaaga acttgctttt gacaaataca    3000
ctgggaacac ttacaaagtg ggtgacactt atgagcgccc taaagattcc atgatctggg    3060
actgtacctg catcggggct gggagaggca ggatcagctg taccattgca agtaagagag    3120
gccttctgtg gagttattga ggtcacatat acacacttcc ctctggcctg tccttgcctt    3180
ttcctgttat ccctgactga atagtgaata cttttttactt caatgaccaa accccatgtc    3240
gtcacccacc tagctcctct acatctggaa gatggatcta agcagagatg gaatctctct    3300
gtctctctct ctgtatgtgt gtgtgtgtgt gtgtgtgtgt gtggacagtg gaagatctct    3360
tggttctttt caataagata tgcccaaggg acctacctat tttaaattat ctgggcctct    3420
ttaagccaga ttgatcattt tatcctctgc agctatgagc cagaagggtt tttgctcttt    3480
gtcatggagt ctggttcttt gtgatgagta gattagattt ggggagaaaa ccttgcggtt    3540
ctcaaattca acacaggctg atgagcacag tgcatctcca aggaacttta ggtcctgggc    3600
tttctctcag gaagtctaca gctgcggcag tctttctcgt gtgactcatt gggttgccag    3660
tacgttctat taataagact ttctctctaa aaaccaactt ttaaatataa gtcctctgtc    3720
caaaagaacc aattagtccc ttctgaatag accaaatcaa tatttccaac atttaacatg    3780
agggtttttt ccaagtttcc tggcaaagcc caagagtcga tggtacactt gtgaccctgc    3840
gtacaattca gccattggat ttcacagcct aagaaagtat cagggtttcc aaccctcatg    3900
agtgtgtctg cttgctttct gccagagtgc tatttccacc ctggagtaga atgcaggctc    3960
tccgtcctcc aggagatcgg aatgctatgc ccaagtagcc caccttgctg tctaggagga    4020
cagttccccc agctcttctc tgtctaggga acagattgcc tgtgatgtct ccggggaacc    4080
acaatttatg acttcttgcc attcagagtt ctccatggct ttccttttg  tgctttaacg    4140 attgacccaa agtgggctga tatggtgtta gccttctttc tgcttttttt ttttttttg     4200 gcaggagagc tgcctgccaa aaaaatccct caggattagg gattgcattt tggccaacat    4260
acatacttat ttatctcagg cagaacatga gatgagcacc ccctgaattc tctcaatccc    4320
ctaacgtttg cctttgatct gtaacagatc gctgccatga agggggtcag tcctacaaga    4380
```

```
ttggcgacaa gtggaggagg ccacatgaga ctggtggcta catgttagag tgtctgtgtc   4440
tgggaaatgg aaaaggggaa tggacctgca aacctatagg taagtggctc gtgtgtgtga   4500
tcgaggggaa cggagccaca agcagatagc ctaagcaaac cagtggccgg gatagctgaa   4560
tcacagcata aaaaccagtg aaatgtgctg cgagtcacca gccttaagga aatcagatcc   4620
tgaactatgg aacataaagg aatcttaatt ttgtttgaaa agcacaaggt ggagttaaaa   4680
tctttaggaa gaagtgattt cttttgttta tatactatgc tgtccccttg gtgaagaaga   4740
catgttattt aaaggaggaa aaattacact attgacacat ttcttgttgg aacacagttt   4800
gttaaagcac aaaatgccac gtggctccgg tcacaccttg gcaatttcct taaaaacaaa   4860
cattaaaggt tgtgggggat ttttgttggt ttgttttatt tatttttttct gtttttttgt   4920 cttagccttg gttgtactct gaagcccaaa gttttgggtt ctctttctta gatctccaag   4980
tcagacgtgt gttttttcaa atttgttttg ttttttgtttt ttacattagt ctaaaattta   5040
aagagcgctc ctctcattct ttgtaagtcg ttcatatttt atagtggttt agtttaggga   5100
cacacagatc agtggtagag agcacttgct gaggctaaca taaggttctg ggttcaattc   5160
ccaggactga attaatgagt taaaagagaa aggttgggat tttgcatagg gtcgtctccc   5220
acagggtaaa gacttgcatt tctttccact tgaaatgtta gtgggaagct tgggacaggc   5280
agaaaaatcc ggtctgtgta ctcattagga caacagaatt tacttgcagc aaggctgggg   5340
cttcctcttg ctccggcttc ttgctccgtg cttagctgca gggcgtgcct gctcatctga   5400
acagagtgcc actttaagaa atgtggctgg ggttttgatt ccatgctaca ctgtaaatta   5460
tagggagacg ctatcatttt aaatcgctct tcctcctttc ttttgctttt cccatttctt   5520
ctccagctga gaagtgtttt gatcatgctg ctgggacgtc ctacgtcgtg ggggagacct   5580
gggaaaagcc ctaccaaggc tggatgatgg tggactgtac ttgtctaggc gaaggcaatg   5640
gacgcatcac ctgtacctcc agaagtaggt ttagctcttt tctgttgaca atgcagccca   5700
ctgttgcttc tggatcccta gagagagttg tgatgccttg gtgactctgt ggtatcataa   5760
gatgtccaga aaaactgtat aaccatcacc ttctgcttct tcagaggaca ctcaataact   5820
aggaaaggca gttctcagtt caaccctgcc ttaggcagtc agctagtaaa aatgaaaaga   5880
gccttagtgg tattcgcttg ctggatgggt cttccttgat ctgggaatta tctcagagat   5940
acctttctgg taccgaggac aattaaatcc ctaaagtagc atgtaaatga atcctttgac   6000 ctggggagc gattggaaat aaaaggctct accccatgtt cggatttcct tctatgtttg    6060
aagtttaaat aaggtttact gactctaaac aagaacctag tggaaatgag tccgtgccca   6120
gtattatcct tcaaatagga aagtggaatg aatttctgtg tgttgtttgt tcatcgattg   6180
ggcagagaga ctgttaaatt ataacccatc cttgctctta cgctacaatg tgggcagtaa   6240
gggtctaact ttgtgactta aatattgctg catttgcagt gtcaggaaaa aaaaatcaac   6300
cattgattca ggcaaatgca tagacacaca agaacagagg tccaagaccc cagctaacag   6360
tgttgtcaaa cctgaacctg ttttcagtat ctttgaatca gtatctcttg aaactcctaa   6420
tgctgagctt tgtaagtgat taatacatga gccttcctca tctttgacct actaagtgtt   6480
ctctgaaggc tgatgcccag ttcgtatttc cctccccata ttgccacata caaagtaagt   6540
acttataaaa ttttgttgat cacatgctat ttgtttgaga aactttgcat gctgtcagaa   6600 gggtttaaa tgataggtaa gagtctgaat tagattcctt tctacatgtg ttttattttgt   6660 gtgtggaggt gggaggcaca cacgccacag tgtgcatgtg gagggcaaag gacagtttgg   6720
```

```
accgcgcagg gtgcagtgac ctcaggttgt caggtttggt ggcaaggttc tttactcact      6780
aagccagctc agtggctcag aattagatgt ctaatttgtc ttcaatgaaa atactgccac      6840
aaacgacttg gaagactgaa gctcatcaca gtttttaaatc aaaagatcta aggatcctat     6900
aagtttgggg gaaacatttg atctttttcc atgacttatt tttgtgtggc aaagaatttg      6960
aacttgggtg gtattttttaa ttactagttt aagctggata acaaaacac attcaagata     7020 tctagatttg actttttttt ttttttgcatg cgttttaaaa ttcatgcttc agcaaattcc     7080
aaggctgttg ttagtttgaa attctaaatg gaactttgaa ggcagaagca gcaattaaga     7140
cttcaagaca atcttagaag cgggagggaa gaaggatgcc tggggccagc tttttacaag     7200
gataataaga gacagcatcc ttaactccag aagagacctt ttaaccgtgg gataagccat     7260
tttgtcgttg ctattggtta ttgtcactgt tattattaca attactatta tacagggagg      7320
attctcataa gcccaggctg gcctagaact tactgtgttg ctgagagaga ccttgggctc     7380
ttaacactcc tgctcctacc tcccagacgc tggggttaac cacgtgggtg actttgtaat     7440
tgtaaaacag gtggttttgg gtggggcaag aaaagagaac cttctagcca gagaagttgt     7500
ttttccacag gaatacttttt acataacaag tggagagatt ggtgtggtta acttttttagc   7560 ttccctgggg cagtcggaag agacctgcct cctttattgtt tattgaaagg agggccatgg    7620
gctgtaatta cagaaaaagg tctggaagac actgaggagt aaagagtaga ttgccagata     7680
attaattgag tcaaagaacc aatgtagaaa atcttaattt ttttttaatca ataaaagaca    7740 ctgaatagta ttttttttcttt ttttcctttg gcaaatggag aggtagggct gtactgtaac   7800
gaaccgggta tctgaatttt aatatatgca tcaccagcac tgggtaggat gtactaacac     7860
caacaacagc cactcagaag cattcaactg cagcattccc atcttagtgt ggatggctgc     7920
gtgtcggtta ctagataact tctatattca atgcttctct cctgaaacag acagatgcaa     7980
cgatcaggac acccggacat cctataggat tggagacacg tggagcaaga aggacaaccg     8040
aggaaacctg cttcagtgtg tctgcacagg caatggcaga ggggagtgga agtgtgagcg     8100
acatgctcta caaagtgctt cagccggtga ggcgctggga ccggggacag ctccacgcca     8160
gggtgattta tagcgtttca gctaagaagc tggaatcgtt cacataactg tttaaaaata    8220
ttcattctat attgtgaaca aagttgagtg gaatgaagtt gagacgtgcc tttagcacag    8280
agggctgggt tggaaaagcat agtgtactct ggtcatggct ctattagtat aggctttggc   8340
ttatgagcat gagactcaga gttcagtcta gaaccaaagt aaatatccaa gtgtgatggt    8400
gttatcccag caccaagaag gtggaggcag gaggatacct ggggattaca gaccagccag    8460
cttacactac tttggaagtg tgggggtggt tccaggttag tgagatggtg tggctggcca    8520
gcccactttt cttgggggag ttgggggaag ttgtgttcta ggtttgtgaa agatggtgtc    8580
atagaaaaca agatggctct gggcataatc cctgccttct acatgcacaa gctctccaca    8640
cgcatgcgca catagataat gtgcatgcac cctccctcac atggacaagc aatagtgagt    8700
gaatgtgtgg tatgtacttg gaatcctcaa gccctgggtt cagttcccag cacccctccca   8760 aaacacccca ataattatta tataaattta aaagaataac taaaacaaag aaaggtatttt    8820 gtatgtatct tggatgcttg gtcagagtct gaggaagggg tcgagcact tgccaaccat     8880 gcgcaaagcc ctggttctgg ttccccatca ctaaataaaa ggagggtgtg ttgtgcctgc    8940
gattccaggg atcaggaagt agagggacgg aggatcagaa gtccagagtc agccttggct    9000
acgtagtgag ttctagtcaa acctgctcaa tgtggctcag tgggtaagag cacccaactg    9060
ctcttccgaa ggtccagagt tcaaatccca gcaaccacat ggtggctcac aaccacccgt    9120
```

```
aacgagatct gacgccctct tctggtgtgt ctgaagacag ctatggtgta cttacatgta   9180
ataaataaat aaatctttaa aaaaaaataa aaaaaaaaaa agatgctgtc tctcatgcac   9240
acacacatcg gaagaaggaa gtgcagctct tgtgggtggt accttccgc tattgcgctc    9300 tgggtttcca tctagctttt actgtgtgat agtccagcct tgttacttag cctcttagca   9360
gtcagtcatt caggcaatag taattagatt ttttccct tttgacgagt ttatctggac     9420
ctaattaatc cttgtgaaag caaacaaggt tacatttgat gatctctaca ttatccaatt   9480
atcatcgata aaacagcta ttggccataa ggcagaggaa gaacagttac gaatgtcagt    9540
cgactgaact acatgaagga ttaactgagc taactgggat taaacaatac gtgttaacta   9600
tttttatggc atcactaata taccgaggtg tttcactatt aaagggtttg agaaacactg   9660
ttaaacgaaa caacctcttc taggagggcc ttgccgtcct tctgtatggt gggccttgac   9720
accattggcg tcctctgtct gagttctctt tgggtatttg tgctcgtcag cgctggggga   9780
agaggctaga ttcattctag aagctcttcc gctgccatac ggactctgac cttcaaaagc   9840
cagatttcta aaagagaagc tagcacaatc tgttgtgtta actatccgag gaaacttgtg   9900
aggattggtt gcttctagga aaacaaacag acatcctaag gaattctgct gagcaccgac   9960
acccaggaag agggataact taggaaatcc gtagctctcc agggtgtcct cctgagagcc  10020
aagttttaga gaaggcagga tatcccctgt gggtcttcag gggtctctca ggaagaggaa  10080
aggccacaca cagagcatat gagagctatg agggaagaca ggcaaggcag accatttcag  10140
atgagtgggg agcctaggg agaaggcagg agcatggtac ccaggaatga tgagcagctc   10200
agtgggttga agcttagaac agggcaggga aggctagcag ccaggcggga ggggagagtg  10260 gtagagggt gtggagctca cagatggatc gcttcctagc gtgactgaag gtttgtgaaa   10320
gataacctgt tgtgttgtgc ggcaggataa tgttgtcgct tagatgtgct gttcaggtgt   10380
ggctccgatg aggattatat gaggagtctt gtgaaccact tcttgggctg agtgcggaag  10440
ttccgggtca agccaagaag actctggact cattgacttc tcccttccag ttttataact  10500
ttttcattct cctgccctta ggatctggct ccttcactga tgtccgaaca gctatttacc  10560
aaccgcagac tcacccccag cccgctccct acggccactg tgtcaccgac agtggtgtgg  10620
tctactctgt gggaatgcag tggctgaagt cgcaaggaaa caagcaaatg ctgtgcacgt  10680
gcctgggcaa tggcgtcagc tgccaggaga caggtaggca ccatctgccc acggatgcca  10740
gaggacctac attcagtgtc tgcagtatct tagctgttcg taaaaaaaaa tgtaaaacca  10800
taaatccaga aaagtttata atcctgtgat aaaaatcata gtagctgaca ttttcttctc   10860
tggtcttttt ttttttttt ggttttttga gacagggttt ctctgtgtat ccctggctgt    10920
ggccttgaac tcagaaatcc ccctgcctct gcttcctgaa tgctgggatt aaaggcgtgt   10980
gccaccacgc ccggctcttc tctagtatta aacttgtat attttcttcc tatcatgagg    11040
atcaaactgc tttgtagtat ctgtatttgc cgaaagggat gctgcaagaa caccatttt    11100 ttcctgtttg tttttgtttt ttctcaacta gccaataatc tgtactctga gttcaatttg   11160
gaattataga tgtctttag cagcacatgg cctcttctgg gtcaaacatg ctctctttta    11220
taattgtttt tctagagcag ccatatatac tgtttcttct gagaatgtaa gcaagcatgt   11280
atcgctctgt gccgtcttca aatcataata atttgtatta ataaagcttt acaagtgggg  11340
aaactgagtc acggtagcag aagtgtctcc caaagacatt aaaaggagaa ctctggctca  11400
cccttaacca gctgactaga ctttcatct tggcccttta gtagcacagt ttccatttaa   11460
```

```
attagaaatt tgtcaccact ggggtcagag gtgagggtgg gaaacaactg tactgactga   11520
gactcttggt tatgcttgta gccgtgaccc agacttatgg tggcaattca aacggggagc   11580
cctgtgtcct cccgttcacc tacaacggta ggaccttcta ttcctgcacc accgaagggc   11640
ggcaagacgg acatctgtgg tgtagcacaa cttccaatta cgaacaagac cagaagtatt   11700
ccttctgcac agaccatgcg ggtgagtgtc ctgggaggaa ccagagaggg cggtcgtctg   11760
tctgtccttg ccgtgcacac ccttctgtgt gccagcagtc agtcagtcat tccgaggctg   11820
cacgggaact atagctttga tctatttgaa cccacagcta atcccttagc agaggcaggc   11880
agtttccatg tcccttagcg ccactgggga aatgtcactg agggaaaagc cctatggttt   11940
gattatttcg acacatgggg attatgatgt gattaaagac actcaagtat tgaaatcagt   12000
ggatgatccc acagagccga tgaacacaca ggataaatgt caagggtgcc ggtacttatc   12060
ttctgtgtag agtcgaattt tacacaaagc tatcatttaa tctttttttt cccccttgg    12120
ctgggaaaat gagaaaacat gagatttaaa tctattttga aagtgaagat gaaaatccac   12180
taagaagctt agggctgtat tatcagatat cttttattt gtggataggc cctctgggac    12240
ttaacagccg gaacctggct ctgtctaagc ctgcggtagt ctctccttgt cgtacacaac   12300
acagctcagc tgtaatcttc gggttgtgt gttgtcttgg gcagttttgg ttcagactcg    12360
aggcggaaat tccaatggtg ctctgtgcca cttcccccttc ctgtacaaca accggaatta  12420
caccgactgt acttctgagg gtcgcaggga caacatgaaa tggtgcggca ccacccagaa   12480
ctacgatgcc gatcagaagt ttggattctg cccaatggct ggtaagagga agccctgtga   12540
gttatgggtg tggacccgct agcagcctgt tgatggtctg ggagagtacg atgtgcatct   12600
atgtattata tcttacattt gcaaattgag aaaactgtca atggcaatgt attctggcaa   12660
atacagagct gtcctcattt tacctggata cagaaagagg aatcagggat tgcttattgt   12720
ttttaagttt cgagagtccg gtagaagaca tcttttccag ttgtagaacc aatagcctga   12780
gggtcatgga gagtcatgtg ctcagacgca aggaaactac acttttttgtt tttctcattt   12840
caacagaaga tgacattggg tttaagaggg acagtcactt ttacctggga ttttatgctc    12900
acagtttccc tttgaacttg agtgaaccag gtgaagtcac aaggctatag ttaaatccag    12960
tcctctagac aacgagaatc aatgagtata tgagattttc ctagtctaat cttcttcagc    13020
cctttttggta tttctctcca atctcctctg gaccggttct ttcctggaga gttcaaaact   13080
ccaccttcat ccagctacat gcatgcaagt cttcttccca aaggagagag aattgtcagg    13140
attatcaaac aagactgcta tcttcacata actatccatt tgtattccat ggctgtttac   13200
caagtgtttc tcctccattt ccaaccagcc cacgaggaga tctgcacaac caatgaaggg    13260
gtcatgtatc gcattgggga tcagtgggat aagcagcatg acctgggcca catgatgagg   13320
tgcacgtgtg tggggaacgg tcgtggagaa tgggcctgca tcccctactc ccagctccga    13380
ggtatgctgg tgtgttgacc agagagtttg tgtgaaagcc tgtagttgca aaagcagaga   13440
gggaagcatg cagtgtgtag ctatccactc acccgctgtg ctgaagaggt ctcttgattc    13500
caggagcccg ctgagaaaag ctggcgagtg agttgaatag ttctagggct ctggaaatat    13560
tctcaggatg taagcattta ggttgagcca aaaggatggc tttcccaaag agagatcaat   13620
atttgaaatc cttttagctc aaggttctgc ccgtgtttat gtctagagaa gatggtatca   13680
tttctccaag ccgggggtgg ggggggtggg gggggtggga ggggcgggaa tggatggata   13740
ttttctattt gtcaaattta aggtgatgaa tacatcacat cctcagacta atttctttt    13800
ttcaaatcag ctttttttcc cctttggact cagatgtgtg ataggaggag ctgttaatgt   13860
```

```
attaaagcaa tttcagcttc tttgattgga aaagtaacat ttaggtggaa ctcagtgggt    13920
aaacagttcc catagccagt ccataaacag tgcgccctac attgattcct ttaatggtgt    13980
ccaatggcta gagatatctg ggagtcctct ttgttactta gaacattcca gagcaggagg    14040
aaaactaata agacatgcaa aacagccctt agtttgacag atgagaaaat ggggtcccaa    14100
agatagaatg taacttattc gggatttctc attgagtgag gaacagcatt gatttacatt    14160
ctaaaacttt ctgaacatca cagatgtcat tgtatttccc agatccaatt accttctgtc    14220
ttaggcttct attgctgtgg aacaccatga gcaaaaccaa accaaaccca accaaaccaa    14280
accatcttgg ggaggaaaag gttaatttta gcttacacct ttcaggccac agtccatcac    14340
tggggagagt cagggcagga agtcaaggca ggcatctgga ggtaggaact gaagcagcag    14400 aggcccaca gaccgaggag cccagcttac aggcttgctc tccctgact tgttcaacct    14460 cctttgttat atagctcagg actacctgcc caggggtaac actacctgcc tgccatggac    14520
tgggtcctcc tccagttaac cactcatcaa atcagttcct cccagactgg cctgcaggcc    14580
agtgttgtgc agacagtttt ctcaatcgag attctctcat ctcagatctg tgtagattat    14640
gtcaagttgg taaaacccaa ccagcgcaca ctgctctcca tcccagaaag gagactacca    14700
catggtggtg tatgctatgt aaatttctct cttcgtctta gggtaacaac caaaaattta    14760
actaaaatca tcaactaaat gaggatgtta gaggaactaa ggcatgcctt tgttgagaaa    14820
ttagtttctc cacaggaaac tatatttttac catggctttt agtttaatgg actgtaatcc    14880
ctgacaatta caagtctatt agtcagaata agagggggagt aaaaattaat attattaagc    14940
tttgaaaaaa agattattct gtgccagtag aaaatgtatt ttagcaggtg ttaaatccag    15000
cagtagaact gactgccttg aaaaaatgca gtttcttttg atttcattag tcaaagctta    15060
tcactcaccc aactgttccc tggacagacc agtgcatcgt tgatgacatt acttacaatg    15120
tgaacgacac gttccacaag cgtcacgagg agggacatat gctgaactgt acctgctttg    15180
gtcagggccg gggcagatgg aagtgtgacc ccattggtaa gtggccgcct ctgcttggtt    15240
ggttttcacc gaggacgttg gctggttggt tggttggttg gttggccact tgcagataag    15300
gaaagctatt tggtatcgcc agacttcctt ctctccaaac ctgcctcatc catcagtctg    15360
cagagagcct tgcaaatgtg ttggtaacaa gggtggcttt actgcagtga gtgagtgggg    15420
ttagctttgt tggttctgag tcatgacaaa ggaagtttcg ttactgactg cagaaaagaa    15480
acatgggtat aggactcagc cagtagatgc ctgcctccgg ccaaaacact tcagcttttg    15540
cctctctgta caataagtag ataaatagat agggctgggc catcactgag cgatcaacat    15600
taaaaggagc ctattcccca aatccaaagt ttaagataat cagttcttac tcctttactg    15660
aaggaggcag actgcttact gagacagcaa attgatccca gcagtttgtt cggcctgcga    15720
ttgtaaagcc gagaggtccc gggaggcttg cttagaaagc tgttcatgct ttaaatttag    15780
ctcattaatg taaagctacc tactgaattc cgaagaagta cacaaaatga aatcattgca    15840
aagttctttt cttattttac agatggcaag ttttaaaact tttaattggt atctagtttc    15900
ctaaaattaa ttttcagatt ttggctatat gctgaaattt taatcttta attttttta    15960 aatttagcaa tgtttcccct gtaggacacc aaatatcctt cccaaaaggt acattttaat    16020
tttaacgact aattttccca taaggtaaat gacttgaata aaatattact ttaggactgg    16080
ggaaatggtt tcacacaaca tatgcacgta tctcacacac aagcacatat cacacacaca    16140
aacacataca cttataactt actttaacta tatttgtaag aactggaatt tttatattca    16200
```

```
tactttaaga atacacttca tcacactaca gtgatgtgtt tgaggctgtt ttaatctttt   16260
ctttgtgttt gttttagacc agtgccaaga ttcagagacc cggacatttt accagattgg   16320
tgactcctgg gagaagtttg tgcatggtgt ccgataccag tgttactgct acggccgtgg   16380
catcggggag tggcactgtc aacctctgca gacctaccca ggtaagtagc tctgagacag   16440
aagcagaccc atggatgcca gtctatgcta ctatttggaa tcccagtggg ggccttgctc   16500
tgtcccatcc cttttcatat tactgtctaa tagttaattg cattttgtc ttaaattgtt    16560 ttatttcacc cttcatcagg gaaaaatcac caaagactat gaaaaagtgc atgctacaat   16620
tttgcatttt acacagttga ggactccatt aggtgaaaac atttcagttc attttatctc   16680
agtcctgtgt gtgtgtgtgt gtgtatctgt gcttgtgcaa acacatgtgt ggatgtgtgt   16740
atgtatgtgc acatgcatgc gtgtgcatgt gtgtacatgt gtgagtgagt gtgtgtgcct   16800
gtgtttgtga gtgtacatgt gtgtgcacat gcgcatacat gggcatgcat gcttgcattc   16860
gtgcatgtgt atgtgtgtgt gttcaagtag agccataaag taactcagac tggaagtgaa   16920
agagttttac attctgtttc ttaaagagaa gtcacatcga cagaaggcaa gaagtacagt   16980
atgaggcata aatttgtttc ctgccatctt aagcccttct ttgtgtcaga tttcatttgt   17040
ttagtgagat gtaatgtgga acaaaatctg gagccaagaa acttggtcaa ctccacccac   17100
accgttcgaa taccttaaaa tatttattgt ggttttgttg ttgatatta ttgctaggtt     17160 ctcattgttt tgtttggttg ttgtttgttc tcccatagac acatcatgcc tagccatagg   17220
cattaattca ttttggggaa acatttaaa attcacacgt tgattatgag tgccatttca    17280
gcagactcct agatttccgt taatgattta tttatttatc tgtatgtgtg tggagagggc   17340
actgggtcac agcacatacg tgaaggtcag agtggacttt gaagttcttt cttcacacac   17400
gattctttat gtggggatca gactcaggtc tacaggcttg tgggaggcga gcaccttacc   17460
ctgagccatc ttgctggccc aaatttaaga catgaaatac cacctgtatt cagaaacaaa   17520
aagatttggg gtgggggag ataatccaca agaatacaaa atattataat aataaattaa     17580
ctccataagt attaagatta aatactaaga ttaaactaat cttcctaaga gtgtcccaaa   17640
gtgaacgatg agagcccaag gcagtgtgag tcctcgctct gactgtgctg tgagagagat   17700
actagttaac ttctcctgtg gacaaaggga gacttgctaa ccacctttaa aattgcttcc   17760
agtccttcac taacagtcag agacccagag caccgtcca ccactcatgc aatcatgttt     17820
tgtttgtttt tcaatgacag ggtttcactg tgtaactctg gctactttgt ggaccaggct   17880
ggcctcagac tcatagagat ccacctgcct cttcctccca agtgctggga ttagagttgc   17940
atgcctccca tatccagaat acgctcattg ttttatgtg ctggggacat cctcctccgc     18000
tcagccctta gacattgtca gggtaggata ggtgattgct tccgcaacta tgtagctcag   18060
agcagcctgc attttgctg gactttggtt taagagtgag ttacttgccg ggcgtggtgg     18120
cgcatgcctt taattccagc acttaggagg cagaggcagg cggatttctg agttcaaggc   18180
cagcctagtc tacaaagtga gttccaggac agccagggct ataacaaagg aaccctgtct   18240
cgaaaaacaa aacaaaacaa aacaaaacaa aacaaaacca agagtgagtt acttaacatt   18300
tttaaaaatt gaatccagtt gctttgtttt gcttttttgag tctcatctag ccctgggtgg   18360
cctcaaactt actatgtagc caatgatgac cttgaacttc tgaccatgcc tcctgtctct   18420
tgtttccaaa aggctggggt cacaggtgtg cacattacac ctggtcaact taatatagtt   18480
taaaaatctg attacaaatg agccataaat tcagaaaaca catatttagg aggattggat   18540
tttccaatga tacaagccaa gaatagaagt ttatttttgt gttcacagtc agttttttgca   18600
```

```
gggcaatttt tgaaatttat tttcttttaa gaccttttct tttaaaaata agtctattca    18660
catatatctt gctgcaagca ttgagggtag atctgctgat ggacaggaag agtcacctag    18720
cgggagtttt acctgttgac tttgttccct gtttctaaaa agggcaatgt caaaaaccca    18780
ttgaacacag aagagatttc agggcaagcg gatgagtgtt tgaccctaga tagcaggctc    18840
agtgtttatc tcaatggagg ctttgctcaa gggctcatgc ctagcctttg aggctccgat    18900
ggctgaaaga ccgtgtctga gccttgccct gtttgttctt cctactaggt tggtagagat    18960
gttcaaacta acaaaaggta gcaggaattt ggtttgtcaa taagcaacca ggaaagcaca    19020
gctctcagca aattaggtag agaaagaacc tttcgggtca aaaaaaatca tgaatgttta    19080
acttctccag ggtcactatt atcggaaatc actctttctg accttactgt caactgattt    19140
tgaaagtgta taatgtggca ccctacaagt gaagatctca cagtgggcat tgctattaga    19200
agtgtaaaag gtccagggag gtggatggtc gggatcacac aactagccag catcaaaggg    19260
gatataaaaa cacttcaatt taagtagtgt aaatgatagc tagcctttt tttaactttc      19320 ccatctttaa atcatgtgtt gtagtgtaga gtatagtgga gagctggaat ttaattgacc    19380
tagaaaacag atgaggggtt ttccttcttc cttccttcct tccttccttc cttccttcct    19440
tccttccttc cttccttcct tccttccttc ccattcctgc acagaaatgc tttaaatccc    19500
ctttgccatt cagggcagtc acttgaaggt ggaccctgtc atcatcttag ggcctggag     19560 agctgagagc tcagaggttg tagtccctac gcagtttaat tcccatccct cccattagac    19620
agcacaattg ctgaaccttc agctcagggg acccatgcct ctgtctcctg ccggcacccg    19680
tactctctca tatgtaggca ttttaaaaat taaaattaaa aataatggga tttcagatct    19740
gcgctgaaag gctgagaaag gaatgaagt tctgagtcac ttgggttaac cattgcgagc     19800
atctttccct ccctcccttt cccgcgtctt ctgtcaccct tgtgaacaca gggtttgatg    19860
actggacaga cagtaaatgt catttatatt ctcttaataa tagatttatc aaggagattt    19920
agttatcaca agttttccag cctcaaattc agtaaataag atgcatgaga catgtctatc    19980
tacctgagag attatactag gattttctca aaacagcaat atttaacagc cttatgcaga    20040
ttgtcactaa taacataagg tctgttttta ctgattcata tgaaacctct ttaaatagtg    20100
tttgaaagaa atgttttaa tgtatttgta tttgtgaggc tcttcatcta tggaaggagc     20160
tattccagag ggctgtgcaa tggacttgag ttgattaatg ggacaaccaa cctgtgtggc    20220
gcgtgggtcc tatgcccctt aggatgcaaa gatgagaatt ttgacatttc agcttgtagc    20280
attaagtgaa atcaagactc aatgaatatg tgttagtctt caacaagctg agttattccc    20340
aatgaagaag ttgagttcaa atcttttga ggtcacataa atatgtaagt tacatattta      20400
ttctgctaaa gaagattttg cttttaaaga atttagaagc ttaagaccat aattaaatct    20460
gaaagtcaat atattttttc caagagcact cagaaatcgc aggtagtgta gagaactcct    20520
ttatcagcat gcagaatttt cttctgtctc acagagcatc agtgagaact ttgtgtctta    20580 ggttttgta aggactttgt acaaatggat tttgactgac aaagaattag agagaagata      20640
aatttccatt ctgtaaacag agttttgat aaaatttcat tattatccta aatggaatct      20700
actatattaa aaaattgatt ccttctctt attttgcctt ttttttcccc ccaaggaaaa      20760
aacctgaatc tatcttaaat tttgttaata acagtcatat caagatctga aaatactgaa    20820
ttttaaatat atgctttcaa atgtcatttc aattgatgat tgcttaaaaa gattttttt      20880 ttgaacaatt cgctcacagt ggctttaaga gtgtacttaa gtaaatgtaa aacgaacaaa    20940
```

```
caaacaaaaa cactaaagga gagaaggctt agactgatgg ggaaataaac cttgggcttt    21000
aattattacc tctgtctgtt tgtccggatt cagccccatt tagaaatgtt tgttttgtgt    21060
cacgccgtaa ggccttggga tcattgcttc tgagcagagt cctctgtccc gaaagcctcc    21120
atgattcgga atttgtctta caagagcctt catgtaatta gcacatgagg tctgtattct    21180
gagctacatt cttcgtgtta aggaaatttc acagttgtcc cacgtcttac tttgaaagcc    21240
agagaagaag gcaagctatg agacactgga gtggtttctc tcgtatttat tagaaaaaga    21300
attctaattg cttttcttat gggaaaggca atgattacca ggtcaaatca gactgtgctt    21360
tttcttcagc taatgtcaca atgtagaagg tttaactaga ctctttgccc acatttcccg    21420
agaagcgaaa agtctttaag gatggacatc catgttttgt aaaactttaa gaccacacaa    21480
gctaaagaga tggcatgttt tcattttcag gcacaactgg acctgtccaa gtaattatca    21540
cggagacccc cagccagccc aattcccacc ccatccagtg gaatgccccg gagccttcac    21600
acatcaccaa gtacattctc agatggagac ctgtgagtaa tagctccgca gccttggact    21660
ctgaccctg acctgatggg actaggatgt gttgccctct gggtttgtta ctgcttttga    21720
gtcgacagat ctgatgccat gtcgaacagt gctgacattt attttcttag tgtctagcca    21780
atatgtagtt agtcgaatca acatgtagat tcagggtttt ttgattgttt ttggtttttt    21840
tgttttgata tgtagaagaa attaaattag gcctttggct taggaaaatc ttagaagcca    21900
taatgctaac aactattctc atccaatgtg gaaagaaaat ttgaaatttt ggtatccatt    21960
tgcaatgtca ttaaaattaa aatcacattt tcaagttatt tccagagttt aaaaccagct    22020
aaatgaacat cgttcttttg actcaactca gttgtcctgt agtcctcttg agttgtgtag    22080
acagaaggga atgaggtatt gagagaagga ggagcgggga agggtttata tttggtttct    22140
aaaaggaccc ccaaacccta gcgttttcta accatccaga tgccaaaacc atagcaagga    22200
gtctctcata ttagtctatt aaccctttgat gtctcgtccc ttctcagact tgccctcttc    22260
catctccaaa gtttatgaca gaatttaaaa ccactacttc agaaaggaga aatgcacttt    22320
taaaaatcaa atctactcaa ttgaactatt attaatccta gactacaaca acctgtctga    22380
cttaggacgt caactcactc ggtcgaattt aaactcttgg ggaattccat tctgctgagc    22440
tcactctttt ccttcagccg tcccatgttg tcactacaaa tgaggcattt ataaataggt    22500
ttcgaaatac acattgagtt gaggcgtctt cacatttgat taaactctca gcaaacattt    22560
tagcttcggt tttgttgtgt ttcgttttga gatgatgacc ccattaggcc aagactgact    22620
tcatattctt acgtagctca cgttgatctc cctgctgagt gcttgattat aggttcagct    22680
cccccttggt atgtgatgct agggactgaa ctcaggactt tggccacctt taggcaagtg    22740
ctctgccaac cgagccgcat ccatggctct gaaaatttaa aaagaatttc tgttgtttcg    22800
tttttttaaa tgtaggccat ctgagagttt atattctcat attttcttct gatggccaat    22860
tgctaatttt taagctaaca aaatggctaa cttcaatttc tttcagcata tttgagctaa    22920
aactaaagat taaagagaac ttgcttggat cacttttatt tatctccaaa ataaaaaacc    22980
gggcattaga acatttgaag tatgtacaaa cttgattaga taacattaaa aaaaaaaatc    23040
actgggcatt aaccatgtat ttgatattta aaccgcttta gaatatttac acttaaaagg    23100
atttcttgtt tgaagtctgg gtgtttcttt tccacacaat ctattgcaat gagttctgtg    23160
gtccatgaca tattaatgaa gctggacagg atataaaaat gtaaactgga gggggaagat    23220
taaacaaacc gaaccctatt cttctgcagt ctttcccaga gttggctaac gactcttgat    23280
gggtcgttca tttccaagga tgagtcacgc caccagacac gttgaacctt gtttgtgatg    23340
```

```
gccccaggat ctgagtccag gcaatgttat tatactttc agtgtctcgc gaggcaagaa   23400
gcttgaaatg tatcccacca agttgaaaga tagagcgtga ggccttttct cacttcagaa   23460
gagagacgtg cctctgttta ccacaaaagt ctagaggctg aattgatggc gctggtctta   23520
aatgattcga ggcctcaagt gtgtaacttt gaaaacctca tttctccacc tgtaaagtgc   23580
agtgaggcac ttcacttccg gcaggaaggt gaagatcagg gggagaaaca aacaagcaaa   23640
acagccctga gtgcttggtc aaccacttgg acgaataatt aattaacatc gacaaactgt   23700
agaggccctg ttcccagtca ggttttccac catctttctt ccaaaacaga gcctcgagaa   23760
tcctatctat cctccattct tctttgaaga tgactaacca ccacgttttt tttccttta   23820 catattcaga aaacctctac gggtcgctgg aaggaagcta ccattcctgg ccaccttaac   23880
tcctatacca tcaaaggcct gaccccaggt gtgatctatg agggacagct catcagcatc   23940
cagcagtatg ccacagaga agtgacacgc ttcgacttca ccaccagcgc cagcacccct   24000
gtgaccagta cgtagccagc atctgttggg gctgtgcctg cactgctcag acgtgggttc   24060
cccagagaag gttctgtcct tagctgcttc tttgctcgga tggtgaacat cctctgaaca   24120
cagagagcgt gggtattcca gataatcaaa ggctcttgtc ccctgctccc attcctctag   24180
gcaacacggt gaccggagag actgcgccct actctcctgt tgtggccact tctgaatctg   24240
taactgaaat cacagccagc agctttgtgg tctcatgggt ctcagcctcc gacaccgtgt   24300
caggcttccg ggtggagtat gagctgagcg aggagggaga tgaaccacag taccttggta   24360
agtagaatgt ctggcttcct cggctcgtgt ttctagatac ttacttggct cgcaggagtt   24420
ttgattccgg aacgcctcca cagttcaaac ggaagacggt cccttcatc agagccagga   24480 gagaggtgac tcctctctgg ccaggctggg attccctggg cacctttgtg gcctctggtg   24540
ctgtgtattt ctcatagcca tggaaggggg accaggatga ggcctatggc tgacaatgtt   24600
atcctttagg ggtgcggagt taccttcttg tttactttta aaatagccca gtgatgaggg   24660
ggtctttaaa aatatttgct ggtgccagtg aggcggctca gtgagtaaag gccctcaccc   24720
ctaagcctta taacccaagt tcaccctcca gtctgacctc catcacgtgt gtacgccccc   24780
cccccaccaa tgtaataatg agaagatact gaacatacat gtgaatagga cccagatcat   24840
aaaaatgaat ctccttccaa cccctgccct gtcatccttc cttccaccat ggctactact   24900
ctgatatcta atgacagctc tgttttaaaa acaaaaaaa cagagagatg ttattaaaaa   24960
ttatacatct tcgggggtgg gggaaagtgg aaaatgaaag aacttactta cattggaaat   25020
tgcaggctat tcactagaac atttctcgtg ggctttcacc ctctgagtat agcgctctta   25080
gaagccgtgg aagattggtt tgctcaggcc actaacctttt gccctgtatt ttaaagatct   25140
cccaagcacg gccacttccg tgaacattcc tgacctgctc ccgggcagaa agtacattgt   25200
caatgtctat cagatatctg aggagggaaa acagagcttg atcctgtcta cctcacagac   25260
tacaggtatg tgggcaccca gccatgataa aagcaacttt aggtatgggg tatggtggta   25320
tggtgggtga tacgatacat acatacatca taatcacaca tacttacact catacataca   25380
gctttgggat gctgagggta gagatccagg ctagcctgca gtaagaacca ctgttttaaa   25440
aaacaaattt ttgaagactc ttttttgtttt tctgtaacgc gtgggcttgt agcaacactg   25500
actgatttcc tttcttcttc tttcagcacc tgacgctcct ccagaccta ccgtggacca   25560 ggttgatgat acttccattg ttgttcggtg gagtagaccc caggcaccta tcacaggtca   25620
tccttggctt ctgtgtttct tttgatgtat agatgtggaa ggggaaaatt ctgatcacac   25680
```

```
tggtaccacc ttaaatcttc cattttaagt ggttggaggt gtgtgtgcat gtgtgtgcat    25740
gtgtgagtgc gtgcgtgggt gtgtccactt caaatcttcc agggattctt cgtttttgat    25800
tcgttttcct tcaagtctgt tcacacgccc ccattcctaa tacctgcatc tgcaacctat    25860
aaggccagcc ccgctgttca ctgcagtggg cagttcccgg gctgtacagg tgggtgattc    25920
ctgcagagct gctgctcact gctgaagagg gagctgagtc gccgctctag cttcaccagt    25980
gaagttccca aaggtgcaaa cactgctcag gctgattcca ttcctctgct ccagaaggg     26040 aaagccgcta gtactatgaa tgtctcacgt catggcatca cttactgaca ttcattaagg    26100
atctctgggt tcaaggatgc tatttgatta ttaaaagctt cctatcaact tattcttatt    26160
tctgtgcccg tcaggcatta tcagaggaag tggtaacatt gaaagacccg gaaagaatct    26220
tgctgattct tagccatgag aaaggagagt tataatttgt ctagcctccg cttctgaaga    26280
ccatgtgtct aaacgctgtt ctcctaaacc tgcagggtat agaattgtct attcaccttc    26340
agtagaaggc agtagcacag agctcaacct ccctgaaacg gccaactccg tcaccctcag    26400
cgacctgcag cccggtgttc agtacaacat cactatctat gctgtggagg agaaccagga    26460
gagcacaccc gttttcatcc aacaagagac cactggcacc ccaagatctg gtaacttaaa    26520
aacagcccat tccctgatgt ctgatctctt aggactagac cagagagccg ctctaacctt    26580
ccaggggaag ataaagccca cgtggattag actcattctt tagccttcag ggaggactga    26640
ggtgcaggtc acgtgggtga cagatccctg agagggagct gttttttgtct ttgccagctc    26700 tttctatgtc ccccatcacc caaatcaatg gctctcaccc ttcctaatgc tgtggtgacc    26760
cccaactata aaattagtgt catgctgctc tatagccaca ctgtcgtgaa tcataatgta    26820
agtatctgtg tagaattctg atggtcttag gtgacccctg tgaaagggtc atctgccacc    26880 aaagggtct caactcacag gttgagaact accgagttaa atgctaaaat gtcagcactt    26940
ggaaggaatt tatttatcca aggcaactat tgggttttct ggttaaaaac tcacagcatc    27000 tcctcttct tttcctggga ggcttaagaa ttactgttct cttaactacc attttcttaa     27060
gaaaatctgt tctcttaact accataaaat gagtcagtta acaaacaca ccagctgtct      27120 tgtaaagtga aaacatttat ttttgtatat tattttaact tggttttatg ttataacatg    27180
cctatctata gatactaaat agagattcca atatcagttt gactaaccat gagtatacac    27240
acacacacac acacacacac acacacacac acacacacac atttatttt tgattaagag      27300 gcaaagccca gtattggcct agaatgagtg ggtctaagag atggcggaat tgttcaggga    27360
gctaacttct agcatcaacc ttcagtggga attgtgactg actgactcat cgctcttgtc    27420
tgctagataa cgtcccccct ccgacggacc tacagtttgt ggaactgact gatgtgaaag    27480
tcaccatcat gtggacccct cctgatagtg tggtgtctgg ataccgtgtg gaggtcctgc    27540
ctgtcagcct gcccggggaa catgggcaga ggctgcctgt caacagaaat acctttgctg    27600
aaatcactgg gctgtcccct ggggtcacgt acctcttcaa agtctttgct gtgcaccagg    27660
gcagggaaag caatcctctg acggcacaac agaccaccag tacgttccag gcctgcctgc    27720
ctgtcttgtg gccccctcct tccagctctg aaccctcagc tctacctggg ataactccat    27780
agcatgctgc tcactcccag gttcacagct cagcagttag ggaacatcga gttgaaagga    27840
atgttgaagg tggaatgaaa ctagcgttct gagaatgctg actccaacat acatgcttcc    27900
aacacgcatg tcatgtccaa catgctcact gctggagtta gagttttctt tgctaatgga    27960
gatgcaattt cagtgctttt gtctctctgt ttccccctccc ttcttccctc ctccttccct    28020
cttttttctt ccttccctcc ctcccttcct ccctccccttc ccttcccta accttccttt    28080
```

```
ctttaagctg tgaatcaaaa aatgctctac cactatacaa catccccagc ccttaagtgc    28140 attttaaaa aatatatggc cgggcgtggt ggtgcacgcc tttaatccca gcactcggga    28200
ggcagaggca ggcggatttc tgagttggag gccagcctgg tctacaaagt gagttccagg    28260
acagccaggg ctacacagag aaaccctgtc tcgaaaaacc aaagggaaaa aaaaatatat    28320
gtagttagat atagtagaat tcatttgagg ctagcagttg ccaggcagca gggtgtgtaa    28380
atgtatgtct gggatgtgtg aggccctggg ttctctctct agcaccacac aacgagttga    28440
taccttaagt aattcatcct aaacatttag tggccctggg cagcgaggta tcatctattt    28500
agctctttat cagcagaacc tggctggctc ttaagtcttt agctgacatg tgcaaaggga    28560
aatgctactt ctgttggatg tgggaagaga cctaaggtct tccctgagga agtgacagtg    28620
gtttggattc caaagctcat gtatgttctc aattacactc gaccacctct ggaaggttct    28680
ttctatcaaa gatgttctaa cttcctatgg gaggcccagt tatcatcctt agaaagaaga    28740
aaaatggtga tctatgtgat tctttctgat actccatggg actggggttc tgcccatctg    28800
ttttagttat tgtaattaga tccatgtgag gcagctttta tttctccagc agaggttagg    28860
tcagccaatg aacatacacg ttagcatatt gcctgcagga cccatggagc ttttcttgcc    28920
ctaactctgt tggacttagc cccctccctt aacctttctg gcccaaaaca aattgtgggg    28980
tttgcaaaat gtttgttttg ctttagaaaa aaaaagtaa tactgttatt ataatgtgac    29040
tataatttcc aagggtggtg ggtaaatctt tactgggaaa agtagccttt ccaaaggatg    29100
atagacaagt gaaaagggtc aacgaatttt cataactgat aaagtttcgg caaaattcta    29160
cactatcctg agtctcccag agccccacgg tatccagggc tgtggctctg actttagttc    29220
caaccttgag taagggagct tgggatgctt aatcaagcgg gaggatttcc gcatggctgt    29280
tactgatcta aacgtttctt gacacatttc atcttatttt ttccccagaa ctcgacgctc    29340
ccactaacct ccagtttgtc aatgaaactg acagaacagt tctggtaacg tggactccac    29400
ctcgagcccg tatagcaggc taccgactga ccgcgggcct gacccgagga ggccagccca    29460
agcagtacaa tgtgggaccc ttggcctcca agtatcccct gagaaatctg cagcctgggt    29520
ctgagtacac cgtgaccttg gtggctgtga agggaaccca gcagagtccc aaagccaccg    29580
gagtctttac tacccgtaag ctaaaattca aatgccttgc tttcgtgaag ctagagttct    29640
caattaactc ttggcttttt ctgtcctttt gcttttcaaa agtgaaccta aaaagccctg    29700
gtgcaccatt taaagccgcc ccattgaagg tgtgccccat ggacaggctg gtgttctctg    29760
agtatttctt gctggtctgc tgtaacatac acagctttgc cagcgtgggc agcacagttc    29820
gtggcctttg cccgggctga taagtgcttg atgaagataa cagtgtgtta atttgcaggt    29880
atttccaggt tctttctatc tttctgggct aacactatga gtcaggagga cttgggaggt    29940
agctcagtgg ataaaacaag tgcggctaac acatgagggc cagagttcgg atccctggca    30000
tggacataaa aggccaggtg ctttggtgga taattgtaat cctagcactg agagacagag    30060
acaagaggat ctggaggctc acagccagtg ttgctgatca gtagctccag gttctccaaa    30120
aatccaccgc cgaggctggt gtggcggcgt acgcttttat tcattcatcc cagcaagtgg    30180
gaggcaaaag caggcggatc tctgagtttg agaccagcct ggtctacata gcgagttcca    30240
gaacagtcag gactatatag aaagaccta tctcaaacaa acaaacaaac aaacaaaaat    30300
acacaaacaa gaaacaaaaa agaaagaaag aaggaaaagg aaatatggtg gagactggtt    30360
aaggaagtca cacgaatcca tgggcgcata gactgaatac aaagtagaaa aggctgagta    30420
```

```
aatactagta gacagaatct aacccatatg catagctcca tcacatcact ctctagacat   30480
caactgagag tcatatatgt ttaaaaaaaa tccacccatg gactgaacag acatcagcaa   30540
atggaaagag aggttaagta tgtgacttcc ttgagagcct ggaccgcccg ccgaaggcta   30600
ccgtccttca cagcagagcc tggtttcctc ttccttaact ttctcttcca catcttccac   30660
acagaggaaa aagacaaggg ttttgggtat gactagcctt tgactcaata ttttagagga   30720
aatggcctta actctcttat ttatccacat tcccataaac tcctgtcttc acaagctgct   30780
ttcctcctac gtacactcca tttacatgac agagagctct gagacttatt tcttgctgag   30840
tacttgttat ttttttgact tgcgggtttg aattatagga ggacctaaca ataagcatgc   30900
tttgggcatt tatggccgtc tacctctggt tcccagcttt ccaggagctt tcagcaagtc   30960
ttgtttgcat taaaaagtaa tctaagccct gcatggtagc acatacctgc ctttagtgct   31020
atcacttggt aggtagactc aggtggatct ctctgagttc aaggccactc tggtcattag   31080
tgaggtctag aacagctagg gctaagcaaa gaggccctgt ctcaaaaaca aacaaataaa   31140
taaataagca acaatttaga aaaactgtca actgttcccc acaggaatct attgtttacc   31200
acaaacttct ttgcatgcac atttggtaat gtgaggttga acaccgaagg cctgtttttt   31260
cctacgaaac tgttcaccag caaatgaagt ctgcttccta gtttgcagac ttcttttaa    31320 atgtttggta tttgacattg cccagttttg agaaagtcta agatccactc ttacagaact   31380
agtatccttg ttttttcttgc aaaacccatt tcttggagct gtcccttaaa ttaatgagca   31440
tggagtttct gtgcacacag cctcttactt ggcctcgtac ccgaggcttc tgggtgtaac   31500
agtaaaactg tatttgctga ccattaatta acataccgaa ttgcgtggag tatcctttcc   31560
aacacggtag ggtaggtgac tgaaagacaa atgagcagct caccgtggct cagatttaaa   31620
taaaccagtg gaaccaagga gttaagcaaa tccatttgga cctcagatag tcttggtata   31680
aacatgagca gggcctagga actttggttt ctgatgcttt accaaaatta gttttggaa    31740 acaaccagtt ttctgacttt tatatctcat gctaaattct taagagcaac tgtgagaaaa   31800 gtgggggggaa taagttattt atagaggagg aatccagcct ccttctgttt ggggggcgtat  31860 gtcatttctc aacagccagg ttgttcctta cctaacaagc cctgccagag cccataattc   31920
atacttacag gcacatcctt tgtttgacaa cactttgtgg gtttgtggct tggtgatttt   31980
cctgtaatgg tcttgtctag gcaagagaat attgtctcaa acatgggca agatttagct     32040 gcttggctga cgcaatagaa aatgcctagg tgtgaaaatg gacagttctg aattgcagga   32100
gcagtatttg gtcctaattg ctgaacattc tctccaggct gttaaaaagt tagaattttc   32160
agccgggcat tggtggcgca cgcctttaat cccagcactc gggaggcaga ggcaggcgga   32220
tttctgagtt cgaggccagc ctggtctata gagtgagttc caggacagcc aggggctaca   32280
cagagaaact ctgtctcgaa aaacaaaaa caaacaaaa caaaaaaagt tagaattttc     32340
agtagaagaa atgatggtgg tgtcaggata ctagaatacc aagcatacta gttataattt   32400
ctatgtctag tggtcaggta ttaagtgtct gtagcatttt tgtttgaatg atcaaccaca   32460
tgttggagga atggatcttt gatgttgatg ataagatccc caaatcatga aaagatacag   32520
atcataaggc ccaagaaatt aaaaggagct tccattgagg tgagcgagcc cctcttcta    32580 ctacctgtga gtgacaggtc tctgccagaa attcaagccc cagcccaaac aaagctggac   32640
ctgcagaatc accacccctcg gccccttcc cgggtctcac caggtcctgg gtgccttgaa   32700
gcagttcaac ttcttagccg atgaatgcac cttagctaca ttctctgtgt acttactggt   32760
tagaccaaag ctctgtttac aatgctcgtt aatctgcagt cctggcctac acctatgcgc   32820
```

```
ctaacgttga acctcatgtt ggttaatttg cagtgcagcc tctgcgctcc attccacctt   32880
acaacaccga ggtgacagag accacaattg tgatcacctg accccccgct ccaaggattg   32940
gcttcaaggt gagtttcaga tgcacctctc atgatccagc ccaggggtgt cttttccattc  33000
ccactacact ttacagacct gggttttaa agttctatgc tcatactcca ggaccttctg    33060
agagcaaagc ctgcattgag gcttctctgt gttgcaaggg aagaaaacca tgagccatgg   33120
aactgtagtg ttgttctgtt ttctgtcctt ctccccaggg aactccattt aaaataaaa    33180
gtatagccaa acctcatttg atgtgttgct ctaaatgggt gtcgagaagc ttatgaaaac   33240
caatttggga agaccaatta aactgagagt cacttaaaaa tcacatttt atccaatcag    33300
tttcatctca acttgttcaa agccctgtgg gtgaatttct taatagaagt taaaattgag   33360
gtcttcgctt tagatatcca gagtcatgtt ctttaaagca gtgataccag ggacgtgatg   33420
gatacaaatg aatatgtttt ttaaaaagaa tcccatcctt aggcatccag aggataaaaa   33480
aaaaagagac acttattatg tctggaatca aagcctgatt gtttaaaaga gagaaaaaag   33540
aaatagaccg agggtcactc tgcttttttag tatgcaaata gccatcttga tgagtgggct  33600
gctcaggtac agaggggacc tttatgaaga ccgccacggc acctttttag ttttcccttaa 33660
taatgtcgtt cagagtttta gaagccacag agaatctgaa gggtttctct ggagctgagt   33720
actgtttgat aatgtcacct aagcttttgt agttaggaac acacggacgt cttcgtggga   33780
atgtgttttt catttccgtg tgtcaaagtg gctgcagata acttattaaa gagagagcct   33840
agagcatttc ttccctgtgt actgctggta tgcaccagaa gggtttgtgt caaacagtta   33900
tactgacatt tctctagaac ctttctatta taaaggaccc tagtaccaaa ggaagatacc   33960
tccagctaat tgcaagatca ctaaagtgag ccctcaatgt gttatccacc cagtaaatgc   34020
agtgtggagt tgtaacggac ttcccctgt gtaaatctac aacctctcgg gatctctgga   34080
atattcatcc ttcatgctga ttttgctgtc ttccttccag ctgggtgtac gaccgagcca   34140
gggaggtgag gcaccccgag aagtgacttc agactctggg agcattgttg tgtctggctt   34200
gactccaggc gtggaataca cttacaccat ccaagtcctg cgagatggcc aggagagaga   34260
tgcaccgatt gtcaacagag tagtgacacg tgaggagagc cttccttctt cttttaactt   34320
gtaaactatt ttaaaagatt gccaaagcca ggtgtggtag ggtgtgcctt taatcctagt   34380
gcttgggaaa gttaagaatg atgatgggag ttcaagacca gccaaaaact ggaggcggag   34440
ctgggtttta taatacacac ctctagtccc agtacttagg aagcagagag aggcagatat   34500
tggagaattt atggctagcc tggtctacat agtaagttct aggccaacca acagtgagag   34560
cctgtccccc caaaaagaa acatattcct ctaattattt gaatgttagc gtcccagctt    34620
tcttttgaga cagaacaagg gaagaacctc tctcttattt atatcagcag agtcttcaga   34680
actggatgta gtttagctgg tgtcatgcag gccacagaat tagaagtgtt ccttccatgt   34740
caaaagtctt ccaaactggc aagatgaaac aatttcagta gtgaattaca atagcgttaa   34800
tcctagagac cacctatcgg ggttactgtc gcctgtattt ttatagaata ctttattttc   34860
ccagtcctag agggaaggga taagaaaagg caaaaaagga gggaggtgcg aggaaagaag   34920
ggtggagaga gggcgtagag gaaacatttc acaggccacg tgttctgtgt tcagtttaac   34980
ttttaagttt tcttttctgt tgtgtagcgc tgtctccacc gaccaacttg catctggagg   35040
caaaccctga cactggagtg cttactgtct cctgggagag gagcactacc ccaggtaaca   35100
aaggggagca ccaccctagg gaagcgtggg gcggatctga gagccgcgta cacataaggc   35160
```

```
tttcccaaga cagatttgga ttccattcag agaaagagag aaagcaagtg ctctgctctc   35220
catgagtgac agaggagaat gagagagttc atgaactacg tgtaaacacg gctgcatctt   35280
ttcttaactc gcaggaaaga gaacaatcaa atgctaggct gtggggcgg gggagactaa    35340 cgtttatact acagggaatt ttgagaggat tagatggaaa gaagattttg ttcagctcgt    35400
taaaaatgcc caaactgggg ctggagggat ggctcagcag ttcagagccc cagctgcctt    35460
tttcagagaa ccctggttca attcccagca cccacatggc agctcacaac tgtctgtaac    35520 tccagttttcc aggggatctg aaaccctcac acatgtaggc acaacacgca tgcacataat   35580
aaataaacaa acaagcaaat aacaaataaa taacaagtaa ataaatgaca aataaataaa    35640
taaatttaaa gcccaatttt aaaggctgaa atcatagtct atagtccata aatcttaagt    35700
tgactgttta ctgaagtttg acagatcgct tggtatctgg gtggggctgg cttcagggtt    35760
cccattgatt ccaaactctg tagctgctca gccaattgca taaaatggtg ttgtgcttgc    35820
gtataaccta tacattgctt gcatacttca actatctgta ggttacttgt agcctaatag    35880
attgcaaatg ctgtggaagt cattgtccca ctggattgtt ttggggacag taacaagaaa    35940
gagtgcatgc atagcataga tccaaattat cttcaaccag tattttcttt taatccatgt    36000
tggttcagta tgcacatctg taacctatga atatgtaatg aattgaacca taagatgtat    36060
gagagacagg gatgggcaga ggctcacatg gggaagaaca tttgatgtgc atgcagaagg    36120
acatagttca tccccagcca ctaggcaaaa agctgggcgt ggctacacga gcagctatga    36180
ttcccctggg agacccgctg ccacaccttg ctacttgaga acatggtcaa tgggagccaa    36240
ctagttggag caatatttt agttcattat ttgattgttg ctaattttac tcattgatca    36300
tttttttttt tgagacaggg tttctctgta tagccctggc tgtcctggaa ctcactctat    36360
agaccaggct ggcctcaaac tcagaaatcc accttcctct gcctcccaag tgctgggatt    36420
aaaggcgtga gccaccatcg cccggtgata atggttttct aaaagtaacg tcacccccaac   36480 actaaggctg aggcaggagg attagcctgg tatatacagc aagtcttaat gctagcctgg    36540
agtcatagtg tgggctatgt cttgacaaaa ctatataaac tatatctgca tctatctcta    36600
tatattatat acatacacat ataataatatc atcttaaagt accttttgtat gatggatgca   36660 tgcctacatg cattttcatg tgtctaagtt caggtggtac agtgtgtgta tggaggtcag    36720
aggataacct tcagtatacg tgactgcctt ccatcttctt taagacagtg agaccaatag    36780
cttctgggaa ctctcctgtc ttcacttccc aatgctctct agcaacattg gggatttcag    36840
acacgctctc gtgtctggct ttatgtggat tctggagata ggaactcagt caggtcctca    36900
tgagtacgtg gccaacagct tatccaccga gccaaatctt tagtctataa tttgtagcta    36960
taatctctta cactgttctt acccttgctc gggcgtaggt gtcaagcagt tatctataaa    37020
tgtgtgtgat tatagtcaca caaaataaaa ctagttttaaa atactccttt taatctcctt    37080
ttgaaataga cagactgagt gatgtttcct tctctgtggc aatgtattgt ataatgtgac    37140
agctacagtg tttccagata agtttctctg ggtttgaaac ttgaagctga caagttcttg    37200
cttctgggca gctggatcat caatctttgg tttcagtggc ctgcccattc aatggtcagg    37260
cgtaaagcaa atgaccgaaa tgttattgac ttcccatccc actgggtttc ctagcacata    37320
acacgttaat gttcaccttc tccccactga caggatatac cctcattccc tgttctcagt    37380
gggtcagtct tgttctgtct tcttccagcc tggccctgca gagctctggc cactactaga    37440
tttattgata tctcctttcc tttaatgcct tcactgccca attttcatga ttctgaagtc    37500
ttctatgatt aatatttgtt ttcgagaatg agcatctaca cttctgtgtt ctgtgccctc    37560
```

```
cagcccctac ccccccccccc ccccgttccc atagttcaaa cttttacact cttcggagaa   37620
tgtttaagtg gaaagcaacc tcagagcatt caaaaaaaaa aatgtagatt tcctagctct   37680
cccacaggtc gcccattaag gaaaaacagg ataaaatagt aaaaagaggc tggaatttgt   37740
agacaggaaa ctctcaggtc ttctctaaga tttccttatc tttgttaaag gtcccatgat   37800
tttactttgt agttaacaca tttatatggg ttgtaagatc gcccaatgga tgcaatgtag   37860
aatgatcgag ttagcatttc catctaaaac attcatgtct aagtgctgga cactctcaga   37920
ctctagttat tatgaaatta tcataagttg ctgtggacta gtcacccggc agagtaattc   37980
ctactttctg actgttggta cattacagcc ctgccccttg gtcccacctt ttcctctcta   38040
ggtccatcat tggtgtacag tttaatatac cctgagtcac attggttctg tatggtaact   38100
tcctctctgc atttactcca gatatcactg gctacagaat aactactacc cccacgaacg   38160
ggcagcaggg gacctctctg gaagaagtgg tccatgctga tcagagttcc tgcacttttg   38220
agaacctgaa tcctggcctg gagtacaacg tcagtgttta cactgtcaaa gatgacaagg   38280
aaagtgcccc tatctctgat accgttgtcc caggtaatag aaaaataagc tgttatcctt   38340
agagtggcag ttttgagtag cgatgggggat aagcatctta atccgagata gctgagtgtg   38400
tcagatacag ttgggattta atgccaacct cccagggcgc tctccaaaac cacaaagcca   38460
aaaagcaact gtttggatga aggctttcct gtttcctctg cttcactatc tgtgcttccc   38520
tgggatgctg tttgttgcca tgggtacctg atgagtgcgg ccacggcatt aactctgtac   38580
tgtttgctca cacggaaaga ttactaaaca gtgtcgcgtg tctgtaccca gtgctgacag   38640
gctaaaagta atgtggtaaa tgcatccctt tggggctttt gtgcccgggt tttacagtcc   38700
atctccacct ccaactgtta tctagaaaac agcctttgtc tccatatgtg agcactgaaa   38760
cacacttggt tgacaatcca aatctttatc ttgcagcttc aaatcctttt taaaattgca   38820
agtggggtga aaaccacag aaaggaaaga agtaaaggcc aggcccccca tggcttgctt   38880
tcttctgaat tgaaagacag cgtcacaaag gcctgtctag ggataggttc attgtttgtc   38940
cccagtcttc tgtagattga aagccctggt cagactctct tacccctctgc agtattttgc   39000 tatgcattta tgaatactaa ttaaattaca tgaattaaaa tgttggcagt ggagtgggct   39060
cagggctctg tgctggctgg ccttggcctg actgtgcatt tgagtggcac attcacaaca   39120
tagattaata ccatggtcat gatgccatca tggcttttga acatgaaaaa taagtcaatt   39180
agccagccaa ttttttttta aaaaacccttt ggaagatttt attttcttac taaaggtttt   39240
gtgttctccc cactcccaac cccccacccc gccaacattg ctagtgtctt ttatagatca   39300
gttcaggctc tgagaatgat tttgacattg taaatgggtt tatgattaat ttttttttaac   39360 acttgagaag ttaaaactgt accattcagg gacattttct aaatgggagg aagccctga   39420 aagaatgtgg taacctgcat tagtctccca ggggagcaaa ttactcatga tgcttgggac   39480
gtcttttcag ataatttggg atacattgca tataccatca ttgcttgagc attccgtcaa   39540
tttcactacc ggtcacctga tgtacactgc tttatttttt cctttgtttt ttgcctctac   39600
ttttcttttg cctcctcttt gcttcgtaac tcaatagagg tgcccagct cactgaccta   39660 agctttgttt atataactga ttcaagcatc ggcctgaggt ggaccccgct aaactcttcc   39720
accattatcg ggtaccgaat cacagtagtt gcggcaggag aagggatccc tatttttgaa   39780
gattttgtgg actcctcagt aggatactac acagttacag ggctggagcc tggcattgac   39840
tatgacatca gcgttatcac tctcattaat ggcggagaga gtgcccctac tacactgaca   39900
```

```
cagcaaacgg gtgaatcttg aagtcttctg tgtttgagac atggatggtg ttgcatgctg   39960
ctcagtcgct gtggttaaat ctggatgttt ccaagccagt gattggctac ggagatgaag   40020
acggggcccg ctcagagata aggatacat tagtctggtt gcatgaaagt atgcgtaaat    40080
agtctcaagc actttcagtc aaagcacaaa cagatgtgaa ggggaagagc tctagatctc   40140
tgatttatga aatgcaaagg agattacatt tgcagatctt gagggtgttt gttttttttt   40200
aaagtatgac tatcaaactg aacaatgagc actcatttac actaagacag gcctccaaag   40260
tgtgccactg cgtgcttcct cttaccttga taagctcctt ttgtagctaa taaaacacct   40320
accaaaaatg agtgtggaac agaaggggag atctcagggt aggatgacga cgagccgtag   40380
ggctttctgg atagtgctgc tctacagggt aaagaaactc ctcttaacc acagtctaga    40440 gacgagcatg caacatctta aaggttctct gccctgcatg gtaagaaaca ttgctgagaa   40500
ccactgtgca tgaatccctc acttgtaagt agagttcact gaatggaatt atggcaatgc   40560
agtagtgtgt agatatctca ctccggggaa actgaggacc ccttgtcttt tttgtcttcg   40620
tgcatgtgtt tcttcggaaa gtactgctat gtgtctttgc tgtgtggcaa cttaagcctc   40680
ttcagcctgg gagaaacatc ttccgtggta tcgatgtact aaaacggcaa tagcagccac   40740 caaaaaaaa gcctacctat ttgaaaagta gactaaaatt cttttaaaat gcattgatca    40800
tggcagaaag gttaagggg cctaacagtg ttctctatag tgttttgttt attttttaa     40860 cagtagcgtg tcatgattta gattagatta gattagactg tttgcatggt tgtaactgtt   40920
tcttttctgc atgaaatact ggttttacc ttttcagcta tttttttttt ttagctttga    40980 cttttaaaatc gcattaactc aatcctcctt atttgatatc agctgtccct cctcccacgg   41040
atctgcgatt caccaatatc ggtccagaca cgatgcgggt cacttgggcc ccgcctccgt   41100
ccatcgagct gaccaacctc ttggtgcgct actcacccgt gaagaatgaa gaggacgttg   41160
cagagctatc catttcacct tcagacaatg ccgtggtcct aacaagtaag ccctcaaaca   41220
tagcttgtcc cgtagatacg cagatcgtta gatctggagc acaaggcatg gatcctgagt   41280
tttcctggag gaccacctaa gagaaggag aactgtgacc gagagacacg ctctccaagt    41340
tcagtaggcg gctctgtaaa ctgtgaaaga tgtaatgatt ctgccggagt ggcagacctt   41400
tgatcgctac aaatcgtagt cgaaggcacg gtctgtgaag caccaaggtg tcagacattc   41460
tctaatcagt gcacaaaaga tacgtgactc ccaagtgaat tctgtaacta aggcaagagt   41520
gagaaacatg gagatcagcg catctggttt attgtccttt cttgtgtgag atctaccacc   41580
accaggggat ctatttagca ctagaaaact tagaatggct tttgcgtgga gacaggcaga   41640
cgtttagttc atatttcaga aagcacgtgt ttgcaccatt tccctgaagc tgggagagtt   41700
tagaaagcaa ctgacatgta ttagacaagt tatagaaatt gtttcttccc gagtcctact   41760
ggaagaggat actttgaatt aaagagaaca agagcttgca acattgtagg aaattgtata   41820
agtacagggg ttctacagga gaggaaagta gttacattca ggcccatttc caaatagggt   41880
cagaaaacat cctctgctct tcagatacgg ctcagaaagc taactacaaa gaggcagcag   41940
cagcagctct cacttggtgg ctaaagacca gaggacccag atacttaacc cgagtgtgga   42000
aatgtctgtc cagtcagtag gaaccacatt gtccaatata ctagacccat cgccacctgt   42060
tggcaccggt ttagccaaac cgtgtcacat gttaattatg tatcttaaag agtcctaatg   42120
ctagaagaaa ctccccctta gagaagtcat tattaccta ttttaaaaat taagcagttt     42180
gagggcagtg gagtgagtcc aggggcacta ggtatgttca ttgtcttgaa tacattcatg   42240
gccccaacaa ggacacatgt caaatttgt ccaactgtac atcttgacat tgcatagcat     42300
```

```
ggaagctgct gaccacctca tgtggttgtt gtgatgggta gatggtaatg tagactccca    42360
caaaagttac atcagtggcc ctcacagatg ccctttcaaa tggacgggag agatagtaac    42420
atcccgtgtt tacacttgac tgagttccat ttatacctgt ggagctgggg cttacagaca    42480
ggacagagcg gcccttattt acagattatg tccagacaga catactcact tagccacagg    42540
taggctatgg gactgaacgc ttggatgttt tatcagatga cggagtcccg gggagcgtta    42600
tgctttctca aagtctcaat caagtttaaa gcaaatccca ctttgcctct tcagatctcc    42660
tgcctgggac agaatactta gtcagtgtct ccagtgtcta cgaacaacat gagagcatcc    42720
ctctccgggg aaggcagaaa acaggtgagc cacgttagct accaacgtta agcaacaaaa    42780
tgataggttg agtctatagt tgcatctcca ccttttgtgg cattgataca ttacttttaa    42840
tttattaatt aatttatgat gacaataatt aattacaact aattaataat taattttagt    42900
tattgtagag tagtggtttt gccatggtat tttcacatgc tctgttgatg ttcctcttcc    42960
gttcctctcc ttgcccctg tcatcctcc tggtcccctt tctccctgta gtaatgtaca    43020
gccccgtttt cactctcgtc atcttgtcac ctctatccta tgaccttttt cactttctac    43080 cctccgcc ttaaagcacc ttctcttctc cccacattcc tttttctagt ttcaggacct    43140
ttgctctgca catacatgta gatgctctat acacacatat gaaaaattaa agctaggatc    43200
caggtaccag aaaactccac ttgtctttct gagactggat tgctttgttt aacataataa    43260
tgttactttg tttaacataa caatagagtt ccctggtttc cttgtgaatt tcactggttt    43320
cttgtcttag ttaaggttgt tgtgatattt gtgaggaaac accatgatca atagcaaact    43380
ggggagggaa gggtttattc gacttacact tccacactgt agtccatcac tgcagggaaa    43440
ccaggacagg aactcaagca gggcaggaac ttggaggcag gagctgatac ccggggccat    43500
ggaggagtgc tgcttactga ctggcttcta ccatgacctg ctcagcctgg tttcttatag    43560
aatccaggac catgagccca gagaaggcac tgtcccgccc acagtgggca gggccctgcc    43620
ctgtcaatca ctgataaaga gaaagcccta caagcttgcc tagatcttac agaggcattt    43680
tcttaattaa cgactccttc ctcttagata actttagctt ggtcaagttt atgatataaa    43740
gctacccaga acaacgctga agccctcaga agtatcagtg tttcggtata atgtagaaat    43800
cggctataat tttacatatt gtttcaatta cttttaaaag gaaaaaaaga aagaaatgct    43860
tgtgtaagct gattgcggtc agctatcagt cccgtataac agtgtcagtt gcgttcccca    43920
catcctccat cctcgatgtc taagctcgtg gttgttgtct tttgctcccc tccttgggtg    43980
ggaaaaacag gtctcgattc cccaactggt tttgattctt ctgatatcac cgccaactca    44040
ttcactgtcc actgggtggc tcctcgggcc cccatcaccg gctacatcat ccgccatcac    44100
gccgagcatt ctgtcggaag acccaggcag gatcgagtgc cgccctcgcg gaattccatc    44160
accctcacca accttaatcc gggcaccgag tacgttgtca gcatcattgc tgttaatggc    44220
agagaggaga gcccgccact gattggccag caagccacag gtaattttgt ttttttaatc    44280
cgcaaagaaa tcccttggtg tggactttgt ataggtttgg tgtagactgt gaaaaagctt    44340
catgttagac acaaagagca gtggtggagc caggcgcagc tgtgcgcgct catgcacgca    44400
ggcacgcgcg cacacacgcg cacacacaca cacacgcacg cgtacgcaca cacacgcacg    44460
cacgcctttg atcccagcgc ttggaggcag gtggatttct ggattggagg tcagcttggt    44520
ctacagagtg agttccagac tagccagagc tacacaacaa gatcttatct caataaaaag    44580
ggaaagagga cagtgataga ctgtgtggta aacatttctc cctctaaaaa catatttatt    44640
```

```
tctctgagag attgtcacct ggttcagcta tgttctggtg tttttgctgg tcagtcttta    44700
tttatgatgg tttgagagag cgtcatagcc cagactgact cagaagctgg ctctgtagcc    44760
caagcttatc taagatactt cgccttgact tgtgagtgct ggagttacag gcatgagcta    44820
ctactactca tggatattta ctggttttta agaaggtttc atacaaaacc ataatatggt    44880
accaaagtta ctgtaaacct atgattttg tttcgttagc tgggcttggt agcacagatg    44940
tgtaatccca ggtacttggg aggctggagc aagaaggcca tcctgggcta ctgtgagttc    45000
aaagttagcc tgtgcaattc agtgaggctc atctcaaagt aaataaaagt ttttaaagg    45060 ggtgcagtgg atgtagtgta gtggtggagt gctctgtgtg gcgtgagtca agccctagat    45120
tttggcttta agcacagata gatatatttt cagtgacaat gactgggaga cctgttatca    45180
gaacaatctg tagcttagct gtgaataggg gcgtgtgtga ccactatttc caaataacac    45240
atagttaagg gtgcatgggg tgggatctct gtgagttcca ggccagcctg gtctacaaag    45300
cgagttccag gacagacagg gctgttataa cacacagaga aaccctgtct tcaaaaacca    45360
aaagaaaaaa gaaaagtgca tggtgagtgc tgctgtagtt tttataactt ctgtgattta    45420
aattatttcc caagagact gttgaggaaa aaaggaattc acaattggga tggtctccat    45480
agccccttcc cttgacctcg ccatagaatt taactctgct aattcagtgt tgcatttaga    45540
tttttgtttg aagaggatgt gtgtaatcgt tatctgggaa aggacaaagt gaacctgagc    45600
tttctttgga agttatacat gtgaagtttt cctgtgattt ttttttttct agtttctgat    45660
attccgagag atctggaggt cattgcctcc acccccacca gcctgctcat cagttgggaa    45720
ccccctgccg tctctgtgcg ctattacaga atcacctacg gagagacagg tctgttcatt    45780
ttgggccatt tcacccttag aggatcaggg ttcgggtggg taacttggaa atctgacagt    45840
gggaacagga ttaaatgcaa acaggcccat ttagaaaacc ccctccttc cctccctccn    45900 tcccntcccc ctcccctccc cctctttctt tcttct ttcttt tcttt    45960 tttcttct tctttcttc tttttctgtc caaaaatgca tgggagctac atttaattga    46020
ttgtaatgaa gttcaaaggt ggtttataca ctacagcaag ggtgggaagc agagctgaga    46080
aaaaaaagtt tatataattta caaatattac cattggtaat tcttactatt ctttcttttc    46140
agtgttctct aaatttaaca aatattctgt taacccttt gtaaagactt cattccattt    46200
taggttgagt gagccacatt cttgtccсcct ttttctattt aatttaaaca attaattaaa    46260
tataattaca tgatttcctc cttcccttc ctcttccaaa ctatcccaca ccctctcgc    46320 tccacttcct ctcagtttct tggcttcttt gtcttactgt tacacacaca cacacacaca    46380
cacacacaca cacacacaca cacagagtgc atgtgcatcc aacaaataag tataaataca    46440
acccaccgag tctgcttact gttgcttata tggacatggt ttcagggctg actgcttggt    46500
atttattatc aaccagggag ctcatttctg gggatttctt cacctttgc ctgttaatct    46560 gcaactcagt gacatttaa cccagggatg ttaatatggc attagcttga gagttctcct    46620
ggtttttata tacttctcag ggcttactac acacataaat acacttgtct gtcaggttgg    46680
gttaaagcag ccactcctta tgatggaacc agcaagctgc agtgacttac ataccgcttt    46740
cgatgtgtta ataatattgg agtaactcct agctcctcaa attctatgct aactcctttc    46800
gtacaggagg aaatagccct gtccaggagt tcactgtgcc cggaagcaag tccacagcca    46860
ccatcaacaa cattaaacca ggagcagact acaccatcac cctgtatgct gtcactggcc    46920
gtggggacag tccagcaagc agcaagccag tttccatcaa ttataaaaca ggtacaaatt    46980
tctcttgggg taacacgggg ttatttatga agatggttat ccctgtattc gtccaaggta    47040
```

```
ttgtcttcac tacacagttg attttccttt agttttgtgt ggtgctgggg accaaaccca   47100
gcatctcata aatatatata tgctgtacca ctgaactaca cccttgaccc tgatttattt   47160
ttcttttttt ttttccgaga cagggttcct ctgtgtacaa agcctgtag  ctaacaacac   47220 cttcaagtaa tagagtcttg agacaaatgt acaaagaaga ccccaagagc agacattttt   47280
gtctgtgttt ttaactgcta ccgctatgta tctacattag acacaagcca gagagtgttt   47340
ataaatacct gtagaaaatg actggatggg ttgactatta ggagacaaag gcctacctga   47400
gatgtaatgc tttgtttgtg gaatgaaaga atcaggttgt aaatagttgt aatagtgact   47460
ggatgcatgg ctttccttct tcaagctaac acccttttatt cttgtcaaaa gaaacatttg   47520
caatacatta atagaagcaa gagaacattc gcatacacac tggaactaaa ggccagggct   47580
tgtccagccc tcccccccaca ctgggacatc actgctttct tttgtactta cagaaattga   47640
caagccgtcc cagatgcagg tgacagatgt ccaggacaac agcatcagtg tcaggtggct   47700
gccttcaact tctcctgtga caggctacag agtgaccacc actcccaaaa atggcctagg   47760
accatcaaaa actaaaactg ccagtccagg taaggataac cacaaggcca cacctagcaa   47820
gagaaacact gtaggagctc agaagttgcc atttgaagtg agtgtcctat gtggtgtgtg   47880
tatgctactc ccattcatag gcttggcacc agctcagtat tggtatccgt gtatctcggg   47940 ttttatttttt tttaatact gtcttgtgta gtaggaagag aaggatatac tgatgttata   48000
gatccttcta gatctgatgt tcttatatga aatggcttgc aaggtctcaa gccagtttct   48060
taagatcaat tttcatttct ttcttgaaat tttcaagaa  tagcctcatt aattttgggg   48120 gatgggcat  catgttaagt tagttgtaaa gcttattctt gaatatgatt ttacttcagt   48180
atgctagatt ttgttttgag atgggggtct catgaagtct gtgctggcct tcactgcact   48240
acgtaggcaa ggatggcgtt aaacttctga tcttgttgtc agtatctcct gagtgctaga   48300
actatagata cgcacacagt ttactgtgcc gcttggttat ctaagcctgg gtttgttcat   48360
gggaacagca ttctaccaac taagccgagc tccccagccc cagttttggt accagtgaac   48420
aagttgtcct gagaggaaac aggcatctga ctttcccaag tggaatgggg gtttcatggt   48480
tattctgcaa atgaaaatta taggctcagc atctgcttct cattgagtcc ttaggagtgg   48540
cttgggtggc tctatagacc tgcaattaat tgcttctccc tccttttcag atcaaacaga   48600
aatgaccatt gaaggtttgc aacccactgt ggagtacgtg gttagtgttt atgctcagaa   48660
ccggaacgga gaaagccagc ccctggttca aactgcagtg accagtacgt aaccaatgct   48720
cggtttccta cttccaaagt catattgtcc tcaggtgtct ctcgatgccc accgcacatc   48780
ttgtgccatt gtatacacac agggaaaggc aatgtgtcag ctggttcata tcttgagatg   48840
agcccttggc ctacatttct tggcgccaaa gcgagcttgc aggaaaaatc actgtagtgt   48900
tgccatcaat ggctgctgtg ctttgaatct cctttgctta aacagcctca gcaaaatctt   48960
atttgctttt agcaaatcta tgaaagatct ctccaggacc tacttttttct atgactggat   49020 ggtaatgttg actgtagtgt gccccaagaa gtggttatgg ttgaaggact gtggctgggt   49080
cagccttgtt ttttttttcct ttttaaagat tttatttttt tcatctatat gagtacactg   49140
tcactgtctt cagacacacc agaagagggc atcggatccc attacagatg gttgtgagcc   49200
accatgtggt tgctaggaat tgaactcagg acctctggaa gagcagtcag tgctcctaac   49260
ctctgagcca tctctccagc ccagggtcag cctttttaaa tataaagact taagagaggg   49320
gaaaaaagaa gaacctaaga caaattatga cttgaggaaa aaaaaaatca actttaccat   49380
```

```
ttccaagata tagaaaatcc aggtccttga gactaacatc acattgcaga atcaaatcta    49440
gaatatcttt aaattgatat aaataaattt ccttggtgga gattttttc ttcagggtgt     49500 ctacatacct tacacacact tgtgtcttaa taagcaacgt gacactgcat atgctaaatc    49560
tcaaaaaaaa aaaaaaagcc ttttaagcag atgtcaagca actttctgtt ttaatagtgt    49620
gataattgga acttaattca tcaaagacaa gagttatctg cagaactgct ttgcatggta    49680
tggaaatatg cttgtttcac aacttgcttt tcacataacc tcttaccatt aatttgccta    49740
acagacattg atcgccctaa aggactggca ttcactgatg tggatgtcga ttccatcaaa    49800
attgcttggg aaagcccaca ggggcaagtt tccaggtaca gggtgaccta ctcgagccct    49860
gaggatggaa tccgggagct tttccctgca cctgatggtg aagacgacac tgcagagctg    49920
cagggcctca ggccgggtc tgagtacaca gtcagtgtgg ttgccttgca cgatgatatg       49980
gagagccagc ccctgattgg aatccagtcc acaggtatat cgttaaccgc acccaccacc    50040
cgggtgcttc tgggaacagt ggctttatgc cttgctggcg ttatacttta ctgggctatt    50100
gagtcccatg taagggagag tagaaaaatg ccttcaaact cttagtaaag aaaggccctc    50160
tttaatgagg aatggttgtg aacaatgaaa gtcaggtgat gtttaggtaa ctaagtctag    50220
gaaagagaaa tttaaagtag ctaagcacag acgtgcaaac atatgaaata tataaatatt    50280
taaagattat gaagcaagac atttgaaggt actaaattac ggattgtttc ctaagtgaga    50340
cacctcggtg gtgacctcc ctctccacac atggaggaaa gaagtctaga atcatagagc        50400
ttactctgag aattgaccct cttaagccag gcattttctt gcaacatgat caagaatac      50460 atgggtaaga cctcccctgg ctagctctcc tgtgctgggc cttcatttgc ttaaaggatg     50520
atgatgcaga tgcacaggac agcgtcatta ggaccagtgc ttcttaccag cctcttatgc     50580
ttttaccgct ggagcaagat tggaatgctc aaagcataca gaggtgacag tctgtggaac     50640
tgctctctgc ttctctctcc tgcctctatt gtaaaccaat tttcttctta tgctacgccg     50700
cagagaatac ttcaaattta gcagtgctat ctgccgtggg gtccaaataa aagagacaaa     50760
taaaaacaat tctatctcta ggatggaata gtctgtgaaa ttgtttcctg tacaagata     50820 atttatatag aaaagggggc cattgctcat cttttttcata caaatggaaa aaaaatcaat    50880
tctaatgact aataagggaa ttcaactctt ggcttctaaa ggcgtagggt agggagataa    50940
gacccaaagt ctctcggaac cctggtgttt atgcagatgt ttgcagtggt tctgagagtt     51000
gctggtataa atactcctct cgttttttatt atctgtttgt gcagactctc ctgggagtct   51060
ccagggagtc caccagtccc tacgaggacc atccattctc cttcttcaag tttgcttttct    51120 ttccccgttc ctcgttccct ataagataac cttttaacca atgaccatcc tgacagccat    51180
tcctgcgccc accaatctga agttcagtca ggtgacaccc accagcttta ctgcccagtg    51240
gatagcaccc agtgttcagc tcactggcta ccgggtgcgg gtgaacccga agagaagac     51300 aggaccaatg aaagaaatca acctttctcc agacagctca tcggtgattg tgtcaggact    51360
catggtaaga agtgagcttc cctctgcaga gtaaggcagg aggtcatttc atagagttca    51420
taggtgcaat ctcataataa acctagtgtt ctttgcttct accatcaaat agggttgtca    51480
caaatgtgta caatagaatt cttttatgta gacctaggat tttctagata ccctaagatg    51540
actattggat tagaatggtg taaatagctt tggatttcgt gcaggtcttt gacagaagta    51600
ttccacttat ttaaagaag tggtattcgg tagggagcaa tttatataca cacacacaca       51660
cacacacaca cacacactct ggctgagttt atggcttta tgagtgatgt ttccctggca       51720
agacgcattc tccagttagt accagcctaa cttgacacta cccccattaa aacatttgac    51780
```

```
aatcagccag ctgtgcttta atcttgggag gcagaataag caggtggatt tctgagttcg   51840
agcccagctt ggtctacaag aatgagttcc aggacagcca gagatacaca aagagaccct   51900
gccgcaaaca agcaagcaag tagtatttaa aacttttttct agccatgcag aaattagcta   51960
ggatcctata agggcttaat gcacatctta acacaaggcc aattcttaga gaagtagcag   52020
tagaatagaa gctttctctt gctttttttg tgatcaggaa aaaagcaaaa cctgatttat   52080
atctgtcata tcataaaggc aaaaaaaaaa aaaggctaag actgatttct ttcttattct   52140 tttttttgctg ctccttgtgg attgtggact taaccctga gaacatttta aaattcactt   52200
aatttaaatg taaatgtatt gtcactcata ggtaacagtg aagttgctct gggaacctgg   52260
gggtttgggg tttgctgggc tatgcagatg gtcttttata atcaccgcat ttctctaatg   52320 cttggtaag aactccgggc atcatgcaac accattgcca aagtttctgg tacctctgct   52380
tccaggtggc cactaaatac gaagtcagtg tctatgctct caaggacaca ctgacaagca   52440
gaccagccca gggagtcatc actactctgg agagtgagta atccgatgag tgacatgttt   52500
taatcctgac acaccctgag tggaagtcaa aagaaaagat ctttacattt aagccactga   52560
cttagcaata gaatttggaa gttgataaga cagcttgtcg tttcgggaat ccatccagga   52620
aatgacctgc cgaaacaaaa tggaatcact tcactgtgtt gtgttggtgc tggtgggtta   52680
aaactcacag ctggcttatg cggtactggt gagggtctgt attcgtaggg ttcaatgtgg   52740
ggaagatgaa ctggcttcca ccatagggaa tgtggggcta aattagatct gtggtctagt   52800
ctgttgatgt ttcatcacct atggaatgat taacacgtga agcctatag aaatgaccga   52860 agattcgcca cccagacaga cgttattact aattgtctgt gttataattc ctaccataca   52920
tccttacata ttagtaaagt aatcattgtc acacttgttt gacatagctc tagacactag   52980
agagtcaacc ctgggcacca ctgatagtat ttagaaagct tttctgttta gtgaacattt   53040
ccatatttcc tcaataccgt taacccatct ttctgtaacc tccacattac ttttttagtgt   53100 atttcctgaa gtggatgtat ttgcataatg aggactcttt ttaaaatatc caaaccttac   53160
atgtatgagc caagcgtgct ttaatctctg gctctgctcc tacacagatg ttagccctcc   53220
aagaagggcc cgtgtgacgg acgctacaga gaccaccatc actattagct ggagaacaaa   53280
gacagagaca atcactggct tccaagtcga tgccatccca gccaatggcc agaccccagt   53340
tcagaggagc atcagcccgg atgttagaag ctacaccatt acaggtcagt gtactcgtgg   53400
tctgcctgtg tgcgcccgca ggagaccctg gctcggtaga tagtctggtc tggtattgag   53460
aatgtgggca ccattccacg atctgttggc ttcctgatgt ttgcttgacc tataaatctc   53520
attcattgaa tttgttgttt tataaatgct cattcattat tgtctaatga aaatctgcac   53580
actgtagtca taggcaggag tctgaggcag gaggatgtga gtttgagact agacatagtg   53640
aaaccctact tttttttaaag ttaatataga gaacataaag atacaaaata gtaaaattag   53700
catgcctaga ttttaaaagg cataatgaaa tttatgatta caaacagcat tatgtataat   53760
aaaaccggaa actgtaatca gagacgattc agtattggga cataagtgag gtgcttttga   53820
gatgagtttt tcattagtag tgacctgtcc accccgtgaa gcccttact cttccctgta   53880 actgcttctg ccagtatagg agtcaaggaa actgtaggca agcatgagaa ctcgcctagt   53940
aaagtaggag tggattaaac aggcgtcttt ttaacttcca ggtttacagc caggcactga   54000
ctacaagatc cacctgtaca ctctgaacga caatgcccgg agctcgcccg tgatcatcga   54060
tgcctccacc ggtaactatg cttttctatgg aggaaatgtc agctgctgca tattgtaatc   54120
```

```
agccgcgtca agtttagaaa cagttaggga gctggaattt ccatgttctg gctcccggga   54180
ctctctgatt ctctctctcc tcctctgttc gctagggctg ggctcaactg tgagaatgga   54240
cattcatttt tctaaggtgt cactttgctt gcctttcagc catcgacgca ccatccaacc   54300
tgcggttcct gaccaccaca cccaactcct tgctggtgtc atggcaggcg ccccgtgcca   54360
ggattactgg ctacattatc aagtatgaga agcctggatc ccctcccaga gaagtggtcc   54420
ctcggcccg cctggtgtc acggaggcca ccattactgg tattgcttcc acactgtgat   54480
tttttttccc ccttaatcat agatgcccca agtccataat actccccaat tgtgtctttg   54540
atgctatttc atgagaatga ggtgcccagc actctagatg ttctgtttag ggacagtagt   54600
tttctcaaga gatatgagca actgagcatg caatttcagt gccgtcctat gacacagctg   54660
tgatgtatta cactctggtg taaattcttc attattcccc cctcccccat aggataaatt   54720
gtgtgtatag attctcctgg atgttgaagt ctctaaaaca cacagatata aggagatcac   54780
agcttctttg ttgcatttat tgaagaagaa aataagagtc tgatatggga agacttaagc   54840
agaagacatc ctaatttttg ctctgtcact gacagctgtc tgagattaga cctaaataga   54900
agtctgaagt ctctgatggc ctctcccaaa tacatatttc attgtcggcc cacagtatag   54960
atagtttatc tacaggctga agaatcctc taggaaggtt gccatgaaac tgctcattca   55020
agtatcagct gtggttgtga aatgactaac tagccaaggg gctttggggt tcgcagagta   55080
gataaacaag gagtgaagct gaaagacttc acaggcagct ggcaggaatg cctgctcccc   55140
agtcgcctct gctgagccaa tcactggccg tgcccgccaa cgtgagtgaa acggccgcgt   55200
ttcccatcag gtctggagcc aggaaccgag tacaccatct acgtcattgc cctgaagaac   55260
aatcagaaga gtgagcccct gattgggagg aagaagacag gtaaagactc ataaccagtg   55320
gttgctttgc agggtgaagt ctctacattt ccacacatca cacatctctc acggatttt   55380
tttatttccc tagcagagtg gcttatatat tttactcttt gacaggaatc acctaacatg   55440
ctctaaaaat gtctgattta tttcttttc tacaaccta agcttcgttt accttgcaga   55500
gattcaaact agatagtttg aattggaagg ggggggaagc tttataatgg tgggagtaaa   55560
acctttctga tttgggtcga tttatttatt atttgatttc tgaacttcaa acacttcagt   55620
tcgttgcaaa gccttaattg gagcagagat ggctttctgt ggggctcagc ggttcaaagc   55680
tttgtctgta tgagaattca tactaacttt ttttttttc tgtctgaact ataaagaaat   55740
ctgtgagaaa aaaaaaatca cgatttcttt ctctaagagt gttttgtgat ctgagaaccg   55800
ctggttgtgt gggagctctg atcgggttga taaacagttg ttgcctgggt tgacagtgat   55860
tggttgcttc ttcttcgagc ttaacttttg cgctttgctt ttttggctct aacctctctt   55920
ggctagatga gcttccccaa ctggttaccc ttccacaccc caatcttcat ggaccagaga   55980
tcttggatgt tccctccaca gttcaaaaga cccccttcat caccaaccct gggtatgaca   56040
ccgaaaatgg tattcagctt cctggcacaa cccaccagca acccagtgtt gggcaacaaa   56100
tgatctttga ggaacatggc tttaggcgga caacgccacc cactgcggcc accccgtca   56160
ggcttaggcc aagaccatac ctgccgaatg tagatgagga ggtccaaatc ggtcatgttc   56220
ccagggggaga cgtagactac cacctctatc ctcatgttcc gggcctcaat ccaaatgcct   56280
ctacaggaca ggaagctctc tctcagacaa ccatctcttg gacgccgttc caggagagtt   56340
ctgagtacat catttcatgc caaccagttg gcaccgacga agagccctta caggtacatg   56400
acagcccttg caaagtgtct ctctatgtaa ctgtgtcttc agaacaacc acagcttcat   56460
gtctgatgcc cactgtctta gtcagggttt ctattcctgc acaaatatca tgaccaagaa   56520
```

```
gcaagttggg gaggaaaggg tttattcggc ttacacttcc atactgctgt tcatcaccaa    56580
aggaagtcag gactgcaatt caagcaggtc aggaagcagg agctgatgca gaagccatgg    56640
agggatgttc cttactggct tgcttcccct ggcttgctca gcctgctctc ttatagaacc    56700
caagtctacc agcccagaga tggtcccacc cacaaggggc ctttgcccct tgatcactaa    56760
ttgagaaaat accccatagc tggatctcat ggaggcattt ccccaactaa agctcctttt    56820
ctttgtgata accccagcct gtgtcaagtt gacacataac accagccagt atacccaccc    56880
tcccagggca gaggctacga ctctgactgg aggttgtttg actcagagag catcactgag    56940
cgtcacgcag tagagaaaac gaaattcttt ttattattct catacactgg agactactta    57000
gtgagatgga tgaaacaatt atcttaggaa gtagaggaaa agtaatttat atgaagtttg    57060
aaatgccacc tttggcgtct gtccttgaag aggcacgctg ttacgtgtct aggaagacga    57120
ggtgaaccgt tggggaccag ctgttatgag agatcgattc tccaaaactc tcttctttaa    57180
tttgtcccac aggtgctaga atcaattttt attgtgttat ttttagaaag tggcagaaat    57240
tttaaaattg actgtaccct aggacattta ttagcttaga aactttagtc tggggatgtg    57300
ccggtatttt aggaaaaccc aagttctact gtgttggcac cttacatggc acatgttgtc    57360
tgtctgtggc actcatgttt atgaaggggc ttttttttcca ggagttctag tggccacagg    57420
attcagagga agctggtata gctgagggtt tctgggaatt gtggaacacc taggtagaaa    57480
aatctagcag aaatgatttt tttttaagtt actcttttaa taattttta tgtaccttgg    57540 tgttttgtct gcatgtatgt cagggtgagg atgtcagaag ctctggaact ggagttacag    57600
atggttgtga gccaccatgt ggctgctggg aattgaaccc aggtcctctg gaagagcatt    57660
tagtgctctt aaccactgag ccatctcccc aatcttaaaa cgatggtttt ttgcactcat    57720
ttaatatctc atcttgacta ggtgggagtc ctatacagcc ctgttctctc ccttcgtctg    57780
tttttaaatg ggagtggggg attgctcata gactaaggaa gctcatgccg attcatcatt    57840
gaaatgcttt ctccctgctt tggatgtata gttccaagtt cctggaactt ctaccagtgc    57900
gactctgact ggccttacca gagggtcac ctacaacatc atagtggagg cactgcagaa    57960
ccagaggagg cacaaggttc gggaagaggt tgtgactgtg ggcaacgctg gtaggtacac    58020
tgctggcctg ttgaggcaca cgcttcttgc tggatcagcc cagagaagac ttggtctgtc    58080
gttctttgtt ggctttaaac ttaggaaaat gagattgcac aacagtcaga gatgtcccct    58140
tatgtaaccc atatgttcac caacacatat tgacaggatg ccaggcctgg gagggacatg    58200
aatattattt actctaatac atttttcccc tcctgttgag gatccagttg acagaggcaa    58260
tggttttttg tacctttttac tattctctca tcccatactg tggtccactt aagcgttcct    58320
aacccgaacc gaacacctat aaacagtcct ccttggcaat cttaagtgat gacttaggtt    58380
ttgtacctaa tgtaaaatgt taccaatatt gcccttgct ttcctaagag cttcccattc    58440
caaatttcaa ctttatatac ttctttgttt tcttcttctt tagatttacg tattttaatg    58500
ttatgtgtac gggtgttttg cctgcatgta tgtgtgcaac atgcattcag cacccatgga    58560
ggccagaaga ggacaccggg tcctctggaa ctggacttat agagggttgt tagtgactat    58620
gtgggtgcta gaacctatgt aatgtcctgt ggaagaggag ccagtgacat aactcctgag    58680
ccatctctcc agccccttta tatgtgtctt aatacataaa ttatatatgt catgttatat    58740
acatgcaagc tcttaaaggt taaatggcca tcatacaaac gtaataaaga tgaaacgacc    58800
cccatgcagc cttttaataa aggttaaatg accagcatgc aacatcttaa taaggttaa    58860
```

```
ataaatttaa tcctgaaaat ttttgataaa ggttgaatga ccctgactct gagaagcctt    58920
ttgaagccag tgatgtgtca tttggcttaa gttgcaatag ctaaagattc accaaggagc    58980
atgagttaag ggctaactga gactggatcc cgagtcctct taccctggaa gggctaactc    59040
ccactttttc cagggagcag gacttctggg taggaccact gccttctttt cagccttctt    59100
cctcttagcg aagactgcta ttatttgact cttcagttaa gcagttgcat gtctggcaat    59160
gcagaagtgg gcagatcttc tgtgttccat ccacagtaat tagcatttgc cttttgtggt    59220
ttcactagta aaatgccact tgaaagggat ttttttcaaa agcatagggg ttttgtggtt    59280
ttccacatca ttttcttgaa ggtgtgtgtg tggtgtgttt cagacagtcc tactgtattg    59340
tatgctgttt gtatatagtg tgctagactg aactgctatg tagcccaggc tcctaatgtt    59400
agggcagacc tcctagatat tttaaaatag tgaaccccca tgagagtttt agccccttttg   59460 ttttctttcc gactcctgtc tttaccaggt cctcttggtt tcaaaacatt ttggatagac    59520 ttttagttc ttccagaatg atggcttttg aaatattagg catttcaaat attgatttca    59580
tttgcacttt tgattttac actattaaaa gaagctatcc acaagtagga ttttttttt     59640 cctgagacag ggtttctctg tatatagccc tggctgtcct ggaactcact ctgtagacta    59700
ggctggcttc gaactcagaa atccgcctgc ctctgcctcc caagtacggg gatgaaatct    59760 tgggaaccc actgcagctt ttctacttat tcctaactgc acggtggtga tttctcttac     59820
ttgaaaatca ggtcttatct agttttacag taaccataag catctaggtt ttcaaactat    59880
ttagcaaaag aaaagctaca atgtaagtaa agattgtgtt ataatgctat ataaagatgc    59940
taagacattg actacagcaa agacgtatct aacaataatt gttaattatt gagtaacagt    60000
agttagtaag tcatctctgc atagtgatac tggtccagag ctttgattcc tcagtttcat    60060
gtagccttta caagatccaa aaaagtgggg ctagttatat tattatcccg taatagatga    60120
gagaagagag acagacaaat gttaattggc tccatgtact caggtgtctt ggggaagcac    60180
cactgcccat attctcagct agttaaaatg cctgacgatc tgcttcatgt catgagaaac    60240
agaagacggg aatgaaggaa gacgtccttt gaccctgctg tgacaagtgc ctactgactg    60300
catcaaagtg ttgccgatga gaacgtctgt gttgttagtg ctgattaggt cacaatatac    60360
agtatggccg tttccccatc aataaccgtc aataaaatgt cttctccttt ttttccttc     60420 tccttctttt cttcatagtc agcgaaggcc tgaaccagcc tacagatgac tcatgctttg    60480
acccttacac ggtttcccat tacgccattg gagaggagtg ggagcggttg tctgacgctg    60540
gctttaagct cacatgccag tgcttgggct ttggcagtgg tcatttcaga tgcgattcat    60600
ctagtgagta gcttgcgttc cccacccctct cactcctcca tctcttctgg tctcatgcgt    60660
tcgcactagg tggccacgga aacatgtttg gcagactcgg gctcttccaa acatgatgca    60720
aacagaagta gactgtttga ctccaagtaa cattttgcat catagaagga tgatgggaaa    60780
ttttacttgt gcaatatgac tgcatttcaa gagttgtgta ctaatctaac tattccttac    60840
aaatatatct gtagtgttga tatgctcctt gtagtgttta gctctatgta aattgaagtt    60900
aaaaaatatc tcattagagt ttggtttaat tgagacaggc aggcagagac tccaaattct    60960
tttcagtctt tagtattgag taaggacaga ggtgaacatt tatactcaca aacaccactt    61020
tttcagcata accagatata catgcacaca tcacacacac acatacacac acacacatct    61080
cacaacccag atatcccaaa cattgctcgt ataaggaaa atgtctctct gtatagccct      61140
ggctgtcctg gaagtcactt tgtagaccag gtcggcctca aactcagaaa tctgcctgcc    61200
tctgccttct gagtgctggg attaaaggcg tgtgccacca cgcctagttt gcattctaca    61260
```

```
tttaaggatc aagttcaggg ctggtgagct aggctaggca tcccatccct ggaacccagg    61320
tggtgccagt ccccacaaat tgtcccttga ccttcacata ttcctggggg gacactaagg    61380
cccatatgta catacatatg tacacacaca tgcaaatcaa taaatctaat aaatgttaag    61440
atcaactttg actgaaaaat aatttgattt tcaaatctta aagaggttaa aatttcaaat    61500
tattagtgaa aatgatccta tgagttatct atgtttctag agatttagta ttggagtata    61560
taaccattca ttctttgttt ttagagctat aattattatt agcttttttaa tgtgcttttt    61620 ttatgtgttc atcatatatc atagatatcc acaggcctat ggacaattat aggtcccata    61680
ttccatggaa tgacatttaa tagatctcta aagttttttg tgtaacattt tccttttcctt   61740 tacatgaaat agcaaaatcc agactggttt caatgtgtgt tgttgggtag agcccagtgg    61800
gcaatatacc atgctgggga caggagggac accatttggc cttgaccagg tgcttttttca  61860 gagagtgaac tgcactgaag tttgcatgtt tttcataact cagtacaaat gtggacgtat    61920
acaatgattt ttatccgtga gcctctgact caccagtctt tgctggatat gtcataactg    61980
ccttatacat ttgctcatcg tttaaggaag gctgaattgt taaagtggaa gaatcactgc    62040
cctggatgag ggtcgtaagt gaactctgtt tagtataaat cttagaggtt aaagggcatt    62100
tttacatctg ccattagaca cagctcgtgg tgacttctta ggacttgtct atttgtacaa    62160
caagcctgat tcatttcatt tgtctttatt ttgttggctg ttatattcgt tcgttcttca    62220
cttatatgaa tcaggtgaca ccagctgttt ttctcttttaa tcttcttgtt tgtttttgtt   62280 tgtttgctttt tgtcgttgtt tcatgagaca gggtttctct gtgtgtccct ggatgtggta   62340
cactcagtct gtagacaggg ctgtcctcaa actcagagat ctgcctgcct ctgcctccct    62400
aatgctggga gcaaattcgt gcacgacgac gcctgccctc tctttaatgt ttaattaaac    62460
tattttgtat ctaggatctc tgcgaaccta aaatatatat ttttttaattc tccaatccca   62520 ttttaatttt ccatatttgt aaaatttaaa aggagctgaa tgaatcactg gttggtcctc    62580
tgaaatgatc ttggtggtag tgttaagtct taacactggc ctggaagata ttaaatgtta    62640
tgatgaagaa atgcttcatc attagaaatg tgatcttgga cttcctgctc tgtatggatt    62700
ttcgtcctgt tccagtgttc tgcccatcct gtgagtcaga acacagagta actctctgcc    62760
tgcgatgtcc ctaccttcca gaatggtgcc atgacaacgg tgtcaactac aagatcggag    62820
agaagtggga tcggcaggga gaaaatggcc agcggatgag ctgcacatgc ctcgggaatg    62880
gaaagggaga attcaagtgt gatccccgta cgtcatccta aaaatgcttt ctagactttt    62940
taagtactcc catgttccta actgagccga acacccatt tacaggctgg gctggacgtg     63000
gtgggcttgt cagtctgtgg ttggtaagtc agtagcttgc ttcagaaagt gaatcatgac    63060
tgaatggcac gtctaagcac tttagcactt tcacaacttg agcactttgg tcatctgcag    63120
tgaagtgcta tgtagactca gttttttaaaa cataacttca aagccaagca gtggtggcac   63180
atgtctttaa tcccagcact tgggaggcag aggcaggagg atttctgagt tggaggacag    63240
cttggtctac acagagagaa cctgtctcaa aaaccaaaa aaaaaaaaag acttcaatcg     63300
ttccatctgg cctagtctac caaggctttg gaacatctcc ttgtgattca cctaagttga    63360
tgagatttgg cccgtgctca ttcaggtcga gggcagatgc atcaacttga gtgtacctga    63420
ttgtccttgg tcttacaact gttcctttct gctctgtgcc cacgtgcaga tgaagcaacg    63480
tgctatgacg atgggaagac ctaccatgta ggagaacagt ggcagaaaga atatctcgga    63540
gccatttgct cctgcacgtg tttcggaggc cagcgggtaa gcctggttgg cgtttagata    63600
```

```
aagcacttag gaggttgcag catggatatg ctttgtgcac aggagccttg ccttttagga    63660
agagtctcta agatgggtgt ctcagttagg gttttgcgttg cttttgaagag acaccatgac   63720 caaggtaact tttataaggg acaatattta attggggctg gcttacagtt tcagaggttc    63780
agtccattat catcatggca ggaagcttgg cagtgtgcag gcagacatgg tactctagaa    63840
agagctgagt gttctgcatc ttgaactgac aaagacagct agaagaaagc tttcttcttc    63900
attgggtaga gcttgaacat aggacctcaa agcccacccc cacagtgact cacttcctct    63960
aacaaagagt gccacttccc atggaccaag catattcaaa ccaccacaat gggtctgtcc    64020
ctcccagttg ataatagctt cagcaccttc tcccatgact aaaattctca ggctgccctg    64080
tttgtcctcg cctggagtgt agcactaagg ccccagctct gagctgatgg actagcatct    64140
gagtattgtt cacatttta ataatactgt gatctaagaa aatttaacta tttttgagcc     64200
tttgttcaat ctaaaaatta ttatcactct aatactgagc taagtaacaa tagacacaca    64260
gggaagggtg gccgttgctc ttgaggatat acttggaggc agcaaattag catacctgc     64320 caagccaagc taatcacagg agattttgac gaatacagtt ctggatggcc tgcaatcagc    64380
aagaaggctt cctagaaaag agaaacataa accagccgcc tggggtttag gatagctatc    64440
attaagtggg gagggaagga agcagagact acatacttcc tggcctaggg agagctggcc    64500
cagcgaggca gtccttccgc tggaatcttt tggtaagaaa ttagatttga ggaggagact    64560
catggaaagc tgggaaagcc atcatttaag acagtaattc tcagtcatgt ctaacgtggg    64620
cccttcttca atataacaac aacttccact ccatctttta ataagtgaaa tatcaaaatg    64680 actttaact  taaatgtaat aggggggctgg agatggtggc atccccttt aatcccagca    64740 ctcagagtag tcagaggcag gtagatctct tgagtacgag ggcagcctgg tccacaaagc    64800
aagttccagg acagccaggg ctacacagag aaaccctgat tcataaaaac gaaacaaaca    64860 aaaaagaaa  atgatcgggc aggtcccaca gtttcccctt tgacctccac acattttggg    64920
cacatgtgta tacatacaca tatgtaaata aatgtgctta attttttagg aattaaattg    64980
ttatgtaaag ggcttgacct taaagggtcc cagaaatctg gggcacaagg aataatgccc    65040 ctcacccca  cagtgaagtt cacccattaa tgctattggc attcatcaat gattaaaagt     65100
agcataatgg acaataacct tttaaaaaaa tgaatctggg agctggagaa atggctcagt    65160
gcttaatggg actcactgtt ctcctgggga cctggacttg gttttctctcc tcacatggtc    65220 cataaccacc attcccagaa gaactgacgt cctcatctgg cttccttgag catcatgcac    65280
acatggtgca cagacataca cacaggcaag cacttatcac ataaaataaa aacatatgat    65340
aaatcctttt taaagaaga  agggcagtta atgtggccac aagaaagact ctatgtatca    65400
tcacaacctt cttaggtctg ggcagccggc aggattgaca atctcgtttt atctgttatt    65460
catggagtgg actgtctgtc cctctgtctc tctgtctctt tctcagacac acagaagcag    65520
atcatatgac tcagtcatca tggtctgaat gagtggcttt gttgggaggc agattttagt    65580
ctttcttcac tccattcttg ttccctatga acgggaatct ctttgggtaa tgcctgtctc    65640
taaagttctg aaacatggtg gcggttgcta tggtctttga gaatcgttat tgattctgca    65700
agcaggccct ctgggaaata ggctcctaaa tggagaaata cgtcaaagat gtttaaatga    65760
ttctataaga aagtgattgt aggatttatt tattttttgag acagagtcta gtagccctga    65820
ctatcctgga acttgctatg tagagcaggc tggccttcag ctcacagaga tctacctgcc    65880
tctgggtgtg tgccaccact ctccagcctg gccttatttc ttcattttgt tgttgttgtt    65940
gttgttgttt tcaacccta  atgtaaagtc ttgctagtta ggcaaaagat ggctaccaac    66000
```

| | | | | | |
|---|---|---|---|---|---|
| atgaactccc | ccattctgtg | aacttcaagg | actactttgc | cccaagagtg | cgcctctctc | 66060
| tgtgtccccc | tagtgtccat | ttctgtgtcc | cctggggctt | ctgctaatgg | tgccatcgtt | 66120
| caccacatca | gctccagatc | ttcctcctcc | cagctcagga | gtgatgagaa | agcaaatgtg | 66180
| tgccagcaaa | actcaggaag | aagcacaggc | ccgctgtggt | gtcttcctgt | acccagcccc | 66240
| acctctggcc | agagctaagg | ctatatagta | taggttaggg | aggttttaga | agggactgga | 66300
| aagagaatgt | ggccaggtac | ccagttctac | ctgggaccca | cggcgtcctt | tctgttcct | 66360
| tccaagtcat | tcctctcctt | caccagaaag | tgatggcatt | tgtccccaca | ctctcaagtc | 66420
| actgtgactg | atttcgcagc | cctaggggtc | tgtgagaaat | cttccaccta | gagcagaaag | 66480
| cctaccaagg | aggaaggtag | gaccaaagat | gagaagagca | aaagaagtga | ggaggatatt | 66540
| tcagcggaaa | ggaaagcata | tgtagacaga | tgaataagcc | aagatctatt | gtaagagtta | 66600
| cgactgtaca | caggcatcat | tgcagtctcc | tgattaactg | cttgtactgc | tgatgggcaa | 66660
| gagctgaaac | tcagtcatga | taccctcagg | ttatcctaaa | ccccatttaa | cttcgtgtct | 66720
| ttcctctcag | ggctggcgct | gtgacaactg | ccgtagacct | ggggctgctg | aacccagtcc | 66780
| cgatggcacc | accggccaca | cctacaacca | gtatacacag | agatacaatc | agagaacaaa | 66840
| cactgtaagt | gtacacatat | ccccacccac | ccccaccacc | gtgactctcc | ctgcatgcag | 66900
| ccaggggcag | gtggatagat | gcttttcttg | aatgaaccaa | atgagtttta | tttggagata | 66960
| agtcttttgc | tcatgagtcc | agtcctcagg | acccatccat | gtaaaagagc | taggcgctac | 67020
| agcaagtgct | tataatctcc | tcactgagga | ggtagaaata | gggtgtgggt | ggtgtccctg | 67080
| gggctgtctg | gccagccact | gtagccttgt | taatgaactt | caggctcatg | aacaaagcag | 67140
| acagcatttg | cttgattaaa | gttaactctt | ggctccttat | acacacaaag | tcatgaatta | 67200
| attataactc | gttataattt | actaaatccc | taagcattgt | ctattgctca | gtacattgct | 67260
| agtcttttga | aactatttat | ccttcctata | aaacacctgt | gacacaaatc | tccactcaac | 67320
| cctccccgaa | acacacacac | ttttggtttt | ccgagtattt | gctactaatg | tttgtcttct | 67380
| attttgacag | aacgtaaatt | gccccattga | gtgcttcatg | ccgctagatg | tgcaagctga | 67440
| cagagacgat | tctcgagagt | aatctttcca | gccccaccct | acaagtgtct | ctctaccaag | 67500
| gtcaatccac | accccagtga | tgttagcaga | ccctccatct | ttgagtggtc | ctttcaccct | 67560
| taagcctttt | gctctggagc | catgttctca | gcttcagcac | aatttacagc | ttctccaagc | 67620
| atcgccccgt | gggatgtttt | gagacttctc | tcctcaatgg | tgacagttgg | tcaccctgtt | 67680
| ctgcttcagg | gtttcagtac | tgctcagtgt | tgtttaagag | aatcaaaagt | tcttatggtt | 67740
| tggtctggga | tcaataggga | aacacaggta | gccaactagg | aggaaatgta | ctgaatgcta | 67800
| gtacccaaga | ccttgagcag | gaaagtcacc | cagacacctc | tgctttcttt | tgccatctga | 67860
| cctgcagcac | tgtcaggaca | tggcctgtgg | ctgtgtgttc | aaacacccct | cccacaggac | 67920
| tcactttgtc | ccaacaattc | agattgccta | gaaatacctt | tctcttacct | gtttgttatt | 67980
| tatcaatttt | tcccagtatt | tttatacgga | aaaaattgta | ttgaagacac | tttgtatgca | 68040
| gttgataaga | ggaattcagt | ataattatgg | ttggtgatta | tttttataag | cacatgccaa | 68100
| cgctttacta | ctgtggaaag | acaagtgttt | taataaaaag | atttacattc | catgatgtgg | 68160
| acgtcatttc | ttttttttt | taacatcatg | tgtttggaga | gaaaaattgt | cttcatgcat | 68220
| gtccttttc | ttttcgatgc | tacaagcatg | tgaagaggca | ctgtgttggg | ctggggtggt | 68280
| ttctgcacat | gagcgcctgc | ctggccttac | agaagcactg | atactttgcg | tcattttgtg | 68340

```
tcctcacttg tggttctgcc ttatcagatt taaatggatt caaatgtggg ctaagcttgc    68400
tagctagcac gttaggagta taaaggaaat aagattcgtg tgtgtgtgtg tgtgtgtgtg    68460
tacatacata caagtgtgtg tgtagctgct catgaaaatc aggaggccag aagggatgc     68520 tgggtccctt agagctggat acaagtgttt gtgagataga tactgggatt tgaactcata    68580
acagagcggc aaatgccctc acctctccag ccctatagtt ctgtttaatc atcacaggcc    68640
tttgcttctt t                                                         68651

<210> SEQ ID NO 30
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 30
gtaagaggtt atgtg                                                     15

<210> SEQ ID NO 31
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 31
ttaatggtaa gaggt                                                     15

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
aatgtctgtt aggcaaat                                                  18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
caatgtctgt taggcaaa                                                  18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
tcaatgtctg ttaggcaa                                                  18

<210> SEQ ID NO 35
<211> LENGTH: 15
<212> TYPE: DNA
<213> ORGANISM: Artificial sequence
<220> FEATURE:
<223> OTHER INFORMATION: Synthetic oligonucleotide
```

```
<400> SEQUENCE: 35
aatgtctgtt aggca                                                    15

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
atcaatgtct gttaggca                                                 18

<210> SEQ ID NO 37
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 37
caatgtctgt taggc                                                    15

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
cgatcaatgt ctgttagg                                                 18

<210> SEQ ID NO 39
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 39
atcaatgtct gttag                                                    15

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
gcgatcaatg tctgttag                                                 18

<210> SEQ ID NO 41
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 41
gatcaatgtc tgtta                                                    15

<210> SEQ ID NO 42
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
ggcgatcaat gtctgtta                                                       18

<210> SEQ ID NO 43
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 43
gccagtcctt taggg                                                          15

<210> SEQ ID NO 44
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 44
gtgaatgcca gtcct                                                          15

<210> SEQ ID NO 45
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 45
acatcagtga atgcc                                                          15

<210> SEQ ID NO 46
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 46
acatccacat cagtg                                                          15

<210> SEQ ID NO 47
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 47
gaatcgacat ccaca                                                          15

<210> SEQ ID NO 48
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 48
```
ttgatggaat cgaca                                                15

<210> SEQ ID NO 49
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 49
gcaattttga tggaa                                                15

<210> SEQ ID NO 50
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 50
tcccaagcaa ttttg                                                15

<210> SEQ ID NO 51
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 51
gggctttccc aagca                                                15

<210> SEQ ID NO 52
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 52
ccctgtgggc tttcc                                                15

<210> SEQ ID NO 53
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 53
acttgcccct gtggg                                                15

<210> SEQ ID NO 54
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 54
ctggaaactt gcccc                                                15

<210> SEQ ID NO 55
<211> LENGTH: 15
<212> TYPE: DNA

```
<213> ORGANISM: Artificial sequence
<220> FEATURE:
<223> OTHER INFORMATION: Synthetic oligonucleotide

<400> SEQUENCE: 55
ctgtacctgg aaact                                               15

<210> SEQ ID NO 56
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 56
gtcaccctgt acctg                                               15

<210> SEQ ID NO 57
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 57
gagtaggtca ccctg                                               15

<210> SEQ ID NO 58
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 58
gggctcgagt aggtc                                               15

<210> SEQ ID NO 59
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 59
tcctcagggc tcgag                                               15

<210> SEQ ID NO 60
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 60
attccatcct caggg                                               15

<210> SEQ ID NO 61
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 61
tcatggattc catcc                                               15
```

<210> SEQ ID NO 62
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 62
aatagctcat ggatt                                                15

<210> SEQ ID NO 63
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 63
gcagggaata gctca                                                15

<210> SEQ ID NO 64
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 64
tcaggtgcag ggaat                                                15

<210> SEQ ID NO 65
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 65
tcaccatcag gtgca                                                15

<210> SEQ ID NO 66
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 66
tcttcttcac catca                                                15

<210> SEQ ID NO 67
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 67
gcagtgtctt cttca                                                15

<210> SEQ ID NO 68
<211> LENGTH: 15
<212> TYPE: DNA
<213> ORGANISM: Artificial sequence
<220> FEATURE:

<223> OTHER INFORMATION: Synthetic oligonucleotide

<400> SEQUENCE: 68
agctctgcag tgtct                                                        15

<210> SEQ ID NO 69
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 69
ccttgcagct ctgca                                                        15

<210> SEQ ID NO 70
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 70
ctgaggcctt gcagc                                                        15

<210> SEQ ID NO 71
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 71
cccggtctga ggcct                                                        15

<210> SEQ ID NO 72
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 72
tcagaacccg gtctg                                                        15

<210> SEQ ID NO 73
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 73
gtgtactcag aaccc                                                        15

<210> SEQ ID NO 74
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 74
ctgactgtgt actca                                                        15

```
<210> SEQ ID NO 75
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 75
accacactga ctgtg                                                    15

<210> SEQ ID NO 76
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 76
aaggcaacca cactg                                                    15

<210> SEQ ID NO 77
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 77
tcgtgcaagg caacc                                                    15

<210> SEQ ID NO 78
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 78
atatcatcgt gcaag                                                    15

<210> SEQ ID NO 79
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 79
ctctccatat catcg                                                    15

<210> SEQ ID NO 80
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 80
ggctggctct ccata                                                    15

<210> SEQ ID NO 81
<211> LENGTH: 15
<212> TYPE: DNA
<213> ORGANISM: Artificial sequence
<220> FEATURE:
<223> OTHER INFORMATION: Synthetic oligonucleotide
```

```
<400> SEQUENCE: 81
gattccaatc agggg                                                      15

<210> SEQ ID NO 82
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 82
actggattcc aatca                                                      15

<210> SEQ ID NO 83
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 83
tggactggat tccaa                                                      15

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
cctgtggact ggattcca                                                   18

<210> SEQ ID NO 85
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 85
ctgtggactg gattc                                                      15

<210> SEQ ID NO 86
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 86
tacctgtgga ctgga                                                      15

<210> SEQ ID NO 87
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 87
aacgatatac ctgtg                                                      15

<210> SEQ ID NO 88
<211> LENGTH: 15
```

<212> TYPE: DNA
<213> ORGANISM: Artificial sequence
<220> FEATURE:
<223> OTHER INFORMATION: Synthetic oligonucleotide

<400> SEQUENCE: 88
aattaatcat aaacc                                                15

<210> SEQ ID NO 89
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 89
ggtgcaatta accat                                                15

<210> SEQ ID NO 90
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 90
cctggtggtg caatt                                                15

<210> SEQ ID NO 91
<211> LENGTH: 20
<212> TYPE: DNA
<213> ORGANISM: Artificial sequence
<220> FEATURE:
<223> OTHER INFORMATION: Primer

<400> SEQUENCE: 91
gccttgcacg atgatatgga                                           20

<210> SEQ ID NO 92
<211> LENGTH: 21
<212> TYPE: DNA
<213> ORGANISM: Artificial sequence
<220> FEATURE:
<223> OTHER INFORMATION: Primer

<400> SEQUENCE: 92
tgtgggtgtg acctgagtga a                                         21

<210> SEQ ID NO 93
<211> LENGTH: 17
<212> TYPE: DNA
<213> ORGANISM: Artificial sequence
<220> FEATURE:
<223> OTHER INFORMATION: Probe

<400> SEQUENCE: 93
attggaaccc agtccac                                              17

<210> SEQ ID NO 94
<211> LENGTH: 21
<212> TYPE: DNA
<213> ORGANISM: Artificial sequence
<220> FEATURE:
<223> OTHER INFORMATION: Primer

<400> SEQUENCE: 94

```
gaatccaagc ggagagagtc a                                              21
```

<210> SEQ ID NO 95
<211> LENGTH: 23
<212> TYPE: DNA
<213> ORGANISM: Artificial sequence
<220> FEATURE:
<223> OTHER INFORMATION: Primer

<400> SEQUENCE: 95

```
acatcagtga atgccagtcc ttt                                            23
```

<210> SEQ ID NO 96
<211> LENGTH: 30
<212> TYPE: DNA
<213> ORGANISM: Artificial sequence
<220> FEATURE:
<223> OTHER INFORMATION: Probe

<400> SEQUENCE: 96

```
ttcagactgc agtaaccaac attgatcgcc                                     30
```

<210> SEQ ID NO 97
<211> LENGTH: 8374
<212> TYPE: DNA
<213> ORGANISM: Homo sapiens

<400> SEQUENCE: 97

```
gcccgcgccg gctgtgctgc acaggggagg gagagggaac cccaggcgcg agcgggaaga    60
ggggacctgc agccacaact tctctggtcc tctgcatccc ttctgtccct ccacccgtcc   120
ccttccccac cctctggccc ccaccttctt ggaggcgaca accccgggga ggcattagaa   180
gggatttttc ccgcaggttg cgaagggaag caaacttggt ggcaacttgc ctcccggtgc   240
gggcgtctct ccccaccgt ctcaacatgc ttaggggtcc ggggcccggg ctgctgctgc    300
tggccgtcca gtgcctgggg acagcggtgc cctccacggg agcctcgaag agcaagaggc   360
aggctcagca aatggttcag ccccagtccc cggtggctgt cagtcaaagc aagcccggtt   420
gttatgacaa tggaaaacac tatcagataa atcaacagtg ggagcggacc tacctaggca   480
atgcgttggt ttgtacttgt tatggaggaa gccgaggttt taactgcgag agtaaacctg   540
aagctgaaga gacttgcttt gacaagtaca ctgggaacac ttaccgagtg ggtgacactt   600
atgagcgtcc taaagactcc atgatctggg actgtacctg catcggggct gggcgaggga   660
gaataagctg taccatcgca aaccgctgcc atgaagggggg tcagtcctac aagattggtg   720
acacctggag gagaccacat gagactggtg gttacatgtt agagtgtgtg tgtcttggta   780
atggaaaagg agaatggacc tgcaagccca tagctgagaa gtgttttgat catgctgctg   840
ggacttccta tgtggtcgga gaaacgtggg agaagcccta ccaaggctgg atgatggtag   900
attgtacttg cctgggagaa ggcagcggac gcatcacttg cacttctaga aatagatgca   960
acgatcagga cacaaggaca tcctatagaa ttggagacac ctggagcaag aaggataatc  1020
gaggaaacct gctccagtgc atctgcacag gcaacggccg aggagagtgg aagtgtgaga  1080
ggcacacctc tgtgcagacc acatcgacg atctggccc cttcaccgat gttcgtgcag   1140
ctgtttacca accgcagcct cacccccagc ctcctcccta tggccactgt gtcacagaca  1200
gtggtgtggt ctactctgtg gggatgcagt ggctgaagac acaaggaaat aagcaaatgc  1260
tttgcacgtg cctgggcaac ggagtcagct gccaagagac agctgtaacc cagacttacg  1320
gtggcaactc aaatgagag ccatgtgtct taccattcac ctacaatggc aggacgttct  1380
```

-continued

```
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattggag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca gtggtcctg    2100 tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatgggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacaccttg cagaagtcac cgggctgtcc cctggggtca   3180
cctattactt caagtctttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccaggagg agaggcacca cgagaagtga   3660
cttcagactc aggaagcatc gttgtgtccg gcttgactcc aggagtagaa tacgtctaca   3720
```

```
ccatccaagt cctgagagat ggacaggaaa gagatgcgcc aattgtaaac aaagtggtga      3780
caccattgtc tccaccaaca aacttgcatc tggaggcaaa ccctgacact ggagtgctca      3840
cagtctcctg ggagaggagc accaccccag acattactgg ttatagaatt accacaaccc      3900
ctacaaacgg ccagcaggga aattctttgg aagaagtggt ccatgctgat cagagctcct      3960
gcacttttga taacctgagt cccggcctgg agtacaatgt cagtgtttac actgtcaagg      4020
atgacaagga aagtgtccct atctctgata ccatcatccc agctgttcct cctcccactg      4080
acctgcgatt caccaacatt ggtccagaca ccatgcgtgt cacctgggct ccacccccat      4140
ccattgattt aaccaacttc ctggtgcgtt actcacctgt gaaaaatgag gaagatgttg      4200
cagagttgtc aatttctcct tcagacaatg cagtggtctt aacaaatctc ctgcctggta      4260
cagaatatgt agtgagtgtc tccagtgtct acgaacaaca tgagagcaca cctcttagag      4320
gaagacagaa acaggtctt gattccccaa ctggcattga cttttctgat attactgcca      4380
actcttttac tgtgcactgg attgctcctc gagccaccat cactggctac aggatccgcc      4440
atcatcccga gcacttcagt gggagacctc gagaagatcg ggtgccccac tctcggaatt      4500
ccatcaccct caccaacctc actccaggca cagagtatgt ggtcagcatc gttgctctta      4560
atggcagaga ggaaagtccc ttattgattg ccaacaatc aacagtttct gatgttccga      4620
gggacctgga agttgttgct gcgaccccca ccagcctact gatcagctgg gatgctcctg      4680
ctgtcacagt gagatattac aggatcactt acggagagac aggaggaaat agccctgtcc      4740
aggagttcac tgtgcctggg agcaagtcta cagctaccat cagcggcctt aaacctggag      4800
ttgattatac catcactgtg tatgctgtca ctggccgtgg agacagcccc gcaagcagca      4860
agccaatttc cattaattac cgaacagaaa ttgacaaacc atcccagatg caagtgaccg      4920
atgttcagga acagcagcatt agtgtcaagt ggctgccttc aagttcccct gttactggtt      4980
acagagtaac caccactccc aaaaatggac caggaccaac aaaaactaaa actgcaggtc      5040
cagatcaaac agaaatgact attgaaggct tgcagcccac agtggagtat gtggttagtg      5100
tctatgctca gaatccaagc ggagagagtc agcctctggt tcagactgca gtaaccaaca      5160
ttgatcgccc taaaggactg gcattcactg atgtggatgt cgattccatc aaaattgctt      5220
gggaaagccc acagggcaa gtttccaggt acagggtgac ctactcgagc cctgaggatg      5280
gaatccatga gctattccct gcacctgatg gtgaagaaga cactgcagag ctgcaaggcc      5340
tcagaccggg ttctgagtac acagtcagtg tggttgcctt gcacgatgat atggagagcc      5400
agccctgat tggaacccag tccacagcta ttcctgcacc aactgacctg aagttcactc      5460
aggtcacacc cacaagcctg agcgcccagt ggacaccacc caatgttcag ctcactggat      5520
atcgagtgcg ggtgaccccc aaggagaaga ccggaccaat gaaagaaatc aaccttgctc      5580
ctgacagctc atccgtggtt gtatcaggac ttatggtggc caccaatat gaagtgagtg      5640
tctatgctct taaggacact ttgacaagca gaccagctca gggagttgtc accactctgg      5700
agaatgtcag cccaccaaga agggctcgtg tgacagatgc tactgagacc accatcacca      5760
ttagctggag aaccaagact gagacgatca ctggcttcca agttgatgcc gttccagcca      5820
atggccagac tccaatccag agaaccatca agccagatgt cagaagctac accatcacag      5880
gtttacaacc aggcactgac tacaagatct acctgtacac cttgaatgac aatgctcgga      5940
gctcccctgt ggtcatcgac gcctccactg ccattgatgc accatccaac ctgcgtttcc      6000
tggccaccac acccaattcc ttgctggtat catggcagcc gccacgtgcc aggattaccg      6060
gctacatcat caagtatgag aagcctgggt ctcctcccag agaagtggtc cctcggcccc      6120
```

```
gccctggtgt cacagaggct actattactg gcctggaacc gggaaccgaa tatacaattt    6180
atgtcattgc cctgaagaat aatcagaaga gcgagcccct gattggaagg aaaaagacag    6240
ttcaaaagac ccctttcgtc acccaccctg ggtatgacac tggaaatggt attcagcttc    6300
ctggcacttc tggtcagcaa cccagtgttg ggcaacaaat gatctttgag gaacatggtt    6360
ttaggcggac cacaccgccc acaacggcca ccccataag gcataggcca agaccatacc     6420
cgccgaatgt aggacaagaa gctctctctc agacaaccat ctcatgggcc ccattccagg    6480
acacttctga gtacatcatt tcatgtcatc ctgttggcac tgatgaagaa cccttacagt    6540
tcagggttcc tggaacttct accagtgcca ctctgacagg cctcaccaga ggtgccacct    6600
acaacatcat agtggaggca ctgaaagacc agcagaggca taaggttcgg aagaggttg     6660 ttaccgtggg caactctgtc aacgaaggct tgaaccaacc tacggatgac tcgtgctttg    6720
acccctacac agtttcccat tatgccgttg gagatgagtg ggaacgaatg tctgaatcag    6780
gctttaaact gttgtgccag tgcttaggct ttggaagtgg tcatttcaga tgtgattcat    6840
ctagatggtg ccatgacaat ggtgtgaact acaagattgg agagaagtgg gaccgtcagg    6900
gagaaaatgg ccagatgatg agctgcacat gtcttgggaa cggaaaagga gaattcaagt    6960
gtgaccctca tgaggcaacg tgttatgatg atgggaagac ataccacgta ggagaacagt    7020
ggcagaagga atatctcggt gccatttgct cctgcacatg cttggaggc cagcggggct    7080 ggcgctgtga caactgccgc agacctgggg gtgaacccag tcccgaaggc actactggcc    7140
agtcctacaa ccagtattct cagagatacc atcagagaac aaacactaat gttaattgcc    7200
caattgagtg cttcatgcct ttagatgtac aggctgacag agaagattcc cgagagtaaa    7260
tcatctttcc aatccagagg aacaagcatg tctctctgcc aagatccatc taaactggag    7320
tgatgttagc agacccagct tagagttctt cttctttct aagccctttt gctctggagg     7380
aagttctcca gcttcagctc aactcacagc ttctccaagc atcaccctgg gagtttcctg    7440
agggttttct cataaatgag ggctgcacat tgcctgttct gcttcgaagt attcaatacc    7500
gctcagtatt ttaaatgaag tgattctaag atttggtttg ggatcaatag gaaagcatat    7560
gcagccaacc aagatgcaaa tgtttgaaa tgatatgacc aaaattttaa gtaggaaagt     7620
cacccaaaca cttctgcttt cacttaagtg tctggcccgc aatactgtag gaacaagcat    7680
gatcttgtta ctgtgatatt ttaaatatcc acagtactca cttttttccaa atgatcctag    7740 taattgccta gaaatatctt tctcttacct gttatttatc aatttttccc agtattttta    7800
tacgaaaaaa attgtattga aaacacttag tatgcagttg ataagaggaa tttggtataa    7860
ttatggtggg tgattatttt ttatactgta tgtgccaaag ctttactact gtggaaagac    7920
aactgtttta ataaaagatt tacattccac aacttgaagt tcatctattt gatataagac    7980
accttcgggg gaaataattc ctgtgaatat tcttttcaa ttcagcaaac atttgaaaat     8040
ctatgatgtg caagtctaat tgttgatttc agtacaagat tttctaaatc agttgctaca    8100
aaaactgatt ggttttgtc acttcatctc ttcactaatg gagatagctt tacactttct     8160
gctttaatag atttaagtgg accccaatat ttattaaaat tgctagttta ccgttcagaa    8220
gtataataga aataatcttt agttgctctt ttctaaccat tgtaattctt cccttcttcc    8280
ctccaccttt ccttcattga ataaacctct gttcaaagag attgcctgca agggaaataa    8340
aaatgactaa gatattaaaa aaaaaaaaaa aaaa                                8374
```

<210> SEQ ID NO 98

```
<211> LENGTH: 24
<212> TYPE: DNA
<213> ORGANISM: Artificial sequence
<220> FEATURE:
<223> OTHER INFORMATION: Primer

<400> SEQUENCE: 98
aaactgcagt gaccaacatt gatc                                              24

<210> SEQ ID NO 99
<211> LENGTH: 18
<212> TYPE: DNA
<213> ORGANISM: Artificial sequence
<220> FEATURE:
<223> OTHER INFORMATION: Primer

<400> SEQUENCE: 99
cttgcccctg tgggcttt                                                     18

<210> SEQ ID NO 100
<211> LENGTH: 18
<212> TYPE: DNA
<213> ORGANISM: Artificial sequence
<220> FEATURE:
<223> OTHER INFORMATION: Probe

<400> SEQUENCE: 100
ctgatgtgga tgtcgatt                                                     18

<210> SEQ ID NO 101
<211> LENGTH: 17
<212> TYPE: DNA
<213> ORGANISM: Artificial sequence
<220> FEATURE:
<223> OTHER INFORMATION: Primer

<400> SEQUENCE: 101
gccagcccct gattgga                                                      17

<210> SEQ ID NO 102
<211> LENGTH: 20
<212> TYPE: DNA
<213> ORGANISM: Artificial sequence
<220> FEATURE:
<223> OTHER INFORMATION: Primer

<400> SEQUENCE: 102
ccggtagcca gtgagctgaa                                                   20

<210> SEQ ID NO 103
<211> LENGTH: 16
<212> TYPE: DNA
<213> ORGANISM: Artificial sequence
<220> FEATURE:
<223> OTHER INFORMATION: Probe

<400> SEQUENCE: 103
caccaatctg aagttc                                                       16

<210> SEQ ID NO 104
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 104
```
gcaaattaat ggtaa                                                15

<210> SEQ ID NO 105
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 105
cgatcaatgt ctgtt                                                15

<210> SEQ ID NO 106
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 106
tccataccat gcaaa                                                15

<210> SEQ ID NO 107
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 107
atatttccat accat                                                15

<210> SEQ ID NO 108
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 108
caagcatatt tccat                                                15

<210> SEQ ID NO 109
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 109
tgaaacaagc atatt                                                15

<210> SEQ ID NO 110
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 110
agttgtgaaa caagc                                                15

<210> SEQ ID NO 111
<211> LENGTH: 15
<212> TYPE: DNA

<213> ORGANISM: Artificial sequence
<220> FEATURE:
<223> OTHER INFORMATION: Synthetic oligonucleotide

<400> SEQUENCE: 111
aagcaagttg tgaaa                                                       15

<210> SEQ ID NO 112
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 112
gtgaaaagca agttg                                                       15

<210> SEQ ID NO 113
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 113
gttatgtgaa aagca                                                       15

<210> SEQ ID NO 114
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 114
aagaggttat gtgaa                                                       15

<210> SEQ ID NO 115
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 115
atggtaagag gttat                                                       15

<210> SEQ ID NO 116
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 116
aattaatggt aagag                                                       15

<210> SEQ ID NO 117
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 117
aggcaaatta atggt                                                       15

<210> SEQ ID NO 118
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 118
ctgttaggca aatta                                                        15

<210> SEQ ID NO 119
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 119
tagggcgatc aatgt                                                        15

<210> SEQ ID NO 120
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 120
tcctttaggg cgatc                                                        15

<210> SEQ ID NO 121
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 121
tgaatgccag tcctt                                                        15

<210> SEQ ID NO 122
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 122
atcagtgaat gccag                                                        15

<210> SEQ ID NO 123
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 123
tccacatcag tgaat                                                        15

<210> SEQ ID NO 124
<211> LENGTH: 15
<212> TYPE: DNA
<213> ORGANISM: Artificial sequence
<220> FEATURE:

```
<223> OTHER INFORMATION: Synthetic oligonucleotide

<400> SEQUENCE: 124
cgacatccac atcag                                                    15

<210> SEQ ID NO 125
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 125
ggaatcgaca tccac                                                    15

<210> SEQ ID NO 126
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 126
caattttgat ggaat                                                    15

<210> SEQ ID NO 127
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 127
ccaagcaatt ttgat                                                    15

<210> SEQ ID NO 128
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 128
ctttcccaag caatt                                                    15

<210> SEQ ID NO 129
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 129
gtgggctttc ccaag                                                    15

<210> SEQ ID NO 130
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 130
cccctgtggg ctttc                                                    15
```

```
<210> SEQ ID NO 131
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 131
tggaaacttg ccccct                                                    15

<210> SEQ ID NO 132
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 132
gtacctggaa acttg                                                     15

<210> SEQ ID NO 133
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 133
accctgtacc tggaa                                                     15

<210> SEQ ID NO 134
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 134
aggtcaccct gtacc                                                     15

<210> SEQ ID NO 135
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 135
cgagtaggtc accct                                                     15

<210> SEQ ID NO 136
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 136
cctcagggct cgagt                                                     15

<210> SEQ ID NO 137
<211> LENGTH: 15
<212> TYPE: DNA
<213> ORGANISM: Artificial sequence
<220> FEATURE:
<223> OTHER INFORMATION: Synthetic oligonucleotide
```

```
<400> SEQUENCE: 137
tccatcctca gggct                                                    15

<210> SEQ ID NO 138
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 138
cggattccat cctca                                                    15

<210> SEQ ID NO 139
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 139
gctcccggat tccat                                                    15

<210> SEQ ID NO 140
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 140
gaaaagctcc cggat                                                    15

<210> SEQ ID NO 141
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 141
gcagggaaaa gctcc                                                    15

<210> SEQ ID NO 142
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 142
caggtgcagg gaaaa                                                    15

<210> SEQ ID NO 143
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 143
accatcaggt gcagg                                                    15

<210> SEQ ID NO 144
<211> LENGTH: 15
```

```
<212> TYPE: DNA
<213> ORGANISM: Artificial sequence
<220> FEATURE:
<223> OTHER INFORMATION: Synthetic oligonucleotide

<400> SEQUENCE: 144
tcttcaccat caggt                                                      15

<210> SEQ ID NO 145
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 145
tgtcgtcttc accat                                                      15

<210> SEQ ID NO 146
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 146
tgcagtgtcg tcttc                                                      15

<210> SEQ ID NO 147
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 147
agctctgcag tgtcg                                                      15

<210> SEQ ID NO 148
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 148
cctgcagctc tgcag                                                      15

<210> SEQ ID NO 149
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 149
gaggccctgc agctc                                                      15

<210> SEQ ID NO 150
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 150
```

-continued

```
ggcctgaggc cctgc                                                    15

<210> SEQ ID NO 151
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 151
accccggcct gaggc                                                    15

<210> SEQ ID NO 152
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 152
ctcagacccc ggcct                                                    15

<210> SEQ ID NO 153
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 153
gtgtactcag acccc                                                    15

<210> SEQ ID NO 154
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 154
tgactgtgta ctcag                                                    15

<210> SEQ ID NO 155
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 155
cacactgact gtgta                                                    15

<210> SEQ ID NO 156
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 156
gcaaccacac tgact                                                    15

<210> SEQ ID NO 157
<211> LENGTH: 15
<212> TYPE: DNA
<213> ORGANISM: Artificial sequence
```

```
<220> FEATURE:
<223> OTHER INFORMATION: Synthetic oligonucleotide

<400> SEQUENCE: 157
gcaaggcaac cacac                                                   15

<210> SEQ ID NO 158
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 158
atcgtgcaag gcaac                                                   15

<210> SEQ ID NO 159
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 159
tctccatatc atcgt                                                   15

<210> SEQ ID NO 160
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 160
ctggctctcc atatc                                                   15

<210> SEQ ID NO 161
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 161
gactggattc caatc                                                   15

<210> SEQ ID NO 162
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 162
tatacctgtg gactg                                                   15

<210> SEQ ID NO 163
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 163
cggttaacga tatac                                                   15
```

<210> SEQ ID NO 164
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 164
gggtgcggtt aacga                                                      15

<210> SEQ ID NO 165
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 165
gtggtgggtg cggtt                                                      15

<210> SEQ ID NO 166
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 166
cccgggtggt gggtg                                                      15

<210> SEQ ID NO 167
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 167
aagcacccgg gtggt                                                      15

<210> SEQ ID NO 168
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 168
cccagaagca cccgg                                                      15

<210> SEQ ID NO 169
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 169
ctgttcccag aagca                                                      15

<210> SEQ ID NO 170
<211> LENGTH: 15
<212> TYPE: DNA
<213> ORGANISM: Artificial sequence
<220> FEATURE:
<223> OTHER INFORMATION: Synthetic oligonucleotide -continued

<400> SEQUENCE: 170
agccactgtt cccag                                                        15

<210> SEQ ID NO 171
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 171
cataaagcca ctgtt                                                        15

<210> SEQ ID NO 172
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 172
caaggcataa agcca                                                        15

<210> SEQ ID NO 173
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 173
gccagcaagg cataa                                                        15

<210> SEQ ID NO 174
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 174
ataacgccag caagg                                                        15

<210> SEQ ID NO 175
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 175
aaagtataac gccag                                                        15

<210> SEQ ID NO 176
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 176
ccagtaaagt ataac                                                        15

<210> SEQ ID NO 177

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
gttaggcaaa ttaatggt                                                 18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
tgttaggcaa attaatgg                                                 18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
ctgttaggca aattaatg                                                 18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
tctgttaggc aaattaat                                                 18

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181
gtctgttagg caaattaa                                                 18

<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
tgtctgttag gcaaatta                                                 18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
```
atgtctgtta ggcaaatt                                                18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
gatcaatgtc tgttaggc                                                18

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185
gggcgatcaa tgtctgtt                                                18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
agggcgatca atgtctgt                                                18

<210> SEQ ID NO 187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 187
tagggcgatc aatgtctg                                                18

<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 188
ttagggcgat caatgtct                                                18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189
tttagggcga tcaatgtc                                                18

<210> SEQ ID NO 190
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 190
ctttagggcg atcaatgt                                                   18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
cctttagggc gatcaatg                                                   18

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
tcctttaggg cgatcaat                                                   18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
gtcctttagg gcgatcaa                                                   18

<210> SEQ ID NO 194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 194
agtcctttag ggcgatca                                                   18

<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
cagtccttta gggcgatc                                                   18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
ggaatcgaca tccacatc                                                   18

```
<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
tggaatcgac atccacat                                                 18

<210> SEQ ID NO 198
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 198
atggaatcga catccaca                                                 18

<210> SEQ ID NO 199
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 199
gatggaatcg acatccac                                                 18

<210> SEQ ID NO 200
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 200
tgatggaatc gacatcca                                                 18

<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
ttgatggaat cgacatcc                                                 18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
tttgatggaa tcgacatc                                                 18

<210> SEQ ID NO 203
<211> LENGTH: 18
<212> TYPE: DNA
<213> ORGANISM: Artificial sequence
<220> FEATURE:
```

<223> OTHER INFORMATION: Synthetic oligonucleotide

<400> SEQUENCE: 203
caattttgat ggaatcga                                            18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
gcaattttga tggaatcg                                            18

<210> SEQ ID NO 205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
agcaattttg atggaatc                                            18

<210> SEQ ID NO 206
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 206
aagcaatttt gatggaat                                            18

<210> SEQ ID NO 207
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 207
caagcaattt tgatggaa                                            18

<210> SEQ ID NO 208
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 208
ccaagcaatt ttgatgga                                            18

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 209
cccaagcaat tttgatgg                                            18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 210
gtcaccctgt acctggaa                                                 18

<210> SEQ ID NO 211
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 211
ggtcaccctg tacctgga                                                 18

<210> SEQ ID NO 212
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 212
aggtcaccct gtacctgg                                                 18

<210> SEQ ID NO 213
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 213
taggtcaccc tgtacctg                                                 18

<210> SEQ ID NO 214
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 214
gtaggtcacc ctgtacct                                                 18

<210> SEQ ID NO 215
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 215
agtaggtcac cctgtacc                                                 18

<210> SEQ ID NO 216
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 216
gagtaggtca ccctgtac    18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 217
cgagtaggtc accctgta    18

<210> SEQ ID NO 218
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 218
tcgagtaggt caccctgt    18

<210> SEQ ID NO 219
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 219
ctcgagtagg tcaccctg    18

<210> SEQ ID NO 220
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 220
gctcgagtag gtcaccct    18

<210> SEQ ID NO 221
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 221
ggctcgagta ggtcaccc    18

<210> SEQ ID NO 222
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 222
gggctcgagt aggtcacc    18

<210> SEQ ID NO 223
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 223
agggctcgag taggtcac                                                   18

<210> SEQ ID NO 224
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 224
cagggctcga gtaggtca                                                   18

<210> SEQ ID NO 225
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 225
tcagggctcg agtaggtc                                                   18

<210> SEQ ID NO 226
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 226
ctcagggctc gagtaggt                                                   18

<210> SEQ ID NO 227
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 227
cctcagggct cgagtagg                                                   18

<210> SEQ ID NO 228
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 228
tcctcagggc tcgagtag                                                   18

<210> SEQ ID NO 229
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 229
```
atcctcaggg ctcgagta                                          18

<210> SEQ ID NO 230
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 230
catcctcagg gctcgagt                                          18

<210> SEQ ID NO 231
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 231
ccatcctcag ggctcgag                                          18

<210> SEQ ID NO 232
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 232
tccatcctca gggctcga                                          18

<210> SEQ ID NO 233
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 233
ttccatcctc agggctcg                                          18

<210> SEQ ID NO 234
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 234
attccatcct cagggctc                                          18

<210> SEQ ID NO 235
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 235
gattccatcc tcagggct                                          18

<210> SEQ ID NO 236
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 236
ggattccatc ctcagggc                                                  18

<210> SEQ ID NO 237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 237
cggattccat cctcaggg                                                  18

<210> SEQ ID NO 238
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 238
ccggattcca tcctcagg                                                  18

<210> SEQ ID NO 239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 239
cccggattcc atcctcag                                                  18

<210> SEQ ID NO 240
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 240
tcccggattc catcctca                                                  18

<210> SEQ ID NO 241
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 241
ctcccggatt ccatcctc                                                  18

<210> SEQ ID NO 242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 242
gctcccggat tccatcct                                                  18

<210> SEQ ID NO 243
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 243
agctcccgga ttccatcc                                                   18

<210> SEQ ID NO 244
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 244
aagctcccgg attccatc                                                   18

<210> SEQ ID NO 245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 245
aaagctcccg gattccat                                                   18

<210> SEQ ID NO 246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 246
aaaagctccc ggattcca                                                   18

<210> SEQ ID NO 247
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 247
gaaaagctcc cggattcc                                                   18

<210> SEQ ID NO 248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 248
ggaaaagctc ccggattc                                                   18

<210> SEQ ID NO 249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 249
gggaaaagct cccggatt                                            18

<210> SEQ ID NO 250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 250
agggaaaagc tcccggat                                            18

<210> SEQ ID NO 251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 251
cagggaaaag ctcccgga                                            18

<210> SEQ ID NO 252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 252
gcagggaaaa gctcccgg                                            18

<210> SEQ ID NO 253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 253
tgcagggaaa agctcccg                                            18

<210> SEQ ID NO 254
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 254
gtgcagggaa aagctccc                                            18

<210> SEQ ID NO 255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 255
ggtgcaggga aaagctcc                                            18

<210> SEQ ID NO 256

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 256
aggtgcaggg aaaagctc                                                   18

<210> SEQ ID NO 257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 257
caggtgcagg gaaaagct                                                   18

<210> SEQ ID NO 258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 258
tcaggtgcag ggaaaagc                                                   18

<210> SEQ ID NO 259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 259
atcaggtgca gggaaaag                                                   18

<210> SEQ ID NO 260
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 260
catcaggtgc agggaaaa                                                   18

<210> SEQ ID NO 261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 261
ccatcaggtg cagggaaa                                                   18

<210> SEQ ID NO 262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 262
```
accatcaggt gcagggaa                                                   18

<210> SEQ ID NO 263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 263
caccatcagg tgcaggga                                                   18

<210> SEQ ID NO 264
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 264
tcaccatcag gtgcaggg                                                   18

<210> SEQ ID NO 265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 265
ttcaccatca ggtgcagg                                                   18

<210> SEQ ID NO 266
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 266
cttcaccatc aggtgcag                                                   18

<210> SEQ ID NO 267
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 267
tcttcaccat caggtgca                                                   18

<210> SEQ ID NO 268
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 268
gtcttcacca tcaggtgc                                                   18

<210> SEQ ID NO 269
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 269
cgtcttcacc atcaggtg                                                18

<210> SEQ ID NO 270
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 270
tcgtcttcac catcaggt                                                18

<210> SEQ ID NO 271
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 271
gtcgtcttca ccatcagg                                                18

<210> SEQ ID NO 272
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 272
tgtcgtcttc accatcag                                                18

<210> SEQ ID NO 273
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 273
gtgtcgtctt caccatca                                                18

<210> SEQ ID NO 274
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 274
agtgtcgtct tcaccatc                                                18

<210> SEQ ID NO 275
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 275
cagtgtcgtc ttcaccat                                                18

<210> SEQ ID NO 276
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 276
gcagtgtcgt cttcacca                                              18

<210> SEQ ID NO 277
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 277
tgcagtgtcg tcttcacc                                              18

<210> SEQ ID NO 278
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 278
ctgcagtgtc gtcttcac                                              18

<210> SEQ ID NO 279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 279
tctgcagtgt cgtcttca                                              18

<210> SEQ ID NO 280
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 280
ctctgcagtg tcgtcttc                                              18

<210> SEQ ID NO 281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 281
gctctgcagt gtcgtctt                                              18

<210> SEQ ID NO 282
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 282
agctctgcag tgtcgtct					18

<210> SEQ ID NO 283
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 283
cagctctgca gtgtcgtc					18

<210> SEQ ID NO 284
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 284
gcagctctgc agtgtcgt					18

<210> SEQ ID NO 285
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 285
tgcagctctg cagtgtcg					18

<210> SEQ ID NO 286
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 286
ctgcagctct gcagtgtc					18

<210> SEQ ID NO 287
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 287
cctgcagctc tgcagtgt					18

<210> SEQ ID NO 288
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 288
ccctgcagct ctgcagtg					18

```
<210> SEQ ID NO 289
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 289
gccctgcagc tctgcagt                                                 18

<210> SEQ ID NO 290
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 290
ggccctgcag ctctgcag                                                 18

<210> SEQ ID NO 291
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 291
aggccctgca gctctgca                                                 18

<210> SEQ ID NO 292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 292
gaggccctgc agctctgc                                                 18

<210> SEQ ID NO 293
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 293
tgaggccctg cagctctg                                                 18

<210> SEQ ID NO 294
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 294
ctgaggccct gcagctct                                                 18

<210> SEQ ID NO 295
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 295
cctgaggccc tgcagctc                                            18

<210> SEQ ID NO 296
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 296
gcaaggcaac cacactga                                            18

<210> SEQ ID NO 297
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 297
tgcaaggcaa ccacactg                                            18

<210> SEQ ID NO 298
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 298
gtgcaaggca accacact                                            18

<210> SEQ ID NO 299
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 299
cgtgcaaggc aaccacac                                            18

<210> SEQ ID NO 300
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 300
tcgtgcaagg caaccaca                                            18

<210> SEQ ID NO 301
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 301
atcgtgcaag gcaaccac                                            18

<210> SEQ ID NO 302
<211> LENGTH: 18

-continued

<212> TYPE: DNA
<213> ORGANISM: Artificial sequence
<220> FEATURE:
<223> OTHER INFORMATION: Synthetic oligonucleotide

<400> SEQUENCE: 302
catcgtgcaa ggcaacca                                                     18

<210> SEQ ID NO 303
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 303
atatcatcgt gcaaggca                                                     18

<210> SEQ ID NO 304
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 304
catatcatcg tgcaaggc                                                     18

<210> SEQ ID NO 305
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 305
ccatatcatc gtgcaagg                                                     18

<210> SEQ ID NO 306
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 306
tccatatcat cgtgcaag                                                     18

<210> SEQ ID NO 307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 307
ctccatatca tcgtgcaa                                                     18

<210> SEQ ID NO 308
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 308

```
tctccatatc atcgtgca                                              18

<210> SEQ ID NO 309
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 309
ctctccatat catcgtgc                                              18

<210> SEQ ID NO 310
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 310
gctctccata tcatcgtg                                              18

<210> SEQ ID NO 311
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 311
ggctctccat atcatcgt                                              18

<210> SEQ ID NO 312
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 312
tggctctcca tatcatcg                                              18

<210> SEQ ID NO 313
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 313
ctggctctcc atatcatc                                              18

<210> SEQ ID NO 314
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 314
gctggctctc catatcat                                              18

<210> SEQ ID NO 315
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 315
atatacctgt ggactgga                                                   18

<210> SEQ ID NO 316
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 316
gatatacctg tggactgg                                                   18

<210> SEQ ID NO 317
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 317
cgatatacct gtggactg                                                   18

<210> SEQ ID NO 318
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 318
acgatatacc tgtggact                                                   18

<210> SEQ ID NO 319
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 319
aacgatatac ctgtggac                                                   18

<210> SEQ ID NO 320
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 320
taacgatata cctgtgga                                                   18

<210> SEQ ID NO 321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 321
ttaacgatat acctgtgg                                                   18
```

<210> SEQ ID NO 322
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 322
gttaacgata tacctgtg                                                 18

<210> SEQ ID NO 323
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 323
ggttaacgat atacctgt                                                 18

<210> SEQ ID NO 324
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 324
cggttaacga tatacctg                                                 18

<210> SEQ ID NO 325
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 325
gcggttaacg atatacct                                                 18

<210> SEQ ID NO 326
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 326
tgcggttaac gatatacc                                                 18

<210> SEQ ID NO 327
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 327
gtgcggttaa cgatatac                                                 18

<210> SEQ ID NO 328
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 328
ggtgcggtta acgatata                                                    18

<210> SEQ ID NO 329
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 329
gggtgcggtt aacgatat                                                    18

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 330
agggaaaagc tcccgg                                                      16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 331
gtcaccctgt acctgg                                                      16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 332
gtaggtcacc ctgtac                                                      16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 333
tcgagtaggt caccct                                                      16

<210> SEQ ID NO 334
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 334
gggctcgagt aggtca                                                      16

<210> SEQ ID NO 335
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 335
ctcagggctc gagtag                                                       16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 336
catcctcagg gctcga                                                       16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 337
attccatcct cagggc                                                       16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 338
ccggattcca tcctca                                                       16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 339
gctcccggat tccatc                                                       16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 340
aaaagctccc ggattc                                                       16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 341
```
gtgcagggaa aagctc                                                 16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 342
tcaggtgcag ggaaaa                                                 16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 343
accatcaggt gcaggg                                                 16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 344
cttcaccatc aggtgc                                                 16

<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 345
tcgtcttcac catcag                                                 16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 346
agtgtcgtct tcacca                                                 16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 347
ctgcagtgtc gtcttc                                                 16

<210> SEQ ID NO 348
<211> LENGTH: 16
<212> TYPE: DNA

-continued

```
<213> ORGANISM: Artificial sequence
<220> FEATURE:
<223> OTHER INFORMATION: Synthetic oligonucleotide

<400> SEQUENCE: 348
agctctgcag tgtcgt                                                      16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 349
ctgcagctct gcagtg                                                      16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 350
ggccctgcag ctctgc                                                      16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 351
ctgaggccct gcagct                                                      16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 352
cggcctgagg ccctgc                                                      16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 353
accccggcct gaggcc                                                      16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 354
tcagaccccg gcctga                                                      16
```

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 355
gtactcagac cccggc                                                     16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 356
ctgtgtactc agaccc                                                     16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
ctgactgtgt actcag                                                     16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 358
cacactgact gtgtac                                                     16

<210> SEQ ID NO 359
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 359
caaccacact gactgt                                                     16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 360
aaggcaacca cactga                                                     16

<210> SEQ ID NO 361
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 361
gtgcaaggca accaca                                                          16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 362
catcgtgcaa ggcaac                                                          16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 363
atatcatcgt gcaagg                                                          16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 364
ctccatatca tcgtgc                                                          16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 365
ggctctccat atcatc                                                          16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 366
ggctggctct ccatat                                                          16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 367
ctggattcca atcagg                                                          16

```
<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 368
tggactggat tccaat                                                       16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 369
cctgtggact ggattc                                                       16

<210> SEQ ID NO 370
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 370
tatacctgtg gactgg                                                       16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 371
acgatatacc tgtgga                                                       16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 372
gttaacgata tacctg                                                       16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 373
tgcggttaac gatata                                                       16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 374
tgggtgcggt taacga                                                  16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 375
aaattaatgg taagag                                                  16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 376
aggcaaatta atggta                                                  16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 377
tgttaggcaa attaat                                                  16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 378
tgtctgttag gcaaat                                                  16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 379
tcaatgtctg ttaggc                                                  16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 380
gcgatcaatg tctgtt                                                  16

<210> SEQ ID NO 381
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 381
tagggcgatc aatgtc                                                      16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 382
cctttagggc gatcaa                                                      16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 383
cagtccttta gggcga                                                      16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 384
atgccagtcc tttagg                                                      16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 385
gtgaatgcca gtcctt                                                      16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 386
atcagtgaat gccagt                                                      16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 387
```

-continued ccacatcagt gaatgc                                          16

<210> SEQ ID NO 388
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 388
acatccacat cagtga                                          16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 389
atcgacatcc acatca                                          16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 390
tggaatcgac atccac                                          16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 391
ttgatggaat cgacat                                          16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 392
aattttgatg gaatcg                                          16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 393 aagcaattttt gatgga                                         16

<210> SEQ ID NO 394
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 394
tcccaagcaa ttttga                                                    16

<210> SEQ ID NO 395
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 395
gctttcccaa gcaatt                                                    16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 396
gtgggctttc ccaagc                                                    16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 397
ccctgtgggc tttccc                                                    16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 398
ttgcccctgt gggctt                                                    16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 399
aaacttgccc ctgtgg                                                    16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 400
ctggaaactt gcccct                                                    16
```

```
<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 401
gtacctggaa acttgc                                                      16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 402
ccctgtacct ggaaac                                                      16

<210> SEQ ID NO 403
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 403
gcctgaggcc ctgcagct                                                    18

<210> SEQ ID NO 404
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 404
cccggcctga ggccctgc                                                    18

<210> SEQ ID NO 405
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 405
agaccccggc ctgaggcc                                                    18

<210> SEQ ID NO 406
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 406
actcagaccc cggcctga                                                    18

<210> SEQ ID NO 407
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 407
gtgtactcag accccggc                                                  18

<210> SEQ ID NO 408
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 408
gactgtgtac tcagaccc                                                  18

<210> SEQ ID NO 409
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 409
cactgactgt gtactcag                                                  18

<210> SEQ ID NO 410
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 410
accacactga ctgtgtac                                                  18

<210> SEQ ID NO 411
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 411
ggcaaccaca ctgactgt                                                  18

<210> SEQ ID NO 412
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 412
atcatcgtgc aaggcaac                                                  18

<210> SEQ ID NO 413
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 413
gactggattc caatcagg                                                  18

<210> SEQ ID NO 414
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 414
tgtggactgg attccaat                                                   18

<210> SEQ ID NO 415
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 415
tacctgtgga ctggattc                                                   18

<210> SEQ ID NO 416
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 416
ggtgggtgcg gttaacga                                                   18

<210> SEQ ID NO 417
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 417
gcaaattaat ggtaagag                                                   18

<210> SEQ ID NO 418
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 418
ttaggcaaat taatggta                                                   18

<210> SEQ ID NO 419
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 419
gccagtcctt tagggcga                                                   18

<210> SEQ ID NO 420
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 420
```

-continued gaatgccagt cctttagg    18

<210> SEQ ID NO 421
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 421
cagtgaatgc cagtcctt    18

<210> SEQ ID NO 422
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 422
acatcagtga atgccagt    18

<210> SEQ ID NO 423
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 423
atccacatca gtgaatgc    18

<210> SEQ ID NO 424
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 424
cgacatccac atcagtga    18

<210> SEQ ID NO 425
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 425
gaatcgacat ccacatca    18

<210> SEQ ID NO 426
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 426
ttttgatgga atcgacat    18

<210> SEQ ID NO 427
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 427
tttcccaagc aattttga                                                 18

<210> SEQ ID NO 428
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 428
gggctttccc aagcaatt                                                 18

<210> SEQ ID NO 429
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 429
ctgtgggctt tcccaagc                                                 18

<210> SEQ ID NO 430
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 430 gccctgtgg gctttccc                                                  18

<210> SEQ ID NO 431
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 431
acttgcccct gtgggctt                                                 18

<210> SEQ ID NO 432
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 432
ggaaacttgc ccctgtgg                                                 18

<210> SEQ ID NO 433
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 433
acctggaaac ttgcccct                                                 18
```

```
<210> SEQ ID NO 434
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 434
ctgtacctgg aaacttgc                                                18

<210> SEQ ID NO 435
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 435
caccctgtac ctggaaac                                                18
```

US 9,828,602 B2

ANTISENSE COMPOUNDS TARGETING GENES ASSOCIATED WITH FIBRONECTIN

CROSS REFERENCED TO RELATED APPLICATIONS

This application is a U.S. National Phase filing under 35 U.S.C. §371 claiming priority to International Serial No. PCT/US2013/043935 filed Jun. 3, 2013, which claims priority to U.S. Provisional Application 61/721,993, filed Nov. 2, 2012, and U.S. Provisional Application 61/654,757, filed Jun. 1, 2012 each of which is incorporated herein by reference in its entirety.

SEQUENCE LISTING

The present application is being filed along with a Sequence Listing in electronic format. The Sequence Listing is provided as a file entitled BIOL0197USASEQ_ST23.txt created Nov. 25, 2014, which is 280 Kb in size. The information in the electronic format of the sequence listing is incorporated herein by reference in its entirety.

BACKGROUND OF THE INVENTION

Fibronectin is a high-molecular weight glycoprotein of the extracellular matrix that binds to membrane-spanning receptor integrin proteins. Fibronectin has been implicated in a number of fibrotic disorders, including renal fibrosis. Alternative splicing of fibronectin pre-mRNA leads to the creation of fibronectin mRNA having a different combination of exons, which in turn leads to the creation of several isoforms of fibronectin protein. In certain instances, alternative splicing of the fibronectin gene results in a fibronectin protein isoform containing the extra type III domain A (EDA). Fibronectin containing extra type III domain A (EDA) is implicated in the formation of fibrosis. See, e.g., Muro et al., *An Essential Role for Fibronectin Extra Type III Domain A in Pulmonary Fibrosis*, American Journal of Respiratory and Critical Care Medicine, Vol. 177, 638 (2008).

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See for example U.S. Pat. No. 7,399,845 and published International Patent Application No. WO 2008/049085, which are hereby incorporated by reference herein in their entirety.

SUMMARY OF THE INVENTION

In certain embodiments, the present invention provides compounds comprising oligonucleotides. In certain embodiments, such oligonucleotides are complementary to a fibronectin transcript. In certain such embodiments, oligonucleotides are complementary to a target region of the fibronectin transcript comprising the EDA exon. In certain such embodiments, oligonucleotides are complementary to a target region of the fibronectin transcript comprising an intron adjacent to the EDA exon. In certain such embodiments, oligonucleotides are complementary to a target region of the fibronectin transcript comprising an intron adjacent to the EDA exon and downstream of the EDA exon. In certain such embodiments, oligonucleotides are complementary to a target region of the fibronectin transcript comprising an intron adjacent to the EDA exon and upstream of the EDA exon. In certain embodiments, the fibronectin transcript comprises an exonic splice enhancer for the EDA exon. In certain embodiments, the fibronectin transcript comprises an exonic splice silencer for the EDA exon. In certain embodiments, oligonucleotides inhibit inclusion of the EDA exon. In certain embodiments, oligonucleotides promote skipping of the of the EDA exon. In certain such embodiments, fibronectin mRNA without EDA mRNA is increased. In certain such embodiments, fibronectin protein without EDA is increased.

The present disclosure provides the following non-limiting numbered embodiments:

Embodiment 1. A compound comprising a modified oligonucleotide consisting of 8 to 30 linked nucleosides and having a nucleobase sequence comprising a complementary region comprising at least 8 contiguous nucleobases complementary to a target region of equal length of a fibronectin transcript.

Embodiment 2. The compound of embodiment 1, wherein the complementary region of the modified oligonucleotide is 100% complementary to the target region.

Embodiment 3. The compound of embodiment 1 or 2, wherein the complementary region of the modified oligonucleotide comprises at least 10 contiguous nucleobases.

Embodiment 4. The compound of embodiment 1 or 2, wherein the complementary region of the modified oligonucleotide comprises at least 12 contiguous nucleobases.

Embodiment 5. The compound of embodiment 1 or 2, wherein the complementary region of the modified oligonucleotide comprises at least 15 contiguous nucleobases.

Embodiment 6. The compound of embodiment 1 or 2, wherein the complementary region of the modified oligonucleotide comprises at least 18 contiguous nucleobases.

Embodiment 7. The compound of embodiment 1 or 2, wherein the complementary region of the modified oligonucleotide comprises at least 20 contiguous nucleobases.

Embodiment 8. The compound of any of embodiments 1-5, wherein the nucleobase sequence of the oligonucleotide is at least 80% complementary to an equal-length region of the fibronectin transcript, as measured over the entire length of the oligonucleotide.

Embodiment 9. The compound of any of embodiments 1-5, wherein the nucleobase sequence of the oligonucleotide is at least 90% complementary to an equal-length region of the fibronectin transcript, as measured over the entire length of the oligonucleotide.

Embodiment 10. The compound of any of embodiments 1-5, wherein the nucleobase sequence of the oligonucleotide is 100% complementary to an equal-length region of the fibronectin transcript, as measured over the entire length of the oligonucleotide.

Embodiment 11. The compound of any of embodiments 1-10, wherein the target region is within nucleobase 55469 and nucleobase 55790 of SEQ ID NO.: 1.

Embodiment 12. The compound of any of embodiments 1-10, wherein the target region is within nucleobase 55469 and nucleobase 55511 of SEQ ID NO.: 1.

Embodiment 13. The compound of any of embodiments 1-10, wherein the target region is within nucleobase 55511 and nucleobase 55732 of SEQ ID NO.: 1.

Embodiment 14. The compound of any of embodiments 1-10, wherein the target region is within nucleobase 55732 and nucleobase 55790 of SEQ ID NO.: 1.

Embodiment 15. The compound of any of embodiments 1-10, wherein the target region is within nucleobase 55491 and nucleobase 55511 of SEQ ID NO.: 1.

Embodiment 16. The compound of any of embodiments 1-10, wherein the target region is within nucleobase 55490 and nucleobase 55510 of SEQ ID NO.: 1.

Embodiment 17. The compound of any of embodiments 1-10, wherein the target region is within nucleobase 55491 and nucleobase 55513 of SEQ ID NO.: 1.

Embodiment 18. The compound of any of embodiments 1-10, wherein the target region is within nucleobase 55536 and nucleobase 55555 of SEQ ID NO.: 1.

Embodiment 19. The compound of any of embodiments 1-10, wherein the target region is within nucleobase 55576 and nucleobase 55600 of SEQ ID NO.: 1.

Embodiment 20. The compound of any of embodiments 1-10, wherein the target region is within nucleobase 55604 and nucleobase 55623 of SEQ ID NO.: 1.

Embodiment 21. The compound of any of embodiments 1-10, wherein the target region is within nucleobase 55610 and nucleobase 55697 of SEQ ID NO.: 1.

Embodiment 22. The compound of any of embodiments 1-10, wherein the target region is within nucleobase 55701 and nucleobase 55737 of SEQ ID NO.: 1.

Embodiment 23. The compound of any of embodiments 1-10, wherein the target region is within nucleobase 55738 and nucleobase 55757 of SEQ ID NO.: 1.

Embodiment 24. The compound of any of embodiments 1-10, wherein the target region is within nucleobase 55753 and nucleobase 55781 of SEQ ID NO.: 1.

Embodiment 25. The compound of any of embodiments 1-24, wherein the antisense oligonucleotide comprises SEQ ID NO: 5.

Embodiment 26. The compound of any of embodiments 1-24, wherein the antisense oligonucleotide comprises SEQ ID NO: 9.

Embodiment 27. The compound of any of embodiments 1-24, wherein the antisense oligonucleotide comprises SEQ ID NO: 13.

Embodiment 28. The compound of any of embodiments 1-24, wherein the antisense oligonucleotide comprises SEQ ID NO: 14.

Embodiment 29. The compound of any of embodiments 1-24, wherein the antisense oligonucleotide comprises SEQ ID NO: 15.

Embodiment 30. The compound of any of embodiments 1-24, wherein the antisense oligonucleotide comprises SEQ ID NO: 18.

Embodiment 31. The compound of any of embodiments 1-24, wherein the antisense oligonucleotide comprises SEQ ID NO: 22.

Embodiment 32. The compound of any of embodiments 1-24, wherein the antisense oligonucleotide comprises SEQ ID NO: 66.

Embodiment 33. The compound of any of embodiments 1-24, wherein the antisense oligonucleotide comprises SEQ ID NO: 67.

Embodiment 34. The compound of any of embodiments 1-24, wherein the antisense oligonucleotide comprises any of SEQ ID NOs: 5 to 24.

Embodiment 35. The compound of any of embodiments 1-24, wherein the antisense oligonucleotide comprises any of SEQ ID NOs: 30 to 90.

Embodiment 36. The compound of any of embodiments 1-24, wherein the antisense oligonucleotide comprises SEQ ID NO: 413.

Embodiment 37. The compound of any of embodiments 1-24, wherein the antisense oligonucleotide comprises SEQ ID NO: 346.

Embodiment 38. The compound of any of embodiments 1-24, wherein the antisense oligonucleotide comprises any of SEQ ID NOs: 104 to 176.

Embodiment 39. The compound of any of embodiments 1-24, wherein the antisense oligonucleotide comprises any of SEQ ID NOs: 177 to 329.

Embodiment 40. The compound of any of embodiments 1-24, wherein the antisense oligonucleotide comprises any of SEQ ID NOs: 403 to 435.

Embodiment 41. The compound of any of embodiments 1-24, wherein the antisense oligonucleotide comprises any of SEQ ID NOs: 105, 87, 126, 133, 134, 140, 141, 147, 149, 157, 159, 190, 223, 238, 244, 268, 285, 300, 302, 303, 308, 319, 327, 381, 382, 339, 346, 348, 364, 365, 367, 368, 369, 370, 268, 276, 280, 406, 407, 412, 413, and 324.

Embodiment 42. The compound of any of embodiments 1-24, wherein the antisense oligonucleotide has a nucleobase sequence comprising CTTCTTCT.

Embodiment 43. The compound of any of embodiments 1-24, wherein the antisense oligonucleotide has a nucleobase sequence comprising GTTCC.

Embodiment 44. The compound of any of embodiments 1-24, wherein the antisense oligonucleotide has a nucleobase sequence comprising GTCCC.

Embodiment 45. The compound of any of embodiments 1-24, wherein the antisense oligonucleotide comprises a sugar motif described by Formula I as follows:

$$[(A)\text{-}(B)_2\text{-}(A)]_n$$

wherein:
each A is independently a bicyclic nucleoside;
each B is independently a 2'-substituted nucleoside or a 2'-deoxynucleoside; and
n is an integer from 3-6.

Embodiment 46. The compound of any of embodiments 1-24, wherein the antisense oligonucleotide comprises a sugar motif described by Formula II as follows:

$$(A)_2\text{-}[(B)_2\text{-}(A)]_n\text{-}(A)$$

wherein:
each A is independently a bicyclic nucleoside;
each B is independently a 2'-substituted nucleoside or a 2'-deoxynucleoside; and
n is an integer from 3-6.

Embodiment 47. The compound of any of embodiments 1-24, wherein the antisense oligonucleotide comprises a sugar motif described by Formula III as follows:

$$(A)_2\text{-}[(B)_2\text{-}(A)]_n$$

wherein:
each A is independently a bicyclic nucleoside;
each B is independently a 2'-substituted nucleoside or a 2'-deoxynucleoside; and
n is an integer from 3-6.

Embodiment 48. The compound of any of embodiments 45 to 47, wherein each A comprises a bicyclic nucleoside selected from among LNA and cEt.

Embodiment 49. The compound of any of embodiments 45 to 47, wherein each A comprises a cEt modification.

Embodiment 50. The compound of any of embodiments 45 to 47, wherein each A comprises an LNA modification.

Embodiment 51. The compound of any of embodiments 45 to 50, wherein each B comprises a 2'-substituted nucleoside having a 2'-modification selected from among 2'-OMe, 2'-F, and 2'-MOE.

Embodiment 52. The compound embodiment 51, wherein the 2'-modification is a 2'-MOE modification.

Embodiment 53. The compound of any of embodiments 45 to 50, wherein each B comprises a 2'-deoxynucleoside.

Embodiment 54. The compound of any of embodiments 1-44, wherein the modified oligonucleotide comprises at least one modified nucleoside.

Embodiment 55. The compound of embodiment 54, wherein at least one modified nucleoside comprises a modified sugar moiety.

Embodiment 56. The compound of embodiment 55, wherein at least one modified sugar moiety is a 2'-substituted sugar moiety.

Embodiment 57. The compound of embodiment 56, wherein the 2'-substituten of at least one 2'-substituted sugar moiety is selected from among: 2'-OMe, 2'-F, and 2'-MOE.

Embodiment 58. The compound of embodiment 57, wherein the 2'-substiuent of at least one 2'-substituted sugar moiety is a 2'-MOE.

Embodiment 59. The compound of any of embodiments 54-56, wherein at least one modified sugar moiety is a bicyclic sugar moiety.

Embodiment 60. The compound of embodiment 59, wherein at least one bicyclic sugar moiety is LNA or cEt.

Embodiment 61. The compound of any of embodiments 54-60, wherein at least one sugar moiety is a sugar surrogate.

Embodiment 62. The compound of embodiment 61, wherein at least one sugar surrogate is a morpholino.

Embodiment 63. The compound of embodiment 61, wherein at least one sugar surrogate is a modified morpholino.

Embodiment 64. The compound of any of embodiment 1-63, wherein the modified oligonucleotide comprises at least 5 modified nucleosides, each independently comprising a modified sugar moiety.

Embodiment 65. The compound of embodiment 64, wherein the modified oligonucleotide comprises at least 10 modified nucleosides, each independently comprising a modified sugar moiety.

Embodiment 66. The compound of embodiment 64, wherein the modified oligonucleotide comprises at least 15 modified nucleosides, each independently comprising a modified sugar moiety.

Embodiment 67. The compound of any of embodiments 1 to 44 or 54 to 66, wherein each nucleoside of the modified oligonucleotide is a modified nucleoside, each independently comprising a modified sugar moiety Embodiment 68. The compound of any of embodiments 1-67, wherein the modified oligonucleotide comprises at least two modified nucleosides comprising modified sugar moieties that are the same as one another.

Embodiment 69. The compound of any of embodiments 1-68, wherein the modified oligonucleotide comprises at least two modified nucleosides comprising modified sugar moieties that are different from one another.

Embodiment 70. The compound of any of embodiments 1-69, wherein the modified oligonucleotide comprises a modified region of at least 5 contiguous modified nucleosides.

Embodiment 71. The compound of any of embodiments 1 to 44 or 54 to 70, wherein the modified oligonucleotide comprises a modified region of at least 10 contiguous modified nucleosides.

Embodiment 72. The compound of any of embodiments 1 to 44 or 54 to 70, wherein the modified oligonucleotide comprises a modified region of at least 15 contiguous modified nucleosides.

Embodiment 73. The compound of any of embodiments 1 to 44 or 54 to 70, wherein the modified oligonucleotide comprises a modified region of at least 20 contiguous modified nucleosides.

Embodiment 74. The compound of any of embodiments 70-73, wherein each modified nucleoside of the modified region has a modified sugar moiety independently selected from among: 2'-F, 2'-OMe, 2'-MOE, cEt, LNA, morpholino, and modified morpholino.

Embodiment 75. The compound of any of embodiments 70-73, wherein the modified nucleosides of the modified region each comprise the same modification as one another.

Embodiment 76. The compound of embodiment 75, wherein the modified nucleosides of the modified region each comprise the same 2'-substituted sugar moiety.

Embodiment 77. The compound of embodiment 75, wherein the 2'-substituted sugar moiety of the modified nucleosides of the region of modified nucleosides is selected from 2'-F, 2'-OMe, and 2'-MOE.

Embodiment 78. The compound of embodiment 77, wherein the 2'-substituted sugar moiety of the modified nucleosides of the region of modified nucleosides is 2'-MOE.

Embodiment 79. The compound of embodiment 75, wherein the modified nucleosides of the region of modified nucleosides each comprise the same bicyclic sugar moiety.

Embodiment 80. The compound of embodiment 79, wherein the bicyclic sugar moiety of the modified nucleosides of the region of modified nucleosides is selected from LNA and cEt.

Embodiment 81. The compound of embodiment 75, wherein the modified nucleosides of the region of modified nucleosides each comprises a sugar surrogate.

Embodiment 82. The compound of embodiment 81, wherein the sugar surrogate of the modified nucleosides of the region of modified nucleosides is a morpholino.

Embodiment 83. The compound of embodiment 81, wherein the sugar surrogate of the modified nucleosides of the region of modified nucleosides is a modified morpholino.

Embodiment 84. The compound of any of embodiments 1-83, wherein the modified nucleotide comprises no more than 4 contiguous naturally occurring nucleosides.

Embodiment 85. The compound of any of embodiments 1 to 44 or 54 to 85, wherein each nucleoside of the modified oligonucleotide is a modified nucleoside.

Embodiment 86. The compound of embodiment 85 wherein each modified nucleoside comprises a modified sugar moiety.

Embodiment 87. The compound of embodiment 86, wherein the modified nucleosides of the modified oligonucleotide comprise the same modification as one another.

Embodiment 88. The compound of embodiment 87, wherein the modified nucleosides of the modified oligonucleotide each comprise the same 2'-substituted sugar moiety.

Embodiment 89. The compound of embodiment 88, wherein the 2'-substituted sugar moiety of the modified oligonucleotide is selected from 2'-F, 2'-OMe, and 2'-MOE.

Embodiment 90. The compound of embodiment 89, wherein the 2'-substituted sugar moiety of the modified oligonucleotide is 2'-MOE.

Embodiment 91. The compound of embodiment 87, wherein the modified nucleosides of the modified oligonucleotide each comprise the same bicyclic sugar moiety.

Embodiment 92. The compound of embodiment 91, wherein the bicyclic sugar moiety of the modified oligonucleotide is selected from LNA and cEt.

Embodiment 93. The compound of embodiment 87, wherein the modified nucleosides of the modified oligonucleotide each comprises a sugar surrogate.

Embodiment 94. The compound of embodiment 93, wherein the sugar surrogate of the modified oligonucleotide is a morpholino.

Embodiment 95. The compound of embodiment 93, wherein the sugar surrogate of the modified oligonucleotide is a modified morpholino.

Embodiment 96. The compound of any of embodiments 1-95, wherein the modified oligonucleotide comprises at least one modified internucleoside linkage.

Embodiment 97. The compound of embodiment 96, wherein each internucleoside linkage is a modified internucleoside linkage.

Embodiment 98. The compound of embodiment 96 or 97, comprising at least one phosphorothioate internucleoside linkage.

Embodiment 99. The compound of embodiment 77, wherein each internucleoside linkage is a modified internucleoside linkage and wherein each internucleoside linkage comprises the same modification.

Embodiment 100. The compound of embodiment 99, wherein each internucleoside linkage is a phosphorothioate internucleoside linkage.

Embodiment 101. The compound of any of embodiments 1-100 comprising at least one conjugate.

Embodiment 102. The compound of any of embodiments 1-101 consisting of the modified oligonucleotide.

Embodiment 103. The compound of any of embodiments 1-102, wherein the compound modulates splicing of the fibronectin transcript.

Embodiment 104. The compound of any of embodiments 1-103, having a nucleobase sequence comprising any of the sequences as set forth in SEQ ID NOs. 5 to 25 or 30 to 90.

Embodiment 105. The compound of any of embodiments 1-103, having a nucleobase sequence comprising the sequence as set forth in SEQ ID NO: 5.

Embodiment 106. The compound of any of embodiments 1-103, having a nucleobase sequence comprising the sequence as set forth in SEQ ID NO: 9.

Embodiment 107. The compound of any of embodiments 1-103, having a nucleobase sequence comprising the sequence as set forth in SEQ ID NO: 13.

Embodiment 108. The compound of any of embodiments 1-103, having a nucleobase sequence comprising the sequence as set forth in SEQ ID NO: 14.

Embodiment 109. The compound of any of embodiments 1-103, having a nucleobase sequence comprising the sequence as set forth in SEQ ID NO: 15.

Embodiment 110. The compound of any of embodiments 1-103, having a nucleobase sequence comprising the sequence as set forth in SEQ ID NO: 18.

Embodiment 111. The compound of any of embodiments 1-103, having a nucleobase sequence comprising the sequence as set forth in SEQ ID NO: 22.

Embodiment 112. The compound of any of embodiments 1-103, having a nucleobase sequence comprising the sequence as set forth in SEQ ID NO: 66.

Embodiment 113. The compound of any of embodiments 1-103, having a nucleobase sequence comprising the sequence as set forth in SEQ ID NO: 67.

Embodiment 114. The compound of any of embodiments 1-103, wherein the antisense oligonucleotide has a nucleobase sequence comprising CTTCTTCT.

Embodiment 115. The compound of any of embodiments 1-103, wherein the antisense oligonucleotide has a nucleobase sequence comprising GTTCC.

Embodiment 116. The compound of any of embodiments 1-103, wherein the antisense oligonucleotide has a nucleobase sequence comprising GTCCC.

Embodiment 117. A pharmaceutical composition comprising a compound according to any of embodiments 1-116 and a pharmaceutically acceptable carrier or diluent.

Embodiment 118. The pharmaceutical composition of embodiment 117, wherein the pharmaceutically acceptable carrier or diluent is sterile saline.

Embodiment 119. A method of decreasing the amount of EDA+ fibronectin protein in a cell, comprising contacting the cell with a compound according to any of embodiments 1-117.

Embodiment 120. A method of increasing the amount of EDA− fibronectin protein in a cell, comprising contacting the cell with a compound according to any of embodiments 1-117.

Embodiment 121. A method of reducing fibrosis, comprising contacting the cell with a compound according to any of embodiments 1-117.

Embodiment 122. A method of reversing fibrosis, comprising contacting the cell with a compound according to any of embodiments 1-117.

Embodiment 123. A method of reducing changes in cell phenotype due to fibrosis, comprising contacting the cell with a compound according to any of embodiments 1-117.

Embodiment 124. A method of reversing changes in cell phenotype due to fibrosis, comprising contacting the cell with a compound according to any of embodiments 1-117.

Embodiment 125. The method of embodiments 123-124, wherein the change in cell phenotype due to fibrosis is the modulation of cadherin expression.

Embodiment 126. The method of embodiments 123-124, wherein the change in cell phenotype due to fibrosis is the induction of α Smooth Muscle Actin (αSMA).

Embodiment 127. The method of embodiments 123-124, wherein the change in cell phenotype due to fibrosis is the alteration of cortical f-actin localization.

Embodiment 128. The method of embodiments 123-124, wherein the change in cell phenotype due to fibrosis is the induction of connexin 43 (Cx 43) expression.

Embodiment 129. The method of embodiments 123-124, wherein the change in cell phenotype due to fibrosis is the increased secretion of MMP2 & MMP9.

Embodiment 130. The method of embodiments 123-124, wherein the change in cell phenotype due to fibrosis is the alteration of the amount vimentin or the arrangement of vimentin within a cell.

Embodiment 131. The method of embodiments 123-124, wherein the change in cell phenotype due to fibrosis is the alteration of the amount tight junction protein ZO-1 or the arrangement of tight junction protein ZO-1 within a cell.

Embodiment 132. A method of reducing loss of cell phenotype due to fibrosis, comprising contacting the cell with a compound according to any of embodiments 1-117.

Embodiment 133. A method of reversing the loss of cell phenotype due to fibrosis, comprising contacting the cell with a compound according to any of embodiments 1-117.

Embodiment 134. A method of increasing the ratio of EDA+/EDA− fibronectin in a cell, comprising contacting the cell with a compound according to any of embodiments 1-117.

Embodiment 135. A method of decreasing the ratio of EDA+/EDA− fibronectin in a cell, comprising contacting the cell with a compound according to any of embodiments 1-117.

Embodiment 136. A method of increasing the ratio of EDA−/EDA+ fibronectin in a cell, comprising contacting the cell with a compound according to any of embodiments 1-117.

Embodiment 137. A method of decreasing the ratio of EDA−/EDA+ fibronectin in a cell, comprising contacting the cell with a compound according to any of embodiments 1-117.

Embodiment 138. A method of increasing the ratio of EDA+/EDA− fibronectin protein in a cell, comprising contacting the cell with a compound according to any of embodiments 1-117.

Embodiment 139. A method of decreasing the ratio of EDA+/EDA− fibronectin protein in a cell, comprising contacting the cell with a compound according to any of embodiments 1-117.

Embodiment 140. A method of increasing the ratio of EDA−/EDA+ fibronectin protein in a cell, comprising contacting the cell with a compound according to any of embodiments 1-117.

Embodiment 141. A method of decreasing the ratio of EDA−/EDA+ fibronectin protein in a cell, comprising contacting the cell with a compound according to any of embodiments 1-117.

Embodiment 142. The method of any of embodiments 119-142, wherein the cell is in vitro.

Embodiment 143. The method of embodiments 119-142, wherein the cell is in an animal.

Embodiment 144. The method of embodiments 119-142, wherein the animal is a mouse.

Embodiment 145. The method of embodiments 119-142, wherein the animal is a human.

Embodiment 146. The method of any of embodiments 119-145, wherein TGFβ1 is present in the cell.

Embodiment 147. The method of any of embodiments 119-146, wherein the healing and/or restoration functions of the cell are not substantially affected.

Embodiment 148. A pharmaceutical composition comprising a compound according to any of embodiments 1-117 and a pharmaceutically acceptable carrier or diluent.

Embodiment 149. The pharmaceutical composition of embodiment 148, wherein the pharmaceutically acceptable carrier or diluent is sterile saline.

Embodiment 150. A method comprising administering the pharmaceutical composition of embodiments 148 or 149 to an animal.

Embodiment 151. The method of embodiment 150, wherein the animal is a mouse.

Embodiment 152. The method of embodiment 150, wherein the animal is a human.

Embodiment 153. The method of embodiment 150, wherein the administration is by injection.

Embodiment 154. The method of embodiment 150, wherein the administration is systemic.

Embodiment 155. The method of embodiment 150 wherein the administration is local.

Embodiment 156. The method of any of embodiments 150-155, wherein the animal has one or more symptom associated with fibrosis.

Embodiment 157. The method of embodiment 156, wherein the administration results in amelioration of at least one symptom associated with fibrosis.

Embodiment 158. The method of embodiment 156-157, wherein the fibrosis is renal fibrosis.

Embodiment 159. The method of embodiment 156-157, wherein the fibrosis is lung fibrosis.

Embodiment 160. The method of embodiment 156-157, wherein the fibrosis is liver fibrosis.

Embodiment 161. The method of embodiment 156-157, wherein the fibrosis is brain fibrosis.

Embodiment 162. The method of embodiment 156-157, wherein the fibrosis is muscular fibrosis.

Embodiment 163. The method of embodiment 156-157, wherein the fibrosis is cardiovascular fibrosis.

Embodiment 164. The method of embodiment 156-157, wherein the fibrosis is in the bone or the bone marrow.

Embodiment 165. The method of embodiment 156-157, wherein the fibrosis is intestinal fibrosis.

Embodiment 166. The method of embodiment 156-157, wherein the fibrosis is epidural fibrosis.

Embodiment 167. The method of any of embodiments 156-167, wherein the animal is a mouse.

Embodiment 168. The method of any of embodiments 156-167, wherein the animal is a human.

Embodiment 169. Use of the compound of any of embodiments 1 to 117 or the composition of embodiments 148-149 for the preparation of a medicament for use in the treatment of of at least one symptom associated with fibrosis.

Embodiment 170. Use of the compound of any of embodiments 1 to 117 or the composition of embodiments 148-149 for the preparation of a medicament for use in the amelioration of one or more symptoms associated with fibrosis.

Embodiment 171. The use of any of embodiment 169-170, wherein the fibrosis is selected from among renal, lung, liver, brain, muscular, cardiovascular, bone or bone marrow, intestinal, and/or epidural fibrosis.

Embodiment 172. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula I as follows:

$$[(A)\text{-}(B)_2\text{-}(A)]_n$$

wherein:
each A is independently a bicyclic nucleoside;
each B is independently a 2'-substituted nucleoside or a 2'-deoxynucleoside; and
n is an integer from 3-6.

Embodiment 173. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula II as follows:

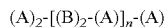

$(A)_2\text{-}[(B)_2\text{-}(A)]_n\text{-}(A)$ wherein:
each A is independently a bicyclic nucleoside;
each B is independently a 2'-substituted nucleoside or a 2'-deoxynucleoside; and
n is an integer from 3-6.

Embodiment 174. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a sugar motif described by Formula III as follows:

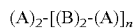

$(A)_2\text{-}[(B)_2\text{-}(A)]_n$ wherein:
each A is independently a bicyclic nucleoside;
each B is independently a 2'-substituted nucleoside or a 2'-deoxynucleoside; and
n is an integer from 3-6.

Embodiment 175. The compound of any of embodiments 172 to 174, wherein each A comprises a bicyclic nucleoside selected from among LNA and cEt.

Embodiment 176. The compound of any of embodiments 172 to 174, wherein each A comprises a cEt modification.

Embodiment 177. The compound of any of embodiments 172 to 174, wherein each A comprises an LNA modification.

Embodiment 178. The compound of any of embodiments 172 to 177, wherein each B comprises a 2'-substituted nucleoside having a 2'-modification selected from among 2'-OMe, 2'-F, and 2'-MOE.

Embodiment 179. The compound embodiments 178, wherein the 2'-modification is a 2'-MOE modification.

Embodiment 180. The compound of any of embodiments 172 to 179, wherein each B comprises a 2'-deoxynucleoside.

Embodiment 181. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a $kd_2kd_2kd_2kd_2kd_2k$ motif, wherein each k comprises a cEt modification and each d comprises a 2'-deoxynucleoside.

Embodiment 182. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkddkddkddkddkddkk motif, wherein each k comprises a cEt modification and each d comprises a 2'-deoxynucleoside.

Embodiment 183. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkeekeekeekeekeeke motif, wherein each k comprises a cEt modification and each e comprises a 2'-MOE modification.

Embodiment 184. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kddkddkddkddkddk motif wherein each k comprises a cEt modification and each d comprises a 2'-deoxynucleoside.

Embodiment 185. A compound comprising a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

In certain embodiments, including, but not limited to any of the above numbered embodiments, the fibronectin transcript is in a human. In certain embodiments, including, but not limited to any of the above numbered embodiments, the fibronectin transcript is in a mouse.

BRIEF DESCRIPTION OF THE FIGURES

FIG. 1 shows a schematic of fibronectin splicing. Exons are represented as boxes and introns are represented as lines. Diagonal lines indicate splicing pathways. As illustrated by the schematic, alternative splicing produces two different mRNA products. Inclusion of the EDA exon results in mRNA containing the EDA exon (EDA+) which results in fibronectin protein having EDA. Alternatively, exclusion of the EDA exon results in mRNA without the EDA exon (EDA−) and results in fibronectin protein without EDA.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety, a bicyclic or tricyclic sugar moiety, or a sugar surrogate.

As used herein, "substituted sugar moiety" means a furanosyl comprising at least one substituent group that differs from that of a naturally occurring sugar moiety. Substituted sugar moieties include, but are not limited to furanosyls comprising substituents at the 2'-position, the 3'-position, the 5'-position and/or the 4'-position.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholino, modified morpholinos, cyclohexenyls and cyclohexitols.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "transcript" means an RNA molecule transcribed from DNA. Transcripts include, but are not limited to mRNA, pre-mRNA, and partially processed RNA.

As used herein, "fibronectin transcript" means a transcript transcribed from a fibronectin gene. In certain embodiments, a fibronectin transcript comprises SEQ ID NO: 1: the complement of GENBANK Accession No. NT_005403.14 truncated from nucleotides 66434501 to 66510708.

As used herein, "fibronectin gene" means a gene that encodes a fibronectin protein and any fibronectin protein isoforms. In certain embodiments, a fibronectin gene is represented by GENBANK Accession No. NT_005403.14 truncated from nucleotides 66434501 to 66510708, or a variant thereof. In certain embodiments, a fibronectin gene is at least 95% identical to GENBANK Accession No. NT_005403.14 truncated from nucleotides 66434501 to 66510708. In certain embodiments, a fibronectin gene is at least 90% identical to GENBANK Accession No. NT_005403.14 truncated from nucleotides 66434501 to 66510708.

As used herein, "EDA− fibronectin protein" means a fibronectin protein isoform that does not contain extra type III domain A.

As used herein, "EDA+ fibronectin protein" means a fibronectin protein isoform that contains extra type III domain A.

As used herein, "EDA− fibronectin mRNA" means a fibronectin transcript that does not contain the extra type III domain A exon.

As used herein, "EDA+ fibronectin mRNA" means a fibronectin transcript that contains the extra type III domain A exon.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino (=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'—O(CH$_2$)$_2$OCH$_3$("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to:, 5'-methyl (R or S); 5'-vinyl; and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

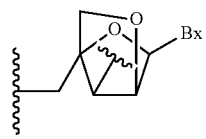
(A)

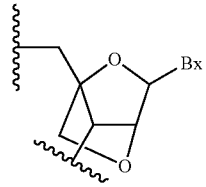
(B)

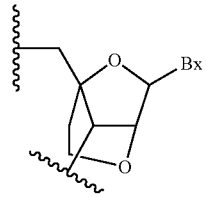
(C)

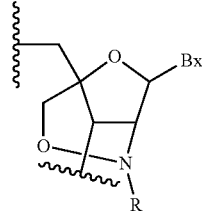
(D)

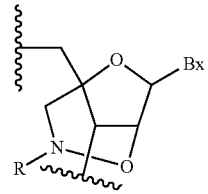
(E)

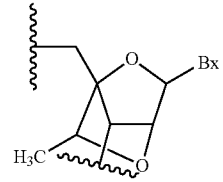
(F)

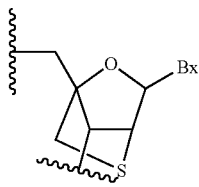
(G)

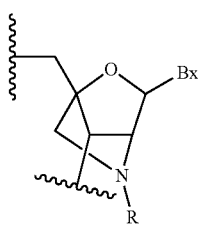
(H)

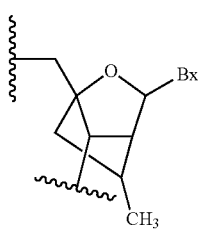
(I)

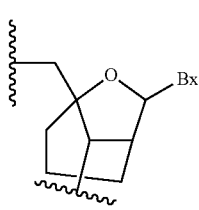
(J)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et A, *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), fluoro HNA (F-HNA), and those compounds having Formula VII:

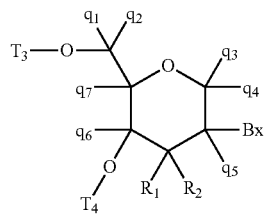

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, Bioorganic & Medicinal Chemistry, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

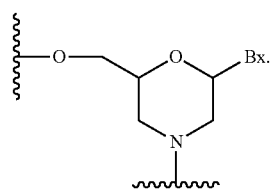

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified nucleosides. In certain embodiments, chemically modified oligonucleotides comprise one or more modified nucleosides comprising modified sugars. In certain embodiments, chemically modified oligonucleotides comprise one or more modified nucleosides comprising one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer). In certain embodiments, oligonucleotides comprise 2'-MOE modified nucleosides in the wings and 2'-F modified nucleosides in the gap.

In certain embodiments, oligonucleotides are fully modified. In certain such embodiments, oligonucleotides are uniformly modified. In certain embodiments, oligonucleotides are uniform 2'-MOE. In certain embodiments, oligonucleotides are uniform 2'-F. In certain embodiments, oligonucleotides are uniform morpholino. In certain embodiments, oligonucleotides are uniform BNA. In certain embodiments, oligonucleotides are uniform LNA. In certain embodiments, oligonucleotides are uniform cEt.

In certain embodiments, oligonucleotides comprise a uniformly modified region and additional nucleosides that are unmodified or differently modified. In certain embodiments, the uniformly modified region is at least 5, 10, 15, or 20 nucleosides in length. In certain embodiments, the uniform region is a 2'-MOE region. In certain embodiments, the uniform region is a 2'-F region. In certain embodiments, the uniform region is a morpholino region. In certain embodiments, the uniform region is a BNA region. In certain embodiments, the uniform region is a LNA region. In certain embodiments, the uniform region is a cEt region.

In certain embodiments, the oligonucleotide does not comprise more than 4 contiguous unmodified 2'-deoxynucleosides. In certain circumstances, antisesense oligonucleotides comprising more than 4 contiguous 2'-deoxynucleosides activate RNase H, resulting in cleavage of the target RNA. In certain embodiments, such cleavage is avoided by not having more than 4 contiguous 2'-deoxynucleosides, for example, where alteration of splicing and not cleavage of a target RNA is desired.

Certain Splicing Motifs

In certain embodiments, oligonucleotides have a certain modification pattern and/or motif designed to alter the splicing of certain nucleic acid transcripts. In certain embodiments, oligonucleotides have a certain modification pattern and/or motif designed to alter the splicing of certain pre-mRNA transcripts. In certain embodiments, oligonucleotides have a certain modification pattern and/or motif designed in such a fashion that the oligonucleotide will not recruit RNase H once bound to a target nucleic acid transcript. For example, in certain such embodiments, an oligonucleotide may have one or more sugar modifications placed throughout the oligonucleotide so as to have no segment comprising more than 4 contiguous 2'-deoxynucleosides. In certain such embodiments, an oligonucleotide may have one or more sugar modifications placed throughout the oligonucleotide so as to have no segment comprising more than 3 contiguous 2'-deoxynucleosides. In certain such embodiments, an oligonucleotide may have one or more sugar modifications placed throughout the oligonucleotide so as to have no segment comprising more than 2 contiguous 2'-deoxynucleosides.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a $Ad_2Ad_2Ad_2Ad_2Ad_2A$ motif, wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AAddAddAddAddAddAA motif, wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AABBABBABBABBABBAB motif, wherein each A independently comprises a bicyclic modification selected from among LNA and cEt and each B independently comprises a 2'-modification selected from among a 2'-OMe, 2'-F, or 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a AddAddAddAddAddA motif wherein each A independently comprises a bicyclic modification selected from among LNA and cEt and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a $kd_2kd_2kd_2kd_2kd_2k$ motif, wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkddkddkddkddkddkk motif, wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kkeekeekeekeekeeke motif, wherein each k comprises a cEt modification and each e comprises a 2'-MOE modification.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a kddkddkddkddkddk motif wherein each k comprises a cEt modification and each d comprises a 2'-deoxynucleoside.

In certain embodiments, the oligonucleotide compound comprises a modified oligonucleotide consisting of 8 to 30 linked nucleosides and having a nucleobase sequence comprising a complementary region comprising at least 8 contiguous nucleobases complementary to a target region of equal length of a target nucleic acid, wherein the modified oligonucleotide comprises a keekeekeekeekeek motif, wherein each k comprises a cEt modification and each e comprises a 2'-MOE modification.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths. In certain embodiments, an antisense oligonucleotide has any of the above lengths.

One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-tri-iodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments antisense compounds and antisense oligonucleotides comprise single-strand compounds. In certain embodiments antisense compounds and antisense oligonucleotides comprise double-strand compounds.

Certain Pathways and Mechanisms Associated with Fibrosis

TGFβ1 and its associated pathways contribute to many processes associated with wound healing and tissue repair. After an injury, TGFβ1 contributes to the healing and restoration of normal tissue by, among other things, stimulating the production of certain extracellular matrix proteins and inhibiting the degradation of certain matrix proteins. In certain embodiments, TGFβ1 stimulates the production of fibronectin. In certain embodiments, TGFβ1 stimulates the production of both the EDA+ and EDA− isoforms of fibronectin.

In certain embodiments, excessive amounts of the EDA+ fibronectin isoform causes tissue fibrosis. In certain embodiments, excessive tissue fibrosis induced by TGFβ1/EDA+ impairs normal organ function, impairs cellular function, and/or causes cells to change or lose their phenotype. In certain embodiments, the release and/or activation of TGFβ1 causes the formation of fibrosis and consequent changes in cell phenotype. In certain embodiments, changes in cell phenotype due to fibrosis include, but are not limited to, modulation of cadherin expression, induction of α Smooth Muscle Actin (αSMA), alteration of cortical f-actin localization, induction of connexin 43 (Cx 43) expression, alteration of vimentin, alteration of tight junction protein ZO-1, and/or increased secretion of MMP2 & MMP9. In certain embodiments, the release and/or activation of TGFβ1 causes a loss of cell phenotype. In certain embodiments, the loss of cell phenotype due to fibrosis impairs the structure or function of a cell. In certain embodiments, the loss of cell phenotype due to fibrosis destroys the function of a cell.

In certain embodiments, it is therefore desirable to reduce fibrosis without affecting the healing and/or restoration process. In certain embodiments, it is therefore desirable to reduce the formation of fibrosis in a cell without reducing or altering the amount and/or activity of TGFβ1 in the cell. In certain embodiments, it is therefore desirable to reduce the amount of EDA+ fibronectin in a cell without reducing or altering the amount of EDA− fibronectin in the cell. In certain embodiments, the reduction of the amount of EDA+ fibronectin in a cell in response to TGFβ1 will result in wound healing and tissue repair without incurring excessive fibrosis. In certain embodiments, the selective reduction of the amount of EDA+ fibronectin in a cell, relative to the amount of EDA− fibronectin in the cell in the response to TGFβ1 will stimulate wound healing and tissue repair without incurring changes in cell phenotype associated with fibrosis. In certain embodiments, the reduction of the amount of EDA+ fibronectin in a cell, relative to the amount of EDA− fibronectin in the cell in response to TGFβ1 will stimulate wound healing and tissue repair without incurring the loss of cell phenotype due to fibrosis.

In certain embodiments, it is desirable to reverse the formation of fibrosis in a cell without reducing or altering the wound healing function of TGFβ1 in the cell. In certain embodiments, it is therefore desirable to reverse the changes caused by fibrosis in the phenotype of a cell without reducing or altering the wound healing function of TGFβ1 in the cell. In certain embodiments, it is therefore desirable to reverse the loss of phenotype in a cell caused by fibrosis without reducing or altering the wound healing function of TGFβ1 in the cell.

Certain Target Nucleic Acids and Mechanisms

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a pre-mRNA. In certain embodiments, the target nucleic acid is a fibronectin transcript. In certain embodiments, the target RNA is a fibronectin pre-mRNA.

In certain embodiments, an antisense compound is complementary to a region of fibronectin pre-mRNA. In certain embodiments, an antisense compound is complementary within a region of fibronectin pre-mRNA comprising an exon encoding EDA. In certain embodiments, an antisense compound is complementary to a region of fibronectin pre-mRNA comprising an intron-exon splice junction. In certain embodiments, an antisense compound is complementary to a region of fibronectin pre-mRNA comprising the intron-exon splice junction adjacent to the EDA exon. In certain embodiments, an antisense compound is complementary within a region of fibronectin pre-mRNA consisting of an exon encoding EDA. In certain embodiments, an antisense compound is complementary within a region of fibronectin pre-mRNA comprising an exonic splicing silencer within an exon encoding EDA. In certain embodiments, an antisense compound is complementary within a region of fibronectin pre-mRNA comprising an exonic splicing enhancer within an exon encoding EDA.

In certain embodiments, an antisense compound comprises a modified oligonucleotide consisting of 8 to 30 linked nucleosides and having a nucleobase sequence comprising a complementary region comprising at least 8 contiguous nucleobases complementary to a target region of equal length of a fibronectin transcript. In certain embodiments, the target region is within nucleobase 55469 and nucleobase 55790 of SEQ ID NO.: 1. In certain embodiments, the target region is within nucleobase 55469 and nucleobase 55511 of SEQ ID NO.: 1. In certain embodiments, the target region is within nucleobase 55511 and nucleobase 55732 of SEQ ID NO.: 1. In certain embodiments, the target region is within nucleobase 55732 and nucleobase 55790 of SEQ ID NO.: 1.

In certain embodiments, an antisense oligonucleotide modulates splicing of a pre-mRNA. In certain embodiments, an antisense oligonucleotide modulates splicing a fibronectin pre-mRNA. In certain embodiments, an antisense oligonucleotide increases the amount of fibronectin mRNA. In certain embodiments, an antisense oligonucleotide increases the amount of EDA− fibronectin mRNA. In certain embodiments, an antisense oligonucleotide decreases the amount of EDA+ fibronectin mRNA. In certain embodiments, an antisense oligonucleotide decreases the amount of EDA+ fibronectin mRNA in the presence of TGFβ1. In certain embodiments, an antisense oligonucleotide decreases the amount of EDA+ fibronectin mRNA in a cell without substantially affecting the healing and/or restoration functions of the cell.

In certain embodiments, an antisense oligonucleotide alters the ratio of EDA+/EDA− fibronectin. In certain embodiments, an antisense oligonucleotide increases the ratio of EDA+/EDA− fibronectin. In certain embodiments, it is desirable to increase the ratio of EDA+/EDA− fibronectin to create a fibrosis model. In certain embodiments, it is desirable to increase the ratio of EDA+/EDA− fibronectin to create a fibrosis phenotype. In certain embodiments, it is desirable to increase the ratio of EDA+/EDA− fibronectin in the presence of TGFβ1 to create a fibrosis model. In certain embodiments, it is desirable to increase the ratio of EDA+/EDA− fibronectin in the presence of TGFβ1 to create a fibrosis phenotype. In certain embodiments, it is desirable to increase the ratio of EDA+/EDA− fibronectin to create a fibrosis mouse model. In certain embodiments, it is desirable to increase the ratio of EDA+/EDA− fibronectin to create a fibrosis mouse phenotype. In certain embodiments, it is desirable to increase the ratio of EDA+/EDA− fibronectin in the presence of TGFβ1 to create a fibrosis mouse model. In certain embodiments, it is desirable to increase the ratio of EDA+/EDA− fibronectin in the presence of TGFβ1 to create a fibrosis mouse phenotype.

In certain embodiments, an antisense oligonucleotide alters the ratio of EDA+/EDA− fibronectin. In certain embodiments, an antisense oligonucleotide decreases the ratio of EDA+/EDA− fibronectin. In certain embodiments, it is desirable to decrease the ratio of EDA+/EDA− fibronectin to create a fibrosis model. In certain embodiments, it is desirable to decrease the ratio of EDA+/EDA− fibronectin to create a fibrosis phenotype. In certain embodiments, it is desirable to decrease the ratio of EDA+/EDA− fibronectin in the presence of TGFβ1 to create a fibrosis model. In certain embodiments, it is desirable to decrease the ratio of EDA+/EDA− fibronectin in the presence of TGFβ1 to create a fibrosis phenotype. In certain embodiments, it is desirable to decrease the ratio of EDA+/EDA− fibronectin to create a fibrosis mouse model. In certain embodiments, it is desirable to decrease the ratio of EDA+/EDA− fibronectin to create a fibrosis mouse phenotype. In certain embodiments, it is desirable to decrease the ratio of EDA+/EDA− fibronectin in the presence of TGFβ1 to create a fibrosis mouse model. In certain embodiments, it is desirable to decrease the ratio of EDA+/EDA− fibronectin in the presence of TGFβ1 to create a fibrosis mouse phenotype.

In certain embodiments, an antisense oligonucleotide alters the ratio of EDA−/EDA+ fibronectin. In certain embodiments, an antisense oligonucleotide increases the ratio of EDA−/EDA+ fibronectin. In certain embodiments, it is desirable to increase the ratio of EDA−/EDA+ fibronectin to create a fibrosis model. In certain embodiments, it is desirable to increase the ratio of EDA−/EDA+ fibronectin to create a fibrosis phenotype. In certain embodiments, it is desirable to increase the ratio of EDA−/EDA+ fibronectin in the presence of TGFβ1 to create a fibrosis model. In certain embodiments, it is desirable to increase the ratio of EDA−/EDA+ fibronectin in the presence of TGFβ1 to create a fibrosis phenotype. In certain embodiments, it is desirable to increase the ratio of EDA−/EDA+ fibronectin to create a fibrosis mouse model. In certain embodiments, it is desirable to increase the ratio of EDA−/EDA+ fibronectin to create a fibrosis mouse phenotype. In certain embodiments, it is desirable to increase the ratio of EDA−/EDA+ fibronectin in the presence of TGFβ1 to create a fibrosis mouse model. In certain embodiments, it is desirable to increase the ratio of EDA−/EDA+ fibronectin in the presence of TGFβ1 to create a fibrosis mouse phenotype.

In certain embodiments, an antisense oligonucleotide alters the ratio of EDA−/EDA+ fibronectin. In certain embodiments, an antisense oligonucleotide decreases the ratio of EDA−/EDA+ fibronectin. In certain embodiments, it is desirable to decrease the ratio of EDA−/EDA+ fibronectin to create a fibrosis model. In certain embodiments, it is desirable to decrease the ratio of EDA−/EDA+ fibronectin to create a fibrosis phenotype. In certain embodiments, it is desirable to decrease the ratio of EDA−/EDA+ fibronectin in the presence of TGFβ1 to create a fibrosis model. In certain embodiments, it is desirable to decrease the ratio of EDA−/EDA+ fibronectin in the presence of TGFβ1 to create a fibrosis phenotype. In certain embodiments, it is desirable to decrease the ratio of EDA−/EDA+ fibronectin to create a fibrosis mouse model. In certain embodiments, it is desirable to decrease the ratio of EDA−/EDA+ fibronectin to create a fibrosis mouse phenotype. In certain embodiments, it is desirable to decrease the ratio of EDA−/EDA+ fibronectin in the presence of TGFβ1 to create a fibrosis mouse model. In certain embodiments, it is desirable to decrease the ratio of EDA−/EDA+ fibronectin in the presence of TGFβ1 to create a fibrosis mouse phenotype.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Further-more, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the eyes, ears).

In certain embodiments, a pharmaceutical composition is administered to an animal having at least one symptom associated with fibrosis. In certain embodiments, such administration results in amelioration of at least one symptom. In certain embodiments, administration of a pharmaceutical composition to an animal results in a decrease of EDA+ fibronectin mRNA in a cell of the animal. In certain embodiments, such administration results in an increase in EDA− fibronectin mRNA. In certain embodiments, such administration results in a decrease in EDA+ fibronectin protein and an increase EDA− fibronectin protein. In certain embodiments, a fibronectin protein lacking EDA amino acids is preferred over a fibronectin protein having EDA amino acids. In certain embodiments, the administration of certain antisense oligonucleotides delays the onset of fibrosis. In certain embodiments, the administration of certain antisense oligonucleotides slows the progression of fibrosis. In certain embodiments, the administration of certain antisense oligonucleotides prevents the formation of fibrosis. In certain embodiments, the administration of certain antisense oligonucleotides reverses fibrosis. In certain embodiments, the administration of certain antisense oligonucleotides rescues cellular phenotype. In certain embodiments, the administration of certain antisense oligonucleotides rescues cellular morphology.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1

In vitro Screening of Human Fibronectin Splicing with Antisense Oligonucleotides in HKC-8 Cells Antisense oligonucleotides were designed targeting a fibronectin nucleic acid and were tested for their effects on the alternative splicing of the fibronectin gene sequence in vitro. The newly designed antisense oligonucleotides in Table 1 were designed as uniform MOE oligonucleotides. Each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Start site" indicates the 5'-most nucleoside to which the oligonucleotide is targeted in the human gene sequence. "Stop site" indicates the 3'-most nucleoside to which the oligonucleotide is targeted human gene sequence. Each oligonucleotide listed in Table 1 is targeted to SEQ ID NO: 1 (the complement of GENBANK Accession No. NT_005403.14 truncated from nucleotides 66434501 to 66510708). ISIS 141923 (CCTTCCCTGAAGGTTCCTCC (SEQ ID NO: 25), no known human target) was used as a negative control.

Cultured HKC-8 cells, which are SV40-transformed human proximal tubular cells, were transfected using 3 μL LipofectAMINE2000®/mL OptiMEM with 200 nM antisense oligonucleotide. After a treatment period of approximately 4 hours, the medium was removed and new medium was added, left in culture overnight, RNA was isolated from the cells and the ratio of Extra Domain A positive fibronectin (EDA$^+$FN) to EDA negative fibronectin (EDA$^-$FN) was measured by conventional PCR. Human primers with forward sequence GGAGAGAGTCAGCCTCTGGTTCAG, designated herein as SEQ ID NO: 2; reverse sequence TGTCAACTGGGCGCTCAGGCTTGTG, designated herein as SEQ ID NO: 3) was used to measure mRNA levels. To compare the efficacy of antisense treatments performed in different experiments and allow for inter-assay variability, ratios were indexed on the corresponding negative control. Results are presented in Table 1 and demonstrate that treatment with antisense oligonucleotides targeted to the EDA region of fibronectin resulted in decreased expression of the EDA$^+$FN isoform compared to the negative control. 'null' indicates that the EDA$^+$ band was undetectable for that sample.

TABLE 1

Ratio of EDA $^+$FN to EDA $^-$FN in HKC-8 cells after treatment with antisense oligonucleotides targeted to SEQ ID NO: 1

| ISIS NO | SEQ ID NO: 1 Start Site | SEQ ID NO: 1 Stop Site | Sequence | EDA $^+$FN/ EDA $^-$FN | SEQ ID NO |
|---|---|---|---|---|---|
| 511399 | 55469 | 55483 | GCAAATTAATGGTAA | 0.07 | 5 |
| 511400 | 55473 | 55487 | TTAGGCAAATTAATG | 0.07 | 6 |
| 511401 | 55477 | 55491 | TCTGTTAGGCAAATT | 0.05 | 7 |
| 511402 | 55480 | 55494 | ATGTCTGTTAGGCAA | 0.09 | 8 |
| 511403 | 55483 | 55497 | TCAATGTCTGTTAGG | 0.04 | 9 |
| 511404 | 55486 | 55500 | CGATCAATGTCTGTT | 0.04 | 10 |
| 511405 | 55489 | 55503 | GGGCGATCAATGTCT | 0.03 | 11 |
| 511406 | 55493 | 55507 | TTTAGGGCGATCAAT | 0.03 | 12 |
| 511407 | 55497 | 55511 | GTCCTTTAGGGCGAT | 0.4 | 13 |

TABLE 1-continued

Ratio of EDA⁺FN to EDA⁻FN in HKC-8 cells after treatment with antisense oligonucleotides targeted to SEQ ID NO: 1

| ISIS NO | SEQ ID NO: 1 Start Site | SEQ ID NO: 1 Stop Site | Sequence | EDA⁺FN/ EDA⁻FN | SEQ ID NO |
|---|---|---|---|---|---|
| 511408 | 55732 | 55746 | CCAATCAGGGGCTGG | 0.02 | 14 |
| 511409 | 55736 | 55750 | GGTTCCAATCAGGGG | null | 15 |
| 511410 | 55740 | 55754 | ACTGGGTTCCAATCA | 0.01 | 16 |
| 511411 | 55743 | 55757 | TGGACTGGGTTCCAA | 0.02 | 17 |
| 511412 | 55746 | 55760 | CTGTGGACTGGGTTC | null | 18 |
| 511413 | 55749 | 55763 | TACCTGTGGACTGGG | 0.06 | 19 |
| 511414 | 55752 | 55766 | ATATACCTGTGGACT | 0.04 | 20 |
| 511415 | 55756 | 55770 | AACCATATACCTGTG | 0.05 | 21 |
| 511416 | 55760 | 55774 | AATTAACCATATACC | 0.15 | 22 |
| 511417 | 55482 | 55499 | GATCAATGTCTGTTAGGC | 0.12 | 23 |
| 511418 | 55744 | 55761 | CCTGTGGACTGGGTTCCA | null | 24 |
| 141923 | n/a | n/a | CCTTCCCTGAAGGTTCCTCC | 1.00 | 25 |

Example 2

In vitro Screening of Human Fibronectin Splicing with Antisense Oligonucleotides in Primary Human Proximal Tubular Cells The antisense oligonucleotides described in Example 1 were also tested for their effects on the alternative splicing of the fibronectin gene sequence in primary human proximal tubular cells (PTEC). Cultured PTEC cells were transfected using 2 µL LipofectAMINE2000®/mL OptiMEM with 100 nM antisense oligonucleotide for 4 hours, the medium was removed and new medium added, left in culture overnight, and then treated with 0.1% BSA (vehicle) or 2.5 ng/mL TGFβ1 in 0.1% BSA for 24 hrs. RNA was isolated from the cells and levels were measured by conventional PCR. The ratio of EDA⁺FN to EDA⁻FN for the given oligonucleotide-treated cells to the ratio for the negative control-treated cells was calculated. Results are presented in Table 2 and indicate that treatment with antisense oligonucleotides targeted to the EDA region of fibronectin resulted in decreased expression of the EDA⁺FN isoform compared to the negative control, even after induction with TGFβ1. 'null' indicates that the EDA⁺ band was undetectable for that sample.

TABLE 2

Ratio of EDA⁺FN to EDA⁻FN in PTEC cells after treatment with antisense oligonucleotides

| ISIS NO | EDA⁺FN/ EDA⁻FN (without TGFβ1) | EDA⁺FN/ EDA⁻FN (with TGFβ1) | SEQ ID NO |
|---|---|---|---|
| 511399 | 0.13 | 0.17 | 5 |
| 511400 | 0.23 | 0.26 | 6 |
| 511401 | 0.14 | 0.26 | 7 |
| 511402 | 0.20 | 0.27 | 8 |
| 511403 | 0.13 | 0.23 | 9 |
| 511404 | 0.09 | 0.11 | 10 |
| 511405 | 0.06 | 0.08 | 11 |
| 511406 | 0.03 | 0.04 | 12 |
| 511407 | 0.41 | 0.66 | 13 |
| 511408 | null | null | 14 |
| 511409 | null | null | 15 |
| 511410 | null | null | 16 |
| 511411 | 0.10 | 0.09 | 17 |
| 511412 | null | null | 18 |
| 511413 | 0.08 | 0.09 | 19 |
| 511414 | 0.15 | 0.13 | 20 |
| 511415 | 0.34 | 0.42 | 21 |
| 511416 | 0.62 | 0.97 | 22 |
| 511417 | 0.17 | 0.20 | 23 |
| 511418 | null | null | 24 |
| 141923 | 1.00 | 1.61 | 25 |

Example 3

Effect of Antisense Oligonucleotides Targeting the EDA Region of Fibronectin on TGFβ1 Induction of EDA⁺FN mRNA Expression in Primary Human Proximal Tubular Cells Antisense oligonucleotides selected from the studies described above were tested for their effects on the alternative splicing of the fibronectin gene sequence in primary human proximal tubular cells (PTEC) treated with TGFβ1. One set of cultured PTEC cells were transfected using 2 µL LipofectAMINE2000®/mL OptiMEM with 100 nM antisense oligonucleotide. These cells were treated for 4 hours with antisense oligonucleotide; the medium was removed and new medium added; left in culture overnight; and then treated with 0.1% BSA (vehicle) or 2.5 ng/mL TGFβ1 in 0.1% BSA for 24 hrs. These cells were designated as pre-TGFβ1. Another set of cells were first treated with 0.1% BSA (vehicle) or 2.5 ng/mL TGFβ1 in 01% BSA for 24 hrs; then transfected using 2 µL LipofectAMINE2000®/mL OptiMEM with 100 nM antisense oligonucleotide for 4 h; the medium was removed and new medium added; and then left in culture overnight. These cells were designated as post-TGFβ1. RNA was isolated from the cells and levels were measured by conventional PCR. The ratio of EDA$^+$FN to EDA$^-$FN for the given oligonucleotide-treated cells to the ratio for the negative control-treated cells was calculated. Results are presented in Tables 3 and 4, and indicate that treatment with antisense oligonucleotides targeted to the EDA region of fibronectin resulted in decreased expression of the EDA$^+$FN isoform compared to the negative control, irrespective of whether the treatment with antisense oligonucleotides took place before or after induction with TGFβ1 'null' indicates that the EDA$^+$ band was undetectable for that sample.

TABLE 3

Ratio of EDA$^+$FN to EDA$^-$FN in pre-TGFβ1 PTEC cells after treatment with antisense oligonucleotides

| ISIS NO | EDA$^+$FN/ EDA$^-$FN (without TGFβ1) | EDA$^+$FN/ EDA$^-$FN (with TGFβ1) | SEQ ID NO |
|---|---|---|---|
| 511399 | 0.13 | 0.17 | 5 |
| 511403 | 0.13 | 0.23 | 9 |
| 511407 | 0.41 | 0.66 | 13 |
| 511408 | null | null | 14 |
| 511412 | null | null | 18 |
| 511416 | 0.62 | 0.97 | 22 |
| 141923 | 1.00 | 1.61 | 25 |

TABLE 4

Ratio of EDA$^+$FN to EDA$^-$FN in post-TGFβ1 PTEC cells after treatment with antisense oligonucleotides

| ISIS NO | EDA$^+$FN/ EDA$^-$FN (without TGFβ1) | EDA$^+$FN/ EDA$^-$FN (with TGFβ1) | SEQ ID NO |
|---|---|---|---|
| 511399 | 0.68 | 0.75 | 5 |
| 511403 | 0.48 | 0.30 | 9 |
| 511407 | 0.68 | 0.68 | 13 |
| 511408 | 0.22 | 0.16 | 14 |
| 511412 | null | null | 18 |
| 511416 | 0.79 | 0.69 | 22 |
| 141923 | 1.00 | 1.57 | 25 |

Example 4

Effect of Antisense Oligonucleotides Targeting the EDA Region of Fibronectin on TGFβ1 Induction of EDA$^+$FN Protein Expression in Primary Human Proximal Tubular Cells The antisense oligonucleotides described above were tested for their effects on the alternative splicing of the fibronectin gene sequence in primary human proximal tubular cells (PTEC) treated with TGFβ1. Cultured PTEC cells were transfected using 2 µL LipofectAMINE2000®/mL OptiMEM with 100 nM antisense oligonucleotide. The cells were treated for 4 hours with antisense oligonucleotide; the medium was removed and new medium added; left in culture overnight; and then treated with 0.1% BSA (vehicle) or 2.5 ng/mL TGFβ1 in 01% BSA for 48 hrs. The cells were lysed in lysis buffer (20 mM Tris-HCl, 150 mM NaCl, 1 mM EDTA, 1% Triton X, 0.5% sodium deoxycholate, 0.1% SDS; pH 7.2) and protein was extracted as described in Phanish M K et al., Biochem J. 2006 Jan. 15; 393(Pt 2):601-7. The protein samples were run on an SDS-PAGE and analyzed via western analysis using the anti-Fibronectin antibody [IST-9] (Abcam, ab6328) that reacts with an epitope located in the ED-A sequence of cellular fibronectin. Results are presented in Table 5, and indicate that treatment with antisense oligonucleotides targeted to the EDA region of fibronectin resulted in decreased protein expression of the EDA$^+$FN isoform compared to the negative control.

TABLE 5

EDA$^+$FN expression in PTEC cells after treatment with antisense oligonucleotides (densitometric analysis on one Western blot)

| ISIS NO | EDA$^+$FN (without TGFβ1) | EDA$^+$FN (with TGFβ1) | SEQ ID NO |
|---|---|---|---|
| 511399 | 0.07 | 0.03 | 5 |
| 511403 | 0.02 | 0.04 | 9 |
| 511407 | 0.13 | 0.75 | 13 |
| 511408 | 0.08 | 0.77 | 14 |
| 511412 | 0.25 | 0.30 | 18 |
| 511416 | 0.61 | 0.58 | 22 |
| 141923 | 0.31 | 0.74 | 25 |

Example 5

Effect of ISIS 511403 on TGFβ1 Induction of Fibrosis in Primary Human Proximal Tubular Cells ISIS 511403 was tested for its effect on the alternative splicing of the fibronectin gene sequence in primary human proximal tubular cells (PTEC) treated with TGFβ1. Cultured PTEC cells were treated with 0.1% BSA (vehicle) or with 2.5 ng/mL TGFβ1 in 01% BSA for 24 hrs and then transfected using 2 µL LipofectAMINE2000®/mL OptiMEM with 100 nM ISIS 511403 or 100 nM ISIS 141923 for 24 h. After a recovery period of 24 h in normal growth medium, RNA was isolated and the ratio of EDA$^+$FN to EDA$^{-\square}$FN was measured by conventional PCR. In addition, the individual expressions of EDA$^+$FN and EDA$^{-\square}$FN normalized to 18s RNA were also measured (human primer probe set for 18S: forward sequence: GTAACCCGTTGAACCCCATT (SEQ ID NO: 26), reverse sequence: CCATCCAATCGG-TAGTAGCG (SEQ ID NO: 27)). In addition, the expression of total fibronectin was also measured by quantitative real-time PCR (probe set Hs01549940_m1, Applied Biosystems). The results are presented in Table 6 and indicate that treatment with ISIS 511403 decreased the ratio of EDA$^+$FN to EDA$^-$FN, decreased expression of EDA$^+$FN, increased expression of EDA$^-$FN, and had no effect on total fibronectin expression compared to that of the negative control cells.

TABLE 6

Effect of ISIS 511403 in PTEC cells treated with TGFβ1

|  |  | without TGFβ1 | with TGFβ1 |
|---|---|---|---|
| EDA+FN/ | ISIS 141923 | 0.90 | 1.54 |
| EDA-□FN | ISIS 511403 | 0.21 | 0.12 |
| EDA+FN/18S | ISIS 141923 | 0.21 | 0.21 |
|  | ISIS 511403 | 0.07 | 0.68 |
| EDA-□FN/18S | ISIS 141923 | 0.23 | 0.11 |
|  | ISIS 511403 | 0.32 | 0.86 |
| Total Fibronectin (range) | ISIS 141923 | 1.00 (0.82-1.23) | 3.98 (3.60-4.40) |
|  | ISIS 511403 | 1.37 (1.17-1.60) | 4.14 (4.05-4.23) |

The effect of treatment with ISIS 511403 on lactate dehydrogenase (LDH) release by the cells was also measured using the CytoTox 96® Non-Radioactive Cytotoxicity Assay (Promega, G1780). The results are presented in Table 7 and indicate the decrease in LDH release in cells treated with ISIS 511403 compared to the cells treated with the negative control. This demonstrates that ISIS 511403 can rescue certain pronounced changes in cell phenotype caused by TGFβ1 induction, e.g. the release of LDH.

TABLE 7

Effect of ISIS 511403 on LDH release in PTEC cells treated with TGFβ1

|  |  | Absorbance at 490 nm |
|---|---|---|
| ISIS 141923 | without TGFβ1 | 0.14 |
|  | with TGFβ1 | 0.12 |
| ISIS 511403 | without TGFβ1 | 0.33 |
|  | with TGFβ1 | 0.16 |

The effect of treatment with ISIS 511403 on αSMA mRNA expression by the cells was also measured by quantitative real-time PCR, using primer probe set Hs00909449_m1 (Applied Biosystems). The results are presented in Table 8 and indicate the decrease in αSMA in cells treated with ISIS 511403 compared to the cells treated with the negative control. The numbers in parentheses indicate the range. This demonstrates that ISIS 511403 can rescue certain pronounced changes in cell phenotype caused by TGFβ1 induction, e.g. the induction of αSMA.

TABLE 8

Effect of ISIS 511403 on αSMA expression in PTEC cells treated with TGFβ1

|  |  | Fold increase over basal levels |
|---|---|---|
| ISIS 141923 | without TGFβ1 | 1.00 (0.79-1.26) |
|  | with TGFβ1 | 1.96 (1.70-2.25) |
| ISIS 511403 | without TGFβ1 | 0.70 (0.59-0.83) |
|  | with TGFβ1 | 0.79 (0.68-0.91) |

The data presented in Tables 7 and 8 indicate that treatment with antisense oligonucleotides inhibiting the splicing and inclusion of the EDA region of fibronectin resulted in decreased fibrosis in primary human PTEC and therefore have therapeutic benefit in the prevention, treatment, or amelioration of fibrosis.

Additionally, by staining it was observed that prevention of EDA inclusion by treatment with ISIS 511403 resulted in a significant reduction in αSMA compared to treatment with a control (ISIS 141923). By western blot analysis, it was also observed that prevention of EDA inclusion by treatment with ISIS 511403 resulted in reduction in secretion of MMP2 & MMP9. The fold-change in the cell motility marker, S100A4 was measured and is presented in Table 9. Treatment with ISIS 511403 resulted in significant reduction in S100A4 in TGF-β-treated cells.

TABLE 9

Effect of ISIS 511403 on S100A4 expression in PTEC cells treated with TGFβ1

|  |  | Fold increase over basal levels |
|---|---|---|
| ISIS 141923 | without TGFβ1 | 1.00 |
|  | with TGFβ1 | 1.45 |
| ISIS 511403 | without TGFβ1 | 0.62 |
|  | with TGFβ1 | 0.74 |

By staining and by western blot analysis, it was also observed that prevention of EDA inclusion by treatment with ISIS 511403 resulted in near complete inhibition of Connexin 43. By staining, it was also observed that prevention of EDA inclusion by treatment with ISIS 511403 resulted in a moderate increase in f-actin localization.

Example 6

Design of Antisense Oligonucleotides Targeting Human and Murine Fibronectin

Antisense oligonucleotides were designed targeting a fibronectin nucleic acid. The newly designed chimeric antisense oligonucleotides in Table 10 were designed as uniform MOE oligonucleotides. Each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Table 10 is targeted to the human fibronectin genomic sequence, SEQ ID NO: 1 (the complement of GENBANK Accession No. NT_005403.14 truncated from nucleotides 66434501 to 66510708) or to murine fibronectin genomic sequence, SEQ ID NO: 29 (the complement of Accession No. NT_039170.2 truncated from nucleotides 20696091 to 20764741), or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the number of nucleotides in the oligonucleotide that are mismatched with the gene sequence. 'n/a' indicates that the oligonucleotide contains more than 2 mismatches with the particular gene sequence.

TABLE 10

Antisense oligonucleotides targeted to SEQ ID NO: 1 and SEQ ID NO: 29

| Human target Start Site (SEQ ID NO: 1) | Mismatches with SEQ ID NO: 1 | Sequence | ISIS No | Mouse Target Start Site (SEQ ID NO: 29) | Mismatches with SEQ ID NO: 29 | SEQ ID NO of oligo |
|---|---|---|---|---|---|---|
| 55458 | 0 | GTAAGAGGTTATGTG | 594692 | 49712 | 0 | 30 |
| 55464 | 0 | TTAATGGTAAGAGGT | 594693 | 49718 | 0 | 31 |
| 55478 | 0 | AATGTCTGTTAGGCAAAT | 594685 | 49732 | 0 | 32 |
| 55479 | 0 | CAATGTCTGTTAGGCAAA | 594686 | 49733 | 0 | 33 |
| 55480 | 0 | TCAATGTCTGTTAGGCAA | 594687 | 49734 | 0 | 34 |
| 55481 | 0 | AATGTCTGTTAGGCA | 594681 | 49735 | 0 | 35 |
| 55481 | 0 | ATCAATGTCTGTTAGGCA | 594688 | 49735 | 0 | 36 |
| 55482 | 0 | CAATGTCTGTTAGGC | 594682 | 49736 | 0 | 37 |
| 55483 | 0 | CGATCAATGTCTGTTAGG | 594689 | 49737 | 0 | 38 |
| 55484 | 0 | ATCAATGTCTGTTAG | 594683 | 49738 | 0 | 39 |
| 55484 | 0 | GCGATCAATGTCTGTTAG | 594690 | 49738 | 0 | 40 |
| 55485 | 0 | GATCAATGTCTGTTA | 594684 | 49739 | 0 | 41 |
| 55485 | 0 | GGCGATCAATGTCTGTTA | 594691 | 49739 | 0 | 42 |
| 55501 | 0 | GCCAGTCCTTTAGGG | 594694 | 49755 | 0 | 43 |
| 55507 | 0 | GTGAATGCCAGTCCT | 594695 | 49761 | 0 | 44 |
| 55513 | 0 | ACATCAGTGAATGCC | 594696 | 49767 | 0 | 45 |
| 55519 | 0 | ACATCCACATCAGTG | 594697 | 49773 | 0 | 46 |
| 55525 | 0 | GAATCGACATCCACA | 594698 | 49779 | 0 | 47 |
| 55531 | 0 | TTGATGGAATCGACA | 594699 | 49785 | 0 | 48 |
| 55537 | 0 | GCAATTTGATGGAA | 594700 | 49791 | 0 | 49 |
| 55543 | 0 | TCCCAAGCAATTTTG | 594701 | 49797 | 0 | 50 |
| 55549 | 0 | GGGCTTTCCCAAGCA | 594702 | 49803 | 0 | 51 |
| 55555 | 0 | CCCTGTGGGCTTTCC | 594703 | 49809 | 0 | 52 |
| 55561 | 0 | ACTTGCCCCTGTGGG | 594704 | 49815 | 0 | 53 |
| 55567 | 0 | CTGGAAACTTGCCCC | 594705 | 49821 | 0 | 54 |
| 55573 | 0 | CTGTACCTGGAAACT | 594706 | 49827 | 0 | 55 |
| 55579 | 0 | GTCACCCTGTACCTG | 594707 | 49833 | 0 | 56 |
| 55585 | 0 | GAGTAGGTCACCCTG | 594708 | 49839 | 0 | 57 |
| 55591 | 0 | GGGCTCGAGTAGGTC | 594709 | 49845 | 0 | 58 |
| 55597 | 0 | TCCTCAGGGCTCGAG | 594710 | 49851 | 0 | 59 |
| 55603 | 0 | ATTCCATCCTCAGGG | 594711 | 49857 | 0 | 60 |
| 55609 | 0 | TCATGGATTCCATCC | 594712 | 49863 | 2 | 61 |
| 55615 | 0 | AATAGCTCATGGATT | 594713 | n/a | n/a | 62 |
| 55621 | 0 | GCAGGGAATAGCTCA | 594714 | 49875 | 2 | 63 |
| 55627 | 0 | TCAGGTGCAGGGAAT | 594715 | 49881 | 1 | 64 |
| 55633 | 0 | TCACCATCAGGTGCA | 594716 | 49887 | 0 | 65 |
| 55639 | 0 | TCTTCTTCACCATCA | 594717 | 49893 | 1 | 66 |

TABLE 10-continued

Antisense oligonucleotides targeted to SEQ ID NO: 1 and SEQ ID NO: 29

| Human target Start Site (SEQ ID NO: 1) | Mismatches with SEQ ID NO: 1 | Sequence | ISIS No | Mouse Target Start Site (SEQ ID NO: 29) | Mismatches with SEQ ID NO: 29 | SEQ ID NO of oligo |
|---|---|---|---|---|---|---|
| 55645 | 0 | GCAGTGTCTTCTTCA | 594718 | 49899 | 1 | 67 |
| 55651 | 0 | AGCTCTGCAGTGTCT | 594719 | 49905 | 1 | 68 |
| 55657 | 0 | CCTTGCAGCTCTGCA | 594720 | 49911 | 1 | 69 |
| 55663 | 0 | CTGAGGCCTTGCAGC | 594721 | 49917 | 1 | 70 |
| 55669 | 0 | CCCGGTCTGAGGCCT | 594722 | 49923 | 2 | 71 |
| 55675 | 0 | TCAGAACCCGGTCTG | 594723 | 49929 | 2 | 72 |
| 55681 | 0 | GTGTACTCAGAACCC | 594724 | 49935 | 1 | 73 |
| 55687 | 0 | CTGACTGTGTACTCA | 594725 | 49941 | 0 | 74 |
| 55693 | 0 | ACCACACTGACTGTG | 594726 | 49947 | 0 | 75 |
| 55699 | 0 | AAGGCAACCACACTG | 594727 | 49953 | 0 | 76 |
| 55705 | 0 | TCGTGCAAGGCAACC | 594728 | 49959 | 0 | 77 |
| 55711 | 0 | ATATCATCGTGCAAG | 594729 | 49965 | 0 | 78 |
| 55717 | 0 | CTCTCCATATCATCG | 594730 | 49971 | 0 | 79 |
| 55723 | 0 | GGCTGGCTCTCCATA | 594731 | 49977 | 0 | 80 |
| 55736 | 1 | GATTCCAATCAGGGG | 594670 | 49990 | 0 | 81 |
| 55740 | 1 | ACTGGATTCCAATCA | 594671 | 49994 | 0 | 82 |
| 55743 | 1 | TGGACTGGATTCCAA | 594672 | 49997 | 0 | 83 |
| 55744 | 1 | CCTGTGGACTGGATTCCA | 594677 | 49998 | 0 | 84 |
| 55746 | 1 | CTGTGGACTGGATTC | 594673 | 50000 | 0 | 85 |
| 55749 | 1 | TACCTGTGGACTGGA | 594674 | 50003 | 0 | 86 |
| 55756 | 1 | AACGATATACCTGTG | 594675 | 50010 | 0 | 87 |
| 55760 | 2 | AATTAATCATAAACC | 594676 | 39337 | 0 | 88 |
| 55765 | 0 | GGTGCAATTAACCAT | 594732 | n/a | n/a | 89 |
| 55771 | 0 | CCTGGTGGTGCAATT | 594733 | n/a | n/a | 90 |

Example 7

In vitro Screening of Uniform MOE Antisense Oligonucleotides Targeting Human and/or Mouse Fibronectin in MHT Cells Some of the antisense oligonucleotides presented in Example 6 were tested for potency in cultured primary PTEC cells. ISIS 511403 was also included in the study.

Cultured PTEC cells were transfected using 2 µL LipofectAMINE2000®/mL OptiMEM with 100 nM antisense oligonucleotide for 4 hours, the medium was removed and new medium added, left in culture overnight, and then treated with 0.1% BSA (vehicle) or 2.5 ng/mL TGFβ1 in 0.1% BSA for 24 hrs. RNA was isolated from the cells and levels of EDA⁺FN mRNA were measured by RT-PCR using primer probe sets RTS3963_MGB (forward sequence GCCTTGCACGATGATATGGA, designated herein as SEQ ID NO: 91; reverse sequence TGTGGGTGTGACCT-GAGTGAA, designated herein as SEQ ID NO: 92; probe sequence ATTGGAACCCAGTCCAC, designated herein as SEQ ID NO: 93), as well as with primer probe set RTS3964 (forward sequence GAATCCAAGCGGAGAGAGTCA, designated herein as SEQ ID NO: 94; reverse sequence ACATCAGTGAATGCCAGTCCTTT, designated herein as SEQ ID NO: 95; probe sequence TTCAGACTGCAG-TAACCAACATTGATCGCC, designated herein as SEQ ID NO: 96), both of which are designed to the EDA+ variant of the FN mRNA transcript (NM_212478.1, designated herein as SEQ ID NO: 97) and which target different regions of the transcript. For data analysis, the levels of EDA⁺FN mRNA were normalized to the levels of the house-keeping gene, the large ribosomal protein transcript (Human RPLPO, Applied Biosystems, cat#4333761F). For each antisense oligonucleotide, the ratio of EDA⁺FN to RPLPO in antisense oligonucleotide-treated cells was then normalized to the ratio of EDA⁺FN mRNA to RPLPO in untreated cells. The results are presented in Table 11. The results indicate that treatment with antisense oligonucleotides reduced expression of the EDA+ transcript compared to untreated cells, both in the presence or absence of TGFβ1.

TABLE 11

EDA+FN mRNA levels compared to untreated cells (designated 1.00) in primary PTEC cells

| ISIS No | PPset Used | without TGFβ1 | with TGFβ1 |
|---|---|---|---|
| 511403 | RTS3963_MGB | 0.21 | 0.21 |
| 594692 | RTS3963_MGB | 0.17 | 0.29 |
| 594693 | RTS3963_MGB | 0.21 | 0.32 |
| 594694 | RTS3963_MGB | 0.02 | 0.03 |
| 594695 | RTS3963_MGB | 0.15 | 0.24 |
| 594696 | RTS3963_MGB | 0.23 | 0.41 |
| 594697 | RTS3963_MGB | 0.40 | 0.70 |
| 594698 | RTS3963_MGB | 0.50 | 0.81 |
| 594699 | RTS3963_MGB | 0.51 | 0.76 |
| 594700 | RTS3963_MGB | 0.13 | 0.18 |
| 594701 | RTS3963_MGB | 0.33 | 0.47 |
| 594702 | RTS3963_MGB | 0.30 | 0.49 |
| 594703 | RTS3963_MGB | 0.16 | 0.32 |
| 594704 | RTS3963_MGB | 0.56 | 0.73 |
| 594705 | RTS3963_MGB | 0.40 | 0.68 |
| 594706 | RTS3963_MGB | 0.40 | 0.81 |
| 594707 | RTS3963_MGB | 0.29 | 0.40 |
| 594708 | RTS3963_MGB | 0.06 | 0.05 |
| 594709 | RTS3963_MGB | 0.03 | 0.02 |
| 594710 | RTS3963_MGB | 0.18 | 0.16 |
| 594711 | RTS3963_MGB | 0.43 | 0.27 |
| 594712 | RTS3963_MGB | 0.36 | 0.31 |
| 594713 | RTS3963_MGB | 0.14 | 0.15 |
| 594714 | RTS3963_MGB | 0.06 | 0.08 |
| 594715 | RTS3963_MGB | 0.05 | 0.07 |
| 594716 | RTS3963_MGB | 0.18 | 0.16 |
| 594717 | RTS3963_MGB | 0.71 | 0.68 |
| 594718 | RTS3963_MGB | 0.22 | 0.33 |
| 594719 | RTS3963_MGB | 0.46 | 0.44 |
| 594720 | RTS3963_MGB | 0.13 | 0.14 |
| 594721 | RTS3963_MGB | 0.14 | 0.13 |
| 594722 | RTS3963_MGB | 0.07 | 0.15 |
| 594723 | RTS3963_MGB | 0.05 | 0.05 |
| 594724 | RTS3963_MGB | 0.11 | 0.17 |
| 594725 | RTS3963_MGB | 0.06 | 0.07 |
| 594726 | RTS3963_MGB | 0.12 | 0.17 |
| 594727 | RTS3964 | 0.06 | 0.10 |
| 594728 | RTS3964 | 0.03 | 0.02 |
| 594729 | RTS3964 | 0.08 | 0.06 |
| 594730 | RTS3964 | 0.39 | 0.38 |
| 594731 | RTS3964 | 0.10 | 0.07 |
| 594732 | RTS3963_MGB | 0.92 | 0.79 |
| 594733 | RTS3963_MGB | 0.37 | 0.38 |

Example 8

In vitro Screening of Uniform MOE Antisense Oligonucleotides Targeting Human and/or Mouse Fibronectin in MHT Cells Antisense oligonucleotides were designed targeting a fibronectin nucleic acid and were tested for their effects on blocking of splicing in vitro. The newly designed chimeric antisense oligonucleotides in Table 12 were designed as uniform MOE oligonucleotides. Each oligonucleotide is 15 nucleosides long and each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Table 12 is targeted to the human fibronectin genomic sequence, SEQ ID NO: 1 or to murine fibronectin genomic sequence, SEQ ID NO: 22, or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a' indicates that the antisense oligonucleotide has more than 3 mismatches with the particular gene sequence.

Cultured MHT cells, a mouse hepatocellular carcinoma cell line (Koller, E. et al., Nucleic Acids Research, 2011, 1-13), were transfected using 5 μl LipofectAMINE2000®/mL OptiMEM with 50 nM antisense oligonucleotide. After a treatment period of approximately 4 hours, the medium was removed and new medium was added, and the cells were left in culture overnight RNA was isolated from the cells and measured by RT-PCR. EDA+FN mRNA expression was measured with mouse primer probe set LTS01050 (forward sequence AAACTGCAGTGACCAACATTGATC, designated herein as SEQ ID NO: 98; reverse sequence CTTGCCCCTGTGGGCTTT, designated herein as SEQ ID NO: 99; probe sequence CTGATGTGGATGTCGATT, designated herein as SEQ ID NO: 100), as well as with LTS01052 (forward sequence GCCAGCCCCTGATTGGA, designated herein as SEQ ID NO: 101; reverse sequence CCGGTAGCCAGTGAGCTGAA, designated herein as SEQ ID NO: 102; probe sequence CACCAATCTGAAGTTC, designated herein as SEQ ID NO: 103). The primer probe sets target different regions of the mouse sequence.

Results are presented in Table 12 and are the average of the values measured in three separate experiments. The results demonstrate blocking of splicing, as represented by EDA+FN expression. The expression value of untreated cells was taken as 1.00. 'n.d.' indicates that the mRNA expression level values were not considered because the oligonucleotide targeted an amplicon region of the specific primer probe set.

TABLE 12

EDA+FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55469 | 0 | GCAAATTAATGGTAA | 49723 | 511399 | 0.43 | 0.44 | 104 |
| 55486 | 0 | CGATCAATGTCTGTT | 49740 | 511404 | n.d. | 0.27 | 105 |
| 55746 | 1 | CTGTGGACTGGATTC | 50000 | 594673 | 0.61 | n.d. | 85 |

TABLE 12-continued

EDA+FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55756 | 1 | AACGATATACCTGTG | 50010 | 594675 | 0.28 | n.d. | 87 |
| 55481 | 0 | AATGTCTGTTAGGCA | 49735 | 594681 | n.d. | 0.37 | 35 |
| 55501 | 0 | GCCAGTCCTTTAGGG | 49755 | 594694 | n.d. | 0.46 | 43 |
| 55531 | 0 | TTGATGGAATCGACA | 49785 | 594699 | n.d. | 0.93 | 48 |
| 55561 | 0 | ACTTGCCCCTGTGGG | 49815 | 594704 | n.d. | 0.94 | 53 |
| 55591 | 0 | GGGCTCGAGTAGGTC | 49845 | 594709 | 0.18 | 0.37 | 58 |
| 55711 | 0 | ATATCATCGTGCAAG | 49965 | 594729 | 0.50 | 0.33 | 78 |
| 55418 | 3 | TCCATACCATGCAAA | 49670 | 598110 | 1.11 | 1.04 | 106 |
| 20288 51489 | 3 3 | ATATTTCCATACCAT | 49675 | 598111 | 1.11 | 1.02 | 107 |
| 17531 19804 23642 42202 | 3 3 3 3 | CAAGCATATTTCCAT | 49680 | 598112 | 0.93 | 1.03 | 108 |
| 43710 55431 | 2 2 | TGAAACAAGCATATT | 49685 | 598113 | 1.04 | 1.15 | 109 |
| 55436 | 1 | AGTTGTGAAACAAGC | 49690 | 598114 | 0.42 | 0.58 | 110 |
| 55441 | 0 | AAGCAAGTTGTGAAA | 49695 | 598115 | 0.08 | 0.35 | 111 |
| 55446 | 0 | GTGAAAAGCAAGTTG | 49700 | 598116 | 0.85 | 0.94 | 112 |
| 55451 | 0 | GTTATGTGAAAAGCA | 49705 | 598117 | 0.63 | 0.68 | 113 |
| 55456 | 0 | AAGAGGTTATGTGAA | 49710 | 598118 | 0.58 | 0.54 | 114 |
| 55461 | 0 | ATGGTAAGAGGTTAT | 49715 | 598119 | 0.47 | 0.43 | 115 |
| 55466 | 0 | AATTAATGGTAAGAG | 49720 | 598120 | 0.49 | 0.53 | 116 |
| 55471 | 0 | AGGCAAATTAATGGT | 49725 | 598121 | 0.27 | 0.29 | 117 |
| 55476 | 0 | CTGTTAGGCAAATTA | 49730 | 598122 | 0.23 | 0.34 | 118 |
| 55491 | 0 | TAGGGCGATCAATGT | 49745 | 598123 | n.d. | 0.29 | 119 |
| 55496 | 0 | TCCTTTAGGGCGATC | 49750 | 598124 | n.d. | 0.39 | 120 |
| 55506 | 0 | TGAATGCCAGTCCTT | 49760 | 598125 | n.d. | 0.70 | 121 |
| 55511 | 0 | ATCAGTGAATGCCAG | 49765 | 598126 | n.d. | 0.54 | 122 |
| 55516 | 0 | TCCACATCAGTGAAT | 49770 | 598127 | n.d. | 0.53 | 123 |
| 55521 | 0 | CGACATCCACATCAG | 49775 | 598128 | n.d. | 0.47 | 124 |
| 55526 | 0 | GGAATCGACATCCAC | 49780 | 598129 | n.d. | 0.32 | 125 |
| 55536 | 0 | CAATTTGATGGAAT | 49790 | 598130 | n.d. | 0.26 | 126 |
| 55541 | 0 | CCAAGCAATTTGAT | 49795 | 598131 | n.d. | 0.45 | 127 |
| 55546 | 0 | CTTTCCCAAGCAATT | 49800 | 598132 | n.d. | 0.51 | 128 |
| 55551 | 0 | GTGGGCTTTCCCAAG | 49805 | 598133 | n.d. | 0.92 | 129 |
| 55556 | 0 | CCCCTGTGGGCTTTC | 49810 | 598134 | n.d. | 0.59 | 130 |
| 55566 | 0 | TGGAAACTTGCCCCT | 49820 | 598135 | n.d. | 0.70 | 131 |
| 55571 | 0 | GTACCTGGAAACTTG | 49825 | 598136 | n.d. | 0.50 | 132 |

TABLE 12-continued

EDA+FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 55576 | 0 | ACCCTGTACCTGGAA | 49830 | 598137 | 78 | 0.27 | 133 |
| 55581 | 0 | AGGTCACCCTGTACC | 49835 | 598138 | 78 | 0.27 | 134 |
| 55586 | 0 | CGAGTAGGTCACCCT | 49840 | 598139 | 71 | 0.41 | 135 |
| 55596 | 0 | CCTCAGGGCTCGAGT | 49850 | 598140 | 73 | 0.42 | 136 |
| 55601 | 0 | TCCATCCTCAGGGCT | 49855 | 598141 | 63 | 0.42 | 137 |
| 55606 | 1 | CGGATTCCATCCTCA | 49860 | 598142 | 52 | 0.35 | 138 |
| 55611 | 2 | GCTCCCGGATTCCAT | 49865 | 598143 | 78 | 0.31 | 139 |
| 48384 55616 | 3 3 | GAAAAGCTCCCGGAT | 49870 | 598144 | 0.20 | 0.28 | 140 |
| 55621 | 2 | GCAGGGAAAAGCTCC | 49875 | 598145 | 0.19 | 0.21 | 141 |
| 55626 | 1 | CAGGTGCAGGGAAAA | 49880 | 598146 | 0.32 | 0.33 | 142 |
| 55631 | 0 | ACCATCAGGTGCAGG | 49885 | 598147 | 0.31 | 0.30 | 143 |
| 55636 | 0 | TCTTCACCATCAGGT | 49890 | 598148 | 0.47 | 0.38 | 144 |
| 55641 | 1 | TGTCGTCTTCACCAT | 49895 | 598149 | 0.39 | 0.37 | 145 |
| 55646 | 1 | TGCAGTGTCGTCTTC | 49900 | 598150 | 0.66 | 0.41 | 146 |
| 55651 | 1 | AGCTCTGCAGTGTCG | 49905 | 598151 | 0.29 | 0.24 | 147 |
| 55656 | 1 | CCTGCAGCTCTGCAG | 49910 | 598152 | 0.40 | 0.42 | 148 |
| 55661 | 1 | GAGGCCCTGCAGCTC | 49915 | 598153 | 0.25 | 0.21 | 149 |
| 55666 | 2 | GGCCTGAGGCCCTGC | 49920 | 598154 | 0.79 | 0.80 | 150 |
| 55671 | 2 | ACCCCGGCCTGAGGC | 49925 | 598155 | 0.48 | 0.54 | 151 |
| 55676 | 2 | CTCAGACCCCGGCCT | 49930 | 598156 | 0.68 | 0.76 | 152 |
| 55681 | 1 | GTGTACTCAGACCCC | 49935 | 598157 | 0.57 | 0.41 | 153 |
| 55686 | 0 | TGACTGTGTACTCAG | 49940 | 598158 | 0.56 | 0.54 | 154 |
| 55691 | 0 | CACACTGACTGTGTA | 49945 | 598159 | 0.59 | 0.51 | 155 |
| 55696 | 0 | GCAACCACACTGACT | 49950 | 598160 | 0.54 | 0.49 | 156 |
| 55701 | 0 | GCAAGGCAACCACAC | 49955 | 598161 | 0.27 | 0.27 | 157 |
| 55706 | 0 | ATCGTGCAAGGCAAC | 49960 | 598162 | 0.56 | 0.49 | 158 |
| 55716 | 0 | TCTCCATATCATCGT | 49970 | 598163 | 0.31 | 0.22 | 159 |
| 55721 | 0 | CTGGCTCTCCATATC | 49975 | 598164 | 0.66 | n.d. | 160 |
| 55741 | 1 | GACTGGATTCCAATC | 49995 | 598165 | 0.56 | n.d. | 161 |
| 55751 | 0 | TATACCTGTGGACTG | 50005 | 598166 | 0.39 | n.d. | 162 |
| 55761 | 3 | CGGTTAACGATATAC | 50015 | 598167 | 0.30 | 0.25 | 163 |
| n/a | n/a | GGGTGCGGTTAACGA | 50020 | 598168 | 0.91 | 0.95 | 164 |
| n/a | n/a | GTGGTGGGTGCGGTT | 50025 | 598169 | 0.95 | 0.51 | 165 |
| 7620 | 3 | CCCGGGTGGTGGGTG | 50030 | 598170 | 0.81 | 0.79 | 166 |
| n/a | n/a | AAGCACCCGGGTGGT | 50035 | 598171 | 0.92 | 1.00 | 167 |
| n/a | n/a | CCCAGAAGCACCCGG | 50040 | 598172 | 1.36 | 1.32 | 168 |

TABLE 12-continued

EDA+FN mRNA levels compared to untreated cells (designated 1.00) in MHT cells

| Human Start Site | Mismatches with human | Sequence | Mouse Start Site | ISIS No | % inhibition with LTS01050 | % inhibition with LTS01052 | SEQ ID NO |
|---|---|---|---|---|---|---|---|
| 50882 | 3 | CTGTTCCCAGAAGCA | 50045 | 598173 | 1.44 | 1.41 | 169 |
| 4 | 4 | | | | | | |
| 23948 | 1 | AGCCACTGTTCCCAG | 50050 | 598174 | 1.11 | 1.14 | 170 |
| 47171 | 1 | | | | | | |
| 55796 | 2 | CATAAAGCCACTGTT | 50055 | 598175 | 0.94 | 0.91 | 171 |
| 64745 | 2 | | | | | | |
| 55801 | 3 | CAAGGCATAAAGCCA | 50060 | 598176 | 1.13 | 0.97 | 172 |
| n/a | n/a | GCCAGCAAGGCATAA | 50065 | 598177 | 0.78 | 0.95 | 173 |
| 61226 | 3 | ATAACGCCAGCAAGG | 50070 | 598178 | 1.08 | 1.10 | 174 |
| n/a | n/a | AAAGTATAACGCCAG | 50075 | 598179 | 1.13 | 1.08 | 175 |
| 3323 | 3 | CCAGTAAAGTATAAC | 50080 | 598180 | 1.09 | 1.20 | 176 |
| 55824 | 3 | | | | | | |
| 60705 | 3 | | | | | | |

Example 9

Antisense Inhibition of Fibronectin mRNA in MHT Cells by Uniform MOE Oligonucleotides Designed by Microwalk Additional antisense oligonucleotides were designed based on the ISIS oligonucleotides that demonstrated significant effect on fibronectin splicing in the studies described above. These oligonucleotides were designed by creating oligonucleotides shifted slightly upstream and downstream (i.e. "microwalk") of ISIS 511417, ISIS 594685, ISIS 594686, ISIS 594686, ISIS 594687, ISIS 594688, ISIS 594689, ISIS 594690, ISIS 594691, and ISIS 598145. The newly designed antisense oligonucleotides in Tables 13 and 14 were designed as uniform MOE oligonucleotides. Each oligonucleotide is 18 nucleosides long and each nucleoside in the oligonucleotide has a 2'-MOE modification. The internucleoside linkages throughout each oligonucleotide are phosphorothioate (P=S) linkages. All cytosine residues throughout each oligonucleotide are 5-methylcytosines. The oligonucleotides are presented in the tables below. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in the tables is targeted to the human fibronectin genomic sequence, SEQ ID NO: 1 or to murine fibronectin genomic sequence, SEQ ID NO: 29, or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a' indicates that the antisense oligonucleotide has more than 3 mismatches with the particular gene sequence.

Cultured MHT cells were transfected using 5 µl LipofectAMINE2000®/mL OptiMEM with 10 nM antisense oligonucleotide. After a treatment period of approximately 4 hours, the medium was removed and new medium was added, left in culture overnight. RNA was isolated from the cells and measured by RT-PCR. EDA+FN mRNA expression was measured with mouse primer probe set LTS01050, as well as with LTS01052.

Results are presented in Tables 13 and 14, and are the average of the values measured in three separate experiments. The results demonstrate blocking of splicing, as represented by EDA+FN expression. The expression value of untreated cells was taken as 1.00. 'n.d.' indicates that the mRNA expression level values were not considered because the oligonucleotide targeted an amplicon region of the specific primer probe set.

TABLE 13

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55471 | 0 | GTTAGGCAAATTAATGGT | 606663 | 49725 | n.d. | 0.77 | 177 |
| 55472 | 0 | TGTTAGGCAAATTAATGG | 606664 | 49726 | n.d. | 0.80 | 178 |

TABLE 13-continued

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55473 | 0 | CTGTTAGGCAAATTAATG | 606665 | 49727 | n.d. | 0.78 | 179 |
| 55474 | 0 | TCTGTTAGGCAAATTAAT | 606666 | 49728 | n.d. | 0.73 | 180 |
| 55475 | 0 | GTCTGTTAGGCAAATTAA | 606667 | 49729 | n.d. | 0.70 | 181 |
| 55476 | 0 | TGTCTGTTAGGCAAATTA | 606668 | 49730 | n.d. | 0.62 | 182 |
| 55477 | 0 | ATGTCTGTTAGGCAAATT | 606669 | 49731 | n.d. | 0.66 | 183 |
| 55478 | 0 | AATGTCTGTTAGGCAAAT | 594685 | 49732 | n.d. | 0.79 | 32 |
| 55479 | 0 | CAATGTCTGTTAGGCAAA | 594686 | 49733 | 0.57 | 0.50 | 33 |
| 55480 | 0 | TCAATGTCTGTTAGGCAA | 594687 | 49734 | 1.21 | 0.99 | 34 |
| 55481 | 0 | ATCAATGTCTGTTAGGCA | 594688 | 49735 | 1.04 | 0.83 | 36 |
| 55482 | 0 | GATCAATGTCTGTTAGGC | 511417 | 49736 | 0.70 | 0.63 | 184 |
| 55483 | 0 | CGATCAATGTCTGTTAGG | 594689 | 49737 | n.d. | 0.66 | 38 |
| 55484 | 0 | GCGATCAATGTCTGTTAG | 594690 | 49738 | n.d. | 0.64 | 40 |
| 55485 | 0 | GGCGATCAATGTCTGTTA | 594691 | 49739 | n.d. | 0.85 | 42 |
| 55486 | 0 | GGGCGATCAATGTCTGTT | 606670 | 49740 | n.d. | 0.83 | 185 |
| 55487 | 0 | AGGGCGATCAATGTCTGT | 606671 | 49741 | n.d. | 0.82 | 186 |
| 55488 | 0 | TAGGGCGATCAATGTCTG | 606672 | 49742 | n.d. | 0.80 | 187 |
| 55489 | 0 | TTAGGGCGATCAATGTCT | 606673 | 49743 | n.d. | 0.56 | 188 |
| 55490 | 0 | TTTAGGGCGATCAATGTC | 606674 | 49744 | n.d. | 0.56 | 189 |
| 55491 | 0 | CTTTAGGGCGATCAATGT | 606675 | 49745 | n.d. | 0.55 | 190 |
| 55492 | 0 | CCTTTAGGGCGATCAATG | 606676 | 49746 | n.d. | 0.47 | 191 |
| 55493 | 0 | TCCTTTAGGGCGATCAAT | 606677 | 49747 | n.d. | 0.57 | 192 |
| 55494 | 0 | GTCCTTTAGGGCGATCAA | 606678 | 49748 | n.d. | 0.62 | 193 |
| 55495 | 0 | AGTCCTTTAGGGCGATCA | 606679 | 49749 | n.d. | 0.94 | 194 |
| 55496 | 0 | CAGTCCTTTAGGGCGATC | 606680 | 49750 | n.d. | 0.92 | 195 |
| 55523 | 0 | GGAATCGACATCCACATC | 606681 | 49777 | n.d. | 0.68 | 196 |
| 55524 | 0 | TGGAATCGACATCCACAT | 606682 | 49778 | n.d. | 0.70 | 197 |
| 55525 | 0 | ATGGAATCGACATCCACA | 606683 | 49779 | n.d. | 0.66 | 198 |
| 55526 | 0 | GATGGAATCGACATCCAC | 606684 | 49780 | n.d. | 0.63 | 199 |
| 55527 | 0 | TGATGGAATCGACATCCA | 606685 | 49781 | n.d. | 0.63 | 200 |
| 55528 | 0 | TTGATGGAATCGACATCC | 606686 | 49782 | n.d. | 0.88 | 201 |
| 55529 | 0 | TTTGATGGAATCGACATC | 606687 | 49783 | n.d. | 0.93 | 202 |
| 55533 | 0 | CAATTTGATGGAATCGA | 606688 | 49787 | n.d. | 1.05 | 203 |
| 55534 | 0 | GCAATTTTGATGGAATCG | 606689 | 49788 | n.d. | 0.81 | 204 |
| 55535 | 0 | AGCAATTTTGATGGAATC | 606690 | 49789 | n.d. | 0.60 | 205 |
| 55536 | 0 | AAGCAATTTTGATGGAAT | 606691 | 49790 | n.d. | 0.66 | 206 |
| 55537 | 0 | CAAGCAATTTTGATGGAA | 606692 | 49791 | n.d. | 0.56 | 207 |
| 55538 | 0 | CCAAGCAATTTTGATGGA | 606693 | 49792 | n.d. | 0.61 | 208 |

TABLE 13-continued

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55539 | 0 | CCCAAGCAATTTTGATGG | 606694 | 49793 | n.d. | 0.84 | 209 |
| 55576 | 0 | GTCACCCTGTACCTGGAA | 606695 | 49830 | n.d. | 0.88 | 210 |
| 55577 | 0 | GGTCACCCTGTACCTGGA | 606696 | 49831 | 1.32 | 1.07 | 211 |
| 55578 | 0 | AGGTCACCCTGTACCTGG | 606697 | 49832 | 0.74 | 0.81 | 212 |
| 55579 | 0 | TAGGTCACCCTGTACCTG | 606698 | 49833 | 0.61 | 0.69 | 213 |
| 55580 | 0 | GTAGGTCACCCTGTACCT | 606699 | 49834 | 0.52 | 0.49 | 214 |
| 55581 | 0 | AGTAGGTCACCCTGTACC | 606700 | 49835 | 0.48 | 0.57 | 215 |
| 55582 | 0 | GAGTAGGTCACCCTGTAC | 606701 | 49836 | 0.45 | 0.59 | 216 |
| 55583 | 0 | CGAGTAGGTCACCCTGTA | 606702 | 49837 | 0.60 | 0.80 | 217 |
| 55584 | 0 | TCGAGTAGGTCACCCTGT | 606703 | 49838 | 0.60 | 0.91 | 218 |
| 55585 | 0 | CTCGAGTAGGTCACCCTG | 606704 | 49839 | 0.60 | 0.78 | 219 |
| 55586 | 0 | GCTCGAGTAGGTCACCCT | 606705 | 49840 | 0.59 | 0.69 | 220 |
| 55587 | 0 | GGCTCGAGTAGGTCACCC | 606706 | 49841 | 0.57 | 0.57 | 221 |
| 55588 | 0 | GGGCTCGAGTAGGTCACC | 606707 | 49842 | 0.53 | 0.58 | 222 |
| 55589 | 0 | AGGGCTCGAGTAGGTCAC | 606708 | 49843 | 0.62 | 0.63 | 223 |
| 55590 | 0 | CAGGGCTCGAGTAGGTCA | 606709 | 49844 | 0.45 | 0.50 | 224 |
| 55591 | 0 | TCAGGGCTCGAGTAGGTC | 606710 | 49845 | 0.60 | 0.60 | 225 |
| 55592 | 0 | CTCAGGGCTCGAGTAGGT | 606711 | 49846 | 0.83 | 0.86 | 226 |
| 55593 | 0 | CCTCAGGGCTCGAGTAGG | 606712 | 49847 | 0.95 | 0.99 | 227 |
| 55594 | 0 | TCCTCAGGGCTCGAGTAG | 606713 | 49848 | 0.95 | 0.83 | 228 |
| 55595 | 0 | ATCCTCAGGGCTCGAGTA | 606714 | 49849 | 0.67 | 0.61 | 229 |
| 55596 | 0 | CATCCTCAGGGCTCGAGT | 606715 | 49850 | 0.58 | 0.59 | 230 |
| 55597 | 0 | CCATCCTCAGGGCTCGAG | 606716 | 49851 | 0.65 | 0.58 | 231 |
| 55598 | 0 | TCCATCCTCAGGGCTCGA | 606717 | 49852 | 0.64 | 0.54 | 232 |
| 55599 | 0 | TTCCATCCTCAGGGCTCG | 606718 | 49853 | 0.65 | 0.62 | 233 |
| 55600 | 0 | ATTCCATCCTCAGGGCTC | 606719 | 49854 | 0.87 | 0.88 | 234 |
| 55601 | 0 | GATTCCATCCTCAGGGCT | 606720 | 49855 | 0.87 | 0.82 | 235 |
| 55602 | 0 | GGATTCCATCCTCAGGGC | 606721 | 49856 | 0.53 | 0.66 | 236 |
| 55603 | 1 | CGGATTCCATCCTCAGGG | 606722 | 49857 | 0.48 | 0.51 | 237 |
| 55604 | 2 | CCGGATTCCATCCTCAGG | 606723 | 49858 | 0.58 | 0.50 | 238 |
| 55605 | 2 | CCCGGATTCCATCCTCAG | 606724 | 49859 | 0.53 | 0.49 | 239 |
| 55606 | 2 | TCCCGGATTCCATCCTCA | 606725 | 49860 | 0.51 | 0.53 | 240 |
| 55607 | 2 | CTCCCGGATTCCATCCTC | 606726 | 49861 | 0.61 | 0.62 | 241 |
| 55608 | 2 | GCTCCCGGATTCCATCCT | 606727 | 49862 | 0.68 | 0.75 | 242 |
| 55609 | 2 | AGCTCCCGGATTCCATCC | 606728 | 49863 | 0.83 | 0.90 | 243 |
| 55610 | 3 | AAGCTCCCGGATTCCATC | 606729 | 49864 | 0.48 | 0.68 | 244 |
| 55611 | 3 | AAAGCTCCCGGATTCCAT | 606730 | 49865 | 0.26 | 0.53 | 245 |

TABLE 13-continued

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55612 | 3 | AAAAGCTCCCGGATTCCA | 606731 | 49866 | 0.32 | 0.52 | 246 |
| 55613 | 3 | GAAAAGCTCCCGGATTCC | 606732 | 49867 | 0.37 | 0.52 | 247 |
| 55614 | 3 | GGAAAAGCTCCCGGATTC | 606733 | 49868 | 0.49 | 0.59 | 248 |
| 55615 | 3 | GGGAAAAGCTCCCGGATT | 606734 | 49869 | 0.61 | 0.57 | 249 |
| 55621 | 2 | GCAGGGAAAAGCTCC | 598145 | 49875 | 0.78 | 0.92 | 141 |

TABLE 14

EDA+FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 48384 | 3 | AGGGAAAAGCTCCCGGAT | 606735 | 49870 | 0.95 | 0.77 | 250 |
| 55617 | 3 | CAGGGAAAAGCTCCCGGA | 606736 | 49871 | 1.04 | 0.83 | 251 |
| 55618 | 3 | GCAGGGAAAAGCTCCCGG | 606737 | 49872 | 0.85 | 0.82 | 252 |
| 55619 | 3 | TGCAGGGAAAAGCTCCCG | 606738 | 49873 | 0.71 | 0.76 | 253 |
| 55620 | 3 | GTGCAGGGAAAAGCTCCC | 606739 | 49874 | 0.65 | 0.68 | 254 |
| 55621 | 2 | GCAGGGAAAAGCTCC | 598145 | 49875 | 0.79 | 0.55 | 141 |
| 55621 | 2 | GGTGCAGGGAAAAGCTCC | 606740 | 49875 | 0.79 | 0.76 | 255 |
| 55622 | 1 | AGGTGCAGGGAAAAGCTC | 606741 | 49876 | 0.88 | 0.83 | 256 |
| 55623 | 1 | CAGGTGCAGGGAAAAGCT | 606742 | 49877 | 0.77 | 0.88 | 257 |
| 55624 | 1 | TCAGGTGCAGGGAAAAGC | 606743 | 49878 | 1.11 | 0.98 | 258 |
| 55625 | 1 | ATCAGGTGCAGGGAAAAG | 606744 | 49879 | 1.05 | 0.97 | 259 |
| 55626 | 1 | CATCAGGTGCAGGGAAAA | 606745 | 49880 | 0.76 | 0.79 | 260 |
| 55627 | 1 | CCATCAGGTGCAGGGAAA | 606746 | 49881 | 0.50 | 0.63 | 261 |
| 55628 | 0 | ACCATCAGGTGCAGGGAA | 606747 | 49882 | 0.53 | 0.73 | 262 |
| 55629 | 0 | CACCATCAGGTGCAGGGA | 606748 | 49883 | 0.70 | 0.77 | 263 |
| 55630 | 0 | TCACCATCAGGTGCAGGG | 606749 | 49884 | 0.83 | 0.85 | 264 |
| 55631 | 0 | TTCACCATCAGGTGCAGG | 606750 | 49885 | 1.11 | 0.94 | 265 |
| 55632 | 0 | CTTCACCATCAGGTGCAG | 606751 | 49886 | 0.88 | 0.82 | 266 |
| 55633 | 0 | TCTTCACCATCAGGTGCA | 606752 | 49887 | 0.68 | 0.71 | 267 |
| 55634 | 1 | GTCTTCACCATCAGGTGC | 606753 | 49888 | 0.49 | 0.55 | 268 |
| 55635 | 1 | CGTCTTCACCATCAGGTG | 606754 | 49889 | 0.90 | 0.53 | 269 |
| 55636 | 1 | TCGTCTTCACCATCAGGT | 606755 | 49890 | 1.17 | 0.49 | 270 |
| 55637 | 1 | GTCGTCTTCACCATCAGG | 606756 | 49891 | 1.58 | 0.57 | 271 |
| 55638 | 1 | TGTCGTCTTCACCATCAG | 606757 | 49892 | 1.48 | 0.64 | 272 |
| 55639 | 1 | GTGTCGTCTTCACCATCA | 606758 | 49893 | 1.27 | 0.96 | 273 |
| 55640 | 1 | AGTGTCGTCTTCACCATC | 606759 | 49894 | 0.78 | 0.75 | 274 |
| 55641 | 1 | CAGTGTCGTCTTCACCAT | 606760 | 49895 | 0.52 | 0.54 | 275 |

TABLE 14-continued

EDA⁺FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55642 | 1 | GCAGTGTCGTCTTCACCA | 606761 | 49896 | 0.47 | 0.53 | 276 |
| 55643 | 1 | TGCAGTGTCGTCTTCACC | 606762 | 49897 | 0.49 | 0.55 | 277 |
| 55644 | 1 | CTGCAGTGTCGTCTTCAC | 606763 | 49898 | 0.61 | 0.54 | 278 |
| 55645 | 1 | TCTGCAGTGTCGTCTTCA | 606764 | 49899 | 0.93 | 0.57 | 279 |
| 55646 | 1 | CTCTGCAGTGTCGTCTTC | 606765 | 49900 | 0.98 | 0.67 | 280 |
| 55647 | 1 | GCTCTGCAGTGTCGTCTT | 606766 | 49901 | 0.72 | 0.83 | 281 |
| 55648 | 1 | AGCTCTGCAGTGTCGTCT | 606767 | 49902 | 0.71 | 0.65 | 282 |
| 55649 | 1 | CAGCTCTGCAGTGTCGTC | 606768 | 49903 | 0.71 | 0.62 | 283 |
| 55650 | 1 | GCAGCTCTGCAGTGTCGT | 606769 | 49904 | 0.64 | 0.60 | 284 |
| 55651 | 1 | TGCAGCTCTGCAGTGTCG | 606770 | 49905 | 0.40 | 0.47 | 285 |
| 55652 | 1 | CTGCAGCTCTGCAGTGTC | 606771 | 49906 | 0.35 | 0.53 | 286 |
| 55653 | 1 | CCTGCAGCTCTGCAGTGT | 606772 | 49907 | 0.47 | 0.56 | 287 |
| 55654 | 1 | CCCTGCAGCTCTGCAGTG | 606773 | 49908 | 0.71 | 0.97 | 288 |
| 55655 | 1 | GCCCTGCAGCTCTGCAGT | 606774 | 49909 | 0.83 | 0.97 | 289 |
| 55656 | 1 | GGCCCTGCAGCTCTGCAG | 606775 | 49910 | 0.91 | 0.73 | 290 |
| 55657 | 1 | AGGCCCTGCAGCTCTGCA | 606776 | 49911 | 0.74 | 0.64 | 291 |
| 55658 | 1 | GAGGCCCTGCAGCTCTGC | 606777 | 49912 | 0.60 | 0.66 | 292 |
| 55659 | 1 | TGAGGCCCTGCAGCTCTG | 606778 | 49913 | 0.49 | 0.50 | 293 |
| 55660 | 1 | CTGAGGCCCTGCAGCTCT | 606779 | 49914 | 0.47 | 0.57 | 294 |
| 55661 | 2 | CCTGAGGCCCTGCAGCTC | 606780 | 49915 | 0.54 | 0.65 | 295 |
| 55698 | 0 | GCAAGGCAACCACACTGA | 606781 | 49952 | 0.60 | 0.71 | 296 |
| 55699 | 0 | TGCAAGGCAACCACACTG | 606782 | 49953 | 0.75 | 0.79 | 297 |
| 55700 | 0 | GTGCAAGGCAACCACACT | 606783 | 49954 | 0.75 | 0.63 | 298 |
| 55701 | 0 | CGTGCAAGGCAACCACAC | 606784 | 49955 | 0.53 | 0.59 | 299 |
| 55702 | 0 | TCGTGCAAGGCAACCACA | 606785 | 49956 | 0.46 | 0.46 | 300 |
| 55703 | 0 | ATCGTGCAAGGCAACCAC | 606786 | 49957 | 0.48 | 0.55 | 301 |
| 55704 | 0 | CATCGTGCAAGGCAACCA | 606787 | 49958 | 0.46 | 0.45 | 302 |
| 55708 | 0 | ATATCATCGTGCAAGGCA | 606788 | 49962 | 0.36 | 0.45 | 303 |
| 55709 | 0 | CATATCATCGTGCAAGGC | 606789 | 49963 | 0.59 | 0.49 | 304 |
| 55710 | 0 | CCATATCATCGTGCAAGG | 606790 | 49964 | 1.00 | 0.72 | 305 |
| 55711 | 0 | TCCATATCATCGTGCAAG | 606791 | 49965 | 1.00 | 0.58 | 306 |
| 55712 | 0 | CTCCATATCATCGTGCAA | 606792 | 49966 | 0.78 | 0.54 | 307 |
| 55713 | 0 | TCTCCATATCATCGTGCA | 606793 | 49967 | 0.61 | 0.46 | 308 |
| 55714 | 0 | CTCTCCATATCATCGTGC | 606794 | 49968 | 0.52 | n.d. | 309 |
| 55715 | 0 | GCTCTCCATATCATCGTG | 606795 | 49969 | 0.69 | n.d. | 310 |
| 55716 | 0 | GGCTCTCCATATCATCGT | 606796 | 49970 | 0.70 | n.d. | 311 |
| 55717 | 0 | TGGCTCTCCATATCATCG | 606797 | 49971 | 0.71 | n.d. | 312 |

TABLE 14-continued

EDA⁺FN mRNA levels compared to untreated cells (designated 1.00) in MHT cells

| Human Start Site | Mismatches with human sequence | Sequence | ISIS No | Murine Start Site | LTS01050 | LTS01052 | SEQ ID NO |
|---|---|---|---|---|---|---|---|
| 55718 | 0 | CTGGCTCTCCATATCATC | 606798 | 49972 | 1.37 | n.d. | 313 |
| 55719 | 0 | GCTGGCTCTCCATATCAT | 606799 | 49973 | 1.82 | n.d. | 314 |
| 55749 | 1 | ATATACCTGTGGACTGGA | 606800 | 50003 | 0.77 | n.d. | 315 |
| 55750 | 1 | GATATACCTGTGGACTGG | 606801 | 50004 | 0.56 | n.d. | 316 |
| 55751 | 1 | CGATATACCTGTGGACTG | 606802 | 50005 | 0.40 | n.d. | 317 |
| 55752 | 1 | ACGATATACCTGTGGACT | 606803 | 50006 | 0.34 | n.d. | 318 |
| 55753 | 1 | AACGATATACCTGTGGAC | 606804 | 50007 | 0.33 | n.d. | 319 |
| 55754 | 1 | TAACGATATACCTGTGGA | 606805 | 50008 | 0.47 | n.d. | 320 |
| 55755 | 1 | TTAACGATATACCTGTGG | 606806 | 50009 | 0.57 | n.d. | 321 |
| 55756 | 2 | GTTAACGATATACCTGTG | 606807 | 50010 | 0.73 | n.d. | 322 |
| 55757 | 3 | GGTTAACGATATACCTGT | 606808 | 50011 | 0.59 | n.d. | 323 |
| 55758 | 3 | CGGTTAACGATATACCTG | 606809 | 50012 | 0.40 | n.d. | 324 |
| 55759 | 3 | GCGGTTAACGATATACCT | 606810 | 50013 | 0.40 | n.d. | 325 |
| 55760 | 3 | TGCGGTTAACGATATACC | 606811 | 50014 | 0.40 | n.d. | 326 |
| 55761 | 3 | GTGCGGTTAACGATATAC | 606812 | 50015 | 0.43 | 0.46 | 327 |
| 55762 | 3 | GGTGCGGTTAACGATATA | 606813 | 50016 | 0.48 | 0.59 | 328 |
| n/a | n/a | GGGTGCGGTTAACGATAT | 606814 | 50017 | 0.77 | 0.83 | 329 |

Example 10

In vitro Screening of Antisense Oligonucleotides with (S)-cEt Modifications Targeting Human and/or Mouse Fibronectin in b.END Cells Antisense oligonucleotides were designed targeting a fibronectin nucleic acid and were tested for their effects on blocking of fibronectin splicing in vitro. ISIS 606793 was also included in the study. The newly designed antisense oligonucleotides in Tables 15-22 were designed as deoxy and (S)-cEt oligonucleotides. Each nucleoside in the oligonucleotide has a 2'-MOE, deoxy, or (S)-cEt modification, as presented in the Chemistry column of the tables. 'e' indicates MOE; 'k' indicates (S)-cEt; 'd' indicates deoxy modifications. The internucleoside linkages throughout each oligonucleotide are phosphorothioate (P=S) linkages. All cytosine residues throughout each oligonucleotide are 5-methylcytosines. "Human Start site" indicates the 5'-most nucleoside to which the oligonucleotide is targeted in the human gene sequence. "Murine Start Site" indicates the 5'-most nucleoside to which the oligonucleotide is targeted murine gene sequence. Each oligonucleotide listed in Tables 15-22 is targeted to the human fibronectin genomic sequence, SEQ ID NO: 1 or to murine fibronectin genomic sequence, SEQ ID NO: 29, or both. Several of the oligonucleotides are cross-reactive with human and mouse gene sequences. The greater the complementarity between the oligonucleotide and the gene sequence, the more likely the oligonucleotide can target the gene sequence. 'Mismatches' indicates the least number of nucleotides in the oligonucleotide that are mismatched with the gene sequence; the antisense oligonucleotide may target the gene sequence with more mismatches. 'n/a' indicates that the antisense oligonucleotide has more than 3 mismatches with the particular gene sequence.

Cultured b.END cells were transfected using 2 µl Cytofectin/mL with 3 nM antisense oligonucleotide. After a treatment period of approximately 4 hours, the medium was removed and new medium was added, left in culture overnight. RNA was isolated from the cells and measured by RT-PCR. EDA mRNA expression was measured with mouse primer probe set LTS01050, as well as with LTS01052.

Results are presented in Tables 15-22, and are the average of the values measured in three separate experiments. The results demonstrate blocking of splicing, as represented by EDA⁺FN expression. The expression value of untreated cells was taken as 1.00. 'n.d.' indicates that the mRNA expression level values were not considered because the oligonucleotide targeted an amplicon region of the specific primer probe set.

TABLE 15

EDA⁺FN mRNA levels compared to untreated cells (designated 1.00) in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 48386 | 3 | 49872 | AGGGAAAAGCTCCCGG | 607180 | kddkddkddkddkddk | 0.80 | 330 |
| 55578 | 0 | 49832 | GTCACCCTGTACCTGG | 607170 | kddkddkddkddkddk | 0.86 | 331 |
| 55582 | 0 | 49836 | GTAGGTCACCCTGTAC | 607171 | kddkddkddkddkddk | 0.71 | 332 |
| 55586 | 0 | 49840 | TCGAGTAGGTCACCCT | 607172 | kddkddkddkddkddk | 0.56 | 333 |
| 55590 | 0 | 49844 | GGGCTCGAGTAGGTCA | 607173 | kddkddkddkddkddk | 0.41 | 334 |
| 55594 | 0 | 49848 | CTCAGGGCTCGAGTAG | 607174 | kddkddkddkddkddk | 0.50 | 335 |
| 55598 | 0 | 49852 | CATCCTCAGGGCTCGA | 607175 | kddkddkddkddkddk | 0.44 | 336 |
| 55602 | 0 | 49856 | ATTCCATCCTCAGGGC | 607176 | kddkddkddkddkddk | 0.42 | 337 |
| 55606 | 2 | 49860 | CCGGATTCCATCCTCA | 607177 | kddkddkddkddkddk | 0.47 | 338 |
| 55610 | 2 | 49864 | GCTCCCGGATTCCATC | 607178 | kddkddkddkddkddk | 0.18 | 339 |
| 55614 | 3 | 49868 | AAAAGCTCCCGGATTC | 607179 | kddkddkddkddkddk | 0.31 | 340 |
| 55622 | 1 | 49876 | GTGCAGGGAAAAGCTC | 607181 | kddkddkddkddkddk | 0.73 | 341 |
| 55626 | 1 | 49880 | TCAGGTGCAGGGAAAA | 607182 | kddkddkddkddkddk | 0.72 | 342 |
| 55630 | 0 | 49884 | ACCATCAGGTGCAGGG | 607183 | kddkddkddkddkddk | 0.36 | 343 |
| 55634 | 0 | 49888 | CTTCACCATCAGGTGC | 607184 | kddkddkddkddkddk | 0.49 | 344 |
| 55638 | 1 | 49892 | TCGTCTTCACCATCAG | 607185 | kddkddkddkddkddk | 0.34 | 345 |
| 55642 | 1 | 49896 | AGTGTCGTCTTCACCA | 607186 | kddkddkddkddkddk | 0.22 | 346 |
| 55646 | 1 | 49900 | CTGCAGTGTCGTCTTC | 607187 | kddkddkddkddkddk | 0.36 | 347 |
| 55650 | 1 | 49904 | AGCTCTGCAGTGTCGT | 607188 | kddkddkddkddkddk | 0.19 | 348 |
| 55654 | 1 | 49908 | CTGCAGCTCTGCAGTG | 607189 | kddkddkddkddkddk | 0.71 | 349 |
| 55658 | 1 | 49912 | GGCCCTGCAGCTCTGC | 607190 | kddkddkddkddkddk | 0.29 | 350 |
| 55662 | 1 | 49916 | CTGAGGCCCTGCAGCT | 607191 | kddkddkddkddkddk | 0.32 | 351 |
| 55666 | 2 | 49920 | CGGCCTGAGGCCCTGC | 607192 | kddkddkddkddkddk | 0.48 | 352 |
| 55670 | 2 | 49924 | ACCCCGGCCTGAGGCC | 607193 | kddkddkddkddkddk | 0.33 | 353 |
| 55674 | 2 | 49928 | TCAGACCCCGGCCTGA | 607194 | kddkddkddkddkddk | 0.34 | 354 |
| 55678 | 2 | 49932 | GTACTCAGACCCCGGC | 607195 | kddkddkddkddkddk | 0.27 | 355 |
| 55682 | 1 | 49936 | CTGTGTACTCAGACCC | 607196 | kddkddkddkddkddk | 0.63 | 356 |
| 55686 | 0 | 49940 | CTGACTGTGTACTCAG | 607197 | kddkddkddkddkddk | 0.61 | 357 |
| 55690 | 0 | 49944 | CACACTGACTGTGTAC | 607198 | kddkddkddkddkddk | 0.57 | 358 |
| 55694 | 0 | 49948 | CAACCACACTGACTGT | 607199 | kddkddkddkddkddk | 0.51 | 359 |
| 55698 | 0 | 49952 | AAGGCAACCACACTGA | 607200 | kddkddkddkddkddk | 0.47 | 360 |
| 55702 | 0 | 49956 | GTGCAAGGCAACCACA | 607201 | kddkddkddkddkddk | 0.28 | 361 |
| 55706 | 0 | 49960 | CATCGTGCAAGGCAAC | 607202 | kddkddkddkddkddk | 0.27 | 362 |
| 55710 | 0 | 49964 | ATATCATCGTGCAAGG | 607203 | kddkddkddkddkddk | 0.44 | 363 |
| 55713 | 0 | 49967 | TCTCCATATCATCGTGCA | 606793 | eeeeeeeeeeeeeeeee | 0.13 | 308 |
| 55714 | 0 | 49968 | CTCCATATCATCGTGC | 607204 | kddkddkddkddkddk | 0.18 | 364 |

TABLE 15-continued

EDA⁺FN mRNA levels compared to untreated cells (designated 1.00) in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55718 | 0 | 49972 | GGCTCTCCATATCATC | 607205 | kddkddkddkddkddk | 0.22 | 365 |
| 55722 | 0 | 49976 | GGCTGGCTCTCCATAT | 607206 | kddkddkddkddkddk | 0.53 | 366 |
| 55738 | 1 | 49992 | CTGGATTCCAATCAGG | 607207 | kddkddkddkddkddk | 0.17 | 367 |
| 55742 | 1 | 49996 | TGGACTGGATTCCAAT | 607208 | kddkddkddkddkddk | 0.17 | 368 |
| 55746 | 1 | 50000 | CCTGTGGACTGGATTC | 607209 | kddkddkddkddkddk | 0.23 | 369 |
| 55750 | 0 | 50004 | TATACCTGTGGACTGG | 607210 | kddkddkddkddkddk | 0.24 | 370 |
| 55754 | 1 | 50008 | ACGATATACCTGTGGA | 607211 | kddkddkddkddkddk | 0.51 | 371 |
| 55758 | 2 | 50012 | GTTAACGATATACCTG | 607212 | kddkddkddkddkddk | 0.40 | 372 |
| 55762 | 3 | 50016 | TGCGGTTAACGATATA | 607213 | kddkddkddkddkddk | 0.18 | 373 |
| n/a | n/a | 50020 | TGGGTGCGGTTAACGA | 607214 | kddkddkddkddkddk | 1.39 | 374 |

TABLE 16

EDA⁺FN mRNA levels compared to untreated cells (designated 1.00) in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55466 | 0 | 49720 | AAATTAATGGTAAGAG | 607142 | kddkddkddkddkddk | 0.19 | 375 |
| 55470 | 0 | 49724 | AGGCAAATTAATGGTA | 607143 | kddkddkddkddkddk | 0.20 | 376 |
| 55474 | 0 | 49728 | TGTTAGGCAAATTAAT | 607144 | kddkddkddkddkddk | 0.53 | 377 |
| 55478 | 0 | 49732 | TGTCTGTTAGGCAAAT | 607145 | kddkddkddkddkddk | 0.59 | 378 |
| 55482 | 0 | 49736 | TCAATGTCTGTTAGGC | 607146 | kddkddkddkddkddk | 0.59 | 379 |
| 55486 | 0 | 49740 | GCGATCAATGTCTGTT | 607147 | kddkddkddkddkddk | 0.65 | 380 |
| 55490 | 0 | 49744 | TAGGGCGATCAATGTC | 607148 | kddkddkddkddkddk | 0.67 | 381 |
| 55494 | 0 | 49748 | CCTTTAGGGCGATCAA | 607149 | kddkddkddkddkddk | 0.68 | 382 |
| 55498 | 0 | 49752 | CAGTCCTTTAGGGCGA | 607150 | kddkddkddkddkddk | 0.68 | 383 |
| 55502 | 0 | 49756 | ATGCCAGTCCTTTAGG | 607151 | kddkddkddkddkddk | 0.71 | 384 |
| 55506 | 0 | 49760 | GTGAATGCCAGTCCTT | 607152 | kddkddkddkddkddk | 0.75 | 385 |
| 55510 | 0 | 49764 | ATCAGTGAATGCCAGT | 607153 | kddkddkddkddkddk | 0.75 | 386 |
| 55514 | 0 | 49768 | CCACATCAGTGAATGC | 607154 | kddkddkddkddkddk | 0.83 | 387 |
| 55518 | 0 | 49772 | ACATCCACATCAGTGA | 607155 | kddkddkddkddkddk | 0.84 | 388 |
| 55522 | 0 | 49776 | ATCGACATCCACATCA | 607156 | kddkddkddkddkddk | 0.88 | 389 |
| 55526 | 0 | 49780 | TGGAATCGACATCCAC | 607157 | kddkddkddkddkddk | 0.90 | 390 |
| 55530 | 0 | 49784 | TTGATGGAATCGACAT | 607158 | kddkddkddkddkddk | 0.91 | 391 |
| 55534 | 0 | 49788 | AATTTTGATGGAATCG | 607159 | kddkddkddkddkddk | 0.91 | 392 |
| 55538 | 0 | 49792 | AAGCAATTTTGATGGA | 607160 | kddkddkddkddkddk | 0.91 | 393 |
| 55542 | 0 | 49796 | TCCCAAGCAATTTTGA | 607161 | kddkddkddkddkddk | 0.95 | 394 |

TABLE 16-continued

EDA⁺FN mRNA levels compared to untreated cells (designated 1.00) in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55546 | 0 | 49800 | GCTTTCCCAAGCAATT | 607162 | kddkddkddkddkddk | 0.96 | 395 |
| 55550 | 0 | 49804 | GTGGGCTTTCCCAAGC | 607163 | kddkddkddkddkddk | 0.97 | 396 |
| 55554 | 0 | 49808 | CCCTGTGGGCTTTCCC | 607164 | kddkddkddkddkddk | 0.97 | 397 |
| 55558 | 0 | 49812 | TTGCCCCTGTGGGCTT | 607165 | kddkddkddkddkddk | 1.00 | 398 |
| 55562 | 0 | 49816 | AAACTTGCCCCTGTGG | 607166 | kddkddkddkddkddk | 1.06 | 399 |
| 55566 | 0 | 49820 | CTGGAAACTTGCCCCT | 607167 | kddkddkddkddkddk | 1.09 | 400 |
| 55570 | 0 | 49824 | GTACCTGGAAACTTGC | 607168 | kddkddkddkddkddk | 1.16 | 401 |
| 55574 | 0 | 49828 | CCCTGTACCTGGAAAC | 607169 | kddkddkddkddkddk | 1.17 | 402 |
| 55713 | 0 | 49967 | TCTCCATATCATCGTGCA | 606793 | eeeeeeeeeeeeeeeee | 0.16 | 308 |

TABLE 17

EDA⁺FN mRNA levels compared to untreated cells (designated 1.00) in b.END cells measured with LTS01050

| Human Start Site | Mismatches to the human sequence | Murine Start Site | Sequence | ISIS No | Chemistry | EDA+FA | SEQ ID NO |
|---|---|---|---|---|---|---|---|
| 55713 | 0 | 49967 | TCTCCATATCATCGTGCA | 606793 | eeeeeeeeeeeeeeeee | 0.16 | 308 |
| 55578 | 0 | 49832 | GTCACCCTGTACCTGG | 607243 | keekeekeekeekeek | 0.83 | 331 |
| 55582 | 0 | 49836 | GTAGGTCACCCTGTAC | 607244 | keekeekeekeekeek | 0.97 | 332 |
| 55586 | 0 | 49840 | TCGAGTAGGTCACCCT | 607245 | keekeekeekeekeek | 0.27 | 333 |
| 55590 | 0 | 49844 | GGGCTCGAGTAGGTCA | 607246 | keekeekeekeekeek | 0.65 | 334 |
| 55594 | 0 | 49848 | CTCAGGGCTCGAGTAG | 607247 | keekeekeekeekeek | 0.71 | 335 |
| 55598 | 0 | 49852 | CATCCTCAGGGCTCGA | 607248 | keekeekeekeekeek | 0.85 | 336 |
| 55602 | 0 | 49856 | ATTCCATCCTCAGGGC | 607249 | keekeekeekeekeek | 0.59 | 337 |
| 55606 | 2 | 49860 | CCGGATTCCATCCTCA | 607250 | keekeekeekeekeek | 0.72 | 338 |
| 55610 | 2 | 49864 | GCTCCCGGATTCCATC | 607251 | keekeekeekeekeek | 0.52 | 339 |
| 55614 | 3 | 49868 | AAAGCTCCCGGATTC | 607252 | keekeekeekeekeek | 0.38 | 340 |
| 48386 | 3 | 49872 | AGGGAAAAGCTCCCGG | 607253 | keekeekeekeekeek | 0.64 | 330 |
| 55622 | 1 | 49876 | GTGCAGGGAAAAGCTC | 607254 | keekeekeekeekeek | 0.61 | 341 |
| 55626 | 1 | 49880 | TCAGGTGCAGGGAAAA | 607255 | keekeekeekeekeek | 0.80 | 342 |
| 55630 | 0 | 49884 | ACCATCAGGTGCAGGG | 607256 | keekeekeekeekeek | 0.47 | 343 |
| 55634 | 0 | 49888 | CTTCACCATCAGGTGC | 607257 | keekeekeekeekeek | 0.83 | 344 |
| 55638 | 1 | 49892 | TCGTCTTCACCATCAG | 607258 | keekeekeekeekeek | 0.53 | 345 |
| 55642 | 1 | 49896 | AGTGTCGTCTTCACCA | 607259 | keekeekeekeekeek | 0.40 | 346 |
| 55646 | 1 | 49900 | CTGCAGTGTCGTCTTC | 607260 | keekeekeekeekeek | 0.84 | 347 |
| 55650 | 1 | 49904 | AGCTCTGCAGTGTCGT | 607261 | keekeekeekeekeek | 0.55 | 348 |

TABLE 17-continued

EDA+FN mRNA levels compared to untreated cells (designated 1.00) in b.END cells measured with LTS01050

| Human Start Site | Mismatches to the human sequence | Murine Start Site | Sequence | ISIS No | Chemistry | EDA+FA | SEQ ID NO |
|---|---|---|---|---|---|---|---|
| 55654 | 1 | 49908 | CTGCAGCTCTGCAGTG | 607262 | keekeekeekeekeek | 0.93 | 349 |
| 55658 | 1 | 49912 | GGCCCTGCAGCTCTGC | 607263 | keekeekeekeekeek | 0.88 | 350 |
| 55662 | 1 | 49916 | CTGAGGCCCTGCAGCT | 607264 | keekeekeekeekeek | 0.87 | 351 |
| 55666 | 2 | 49920 | CGGCCTGAGGCCCTGC | 607265 | keekeekeekeekeek | 0.82 | 352 |
| 55670 | 2 | 49924 | ACCCCGGCCTGAGGCC | 607266 | keekeekeekeekeek | 0.46 | 353 |
| 55674 | 2 | 49928 | TCAGACCCCGGCCTGA | 607267 | keekeekeekeekeek | 0.84 | 354 |
| 55678 | 2 | 49932 | GTACTCAGACCCCGGC | 607268 | keekeekeekeekeek | 0.67 | 355 |
| 55682 | 1 | 49936 | CTGTGTACTCAGACCC | 607269 | keekeekeekeekeek | 0.78 | 356 |
| 55686 | 0 | 49940 | CTGACTGTGTACTCAG | 607270 | keekeekeekeekeek | 0.75 | 357 |
| 55690 | 0 | 49944 | CACACTGACTGTGTAC | 607271 | keekeekeekeekeek | 0.90 | 358 |
| 55694 | 0 | 49948 | CAACCACACTGACTGT | 607272 | keekeekeekeekeek | 0.41 | 359 |
| 55698 | 0 | 49952 | AAGGCAACCACACTGA | 607273 | keekeekeekeekeek | 0.30 | 360 |
| 55702 | 0 | 49956 | GTGCAAGGCAACCACA | 607274 | keekeekeekeekeek | 0.35 | 361 |
| 55706 | 0 | 49960 | CATCGTGCAAGGCAAC | 607275 | keekeekeekeekeek | 0.24 | 362 |
| 55710 | 0 | 49964 | ATATCATCGTGCAAGG | 607276 | keekeekeekeekeek | 0.24 | 363 |
| 55714 | 0 | 49968 | CTCCATATCATCGTGC | 607277 | keekeekeekeekeek | 0.20 | 364 |
| 55718 | 0 | 49972 | GGCTCTCCATATCATC | 607278 | keekeekeekeekeek | 0.35 | 365 |
| 55722 | 0 | 49976 | GGCTGGCTCTCCATAT | 607279 | keekeekeekeekeek | 0.84 | 366 |
| 55738 | 1 | 49992 | CTGGATTCCAATCAGG | 607280 | keekeekeekeekeek | 0.28 | 367 |
| 55742 | 1 | 49996 | TGGACTGGATTCCAAT | 607281 | keekeekeekeekeek | 0.54 | 368 |
| 55746 | 1 | 50000 | CCTGTGGACTGGATTC | 607282 | keekeekeekeekeek | 0.42 | 369 |
| 55750 | 0 | 50004 | TATACCTGTGGACTGG | 607283 | keekeekeekeekeek | 0.50 | 370 |
| 55754 | 1 | 50008 | ACGATATACCTGTGGA | 607284 | keekeekeekeekeek | 0.16 | 371 |
| 55758 | 2 | 50012 | GTTAACGATATACCTG | 607285 | keekeekeekeekeek | 0.18 | 372 |
| 55762 | 3 | 50016 | TGCGGTTAACGATATA | 607286 | keekeekeekeekeek | 0.20 | 373 |
| n/a | n/a | 50020 | TGGGTGCGGTTAACGA | 607287 | keekeekeekeekeek | 1.28 | 374 |

TABLE 18

EDA+FN mRNA levels compared to untreated cells (designated 1.00) in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55713 | 0 | 49967 | TCTCCATATCATCGTGCA | 606793 | eeeeeeeeeeeeeeee | 0.19 | 308 |
| 55466 | 0 | 49720 | AAATTAATGGTAAGAG | 607215 | keekeekeekeekeek | 0.55 | 375 |
| 55470 | 0 | 49724 | AGGCAAATTAATGGTA | 607216 | keekeekeekeekeek | 0.39 | 376 |
| 55474 | 0 | 49728 | TGTTAGGCAAATTAAT | 607217 | keekeekeekeekeek | 0.67 | 377 |

TABLE 18-continued

EDA⁺FN mRNA levels compared to untreated cells (designated 1.00)
in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55478 | 0 | 49732 | TGTCTGTTAGGCAAAT | 607218 | keekeekeekeekeek | 0.87 | 378 |
| 55482 | 0 | 49736 | TCAATGTCTGTTAGGC | 607219 | keekeekeekeekeek | 0.74 | 379 |
| 55486 | 0 | 49740 | GCGATCAATGTCTGTT | 607220 | keekeekeekeekeek | 0.60 | 380 |
| 55490 | 0 | 49744 | TAGGGCGATCAATGTC | 607221 | keekeekeekeekeek | 0.59 | 381 |
| 55494 | 0 | 49748 | CCTTTAGGGCGATCAA | 607222 | keekeekeekeekeek | 0.71 | 382 |
| 55498 | 0 | 49752 | CAGTCCTTTAGGGCGA | 607223 | keekeekeekeekeek | 0.97 | 383 |
| 55502 | 0 | 49756 | ATGCCAGTCCTTTAGG | 607224 | keekeekeekeekeek | 0.83 | 384 |
| 55506 | 0 | 49760 | GTGAATGCCAGTCCTT | 607225 | keekeekeekeekeek | 1.00 | 385 |
| 55510 | 0 | 49764 | ATCAGTGAATGCCAGT | 607226 | keekeekeekeekeek | 1.09 | 386 |
| 55514 | 0 | 49768 | CCACATCAGTGAATGC | 607227 | keekeekeekeekeek | 0.84 | 387 |
| 55518 | 0 | 49772 | ACATCCACATCAGTGA | 607228 | keekeekeekeekeek | 0.96 | 388 |
| 55522 | 0 | 49776 | ATCGACATCCACATCA | 607229 | keekeekeekeekeek | 0.84 | 389 |
| 55526 | 0 | 49780 | TGGAATCGACATCCAC | 607230 | keekeekeekeekeek | 0.95 | 390 |
| 55530 | 0 | 49784 | TTGATGGAATCGACAT | 607231 | keekeekeekeekeek | 0.96 | 391 |
| 55534 | 0 | 49788 | AATTTTGATGGAATCG | 607232 | keekeekeekeekeek | 0.83 | 392 |
| 55538 | 0 | 49792 | AAGCAATTTTGATGGA | 607233 | keekeekeekeekeek | 0.65 | 393 |
| 55542 | 0 | 49796 | TCCCAAGCAATTTTGA | 607234 | keekeekeekeekeek | 0.73 | 394 |
| 55546 | 0 | 49800 | GCTTTCCCAAGCAATT | 607235 | keekeekeekeekeek | 0.96 | 395 |
| 55550 | 0 | 49804 | GTGGGCTTTCCCAAGC | 607236 | keekeekeekeekeek | 0.93 | 396 |
| 55554 | 0 | 49808 | CCCTGTGGGCTTTCCC | 607237 | keekeekeekeekeek | 0.99 | 397 |
| 55558 | 0 | 49812 | TTGCCCCTGTGGGCTT | 607238 | keekeekeekeekeek | 0.92 | 398 |
| 55562 | 0 | 49816 | AAACTTGCCCCTGTGG | 607239 | keekeekeekeekeek | 0.95 | 399 |
| 55566 | 0 | 49820 | CTGGAAACTTGCCCCT | 607240 | keekeekeekeekeek | 0.79 | 400 |
| 55570 | 0 | 49824 | GTACCTGGAAACTTGC | 607241 | keekeekeekeekeek | 0.68 | 401 |
| 55574 | 0 | 49828 | CCCTGTACCTGGAAAC | 607242 | keekeekeekeekeek | 0.84 | 402 |

TABLE 19

EDA⁺FN mRNA levels compared to untreated cells (designated 1.00)
in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55713 | 0 | 49967 | TCTCCATATCATCGTGCA | 606793 | eeeeeeeeeeeeeeee | 0.20 | 308 |
| 55578 | 0 | 49832 | AGGTCACCCTGTACCTGG | 607388 | kkeekeekeekeekeeke | 0.76 | 212 |
| 55582 | 0 | 49836 | GAGTAGGTCACCCTGTAC | 607389 | kkeekeekeekeekeeke | 0.76 | 216 |
| 55586 | 0 | 49840 | GCTCGAGTAGGTCACCCT | 607390 | kkeekeekeekeekeeke | 0.83 | 220 |

TABLE 19-continued

EDA⁺FN mRNA levels compared to untreated cells (designated 1.00)
in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55590 | 0 | 49844 | CAGGGCTCGAGTAGGTCA | 607391 | kkeekeekeekeekeeke | 1.03 | 224 |
| 55594 | 0 | 49848 | TCCTCAGGGCTCGAGTAG | 607392 | kkeekeekeekeekeeke | 0.88 | 228 |
| 55598 | 0 | 49852 | TCCATCCTCAGGGCTCGA | 607393 | kkeekeekeekeekeeke | 0.74 | 232 |
| 55602 | 0 | 49856 | GGATTCCATCCTCAGGGC | 607394 | kkeekeekeekeekeeke | 1.16 | 236 |
| 55606 | 2 | 49860 | TCCCGGATTCCATCCTCA | 607395 | kkeekeekeekeekeeke | 0.81 | 240 |
| 55610 | 3 | 49864 | AAGCTCCCGGATTCCATC | 607396 | kkeekeekeekeekeeke | 0.71 | 244 |
| 55614 | 3 | 49868 | GGAAAAGCTCCCGGATTC | 607397 | kkeekeekeekeekeeke | 0.74 | 248 |
| 55618 | 3 | 49872 | GCAGGGAAAAGCTCCCGG | 607398 | kkeekeekeekeekeeke | 0.69 | 252 |
| 55622 | 1 | 49876 | AGGTGCAGGGAAAAGCTC | 607399 | kkeekeekeekeekeeke | 0.57 | 256 |
| 55626 | 1 | 49880 | CATCAGGTGCAGGGAAAA | 607400 | kkeekeekeekeekeeke | 0.80 | 260 |
| 55630 | 0 | 49884 | TCACCATCAGGTGCAGGG | 607401 | kkeekeekeekeekeeke | 0.64 | 264 |
| 55634 | 1 | 49888 | GTCTTCACCATCAGGTGC | 607402 | kkeekeekeekeekeeke | 0.65 | 268 |
| 55638 | 1 | 49892 | TGTCGTCTTCACCATCAG | 607403 | kkeekeekeekeekeeke | 0.46 | 272 |
| 55642 | 1 | 49896 | GCAGTGTCGTCTTCACCA | 607404 | kkeekeekeekeekeeke | 0.51 | 276 |
| 55646 | 1 | 49900 | CTCTGCAGTGTCGTCTTC | 607405 | kkeekeekeekeekeeke | 0.39 | 280 |
| 55650 | 1 | 49904 | GCAGCTCTGCAGTGTCGT | 607406 | kkeekeekeekeekeeke | 0.75 | 284 |
| 55654 | 1 | 49908 | CCCTGCAGCTCTGCAGTG | 607407 | kkeekeekeekeekeeke | 0.40 | 288 |
| 55658 | 1 | 49912 | GAGGCCCTGCAGCTCTGC | 607408 | kkeekeekeekeekeeke | 1.00 | 292 |
| 55662 | 2 | 49916 | GCCTGAGGCCCTGCAGCT | 607409 | kkeekeekeekeekeeke | 0.64 | 403 |
| 55666 | 2 | 49920 | CCCGGCCTGAGGCCCTGC | 607410 | kkeekeekeekeekeeke | 0.24 | 404 |
| 55670 | 2 | 49924 | AGACCCCGGCCTGAGGCC | 607411 | kkeekeekeekeekeeke | 0.47 | 405 |
| 55674 | 2 | 49928 | ACTCAGACCCCGGCCTGA | 607412 | kkeekeekeekeekeeke | 0.62 | 406 |
| 55678 | 2 | 49932 | GTGTACTCAGACCCCGGC | 607413 | kkeekeekeekeekeeke | 0.74 | 407 |
| 55682 | 1 | 49936 | GACTGTGTACTCAGACCC | 607414 | kkeekeekeekeekeeke | 0.53 | 408 |
| 55686 | 0 | 49940 | CACTGACTGTGTACTCAG | 607415 | kkeekeekeekeekeeke | 1.03 | 409 |
| 55690 | 0 | 49944 | ACCACACTGACTGTGTAC | 607416 | kkeekeekeekeekeeke | 0.95 | 410 |
| 55694 | 0 | 49948 | GGCAACCACACTGACTGT | 607417 | kkeekeekeekeekeeke | 0.83 | 411 |
| 55698 | 0 | 49952 | GCAAGGCAACCACACTGA | 607418 | kkeekeekeekeekeeke | 0.80 | 296 |
| 55702 | 0 | 49956 | TCGTGCAAGGCAACCACA | 607419 | kkeekeekeekeekeeke | 0.78 | 300 |
| 55706 | 0 | 49960 | ATCATCGTGCAAGGCAAC | 607420 | kkeekeekeekeekeeke | 0.88 | 412 |
| 55710 | 0 | 49964 | CCATATCATCGTGCAAGG | 607421 | kkeekeekeekeekeeke | 0.71 | 305 |
| 55714 | 0 | 49968 | CTCTCCATATCATCGTGC | 607422 | kkeekeekeekeekeeke | 0.84 | 309 |
| 55718 | 0 | 49972 | CTGGCTCTCCATATCATC | 607423 | kkeekeekeekeekeeke | 0.42 | 313 |
| 55738 | 1 | 49992 | GACTGGATTCCAATCAGG | 607424 | kkeekeekeekeekeeke | 0.47 | 413 |
| 55742 | 1 | 49996 | TGTGGACTGGATTCCAAT | 607425 | kkeekeekeekeekeeke | 0.49 | 414 |
| 55746 | 1 | 50000 | TACCTGTGGACTGGATTC | 607426 | kkeekeekeekeekeeke | 0.48 | 415 |

TABLE 19-continued

EDA+FN mRNA levels compared to untreated cells (designated 1.00) in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55750 | 1 | 50004 | GATATACCTGTGGACTGG | 607427 | kkeekeekeekeekeeke | 0.30 | 316 |
| 55754 | 1 | 50008 | TAACGATATACCTGTGGA | 607428 | kkeekeekeekeekeeke | 0.19 | 320 |
| 55758 | 3 | 50012 | CGGTTAACGATATACCTG | 607429 | kkeekeekeekeekeeke | 0.19 | 324 |
| 55762 | 3 | 50016 | GGTGCGGTTAACGATATA | 607430 | kkeekeekeekeekeeke | 0.41 | 328 |
| n/a | n/a | 50020 | GGTGGGTGCGGTTAACGA | 607431 | kkeekeekeekeekeeke | 0.44 | 416 |

TABLE 20

EDA+FN mRNA levels compared to untreated cells (designated 1.00) in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55713 | 0 | 49967 | TCTCCATATCATCGTGCA | 606793 | eeeeeeeeeeeeeeeee | 0.19 | 308 |
| 55466 | 0 | 49720 | GCAAATTAATGGTAAGAG | 607360 | kkeekeekeekeekeeke | 0.51 | 417 |
| 55470 | 0 | 49724 | TTAGGCAAATTAATGGTA | 607361 | kkeekeekeekeekeeke | 0.53 | 418 |
| 55474 | 0 | 49728 | TCTGTTAGGCAAATTAAT | 607362 | kkeekeekeekeekeeke | 0.64 | 180 |
| 55478 | 0 | 49732 | AATGTCTGTTAGGCAAAT | 607363 | kkeekeekeekeekeeke | 1.06 | 32 |
| 55482 | 0 | 49736 | GATCAATGTCTGTTAGGC | 607364 | kkeekeekeekeekeeke | 0.85 | 184 |
| 55486 | 0 | 49740 | GGGCGATCAATGTCTGTT | 607365 | kkeekeekeekeekeeke | 1.12 | 185 |
| 55490 | 0 | 49744 | TTTAGGGCGATCAATGTC | 607366 | kkeekeekeekeekeeke | 0.44 | 189 |
| 55494 | 0 | 49748 | GTCCTTTAGGGCGATCAA | 607367 | kkeekeekeekeekeeke | 0.88 | 193 |
| 55498 | 0 | 49752 | GCCAGTCCTTTAGGGCGA | 607368 | kkeekeekeekeekeeke | 1.09 | 419 |
| 55502 | 0 | 49756 | GAATGCCAGTCCTTTAGG | 607369 | kkeekeekeekeekeeke | 1.04 | 420 |
| 55506 | 0 | 49760 | CAGTGAATGCCAGTCCTT | 607370 | kkeekeekeekeekeeke | 0.97 | 421 |
| 55510 | 0 | 49764 | ACATCAGTGAATGCCAGT | 607371 | kkeekeekeekeekeeke | 0.95 | 422 |
| 55514 | 0 | 49768 | ATCCACATCAGTGAATGC | 607372 | kkeekeekeekeekeeke | 1.05 | 423 |
| 55518 | 0 | 49772 | CGACATCCACATCAGTGA | 607373 | kkeekeekeekeekeeke | 1.04 | 424 |
| 55522 | 0 | 49776 | GAATCGACATCCACATCA | 607374 | kkeekeekeekeekeeke | 0.94 | 425 |
| 55526 | 0 | 49780 | GATGGAATCGACATCCAC | 607375 | kkeekeekeekeekeeke | 1.07 | 199 |
| 55530 | 0 | 49784 | TTTTGATGGAATCGACAT | 607376 | kkeekeekeekeekeeke | 1.05 | 426 |
| 55534 | 0 | 49788 | GCAATTTGATGGAATCG | 607377 | kkeekeekeekeekeeke | 0.89 | 204 |
| 55538 | 0 | 49792 | CCAAGCAATTTTGATGGA | 607378 | kkeekeekeekeekeeke | 0.88 | 208 |
| 55542 | 0 | 49796 | TTTCCCAAGCAATTTTGA | 607379 | kkeekeekeekeekeeke | 0.97 | 427 |
| 55546 | 0 | 49800 | GGGCTTTCCCAAGCAATT | 607380 | kkeekeekeekeekeeke | 1.09 | 428 |
| 55550 | 0 | 49804 | CTGTGGGCTTTCCCAAGC | 607381 | kkeekeekeekeekeeke | 1.05 | 429 |
| 55554 | 0 | 49808 | GCCCCTGTGGGCTTTCCC | 607382 | kkeekeekeekeekeeke | 1.26 | 430 |
| 55558 | 0 | 49812 | ACTTGCCCCTGTGGGCTT | 607383 | kkeekeekeekeekeeke | 1.26 | 431 |

TABLE 20-continued

EDA⁺FN mRNA levels compared to untreated cells (designated 1.00) in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55562 | 0 | 49816 | GGAAACTTGCCCCTGTGG | 607384 | kkeekeekeekeekeeke | 1.07 | 432 |
| 55566 | 0 | 49820 | ACCTGGAAACTTGCCCCT | 607385 | kkeekeekeekeekeeke | 0.91 | 433 |
| 55570 | 0 | 49824 | CTGTACCTGGAAACTTGC | 607386 | kkeekeekeekeekeeke | 0.85 | 434 |
| 55574 | 0 | 49828 | CACCCTGTACCTGGAAAC | 607387 | kkeekeekeekeekeeke | 1.03 | 435 |

TABLE 21

EDA⁺FN mRNA levels compared to untreated cells (designated 1.00) in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55713 | 0 | 49967 | TCTCCATATCATCGTGCA | 606793 | eeeeeeeeeeeeeeeee | 0.15 | 308 |
| 55578 | 0 | 49832 | AGGTCACCCTGTACCTGG | 607316 | kkddkddkddkddkddkk | 0.47 | 212 |
| 55582 | 0 | 49836 | GAGTAGGTCACCCTGTAC | 607317 | kkddkddkddkddkddkk | 0.66 | 216 |
| 55586 | 0 | 49840 | GCTCGAGTAGGTCACCCT | 607318 | kkddkddkddkddkddkk | 0.78 | 220 |
| 55590 | 0 | 49844 | CAGGGCTCGAGTAGGTCA | 607319 | kkddkddkddkddkddkk | 0.78 | 224 |
| 55594 | 0 | 49848 | TCCTCAGGGCTCGAGTAG | 607320 | kkddkddkddkddkddkk | 0.60 | 228 |
| 55598 | 0 | 49852 | TCCATCCTCAGGGCTCGA | 607321 | kkddkddkddkddkddkk | 0.72 | 232 |
| 55602 | 0 | 49856 | GGATTCCATCCTCAGGGC | 607322 | kkddkddkddkddkddkk | 0.68 | 236 |
| 55606 | 2 | 49860 | TCCCGGATTCCATCCTCA | 607323 | kkddkddkddkddkddkk | 0.69 | 240 |
| 55610 | 3 | 49864 | AAGCTCCCGGATTCCATC | 607324 | kkddkddkddkddkddkk | 0.31 | 244 |
| 55614 | 3 | 49868 | GGAAAAGCTCCCGGATTC | 607325 | kkddkddkddkddkddkk | 0.58 | 248 |
| 55618 | 3 | 49872 | GCAGGGAAAAGCTCCCGG | 607326 | kkddkddkddkddkddkk | 0.52 | 252 |
| 55622 | 1 | 49876 | AGGTGCAGGGAAAAGCTC | 607327 | kkddkddkddkddkddkk | 0.28 | 256 |
| 55626 | 1 | 49880 | CATCAGGTGCAGGGAAAA | 607328 | kkddkddkddkddkddkk | 0.45 | 260 |
| 55630 | 0 | 49884 | TCACCATCAGGTGCAGGG | 607329 | kkddkddkddkddkddkk | 0.34 | 264 |
| 55634 | 1 | 49888 | GTCTTCACCATCAGGTGC | 607330 | kkddkddkddkddkddkk | 0.16 | 268 |
| 55638 | 1 | 49892 | TGTCGTCTTCACCATCAG | 607331 | kkddkddkddkddkddkk | 0.23 | 272 |
| 55642 | 1 | 49896 | GCAGTGTCGTCTTCACCA | 607332 | kkddkddkddkddkddkk | 0.18 | 276 |
| 55646 | 1 | 49900 | CTCTGCAGTGTCGTCTTC | 607333 | kkddkddkddkddkddkk | 0.17 | 280 |
| 55650 | 1 | 49904 | GCAGCTCTGCAGTGTCGT | 607334 | kkddkddkddkddkddkk | 0.41 | 284 |
| 55654 | 1 | 49908 | CCCTGCAGCTCTGCAGTG | 607335 | kkddkddkddkddkddkk | 0.44 | 288 |
| 55658 | 1 | 49912 | GAGGCCCTGCAGCTCTGC | 607336 | kkddkddkddkddkddkk | 0.42 | 292 |
| 55662 | 2 | 49916 | GCCTGAGGCCCTGCAGCT | 607337 | kkddkddkddkddkddkk | 0.23 | 403 |
| 55666 | 2 | 49920 | CCCGGCCTGAGGCCCTGC | 607338 | kkddkddkddkddkddkk | 0.14 | 404 |
| 55670 | 2 | 49924 | AGACCCCGGCCTGAGGCC | 607339 | kkddkddkddkddkddkk | 0.15 | 405 |

TABLE 21-continued

EDA+FN mRNA levels compared to untreated cells (designated 1.00)
in b.END cells measured with LTS01050

| Human Start Site | Mismatches to the human sequence | Murine Start Site | Sequence | ISIS No | Chemistry | EDA+FN | SEQ ID NO |
|---|---|---|---|---|---|---|---|
| 55674 | 2 | 49928 | ACTCAGACCCCGGCCTGA | 607340 | kkddkddkddkddkddkk | 0.15 | 406 |
| 55678 | 2 | 49932 | GTGTACTCAGACCCCGGC | 607341 | kkddkddkddkddkddkk | 0.22 | 407 |
| 55682 | 1 | 49936 | GACTGTGTACTCAGACCC | 607342 | kkddkddkddkddkddkk | 0.17 | 408 |
| 55686 | 0 | 49940 | CACTGACTGTGTACTCAG | 607343 | kkddkddkddkddkddkk | 0.39 | 409 |
| 55690 | 0 | 49944 | ACCACACTGACTGTGTAC | 607344 | kkddkddkddkddkddkk | 0.58 | 410 |
| 55694 | 0 | 49948 | GGCAACCACACTGACTGT | 607345 | kkddkddkddkddkddkk | 0.38 | 411 |
| 55698 | 0 | 49952 | GCAAGGCAACCACACTGA | 607346 | kkddkddkddkddkddkk | 0.43 | 296 |
| 55702 | 0 | 49956 | TCGTGCAAGGCAACCACA | 607347 | kkddkddkddkddkddkk | 0.56 | 300 |
| 55706 | 0 | 49960 | ATCATCGTGCAAGGCAAC | 607348 | kkddkddkddkddkddkk | 0.20 | 412 |
| 55710 | 0 | 49964 | CCATATCATCGTGCAAGG | 607349 | kkddkddkddkddkddkk | 0.22 | 305 |
| 55714 | 0 | 49968 | CTCTCCATATCATCGTGC | 607350 | kkddkddkddkddkddkk | 0.44 | 309 |
| 55718 | 0 | 49972 | CTGGCTCTCCATATCATC | 607351 | kkddkddkddkddkddkk | 0.29 | 313 |
| 55738 | 1 | 49992 | GACTGGATTCCAATCAGG | 607352 | kkddkddkddkddkddkk | 0.15 | 413 |
| 55742 | 1 | 49996 | TGTGGACTGGATTCCAAT | 607353 | kkddkddkddkddkddkk | 0.51 | 414 |
| 55746 | 1 | 50000 | TACCTGTGGACTGGATTC | 607354 | kkddkddkddkddkddkk | 0.23 | 415 |
| 55750 | 1 | 50004 | GATATACCTGTGGACTGG | 607355 | kkddkddkddkddkddkk | 0.24 | 316 |
| 55754 | 1 | 50008 | TAACGATATACCTGTGGA | 607356 | kkddkddkddkddkddkk | 0.21 | 320 |
| 55758 | 3 | 50012 | CGGTTAACGATATACCTG | 607357 | kkddkddkddkddkddkk | 0.14 | 324 |
| 55762 | 3 | 50016 | GGTGCGGTTAACGATATA | 607358 | kkddkddkddkddkddkk | 0.23 | 328 |
| n/a | n/a | 50020 | GGTGGGTGCGGTTAACGA | 607359 | kkddkddkddkddkddkk | 0.25 | 416 |

TABLE 22

EDA+FN mRNA levels compared to untreated cells (designated 1.00)
in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55713 | 0 | 49967 | TCTCCATATCATCGTGCA | 606793 | eeeeeeeeeeeeeeeee | 0.14 | 308 |
| 55466 | 0 | 49720 | GCAAATTAATGGTAAGAG | 607288 | kkddkddkddkddkddkk | 0.75 | 417 |
| 55470 | 0 | 49724 | TTAGGCAAATTAATGGTA | 607289 | kkddkddkddkddkddkk | 0.62 | 418 |
| 55474 | 0 | 49728 | TCTGTTAGGCAAATTAAT | 607290 | kkddkddkddkddkddkk | 0.47 | 180 |
| 55478 | 0 | 49732 | AATGTCTGTTAGGCAAAT | 607291 | kkddkddkddkddkddkk | 0.88 | 32 |
| 55482 | 0 | 49736 | GATCAATGTCTGTTAGGC | 607292 | kkddkddkddkddkddkk | 0.4 | 184 |
| 55486 | 0 | 49740 | GGGCGATCAATGTCTGTT | 607293 | kkddkddkddkddkddkk | 0.49 | 185 |
| 55490 | 0 | 49744 | TTAGGGCGATCAATGTC | 607294 | kkddkddkddkddkddkk | 0.35 | 189 |
| 55494 | 0 | 49748 | GTCCTTTAGGGCGATCAA | 607295 | kkddkddkddkddkddkk | 0.53 | 193 |
| 55498 | 0 | 49752 | GCCAGTCCTTTAGGGCGA | 607296 | kkddkddkddkddkddkk | 0.66 | 419 |

TABLE 22-continued

EDA+FN mRNA levels compared to untreated cells (designated 1.00)
in b.END cells measured with LTS01052

| Human Start Site | Mismatches to the human sequence | Murine Start Site | Sequence | ISIS No | Chemistry | EDA+FN | SEQ ID NO |
|---|---|---|---|---|---|---|---|
| 55502 | 0 | 49756 | GAATGCCAGTCCTTTAGG | 607297 | kkddkddkddkddkddkk | 0.58 | 420 |
| 55506 | 0 | 49760 | CAGTGAATGCCAGTCCTT | 607298 | kkddkddkddkddkddkk | 0.67 | 421 |
| 55510 | 0 | 49764 | ACATCAGTGAATGCCAGT | 607299 | kkddkddkddkddkddkk | 0.67 | 422 |
| 55514 | 0 | 49768 | ATCCACATCAGTGAATGC | 607300 | kkddkddkddkddkddkk | 0.78 | 423 |
| 55518 | 0 | 49772 | CGACATCCACATCAGTGA | 607301 | kkddkddkddkddkddkk | 0.72 | 424 |
| 55522 | 0 | 49776 | GAATCGACATCCACATCA | 607302 | kkddkddkddkddkddkk | 0.65 | 425 |
| 55526 | 0 | 49780 | GATGGAATCGACATCCAC | 607303 | kkddkddkddkddkddkk | 0.84 | 199 |
| 55530 | 0 | 49784 | TTTTGATGGAATCGACAT | 607304 | kkddkddkddkddkddkk | 0.88 | 426 |
| 55534 | 0 | 49788 | GCAATTTTGATGGAATCG | 607305 | kkddkddkddkddkddkk | 0.62 | 204 |
| 55538 | 0 | 49792 | CCAAGCAATTTTGATGGA | 607306 | kkddkddkddkddkddkk | 0.78 | 208 |
| 55542 | 0 | 49796 | TTTCCCAAGCAATTTTGA | 607307 | kkddkddkddkddkddkk | 0.59 | 427 |
| 55546 | 0 | 49800 | GGGCTTTCCCAAGCAATT | 607308 | kkddkddkddkddkddkk | 0.61 | 428 |
| 55550 | 0 | 49804 | CTGTGGGCTTTCCCAAGC | 607309 | kkddkddkddkddkddkk | 1.08 | 428 |
| 55554 | 0 | 49808 | GCCCCTGTGGGCTTTCCC | 607310 | kkddkddkddkddkddkk | 1.13 | 430 |
| 55558 | 0 | 49812 | ACTTGCCCCTGTGGGCTT | 607311 | kkddkddkddkddkddkk | 1.14 | 431 |
| 55562 | 0 | 49816 | GGAAACTTGCCCCTGTGG | 607312 | kkddkddkddkddkddkk | 0.94 | 432 |
| 55566 | 0 | 49820 | ACCTGGAAACTTGCCCCT | 607313 | kkddkddkddkddkddkk | 0.65 | 433 |
| 55570 | 0 | 49824 | CTGTACCTGGAAACTTGC | 607314 | kkddkddkddkddkddkk | 0.68 | 434 |
| 55574 | 0 | 49828 | CACCCTGTACCTGGAAAC | 607315 | kkddkddkddkddkddkk | 0.77 | 435 |

Example 11

Dose-dependent Antisense Inhibition of Fibronectin with Deoxy, MOE and (S)-cEt Antisense Oligonucleotides in b.END Cells Antisense oligonucleotides from the studies described above exhibiting significant in vitro inhibition of EDA+FN mRNA were selected and tested at various doses in b.END cells. Cells were transfected using Cytofectin reagent with 0.19 nM, 0.39 nM, 0.78 nM, 1.56 nM, 3.125 nM, or 6.25 nM concentrations of antisense oligonucleotide, as specified in Tables 23-27. After a treatment period of approximately 16 hours, RNA was isolated from the cells and EDA+FN mRNA levels were measured by quantitative real-time PCR. Primer probe sets LTS01050 and LTS01052 were used to measure mRNA levels. EDA+FN mRNA levels were adjusted according to total RNA content, as measured by RIBOGREEN®. The results demonstrate blocking of splicing, as represented by EDA+FN expression. The expression value of untreated cells was taken as 1.00. Different primer probe sets were used for different antisense oligonucleotide-treated cells to avoid the amplicon effect. Each table represents a separate experiment.

The half maximal inhibitory concentration (IC$_{50}$) of each oligonucleotide is also presented in Tables 23-27. As illustrated in the tables, EDA+FN mRNA levels were significantly reduced in a dose-dependent manner in antisense oligonucleotide treated cells.

TABLE 23

EDA+FN mRNA levels compared to untreated cells (designated 1.00) by 16-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607178 | 0.7 | 0.6 | 0.5 | 0.3 | 0.2 | 0.1 | 0.59 |
| 607186 | 0.6 | 0.5 | 0.4 | 0.2 | 0.2 | 0.1 | 0.39 |
| 607188 | 0.8 | 0.6 | 0.4 | 0.3 | 0.2 | 0.1 | 0.67 |
| 607204 | 0.6 | 0.4 | 0.3 | 0.2 | 0.1 | 0.1 | 0.27 |
| 607205 | 0.6 | 0.5 | 0.4 | 0.3 | 0.2 | 0.1 | 0.34 |

TABLE 23-continued

EDA⁺FN mRNA levels compared to untreated cells (designated 1.00) by 16-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607207 | 0.5 | 0.4 | 0.3 | 0.2 | 0.1 | 0.1 | 0.21 |
| 607208 | 0.9 | 0.5 | 0.4 | 0.3 | 0.2 | 0.2 | 0.62 |
| 607209 | 0.7 | 0.6 | 0.5 | 0.3 | 0.3 | 0.2 | 0.68 |
| 607210 | 0.8 | 0.6 | 0.5 | 0.3 | 0.3 | 0.2 | 0.77 |

TABLE 24

EDA⁺FN mRNA levels compared to untreated cells (designated 1.00) by 16-mer MOE, deoxy and (S)-cEt antisense oligonucleotides in b.END cells measured with LTS01052

| ISIS No | 0.19 nM | 0.39 nM | 0.78 nM | 1.56 nM | 3.125 nM | 6.25 nM | IC$_{50}$ |
|---|---|---|---|---|---|---|---|
| 607148 | 0.6 | 0.5 | 0.6 | 0.4 | 0.2 | 0.1 | 0.60 |
| 607149 | 0.7 | 0.5 | 0.3 | 0.3 | 0.1 | 0.1 | 0.44 |

TABLE 25

EDA⁺FN mRNA levels compared to untreated cells (designated 1.00) by 18-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607330 | 0.6 | 0.4 | 0.3 | 0.2 | 0.2 | 0.1 | 0.28 |
| 607332 | 0.6 | 0.5 | 0.3 | 0.2 | 0.1 | 0.1 | 0.35 |
| 607333 | 0.6 | 0.6 | 0.5 | 0.3 | 0.2 | 0.2 | 0.59 |
| 607338 | 0.8 | 0.9 | 0.8 | 0.7 | 0.5 | 0.4 | 3.64 |
| 607339 | 0.8 | 0.8 | 0.7 | 0.6 | 0.6 | 0.5 | 5.89 |
| 607340 | 0.7 | 0.6 | 0.5 | 0.3 | 0.3 | 0.2 | 0.63 |
| 607341 | 0.6 | 0.5 | 0.4 | 0.3 | 0.2 | 0.1 | 0.44 |
| 607342 | 0.9 | 0.7 | 0.5 | 0.5 | 0.4 | 0.4 | 1.54 |
| 607348 | 0.9 | 0.7 | 0.5 | 0.3 | 0.2 | 0.2 | 0.96 |
| 607352 | 0.4 | 0.4 | 0.2 | 0.1 | 0.1 | 0.1 | 0.16 |
| 607357 | 0.7 | 0.5 | 0.4 | 0.2 | 0.2 | 0.1 | 0.48 |

TABLE 26

EDA⁺FN mRNA levels compared to untreated cells (designated 1.00) by 16-mer MOE, deoxy and (S)-cEt antisense oligonucleotides in b.END cells measured with LTS01050

| ISIS No | 0.19 nM | 0.39 nM | 0.78 nM | 1.56 nM | 3.125 nM | 6.25 nM | IC$_{50}$ |
|---|---|---|---|---|---|---|---|
| 607245 | 0.9 | 0.9 | 0.5 | 0.5 | 0.4 | 0.4 | 2.04 |
| 607275 | 0.8 | 0.8 | 0.5 | 0.5 | 0.2 | 0.2 | 1.09 |
| 607276 | 0.8 | 0.6 | 0.4 | 0.3 | 0.2 | 0.2 | 0.57 |
| 607277 | 0.7 | 0.6 | 0.4 | 0.2 | 0.2 | 0.1 | 0.48 |
| 607284 | 0.6 | 0.6 | 0.3 | 0.1 | 0.1 | 0.1 | 0.37 |
| 607285 | 0.4 | 0.4 | 0.2 | 0.1 | 0.1 | 0.1 | 0.12 |
| 607286 | 0.7 | 0.4 | 0.3 | 0.2 | 0.1 | 0.1 | 0.36 |

TABLE 27

EDA⁺FN mRNA levels compared to untreated cells (designated 1.00) by MOE, deoxy and (S)-cEt antisense oligonucleotides in b.END cells measured with LTS01050

| ISIS No | Length (nt) | 0.19 nM | 0.39 nM | 0.78 nM | 1.56 nM | 3.125 nM | 6.25 nM | IC$_{50}$ |
|---|---|---|---|---|---|---|---|---|
| 607428 | 18 | 0.5 | 0.3 | 0.1 | 0.1 | 0.1 | 0.1 | 0.16 |
| 607429 | 18 | 0.6 | 0.7 | 0.5 | 0.3 | 0.2 | 0.1 | 0.58 |
| 607213 | 16 | 0.9 | 0.8 | 0.5 | 0.3 | 0.2 | 0.2 | 0.95 |

Example 12

Dose-dependent Antisense Inhibition of Fibronectin with Uniform MOE Antisense Oligonucleotides in b.END Cells Antisense oligonucleotides from the studies described above exhibiting significant in vitro inhibition of EDA⁺FN mRNA were selected and tested at various doses in b.END cells. Cells were transfected using Cytofectin reagent with 0.39 nM, 0.78 nM, 1.56 nM, 3.125 nM, 6.25 nM or 12.5 nM concentrations of antisense oligonucleotide, as specified in Tables 28-31. After a treatment period of approximately 16 hours, RNA was isolated from the cells and EDA⁺FN mRNA levels were measured by quantitative real-time PCR. Primer probe sets LTS01050 and LTS01052 were used to measure mRNA levels. EDA⁺FN mRNA levels were adjusted according to total RNA content, as measured by RIBOGREEN®. The results demonstrate blocking of splicing, as represented by EDA⁺FN expression. The expression value of untreated cells was taken as 1.00. Different primer probe sets were used for different antisense oligonucleotide-treated cells to avoid the amplicon effect. Each table represents a separate experiment.

The half maximal inhibitory concentration ($IC_{50}$) of each oligonucleotide is also presented in Tables 28-31. As illustrated in the tables, EDA⁺FN mRNA levels were significantly reduced in a dose-dependent manner in antisense oligonucleotide treated cells.

TABLE 28

EDA⁺FN mRNA levels compared to untreated cells (designated 1.00) by 18-mer uniform MOE oligonucleotides in b.END cells measured with LTS01050

| ISIS No | 0.39 nM | 0.78 nM | 1.56 nM | 3.125 nM | 6.25 nM | 12.5 nM | $IC_{50}$ |
|---|---|---|---|---|---|---|---|
| 606708 | 1.1 | 0.8 | 0.6 | 0.4 | 0.3 | 0.2 | 2.79 |
| 606723 | 0.8 | 0.8 | 0.6 | 0.4 | 0.2 | 0.1 | 2.39 |
| 606729 | 0.8 | 0.6 | 0.3 | 0.2 | 0.1 | 0.1 | 1.10 |
| 606753 | 0.8 | 0.5 | 0.4 | 0.3 | 0.2 | 0.1 | 1.09 |
| 606770 | 0.7 | 0.5 | 0.4 | 0.2 | 0.1 | 0.1 | 0.87 |
| 606785 | 0.5 | 0.3 | 0.2 | 0.1 | 0.1 | 0.1 | 0.37 |
| 606787 | 0.5 | 0.3 | 0.3 | 0.1 | 0.1 | 0.1 | 0.30 |
| 606788 | 0.4 | 0.2 | 0.2 | 0.1 | 0.1 | 0.1 | 0.21 |
| 606793 | 0.3 | 0.3 | 0.2 | 0.1 | 0.1 | 0.1 | 0.09 |
| 606804 | 0.5 | 0.3 | 0.3 | 0.1 | 0.1 | 0.1 | 0.40 |
| 606812 | 0.4 | 0.3 | 0.2 | 0.1 | 0.1 | 0.1 | 0.23 |

TABLE 29

EDA⁺FN mRNA levels compared to untreated cells (designated 1.00) by ISIS 606675 in b.END cells measured with LTS01052

| | |
|---|---|
| 0.39 nM | 0.8 |
| 0.78 nM | 0.6 |
| 1.56 nM | 0.5 |
| 3.125 nM | 0.3 |
| 6.25 nM | 0.1 |
| 12.5 nM | 0.1 |
| $IC_{50}$ | 1.38 |

TABLE 30

EDA⁺FN mRNA levels compared to untreated cells (designated 1.00) by 15-mer uniform MOE oligonucleotides in b.END cells measured with LTS01050

| ISIS No | 0.39 nM | 0.78 nM | 1.56 nM | 3.125 nM | 6.25 nM | 12.5 nM | $IC_{50}$ |
|---|---|---|---|---|---|---|---|
| 598137 | 1.0 | 0.8 | 0.7 | 0.5 | 0.4 | 0.2 | 4.08 |
| 598138 | 0.8 | 0.9 | 0.6 | 0.6 | 0.4 | 0.2 | 4.11 |
| 598144 | 0.9 | 0.7 | 0.4 | 0.4 | 0.2 | 0.1 | 1.75 |
| 598151 | 0.7 | 0.5 | 0.3 | 0.2 | 0.1 | 0.1 | 0.79 |
| 598153 | 0.9 | 0.6 | 0.5 | 0.3 | 0.2 | 0.1 | 1.54 |
| 598161 | 0.9 | 0.5 | 0.5 | 0.3 | 0.2 | 0.2 | 1.50 |
| 598163 | 0.6 | 0.5 | 0.4 | 0.3 | 0.1 | 0.1 | 0.60 |
| 594675 | 0.8 | 0.6 | 0.4 | 0.3 | 0.1 | 0.1 | 1.18 |
| 598145 | 0.9 | 0.7 | 0.5 | 0.3 | 0.2 | 0.1 | 1.58 |

TABLE 31

EDA⁺FN mRNA levels compared to untreated cells (designated 1.00) by 15-mer uniform MOE oligonucleotides in b.END cells measured with LTS01052

| ISIS No | 0.39 nM | 0.78 nM | 1.56 nM | 3.125 nM | 6.25 nM | 12.5 nM | $IC_{50}$ |
|---|---|---|---|---|---|---|---|
| 511404 | 0.9 | 0.8 | 0.7 | 0.4 | 0.3 | 0.2 | 2.81 |
| 598130 | 0.9 | 1.0 | 0.9 | 0.9 | 0.7 | 0.5 | 13.18 |

Example 13

Efficacy and Tolerability of Antisense Oligonucleotides Targeting Fibronectin in C57BL/6 Mice C57BL/6 mice are a multipurpose mice model, frequently utilized for safety and efficacy testing. The mice were treated with ISIS antisense oligonucleotides selected from studies described above and evaluated for efficacy, as well as changes in the levels of various plasma chemistry markers.

Study with Uniform MOE Oligonucleotides

Treatment

Groups of eight-week old C57BL/6 mice were injected subcutaneously twice a week for 3 weeks with 100 mg/kg of ISIS 594675, ISIS 598145, ISIS 598151, ISIS 598153, ISIS 598163, ISIS 606770, ISIS 606785, ISIS 606787, ISIS 606788, ISIS 606793, ISIS 606804, or ISIS 606812. One group of eight-week old C57BL/6 mice was injected subcutaneously twice a week for 3 weeks with PBS. Mice were euthanized 48 hours after the last dose, and organs and plasma were harvested for further analysis.

RNA Analysis

To evaluate the effect of ISIS oligonucleotides on blocking fibronectin splicing, mRNA levels of EDA$^+$FN were measured by RT-PCR using mouse primer probe set LTS01050 and LTS01052. The results are presented in Table 32, normalized to total fibronectin. The results demonstrate blocking of splicing, as represented by EDA$^+$FN expression. The expression value in untreated mice was taken as 1.00. 'n.d.' indicates that the mRNA expression level values were not considered because the oligonucleotide targeted an amplicon region of the specific primer probe set.

TABLE 32

EDA$^+$FN expression after antisense oligonucleotide treatment in C57BL/6 mice

|  | Lungs | | Kidneys | |
| --- | --- | --- | --- | --- |
| ISIS No | EDA$^+$FN/total FN (LTS01050) | EDA$^+$FN/total FN (LTS01052) | EDA$^+$FN/total FN (LTS01050) | EDA$^+$FN/total FN (LTS01052) |
| 594675 | 0.43 | 0.43 | 0.52 | 0.57 |
| 598145 | 0.65 | 0.61 | 0.61 | 0.64 |
| 598151 | 0.40 | 0.33 | 0.43 | 0.36 |
| 598153 | 0.75 | 0.57 | 1.07 | 0.69 |
| 598163 | 0.24 | 0.23 | 0.15 | 0.17 |
| 606770 | 0.50 | 0.38 | 0.54 | 0.52 |
| 606785 | 0.31 | 0.33 | 0.22 | 0.29 |
| 606787 | 0.36 | 0.32 | 0.26 | 0.32 |
| 606788 | 0.40 | 0.36 | 0.19 | 0.22 |
| 606793 | 0.28 | 0.23 | 0.12 | 0.14 |
| 606804 | 0.32 | n.d. | 0.27 | n.d. |
| 606812 | 0.39 | n.d. | 0.42 | n.d. |

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 33. ISIS oligonucleotides did not cause any changes in the levels of any of the liver or kidney function markers outside the expected range for antisense oligonucleotides.

TABLE 33

Plasma chemistry markers in C57BL/6 mice plasma

| | ALT (IU/L) | AST (IU/L) | Bilirubin (mg/dL) | BUN (mg/dL) |
| --- | --- | --- | --- | --- |
| PBS | 26 | 46 | 0.19 | 35 |
| ISIS 594675 | 19 | 42 | 0.20 | 31 |
| ISIS 598145 | 25 | 49 | 0.20 | 29 |
| ISIS 598151 | 30 | 67 | 0.18 | 35 |
| ISIS 598153 | 26 | 71 | 0.17 | 34 |
| ISIS 598163 | 64 | 102 | 0.19 | 38 |
| ISIS 606770 | 22 | 54 | 0.18 | 29 |
| ISIS 606785 | 48 | 94 | 0.17 | 32 |
| ISIS 606787 | 30 | 71 | 0.15 | 30 |
| ISIS 606788 | 82 | 116 | 0.15 | 33 |
| ISIS 606793 | 50 | 83 | 0.15 | 32 |
| ISIS 606804 | 31 | 56 | 0.16 | 28 |
| ISIS 606812 | 29 | 49 | 0.15 | 27 |

Organ Weights

Liver, spleen and kidney weights were measured at the end of the study, and are presented in Table 34. ISIS oligonucleotides did not cause any changes in organ weights outside the expected range for antisense oligonucleotides.

TABLE 34

Organ weights (% of the PBS control) of C57BL/6 mice

| ISIS No | Liver | Kidneys | Spleen |
| --- | --- | --- | --- |
| 594675 | 102 | 102 | 99 |
| 598145 | 98 | 105 | 117 |
| 598151 | 108 | 103 | 90 |
| 598153 | 106 | 100 | 88 |
| 598163 | 102 | 102 | 94 |
| 606770 | 106 | 104 | 93 |
| 606785 | 101 | 102 | 98 |
| 606787 | 108 | 99 | 93 |
| 606788 | 98 | 97 | 99 |
| 606793 | 103 | 94 | 99 |
| 606804 | 95 | 98 | 89 |
| 606812 | 105 | 101 | 86 |

Study with Deoxy, (S)-cEt and MOE Oligonucleotides

Treatment

Groups of eight-week old C57BL/6 mice were injected subcutaneously twice a week for 3 weeks with 100 mg/kg of ISIS 607149, ISIS 607186, ISIS 607204, ISIS 607205, ISIS 607207, ISIS 607277, ISIS 607285, ISIS 607286, ISIS 607330, ISIS 607332, ISIS 607341, ISIS 607352, ISIS 607428, or ISIS 607429. One group of eight-week old C57BL/6 mice was injected subcutaneously twice a week for 3 weeks with PBS. Mice were euthanized 48 hours after the last dose, and organs and plasma were harvested for further analysis.

RNA Analysis

To evaluate the effect of ISIS oligonucleotides on blocking fibronectin splicing, mRNA levels of EDA$^+$FN were measured by RT-PCR using mouse primer probe set LTS01050 and LTS01052. The results are presented in Table 35, normalized to total fibronectin. The results demonstrate blocking of splicing, as represented by EDA$^+$FN expression. The expression value in untreated mice was taken as 1.00. 'n.d.' indicates that the mRNA expression level values were not considered because the oligonucleotide targeted an amplicon region of the specific primer probe set.

TABLE 35

EDA+FN expression after antisense oligonucleotide treatment in C57BL/6 mice

| ISIS No | Lungs | | Kidneys | |
|---|---|---|---|---|
| | EDA+FN/total FN (LTS01050) | EDA+FN/total FN (LTS01052) | EDA+FN/total FN (LTS01050) | EDA+FN/total FN (LTS01052) |
| 607149 | n.d. | 0.32 | n.d. | 0.07 |
| 607186 | 0.26 | 0.14 | 0.02 | 0.02 |
| 607204 | 0.15 | 0.13 | 0.02 | 0.03 |
| 607205 | 0.30 | n.d. | 0.03 | n.d. |
| 607207 | 0.42 | n.d. | 0.04 | n.d. |
| 607277 | 0.33 | 0.27 | 0.05 | 0.08 |
| 607285 | 0.21 | n.d. | 0.29 | n.d. |
| 607286 | 0.13 | n.d. | 0.02 | n.d. |
| 607330 | 0.29 | 0.27 | 0.02 | 0.06 |
| 607332 | 0.08 | 0.13 | 0.01 | 0.05 |
| 607341 | 0.15 | 0.24 | 0.10 | 0.16 |
| 607352 | 0.11 | n.d. | 0.01 | n.d. |
| 607357 | 0.12 | n.d. | 0.09 | n.d. |
| 607428 | 0.12 | n.d. | 0.07 | n.d. |
| 607429 | 0.33 | n.d. | 0.20 | n.d. |

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 36. ISIS oligonucleotides that caused any changes in organ weights outside the expected range for antisense oligonucleotides were excluded from further studies.

TABLE 36

Plasma chemistry markers in C57BL/6 mice plasma

| | ALT (IU/L) | AST (IU/L) | Bilirubin (mg/dL) | BUN (mg/dL) |
|---|---|---|---|---|
| PBS | 38 | 96 | 0.18 | 36 |
| ISIS 607149 | 35 | 170 | 0.29 | 31 |
| ISIS 607186 | 22 | 73 | 0.21 | 26 |
| ISIS 607204 | 41 | 75 | 0.15 | 29 |
| ISIS 607205 | 38 | 83 | 0.15 | 32 |
| ISIS 607207 | 70 | 92 | 0.19 | 32 |
| ISIS 607277 | 54 | 108 | 0.16 | 30 |
| ISIS 607285 | 78 | 139 | 0.32 | 28 |
| ISIS 607286 | 40 | 94 | 0.38 | 27 |
| ISIS 607330 | 23 | 40 | 0.16 | 30 |
| ISIS 607332 | 41 | 66 | 0.20 | 28 |
| ISIS 607341 | 70 | 102 | 0.24 | 28 |
| ISIS 607352 | 20 | 75 | 0.13 | 27 |
| ISIS 607357 | 85 | 100 | 0.15 | 26 |
| ISIS 607428 | 21 | 82 | 0.24 | 25 |
| ISIS 607429 | 21 | 50 | 0.17 | 26 |

Organ Weights

Liver, spleen and kidney weights were measured at the end of the study, and are presented in Table 37. ISIS oligonucleotides that caused any changes in organ weights outside the expected range for antisense oligonucleotides were excluded from further studies.

TABLE 37

Organ weights (% of the PBS control) of C57BL/6 mice

| ISIS No. | Liver | Kidneys | Spleen |
|---|---|---|---|
| 607149 | 103 | 103 | 99 |
| 607186 | 91 | 106 | 101 |
| 607204 | 93 | 97 | 116 |
| 607205 | 112 | 114 | 276 |
| 607207 | 98 | 99 | 96 |
| 607277 | 98 | 100 | 108 |
| 607285 | 99 | 97 | 105 |
| 607286 | 96 | 103 | 98 |
| 607330 | 97 | 101 | 85 |
| 607332 | 102 | 98 | 97 |
| 607341 | 93 | 98 | 92 |
| 607352 | 98 | 101 | 84 |
| 607357 | 88 | 101 | 113 |
| 607428 | 96 | 101 | 90 |
| 607429 | 91 | 101 | 99 |

The invention claimed is:

1. A compound comprising a modified oligonucleotide consisting of 8 to 30 linked nucleosides and having a nucleobase sequence comprising a complementary region comprising at least 8 contiguous nucleobases complementary to a target region of equal length of a fibronectin transcript, wherein the target region is within nucleobase 55441 and nucleobase 55790 of SEQ ID NO.: 1, and wherein the modified oligonucleotide comprises a region having a sugar motif described by Formula I as follows:

$$[(A)-(B)_2]_n$$

wherein:
each A is independently a bicyclic nucleoside;
each B is independently a 2'-substituted nucleoside or a 2'-deoxynucleoside; and
n is an integer from 3-6.

2. The compound of claim 1, wherein the antisense oligonucleotide comprises a region having a sugar motif described by Formula II as follows:

$$(A)_2-[(B)_2-(A)]_n-(A)$$

wherein:
each A is independently a bicyclic nucleoside;
each B is independently a 2'-substituted nucleoside or a 2'-deoxynucleoside; and
n is an integer from 3-6.

3. The compound of claim 1, wherein the antisense oligonucleotide comprises a region having a sugar motif described by Formula III as follows:

$$(A)_2-[(B)_2-(A)]_n$$

wherein:
each A is independently a bicyclic nucleoside;
each B is independently a 2'-substituted nucleoside or a 2'-deoxynucleoside; and
n is an integer from 3-6.

4. The compound of claim 1, wherein each A comprises a bicyclic nucleoside selected from among LNA and cEt.

5. The compound of claim 4, wherein each A comprises a cEt modification.

6. The compound of claim 1, wherein each B comprises a 2'-substituted nucleoside having a 2'-modification selected from among 2'-OMe, 2'-F, and 2'-MOE.

7. The compound of claim 6, wherein the 2'-modification is a 2'-MOE modification.

8. The compound of claim 1, wherein each B comprises a 2'-deoxynucleoside.

9. A pharmaceutical composition comprising a compound according to claim 1 and a pharmaceutically acceptable carrier or diluent.

* * * * *